United States Patent
Lo et al.

(10) Patent No.: US 9,642,851 B2
(45) Date of Patent: May 9, 2017

(54) INDOLINONE DERIVATIVE AS TYROSINE KINASE INHIBITOR

(71) Applicant: KBP Biosciences Co., Ltd., Jinan, Shandong Province (CN)

(72) Inventors: Hoyin Lo, Jinan (CN); Aichen Wang, Jinan (CN); Qian Zhang, Jinan (CN)

(73) Assignee: KBP BioSciences Co., Ltd., Jinan, Shandong Province (CN)

( * ) Notice: Subject to any disclaimer, the term of this patent is extended or adjusted under 35 U.S.C. 154(b) by 0 days.

(21) Appl. No.: 14/650,270

(22) PCT Filed: Dec. 6, 2013

(86) PCT No.: PCT/CN2013/001512
§ 371 (c)(1),
(2) Date: Jun. 5, 2015

(87) PCT Pub. No.: WO2014/086102
PCT Pub. Date: Jun. 12, 2014

(65) Prior Publication Data
US 2015/0306095 A1    Oct. 29, 2015

(30) Foreign Application Priority Data

Dec. 6, 2012 (CN) .......................... 2012 1 0519315

(51) Int. Cl.
| | | |
|---|---|---|
| *C07D 209/14* | (2006.01) | |
| *C07D 413/12* | (2006.01) | |
| *C07D 413/14* | (2006.01) | |
| *C07D 403/12* | (2006.01) | |
| *A61K 31/4045* | (2006.01) | |

(Continued)

(52) U.S. Cl.
CPC ........ *A61K 31/496* (2013.01); *A61K 31/4045* (2013.01); *A61K 31/4155* (2013.01); *A61K 31/4196* (2013.01); *A61K 31/433* (2013.01); *A61K 31/435* (2013.01); *A61K 31/438* (2013.01); *A61K 31/439* (2013.01); *A61K 31/4439* (2013.01); *A61K 31/454* (2013.01); *A61K 31/4995* (2013.01); *A61K 31/506* (2013.01); *A61K 31/5377* (2013.01); *A61K 31/5383* (2013.01); *A61K 45/06* (2013.01); *C07D 209/30* (2013.01); *C07D 209/34* (2013.01); *C07D 401/12* (2013.01); *C07D 401/14* (2013.01); *C07D 403/12* (2013.01); *C07D 403/14* (2013.01); *C07D 405/04* (2013.01); *C07D 405/12* (2013.01); *C07D 405/14* (2013.01); *C07D 409/14* (2013.01); *C07D 413/14* (2013.01); *C07D 417/14* (2013.01); *C07D 471/04* (2013.01); *C07D 471/10* (2013.01); *C07D 471/14* (2013.01); *C07D 487/04* (2013.01); *C07D 487/08* (2013.01); *C07D 487/10* (2013.01); *C07D 491/107* (2013.01); *C07D 498/04* (2013.01)

(58) Field of Classification Search
CPC .. C07D 413/14; C07D 413/02; C07D 209/14; C07D 413/12; C07D 403/12; A61K 8/492; A61K 31/5377; A61K 31/4045; A61K 31/407
USPC .................. 514/414, 418; 548/456, 506, 486
See application file for complete search history.

(56) References Cited

U.S. PATENT DOCUMENTS

| | | | |
|---|---|---|---|
| 6,043,254 | A | 3/2000 | Grell et al. |
| 7,148,249 | B2 | 12/2006 | Kley et al. |
| 2005/0009898 | A1 | 1/2005 | Roth et al. |
| 2005/0054710 | A1 | 3/2005 | Kley et al. |
| 2012/0190009 | A1 | 7/2012 | Kashanchi et al. |

FOREIGN PATENT DOCUMENTS

| | | |
|---|---|---|
| AU | 781939 B2 | 6/2005 |
| CN | 1668589 A | 9/2005 |

(Continued)

OTHER PUBLICATIONS

State Intellectual Property Office of the People's Republic of China, Office Action (Non-English) issued Feb. 1, 2016 in corresponding Chinese Patent Application 2013800639362 (8 pages).

(Continued)

*Primary Examiner* — Alicia L Otton
*Assistant Examiner* — Sagar Patel
(74) *Attorney, Agent, or Firm* — Fitch, Even, Tabin & Flannery, LLP

(57) ABSTRACT

The present invention relates to a compound represented by general formula (I), a method for preparing said compound, a pharmaceutical formulation containing said compound, and the use of said compound in manufacture of a medicament for treating or preventing the fibrous degeneration disease and treating the excessive proliferation disease:

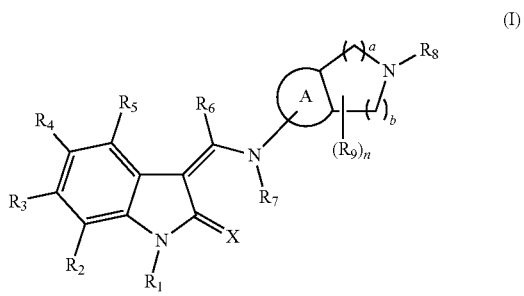

(I)

wherein ring A, X, $R_1$, $R_2$, $R_3$, $R_4$, $R_5$, $R_6$, $R_7$, $R_8$, $R_9$, a, b and n are defined as those in the description.

15 Claims, No Drawings

(51) Int. Cl.

| | | |
|---|---|---|
| A61K 31/407 | (2006.01) | |
| A61K 31/496 | (2006.01) | |
| C07D 405/14 | (2006.01) | |
| C07D 401/12 | (2006.01) | |
| C07D 405/12 | (2006.01) | |
| C07D 417/14 | (2006.01) | |
| C07D 209/34 | (2006.01) | |
| A61K 45/06 | (2006.01) | |
| A61K 31/5377 | (2006.01) | |
| C07D 409/14 | (2006.01) | |
| C07D 487/04 | (2006.01) | |
| C07D 498/04 | (2006.01) | |
| C07D 209/30 | (2006.01) | |
| C07D 401/14 | (2006.01) | |
| A61K 31/435 | (2006.01) | |
| A61K 31/438 | (2006.01) | |
| A61K 31/439 | (2006.01) | |
| A61K 31/4439 | (2006.01) | |
| A61K 31/4995 | (2006.01) | |
| A61K 31/506 | (2006.01) | |
| C07D 403/14 | (2006.01) | |
| C07D 471/10 | (2006.01) | |
| C07D 471/14 | (2006.01) | |
| C07D 487/08 | (2006.01) | |
| C07D 487/10 | (2006.01) | |
| C07D 491/107 | (2006.01) | |
| A61K 31/4155 | (2006.01) | |
| A61K 31/4196 | (2006.01) | |
| A61K 31/433 | (2006.01) | |
| A61K 31/454 | (2006.01) | |
| A61K 31/5383 | (2006.01) | |
| C07D 471/04 | (2006.01) | |
| C07D 405/04 | (2006.01) | |

(56) References Cited

FOREIGN PATENT DOCUMENTS

| | | | |
|---|---|---|---|
| CN | 103102352 A | * | 5/2013 |
| CN | 103130775 A | | 6/2013 |
| JP | 2003-511441 A | | 3/2003 |
| WO | 03/027102 A1 | | 4/2003 |

OTHER PUBLICATIONS

PCT International Search Report of the International Searching Authority dated Mar. 13, 2014 for International Application No. PCT/CN2013/001512 and English Translation, 8 pages.
Roberto Barrios et al., "Upregulation of acidic fibroblast growth factor during development of experimental lung fibrosis," American Physiological Society, 1997, pp. L451-L458.
Ulrike Bartram and Christian P. Speer, "The Role of Transforming Growth Factor β in Lung Development and Disease," Chest Journal, 2004, vol. 125, No. 2, pp. 754-765.
Erawan Borkham-Kamphorst et al., "Inhibitory effect of soluble PDGF-β receptor in culture-activated hepatic stellate cells," Biochemical and Biophysical Research Communications, 2004, vol. 317, pp. 451-462.
Erawan Borkham-Kamphorst et al., "Antisense strategy against PDGF B-chain proves effective in preventing experimental liver fibrogenesis," Biochemical and Biophysical Research Communications, 2004, vol. 321, pp. 413-423.
Thomas J. Broekelmann et al., "Transforming growth factor β1 is present at sites of extracellular matrix gene expression in human pulmonary fibrosis," Proceedings of the National Academy of Sciences, Aug. 1991, vol. 88, pp. 6642-6646.
Judah Folkman, "Tumor Angiogenesis: Therapeutic Implications," The New England Journal of Medicine, Nov. 18, 1971, vol. 285, No. 21, pp. 1182-1186.
Nicholas J. Laping, "ALK5 inhibition in renal disease," Current Opinion in Pharmacology, 2003, vol. 3, pp. 204-208.
Andrew Leask and David J. Abraham, "TGF-β signaling and the fibrotic response," The FASEB Journal, May 2004, vol. 18, pp. 816-827.
Alexander Levitzki, "PDGF receptor kinase inhibitors for the treatment of PDGF driven diseases," Cytokine & Growth Factor Reviews, 2004, vol. 15, pp. 229-235.
Xue-Mei Ou et al., "VEGFR-2 antagonist SU5416 attenuates bleomycin-induced pulmonary fibrosis in mice," International Immunopharmacology, 2009, vol. 9, pp. 70-79.
Annette B. Rice et al., "Specific Inhibitors of Platelet-Derived Growth Factor or Epidermal Growth Factor Receptor Tyrosine Kinase Reduce Pulmonary Fibrosis in Rats," American Journal of Pathology, Jul. 1999, vol. 155, No. 1, pp. 213-221.
Gerald J. Roth et al., "Design, Synthesis, and Evaluation of Indolinones as Triple Angiokinase Inhibitors and the Discovery of a Highly Specific 6-Methoxycarbonyl-Substituted Indolinone (BIBF 1120)," Journal of Medicinal Chemistry, 2009, vol. 52, pp. 4466-4480.
Frank Strutz et al., "Basic fibroblast growth factor expression is increased in human renal fibrogenesis and may mediate autocrine fibroblast proliferation," Kidney International, 2000, vol. 57, pp. 1521-1538.
Frank Strutz and Eric G. Neilson, "New insights into mechanisms of fibrosis in immune renal injury," Springer Seminars in Immunopathology, 2003, No. 24, pp. 459-476.
Qingjian Wang et al., "Effects of Delayed Treatment with Transforming Growth Factor-β Soluble Receptor in a Three-Dose Bleomycin Model of Lung Fibrosis in Hamsters," Experimental Lung Research, 2002, vol. 28, pp. 405-417.
Thomas A. Wynn, "Fibrotic Disease and the TH1/TH2 Paradigm," Nature Reviews | Immunology, Aug. 2004, vol. 4, pp. 583-594.
Chundong Yu et al., "Role of Fibroblast Growth Factor Type 1 and 2 in Carbon Tetrachloride-Induced Hepatic Injury and Fibrogenesis," American Journal of Pathology, Oct. 2003, vol. 163, No. 4, pp. 1653-1662.
PCT Transmittal and Written Opinion of the International Searching Authority for International Application PCT/CN2013/001512 dated Mar. 13, 2014, 9 pages, and English Translation 8 pages.
Mathieu Sassatelli et al., "Snythesis and antiproliferative activities of indolin-2-one derivatives bearing amino acid moieties," European Journal of Medicinal Chemistry, 2006, vol. 41, No. 6, pp. 709-716.
Chao-Cheng Chiang et al., "Discovery of Pyrrole—Indoline-2-ones as Aurora Kinase Inhibitors with a Different Inhibition Profile," Journal of Medicinal Chemistry, 2010, vol. 53, No. 16, pp. 5929-5941.
Tomoya Miura et al., "Stereoselective Oxindole Synthesis by Palladium-Catalyzed Cyclization Reaction of 2-(Alkynyl) aryl Isocyanates with Amides," Organic Letters, 2009, vol. 11, No. 10, pp. 2141-2143.
Japanese Patent Office, Office Action issued on Oct. 4, 2016 for Japanese Patent Application No. 2015-545634 (5 pages).
European Patent Office Extended European Search Report dated Jul. 6, 2016 for European Patent Application No. 13860630.6 (8 pages).

* cited by examiner

INDOLINONE DERIVATIVE AS TYROSINE KINASE INHIBITOR

CROSS-REFERENCE TO RELATED APPLICATIONS

This application is a U.S. national phase application filed under 35 U.S.C. §371 of International Application PCT/CN2013/001512, filed Dec. 6, 2013, designating the United States, which claims priority from Chinese Application CN 201210519315.8, filed Dec. 6, 2012, which are all hereby incorporated herein by reference in their entirety.

1. TECHNICAL FIELD

The present invention belongs to the field of pharmaceutical technology, specifically relates to an indolinone derivative as tyrosine kinase inhibitor, or a pharmaceutically acceptable salt, a deuteride or a stereoisomer thereof, a method for preparing the compound, a pharmaceutical composition containing the present compound, a pharmaceutical formulation containing the present compound, and the use of in manufacture of a medicament for treating or preventing the fibrous degeneration disease and treating the excessive proliferation disease.

2. BACKGROUNDS

Angiogenesis is the generation of new blood vessels in a tissue or organ. Under normal physiological conditions, humans and animals undergo angiogenesis only in very specific, restricted situations. For example, angiogenesis is normally observed in wound healing, fetal and embryonal development, and formation of the corpus luteum, endometrium and placenta.

Capillary blood vessels are composed of endothelial cells and pericytes, surrounded by a basement membrane. Angiogenesis begins with the erosion of the basement membrane by enzymes released from endothelial cells and leukocytes. Endothelial cells, lining the lumen of blood vessels, then protrude through the basement membrane. Angiogenic stimulants induce the endothelial cells to migrate through the eroded basement membrane. The migrating cells form a "sprout" off the parent blood vessel where the endothelial cells undergo mitosis and proliferate. The endothelial sprouts merge with each other to form capillary loops, creating a new blood vessel.

Protein tyrosine kinases are a class of enzymes that catalyze the transfer of a phosphate group from ATP to a tyrosine residue located on a protein substrate. Protein tyrosine kinases clearly play a role in normal cell growth. Many of the growth factor receptor proteins function as tyrosine kinases and it is by this process that they effect signaling. The interaction of growth factors with these receptors is a necessary event in normal regulation of cell growth. For example, FGFR (Fibroblast growth factor receptor), VEGFR (Vascular endothelial growth factor receptor) and PDGFR (Platelet-derived growth factor receptor). However, under certain conditions, as a result of either mutation or overexpression, these receptors can become deregulated; the result of which is uncontrolled cell proliferation which can lead to tumor growth and ultimately to the disease known as cancer. The growth factor receptor protein tyrosine kinase inhibitor can inhibit the above phosphorylation process and will have therapeutic value for the treatment of cancer and other diseases characterized by uncontrolled or abnormal cell growth.

Uncontrolled angiogenesis is a hallmark of cancer. In 1971, Dr. Judah Folkman proposed that tumor growth is dependent upon angiogenesis. See, e.g., Folkman, New England Journal of Medicine, 285:1182-86 (1971). According to Dr. Folkman, a tumor can only grow to a certain size without the growth of additional blood vessels to nourish the tumor. In its simplest terms, this proposition states: that "once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume, and not exceeding a few million cells, can survive on existing host microvessels.

It has been shown that tumors can be treated by inhibiting angiogenesis rather than inhibiting proliferation of the tumor cells themselves. Angiogenesis has been associated with a number of different types of cancer, including solid tumors and blood-borne tumors. Solid tumors with which angiogenesis has been associated include, but are not limited to, rhabdomyosarcomas, retinoblastoma, Ewing's sarcoma, neuroblastoma, and osteosarcoma. Angiogenesis also has been linked with breast cancer, prostate cancer, lung cancer, and colon cancer. Angiogenesis is also associated with blood-borne tumors, such as leukemias, lymphomas, multiple myelomas, and any of various acute or chronic neoplastic diseases of the bone marrow in which unrestrained proliferation of white blood cells occurs, usually accompanied by anemia, impaired blood clotting, and enlargement of the lymph nodes, liver and spleen. It is believed too that angiogenesis plays a role in the abnormalities in the bone marrow that give rise to leukemia and lymphoma tumors and multiple myeloma diseases.

Angiogenesis plays a major role in the metastasis of cancer. If this angiogenic activity could be repressed or eliminated, then the tumor, although present, would not grow. In the disease state, prevention of angiogenesis could overt the damage caused by the invasion of the new micro vascular system. Therapies directed at control of angiogenic processes could lead to the abrogation or mitigation of these diseases.

Among others, the studies on the inhibition of angiogenesis with the inhibitors for FGFR (Fibroblast growth factor receptor), VEGFR (Vascular endothelial growth factor receptor) and PDGFR (Platelet-derived growth factor receptor) become more and more mature.

Moreover, a large body of literature implicates FGF (Fibroblast growth factor), VEGF (Vascular endothelial growth factor) and PDGF (Platelet-derived growth factor) in the induction or persistence of fibrosis (Levitzki, Cytokine & Growth Factor Rev, 2004, 15(4): 229-35; Strutz et al., Kidney Int, 2000, 57: 1521-38; Strutz et al., 2003, Springer Semin Immunopathol, 24: 459-76; Rice et al., 1999, Amer J Pathol, 155(1): 213-221; Broekelmann et al., 1991, Proc Nat Acad Sci, 88: 6642-6; Wynn, 2004, Nat Rev Immunol, 4(8): 583-94).

FGF1/FGF2-deficient mice show dramatically decreased liver fibrosis after chronic carbon tetrachloride (CC14) exposure (Yu et al., 2003, Am J Pathol, 163(4): 1653-62). FGF expression is increased in human renal interstitial fibrosis where it strongly correlates with interstitial scarring (Strutz et al., 2000, Kidney Intl, 57:1521-38) as well as in a model of experimental lung fibrosis (Barrios et al., 1997, Am J Physiol, 273 (2 Pt 1): L451-8), again lending credence to the idea that fibrosis in various tissues has a common basis.

The increased expression of VEGF/VEGFR is relevant to a great number of microvascular and pulmonary fibrosis (X.-M Ou et al. International Immunopharmacology 9 (2009): 70-79), and the VEGFR-2 inhibitor, SU5416, alleviates the fibrous tissue pathology of the belomycin-induced pulmonary fibrosis in mice.

Inhibition of PDGF attenuates both liver fibrosis and lung fibrosis in experimental models, suggesting fibrosis in different organs may have a common origin (Borkham-Kamphorst et al. 2004, Biochem Biophys Res Commun; Rice et al., 1999, Amer J Pathol, 155(1): 213-221).

Finally, TGFβ stimulates production of extracellular matrix proteins including fibronectin and collagens and is believed to play an important role in fibrosis in many tissues (Leask et al., 2004, FaSEB J 18(7): 816-27; Bartram et al., 2004, Chest 125(2): 754-65; Strutz et al., 2003, Springer Semin Immunopathol, 24: 459-76; Wynn, 2004, Nat Rev Immunol, 4(8): 583-94). Inhibitors of TGFβ production and signaling pathways are active in a number of fibrosis animal models (Wang et al., 2002, Exp Lung Res, 28:405-17; Laping, 2003, Curr Opin Pharmacol, 3(2): 204-8).

As summarized above, several growth factors are upregulated in fibrosis and the inhibition of a single factor seems to reduce the severity of fibrosis in the fibrosis models.

Pulmonary fibrosis is one of the four largest respiratory diseases. It is caused by several pathogenic factors, and is a severe pathological condition faced or experienced by the pulmonary patient. Since the cause of disease is complex, there is lacking an efficient way to treat it clinically. Besides Pirfenidone, there is no other medicament for treating the pulmonary fibrosis all over the world. Pirfenidone has the following structure and has the anti-fibrosis function by inhibiting the TGFβ signal pathway.

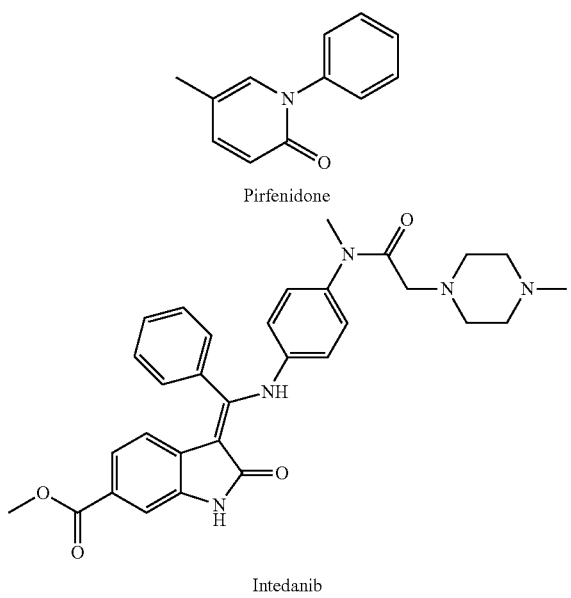

Currently, there is no small molecule tyrosine kinase inhibitor for treating tumor and fibrosis on the market. Intedanib, a compound that is now being fastest developed, is in Phase III clinical trial. Its structure is shown as above.

The object of the present invention is to develop a medicament having both the good anti-tumor activity and the good anti-fibrosis function, and therefore a small molecule tyrosine kinase inhibitor was found.

3. SUMMARY OF THE INVENTION

The object of the present invention is to provide an indolinone derivative tyrosine kinaase inhibitor, which has a good anti-tumor activity and a good anti-fibrosis function, and is easy to be synthesized, and a method for preparing the same.

The technical solutions of the present invention are as follows:

A compound represented by general formula (I), a pharmaceutically acceptable salt, a deuteride or a stereoisomer thereof:

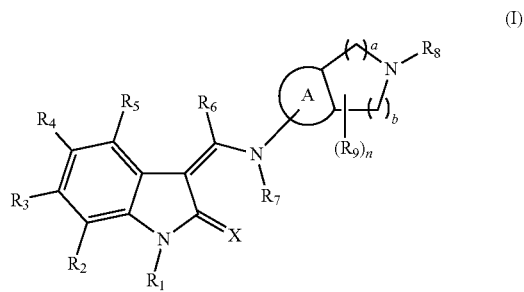

wherein, X represents O or S;
$R_1$ represents H or a prodrug group thereof;
$R_2$, $R_4$ and $R_5$ each independently represent H, hydroxy, amino, halogen, $C_{1-6}$alkyl or $C_{1-6}$alkyloxy;
$R_3$ represents H, carboxyl, or $C_{1-6}$alkyl-OC(O)—, $C_{1-6}$alkyl-SC(O)—, 3-14-membered cycloalkyl-OC(O)—, carbamoyl, $C_{1-3}$alkylcarbamoyl, di($C_{1-3}$alkyl)carbamoyl, 6-14-membered aryl-OC(O)—, or 6-14-membered aryl($C_{1-3}$alkyl)-OC(O)—, which is unsubstituted or substituted by 1-3 groups represented by $Q_1$;
$Q_1$ represents halogen, hydroxy, amino, 6-14-membered aryl, 3-14-membered cycloalkyl, 3-14-membered heterocyclyl, carboxyl, $C_{1-3}$alkyloxy, $C_{1-3}$alkyloxycarbonyl, $C_{1-3}$alkylamino, di($C_{1-3}$alkyl)amino, carbamoyl, $C_{1-3}$alkylcarbamoyl or di($C_{1-3}$alkyl)carbamoyl;
$R_6$ represents H, or $C_{1-6}$alkyl, 3-14-membered cycloalkyl, 6-14-membered aryl, 7-12-membered bridged ring group-$C_{0-3}$alkyl, 7-12-membered spiro ring group-$C_{0-3}$alkyl or 3-14-membered heterocyclyl$C_{0-3}$alkyl, which is unsubstituted or substituted by 1-3 groups represented by $Q_2$,
$Q_2$ represents halogen, hydroxy, cyano, carboxyl, amino, nitro, trifluoromethyl, $C_{1-3}$alkyl, $C_{1-3}$alkyloxy, hydroxy$C_{1-3}$alkyl, amino$C_{1-3}$alkyl, $C_{1-3}$alkyloxy$C_{1-3}$alkyl, carboxyl$C_{1-3}$alkyloxy, $C_{1-3}$alkylamino, di($C_{1-3}$alkyl)amino, $C_{1-3}$alkyloxycarbonyl, carbamoyl, $C_{1-3}$alkylcarbamoyl, di($C_{1-3}$alkyl)carbamoyl, $C_{1-3}$alkylcarbonylamino, N-($C_{1-3}$alkyl)$C_{1-3}$alkylcarbonylamino, $C_{1-3}$alkylsulfonylamino, N-($C_{1-3}$alkyl)$C_{1-3}$alkylsulfonylamino, or 6-14-membered aryl$C_{1-3}$alkylsulfonylamino;
$R_7$ represents H, or $C_{1-3}$alkyl, 3-14-membered cycloalkyl, or 3-14-membered heterocyclyl, which is unsubstituted or substituted by 1-3 groups represented by $Q_3$;
Ring A represents phenyl or 5-7-membered heterocyclyl;
$R_8$ represents formula (IIa),

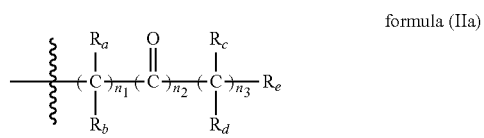

wherein,
$R_a$, $R_b$, $R_c$ and $R_d$ each independently represent H, $C_{1-3}$alkyl, $C_{1-3}$alkyloxy, amino, $C_{1-3}$alkylamino, di($C_{1-3}$alkyl)

amino, phenylamino, N-($C_{1-3}$alkyl)phenylamino, benzylamino, or N-($C_{1-3}$alkyl)benzylamino, $R_e$ represents H, $C_{1-3}$alkyl, $C_{1-3}$alkyloxy, amino, $C_{1-3}$alkylamino, di($C_{1-3}$alkyl)amino, phenylamino, N-($C_{1-3}$alkyl)phenylamino, benzylamino, N-($C_{1-3}$alkyl)benzylamino, phenyl, or 3-8-membered monocyclic heterocyclyl, the carbon atom on the 3-8-membered monocyclic heterocyclyl can be replaced with 1-3 same or different groups selected from $S(O)_m$ and $C(O)$, the $C_{1-3}$alkyl and the 3-8-membered monocyclic heterocyclyl can be substituted by 1-3 groups as represented by $Q_3$, $Q_3$ represents halogen, hydroxy, cyano, carboxyl, amino, nitro, trifluoromethyl, $C_{1-3}$alkyl, $C_{1-3}$alkyloxy, di($C_{1-3}$alkyl)amino, $C_{1-3}$alkyloxycarbonyl, carbamoyl, $C_{1-3}$alkylcarbamoyl, di($C_{1-3}$alkyl)carbamoyl or $C_{1-3}$alkylcarbonylamino;

$R_9$ represents H, halogen, hydroxy, cyano, carboxyl, amino, nitro, $C_{1-3}$alkyl, trifluoromethyl, $C_{1-3}$alkyloxy, $C_{1-3}$alkyloxycarbonyl, acetamido, $C_{1-3}$alkylsulfonylamino, carbamoyl, $C_{1-3}$alkylcarbamoyl, di($C_{1-3}$alkyl)carbamoyl, aminosulfonyl, $C_{1-3}$alkylaminosulfonyl or di($C_{1-3}$alkyl)aminosulfonyl;

a and b each independently represent 0, 1, 2 or 3;

n represents 0, 1 or 2, when n is 2, the substituents represented by $R_9$ can be identical or different;

$n_1$ represents 0, 1, 2 or 3;

$n_2$ represents 0 or 1;

$n_3$ represents 0, 1, 2 or 3;

m represents 1 or 2.

Another preferable embodiment of the present invention is as follows:

A compound represented by general formula (I), or a pharmaceutically acceptable salt, a deuteride or a stereoisomer thereof:

wherein, X represents O or S;

$R_1$ represents H or a prodrug group thereof;

$R_2$, $R_4$ and $R_5$ each independently represent H;

$R_3$ represents carboxyl, or $C_{1-3}$alkyl-OC(O)—, 3-8-membered monocyclic cycloalkylOC(O)—, carbamoyl, or benzyl-OC(O)—, which is unsubstituted or substituted by 1-3 groups represented by $Q_1$, $Q_1$ represents halogen, hydroxy, amino, phenyl, 3-6-membered cycloalkyl, $C_{1-3}$alkyloxy, $C_{1-3}$alkylamino or di($C_{1-3}$alkyl)amino;

$R_6$ represents the following groups, which are unsubstituted or substituted by 1-3 groups represented by $Q_2$:

(1) $C_{1-3}$alkyl, 3-8-membered monocyclic cycloalkyl, aryl, the carbon atom on the cycloalkyl and the aryl can be replaced with 1-3 identical or different groups selected from N, NH, N($C_{1-3}$alkyl), O, $S(O)_m$, and C(O), (2)

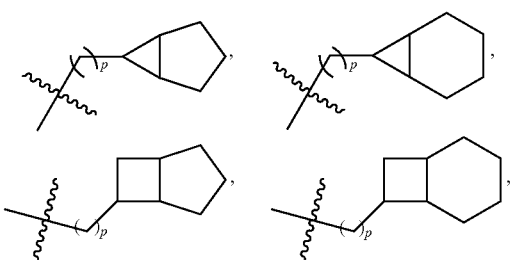
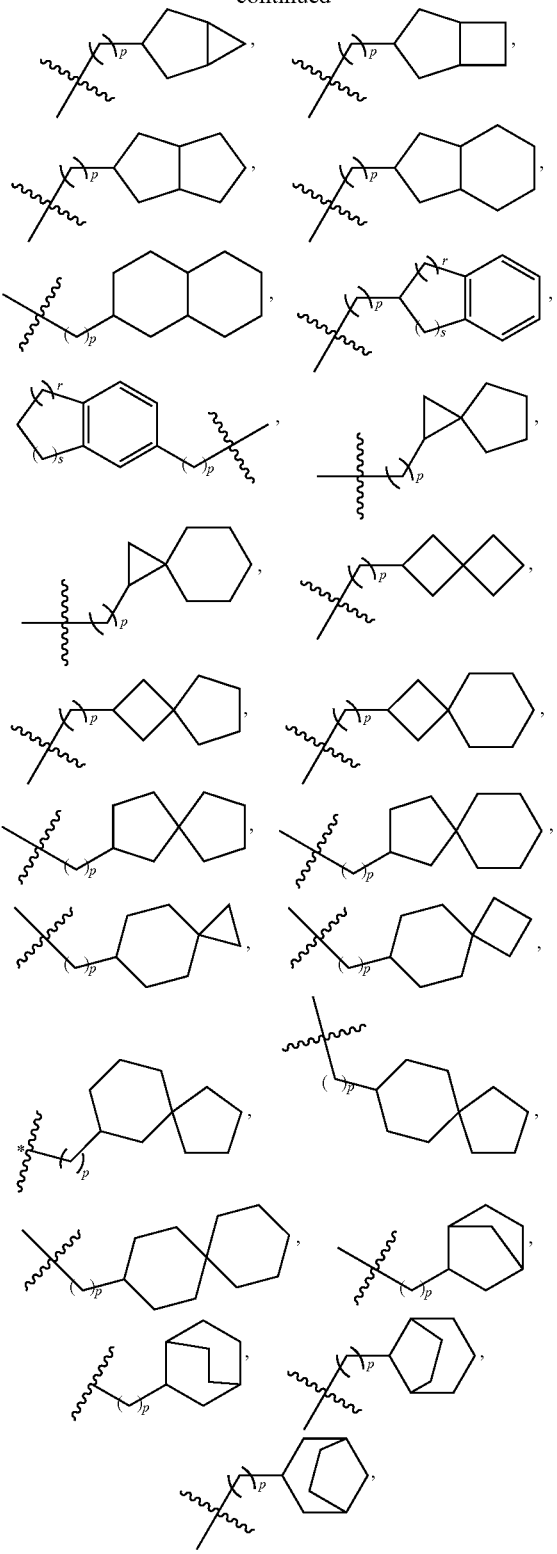

and the carbon atom on the ring can be replaced with 1-3 identical or different groups selected from NH, N($C_{1-3}$alkyl), O, $S(O)_m$, and C(O), p represents 0, 1, 2 or 3, r represents 0, 1 or 2, s represents 0, 1 or 2, $Q_2$ represents halogen, hydroxy, cyano, carboxyl, amino, nitro, trifluoromethyl, $C_{1-3}$alkyl, $C_{1-3}$alkyloxy, hydroxy$C_{1-3}$alkyl, amino$C_{1-3}$alkyl, $C_{1-3}$alkyloxy$C_{1-3}$alkyl, carboxyl$C_{1-3}$alkyloxy, $C_{1-3}$alkylamino, di($C_{1-3}$alkyl)amino, $C_{1-3}$alkyloxycarbonyl, carbamoyl, $C_{1-3}$alkylcarbamoyl, di($C_{1-3}$alkyl)carbamoyl, $C_{1-3}$alkylcarbonylamino, N-($C_{1-3}$alkyl)$C_{1-3}$alkylcarbonylamino, $C_{1-3}$alkylsulfonylamino, N-($C_{1-3}$alkyl)$C_{1-3}$alkylsulfonylamino or phenyl$C_{1-3}$alkylsulfonylamino;

$R_7$ represents H, or $C_{1-3}$alkyl, 3-6-membered monocyclic cycloalkyl, or 3-8-membered monocyclic heterocyclyl, which is unsubstituted or substituted by 1-3 groups represented by $Q_3$;

Ring A represents phenyl, pyrrolyl, pyridyl, pyrimidinyl, pyrrolidinyl, piperidinyl, piperazinyl or morpholinyl;

$R_8$ represents formula (IIa)

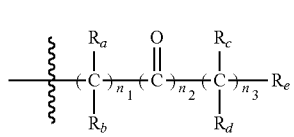

formula (IIa)

wherein, $R_a$, $R_b$, $R_c$ and $R_d$ each independently represent H, $C_{1-3}$alkyl, $C_{1-3}$alkyloxy, amino or $C_{1-3}$alkylamino, $R_e$ represents H, $C_{1-3}$alkyl, $C_{1-3}$alkyloxy, amino, $C_{1-3}$alkylamino, di($C_{1-3}$alkyl)amino, phenylamino, N-($C_{1-3}$alkyl)phenylamino, benzylamino, N-($C_{1-3}$alkyl)benzylamino, phenyl or 5-7-membered monocyclic heterocyclyl, the carbon atom on the 5-7-membered monocyclic heterocyclyl can be replaced with 1-3 same or different groups selected from $S(O)_m$ and $C(O)$, the $C_{1-3}$alkyl and the 5-7-membered monocyclic heterocyclyl can be substituted by 1-3 groups represented by $Q_3$, $Q_3$ represents halogen, hydroxy, cyano, carboxyl, amino, nitro, trifluoromethyl or $C_{1-3}$alkyl;

$R_9$ represents H, halogen, hydroxy, cyano, carboxyl, amino, nitro, $C_{1-3}$alkyl, trifluoromethyl or $C_{1-3}$alkyloxy;

a and b each independently represent 0, 1 or 2;

n represents 0, 1 or 2, when n is 2, the substituents represented by $R_9$ can be identical or different;

$n_1$ represents 0, 1 or 2;

$n_2$ represents 0 or 1;

$n_3$ represents 0, 1 or 2;

m represents 1 or 2.

In a preferable embodiment, the present invention provides a compound represented by the above general formula (I), or a pharmaceutically acceptable salt, a deuteride or a stereoisomer thereof, wherein:

X represents O;

$R_1$ represents H;

$R_2$, $R_4$ and $R_5$ each independently represent H;

$R_3$ represents $C_{1-3}$alkylOC(O)— or carbamoyl, which is unsubstituted or substituted by 1-2 groups represented by $Q_1$, $Q_1$ represents halogen, hydroxy, amino, $C_{1-3}$alkyloxy, $C_{1-3}$alkylamino or di($C_{1-3}$alkyl)amino;

$R_6$ represents the following groups, which are unsubstituted or substituted by 1-3 groups represented by $Q_2$:

(1) 4-7 membered monocyclic cycloalkyl, or phenyl, the carbon atom on the phenyl and the cycloalkyl can be replaced with 1-3 same or different groups selected from N, NH, N($C_{1-3}$alkyl), O, $S(O)_m$, and C(O), (2)

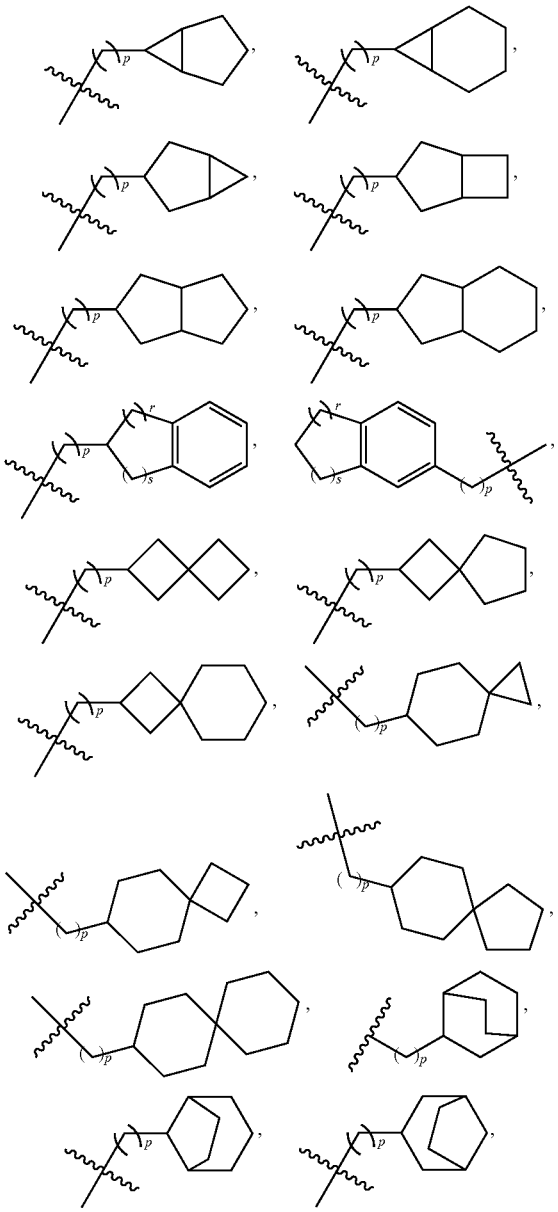

and the carbon atom on the ring can be replaced with 1-3 identical or different groups selected from NH, N($C_{1-3}$alkyl), O, $S(O)_m$, and C(O), p represents 0, 1, 2 or 3, r represents 1, s represents 1, $Q_2$ represents halogen, hydroxy, cyano, carboxyl, amino, nitro, trifluoromethyl, $C_{1-3}$alkyl, $C_{1-3}$alkyloxy, hydroxy$C_{1-3}$alkyl, amino$C_{1-3}$alkyl or $C_{1-3}$alkyloxy$C_{1-3}$alkyl;

$R_7$ represents H or 3-5 membered monocyclic cycloalkyl;

Ring A represents phenyl or pyridyl;

$R_8$ represents formula (IIa)

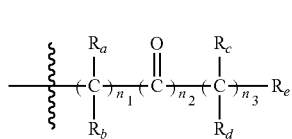

formula (IIa)

wherein, $R_a$, $R_b$, $R_c$ and $R_d$ each independently represent H, methyl or ethyl, $R_e$ represents H, $C_{1-3}$alkyl, $C_{1-3}$alkyloxy, amino, $C_{1-3}$alkylamino, di($C_{1-3}$alkyl)amino, phenylamino, N-($C_{1-3}$alkyl)phenylamino, benzylamino, N-($C_{1-3}$alkyl)benzylamino, phenyl or 5-7-membered monocyclic heterocyclyl, the carbon atom on the 5-7-membered monocyclic heterocyclyl can be replaced with 1-3 same or different groups selected from $S(O)_m$ and $C(O)$, the $C_{1-3}$alkyl and the 5-7-membered monocyclic heterocyclyl can be substituted by 1-3 groups represented by $Q_3$, $Q_3$ represents halogen, hydroxy, cyano, carboxyl, amino, nitro, trifluoromethyl or methyl;

$R_9$ represents H, halogen, hydroxy, cyano, carboxyl, amino or methyl;

a and b each independently represent 0, 1 or 2;
n represents 0 or 1;
$n_1$ represents 0 or 1;
$n_2$ represents 1;
$n_3$ represents 0, 1 or 2;
m represents 1 or 2.

In another preferable embodiment, the present invention provides a compound represented by the general formula (II), a pharmaceutically acceptable salt, a deuteride or a stereoisomer thereof, wherein:

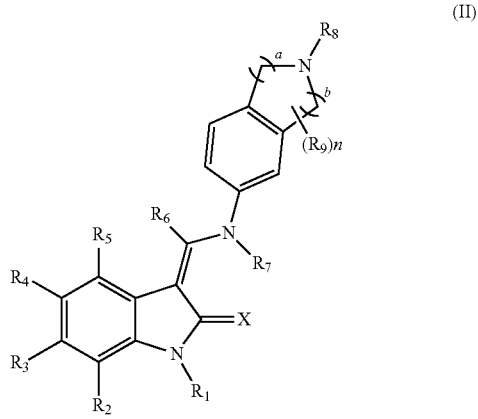

(II)

X represents O;
$R_1$ represents H;
$R_2$, $R_4$ and $R_5$ each independently represent H;
$R_3$ represents $CH_3OC(O)$—, $CH_3CH_2OC(O)$—, $(CH_3)_2CHOC(O)$— or $NH_3C(O)$—;
$R_6$ represents the following groups, which are unsubstituted or substituted by 1-3 groups represented by $Q_2$:
phenyl, tetrahydrofuran, tetrahydropyran,

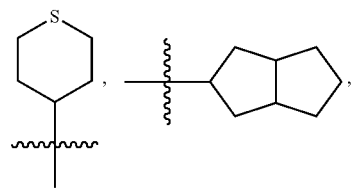

-continued

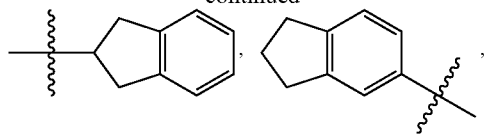

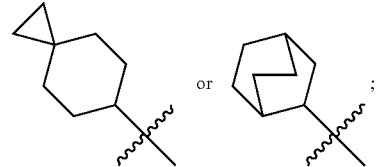

$Q_2$ represents halogen, hydroxy, cyano, carboxyl, amino, nitro, trifluoromethyl, methyl, methoxy or methoxymethyl;
$R_7$ represents H or cyclopropyl;
$R_8$ represents formula (IIb)

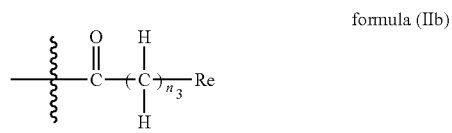

formula (IIb)

wherein, $R_e$ represents $C_{1-3}$alkyl, $C_{1-3}$alkyloxy, di($C_{1-3}$alkyl)amino, di($C_{1-3}$alkyl)carbamoyl, phenylamino, benzylamino, pyrrolyl, pyrazolyl, imidazolyl, triazolyl, pyridyl, pyrimidinyl, pyrrolidinyl, pyrrolidonyl, piperidinyl, piperazinyl or morpholinyl, said pyrrolyl, pyrazolyl, imidazolyl, triazolyl, pyridyl, pyrimidinyl, pyrrolidinyl, pyrrolidonyl, piperidinyl, piperazinyl, and morpholinyl can be substituted by 1-3 groups represented by $Q_3$, $Q_3$ represents halogen, hydroxy, amino, trifluoromethyl or methyl;

$R_9$ represents H;
a and b each independently represent 0, 1 or 2;
n represents 0;
$n_3$ represents 1 or 2.

In another preferable embodiment, the present invention provides a compound represented by the above general formula (II), a pharmaceutically acceptable salt, a deuteride or a stereoisomer thereof, wherein:

X represents O;
$R_1$ represents H;
$R_2$, $R_4$ and $R_5$ each independently represent H;
$R_3$ represents $CH_3OC(O)$— or $CH_3CH_2OC(O)$—;
$R_6$ represents the following groups, which are unsubstituted or substituted by 1-3 groups selected from halogen, trifluoromethyl and methoxy:
phenyl, tetrahydrofuryl, tetrahydropyranyl or

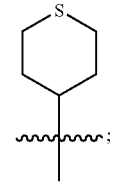

;

$R_7$ represents H or cyclopropyl;
Ring A represents phenyl;
$R_8$ represents formula (IIb)

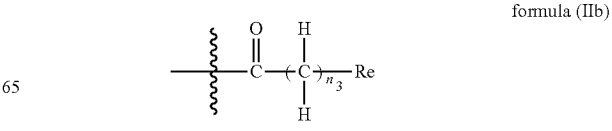

formula (IIb)

wherein R_e represents dimethylamino, dimethylcarbamoyl, pyrrolyl, pyrazolyl, imidazolyl, triazolyl, pyridyl, pyrimidinyl, pyrrolidinyl, pyrrolidonyl, piperidinyl, piperazinyl or morpholinyl, said pyrrolyl, pyrazolyl, imidazolyl, triazolyl, pyridyl, pyrimidinyl, pyrrolidinyl, pyrrolidonyl, piperidinyl, piperazinyl, and morpholinyl can be substituted by 1-2 groups selected from $Q_3$, $Q_3$ represents hydroxy, trifluoromethyl or methyl;
$R_9$ represents H;
a represents 0;
b represents 2;
n represents 0;
$n_3$ represents 1 or 2.

In another preferable embodiment, the present invention provides a compound represented by the above general formula (II); a pharmaceutically acceptable salt, a deuteride or a stereoisomer thereof, wherein:
X represents O;
$R_1$ represents H;
$R_2$, $R_4$ and $R_5$ each independently represent H;
$R_3$ represents $CH_3OC(O)$—, or $CH_3CH_2OC(O)$—;

$R_6$ represents phenyl, 4-fluorophenyl, 4-trifluoromethylphenyl, or 4-methoxyphenyl;
$R_7$ represents H;
$R_8$ represents formula (IIb)

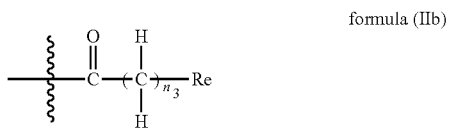

formula (IIb)

wherein $R_e$ represents dimethylamino, dimethylcarbamoyl, pyrazolyl, triazolyl, pyrrolidinyl, pyrrolidonyl, piperidinyl, N-methylpiperidinyl, 4-hydroxypiperidinyl, N-methylpiperazinyl, morpholinyl, or 3,5-dimethylmorpholinyl;
$R_9$ represents H;
a represents 0;
b represents 2;
n represents 0;
$n_3$ represents 1 or 2.

The particularly preferable compound according to the present invention are:

| Compound | Structure |
| --- | --- |
| 1 | 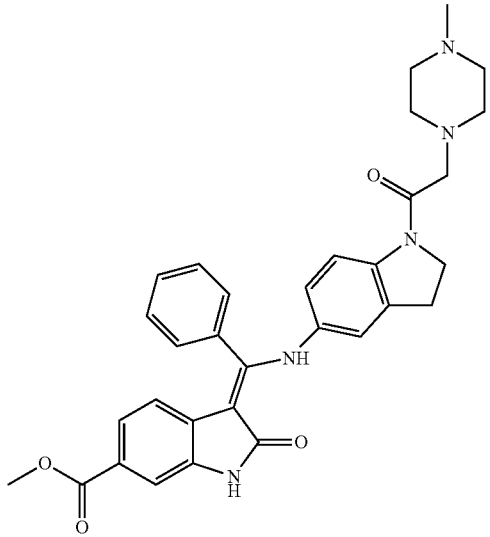 [SMILES: COC(=O)c1ccc2c(c1)NC(=O)/C2=C(\Nc1ccc2c(c1)CCN2C(=O)CN1CCN(C)CC1)c1ccccc1] |
| 2 | 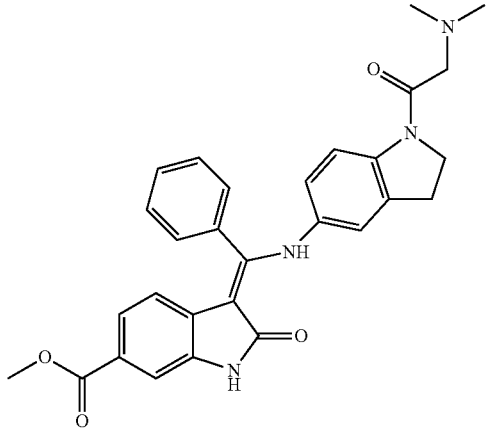 |

-continued
| Compound | Structure |
|---|---|
| 3 | 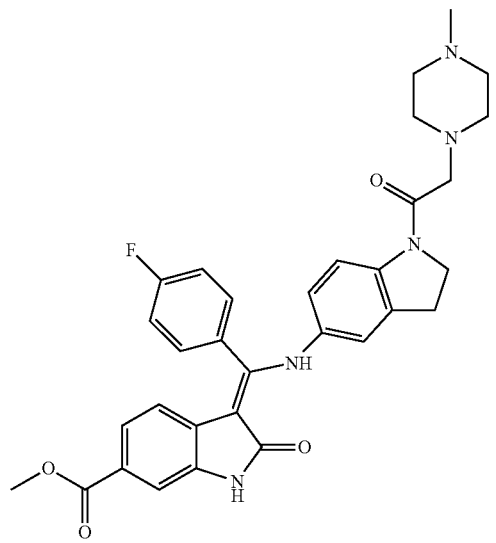 [SMILES: COC(=O)c1ccc2c(c1)NC(=O)/C2=C(\Nc1ccc2c(c1)CCN2C(=O)CN1CCN(C)CC1)c1ccc(F)cc1] |
| 4 | 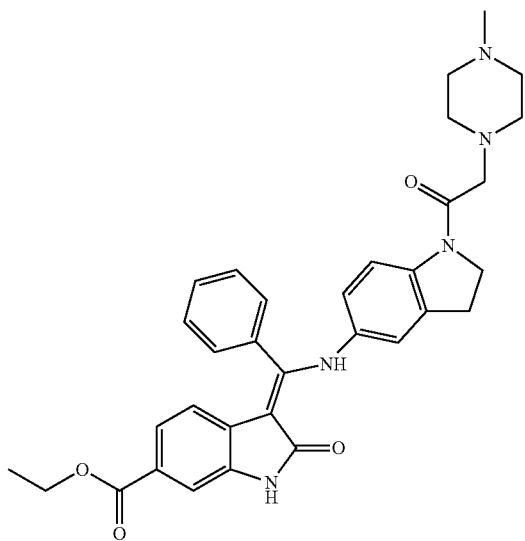 [SMILES: CCOC(=O)c1ccc2c(c1)NC(=O)/C2=C(\Nc1ccc2c(c1)CCN2C(=O)CN1CCN(C)CC1)c1ccccc1] |
| 5 | 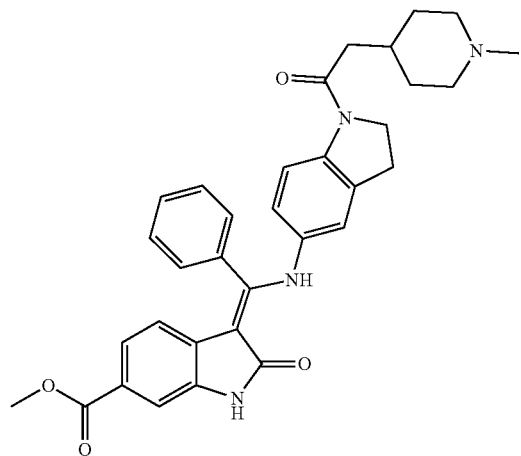 |

-continued
| Compound | Structure |
|---|---|
| 6 | 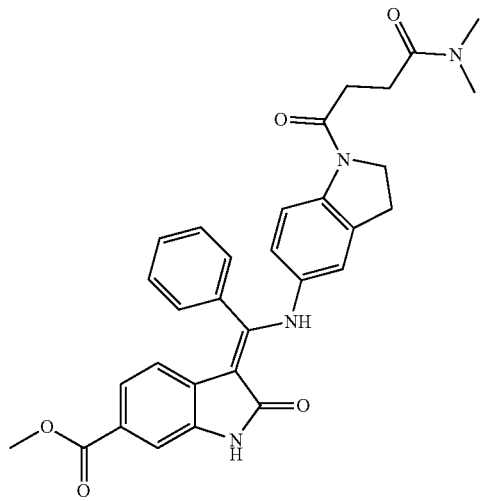 |
| 7 | 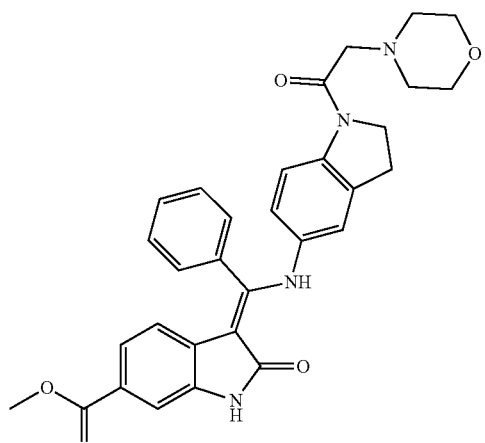 |
| 8 | 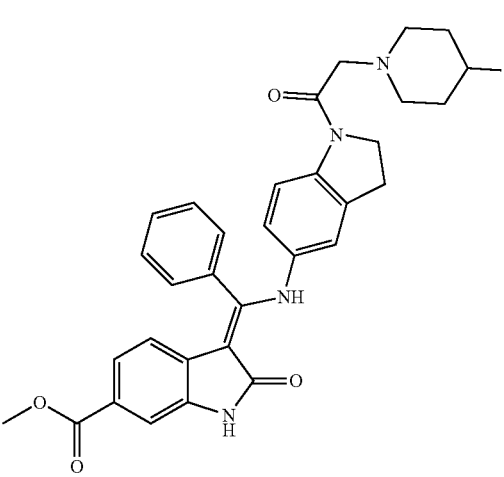 |

-continued
| Compound | Structure |
|---|---|
| 9 | 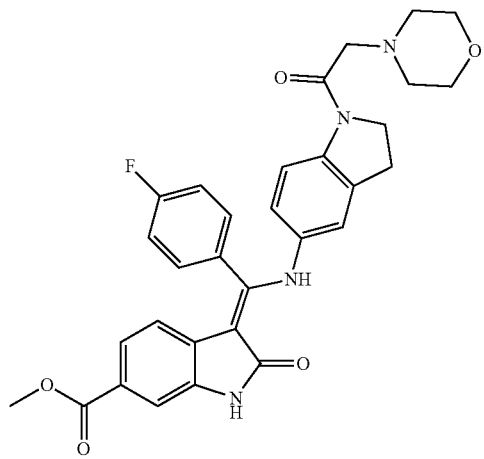 [SMILES: COC(=O)c1ccc2c(c1)NC(=O)/C2=C(\Nc1ccc2c(c1)CCN2C(=O)CN1CCOCC1)c1ccc(F)cc1] |
| 10 | 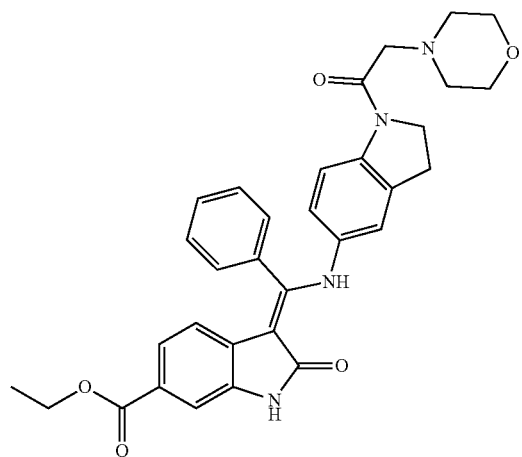 [SMILES: CCOC(=O)c1ccc2c(c1)NC(=O)/C2=C(\Nc1ccc2c(c1)CCN2C(=O)CN1CCOCC1)c1ccccc1] |
| 11 | 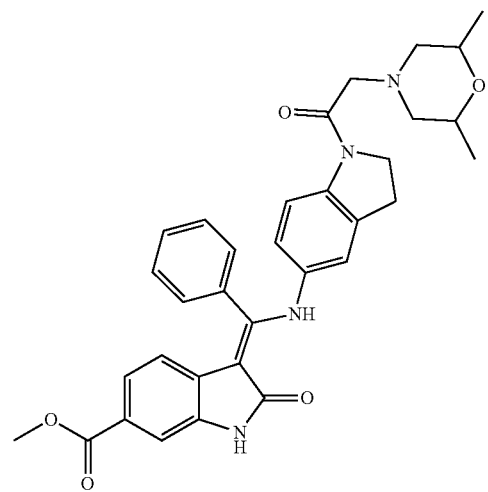 |

-continued
| Compound | Structure |
|---|---|
| 12 | 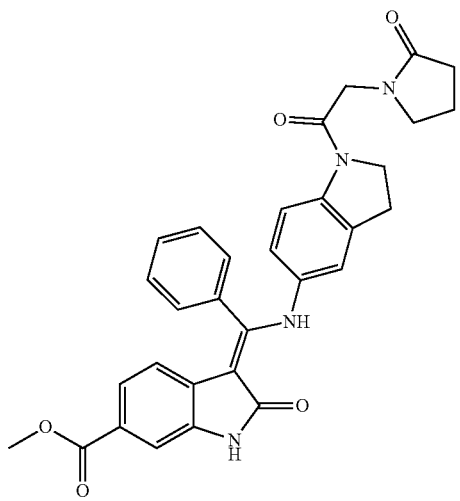 [SMILES: COC(=O)c1ccc2c(c1)NC(=O)/C2=C(\Nc1ccc2c(c1)CCN2C(=O)CN1CCCC1=O)c1ccccc1] |
| 13 | 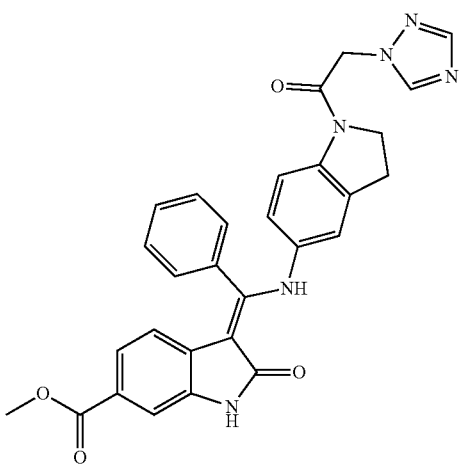 [SMILES: COC(=O)c1ccc2c(c1)NC(=O)/C2=C(\Nc1ccc2c(c1)CCN2C(=O)Cn1cncn1)c1ccccc1] |
| 14 | 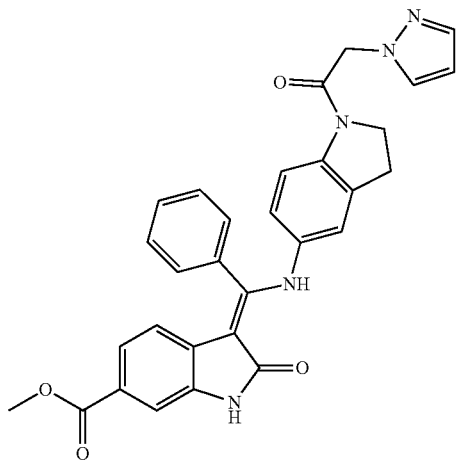 [SMILES: COC(=O)c1ccc2c(c1)NC(=O)/C2=C(\Nc1ccc2c(c1)CCN2C(=O)Cn1cccn1)c1ccccc1] |

-continued
| Compound | Structure |
|---|---|
| 15 | 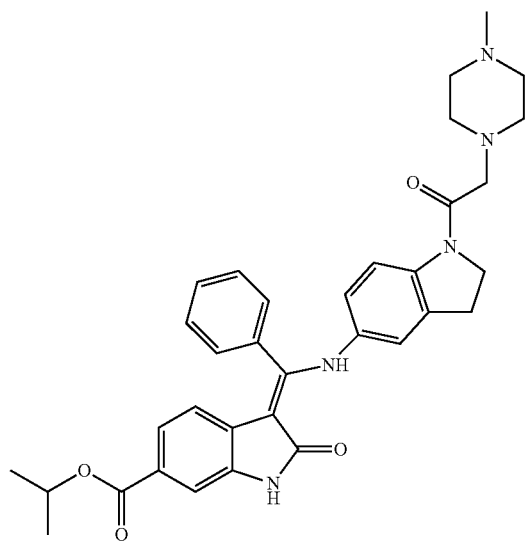 [SMILES: CC(C)OC(=O)c1ccc2c(c1)NC(=O)/C2=C(\Nc1ccc2c(c1)CCN2C(=O)CN1CCN(C)CC1)c1ccccc1] |
| 16 | 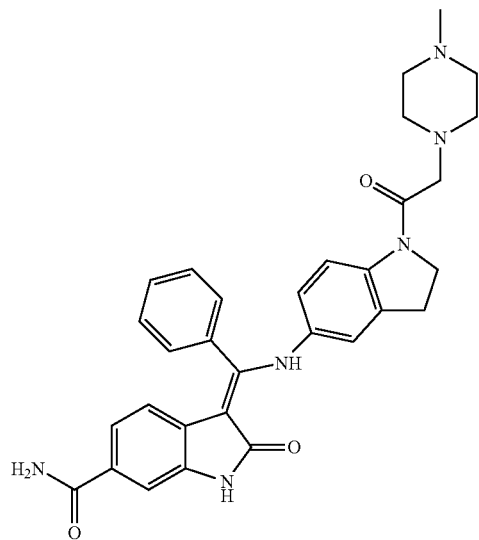 [SMILES: CN1CCN(CC(=O)N2CCc3cc(N/C(=C4\C(=O)Nc5cc(C(N)=O)ccc54)c4ccccc4)ccc32)CC1] |
| 17 | 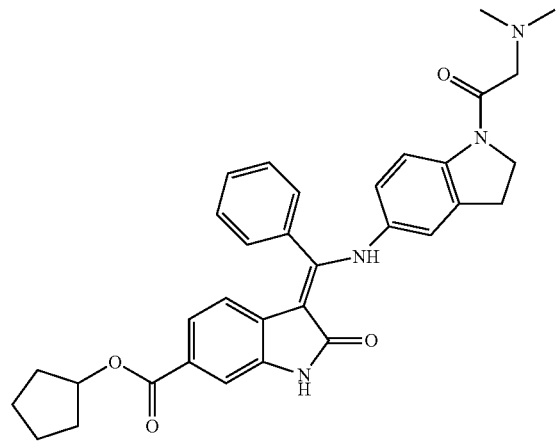 [SMILES: CN(C)CC(=O)N1CCc2cc(N/C(=C3\C(=O)Nc4cc(C(=O)OC5CCCC5)ccc43)c3ccccc3)ccc21] |

-continued
| Compound | Structure |
|---|---|
| 18 | 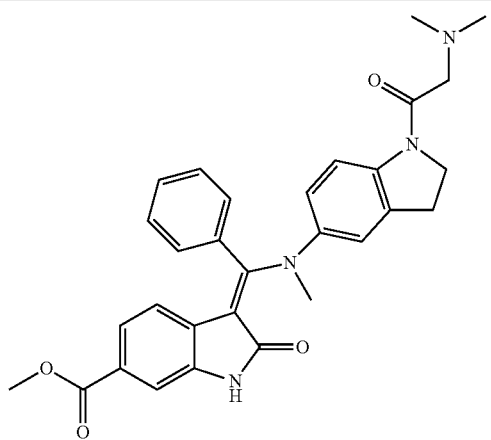 |
| 19 | 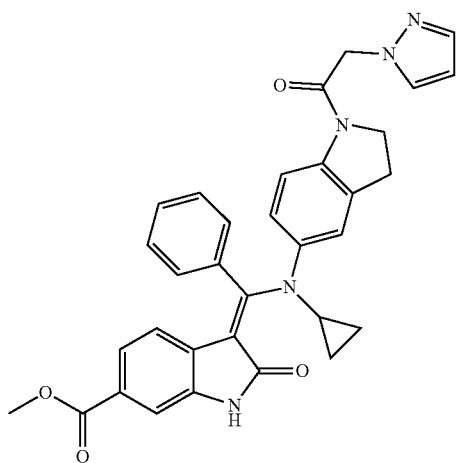 [SMILES: COC(=O)c1ccc2c(c1)NC(=O)/C2=C(/c1ccccc1)N(c1ccc2c(c1)CCN2C(=O)Cn1cccn1)C1CC1] |
| 20 | 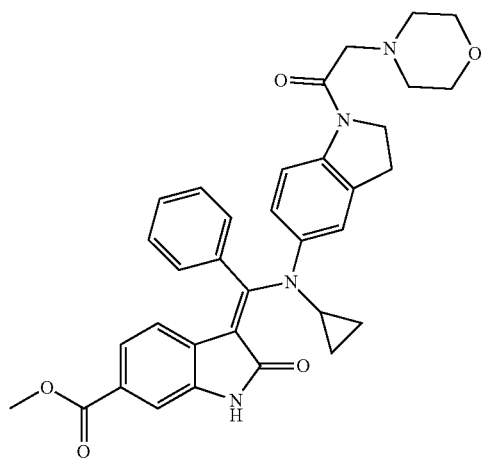 [SMILES: COC(=O)c1ccc2c(c1)NC(=O)/C2=C(/c1ccccc1)N(c1ccc2c(c1)CCN2C(=O)CN1CCOCC1)C1CC1] |

-continued

| Compound | Structure |
|---|---|
| 21 | 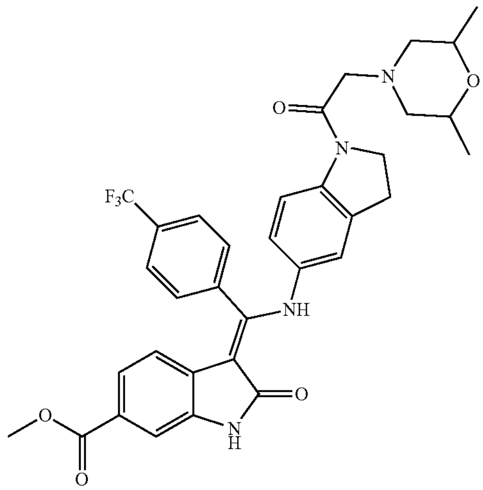 |
| 22 | 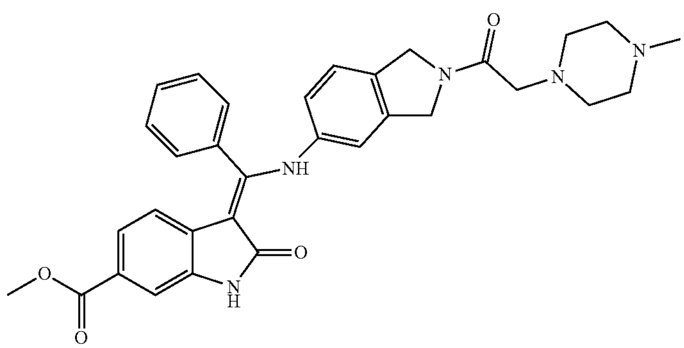 |
| 23 | 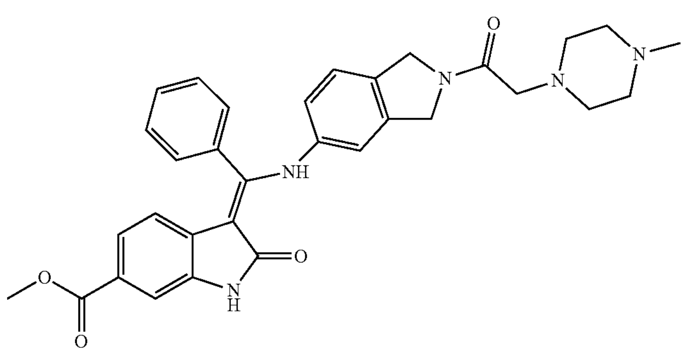 |
| 24 | 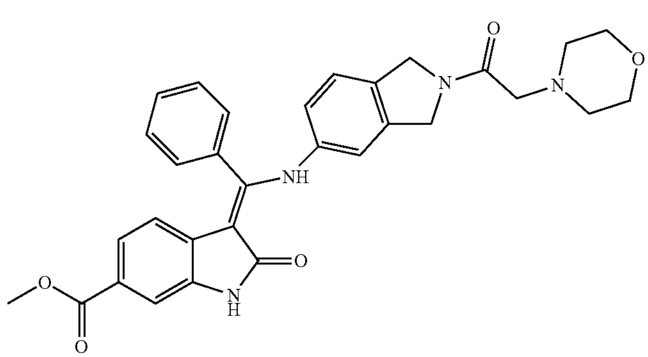 [SMILES: COC(=O)c1ccc2c(c1)NC(=O)/C2=C(\Nc1ccc2c(c1)CN(C(=O)CN1CCOCC1)C2)c1ccccc1] |

| Compound | Structure |
|---|---|
| 25 | 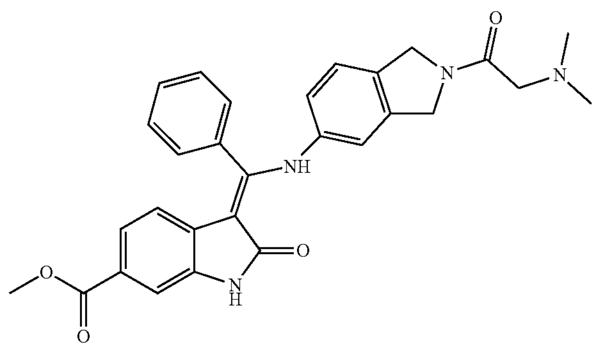 |
| 26 | 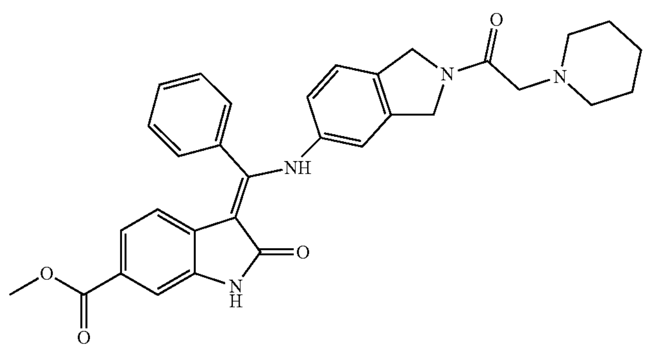 [SMILES: COC(=O)c1ccc2c(c1)NC(=O)/C2=C(\Nc1ccc2c(c1)CN(C(=O)CN1CCCCC1)C2)c1ccccc1] |
| 27 | 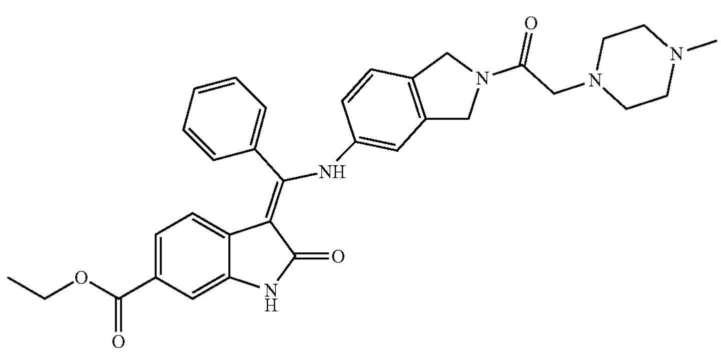 [SMILES: CCOC(=O)c1ccc2c(c1)NC(=O)/C2=C(\Nc1ccc2c(c1)CN(C(=O)CN1CCN(C)CC1)C2)c1ccccc1] |
| 28 | 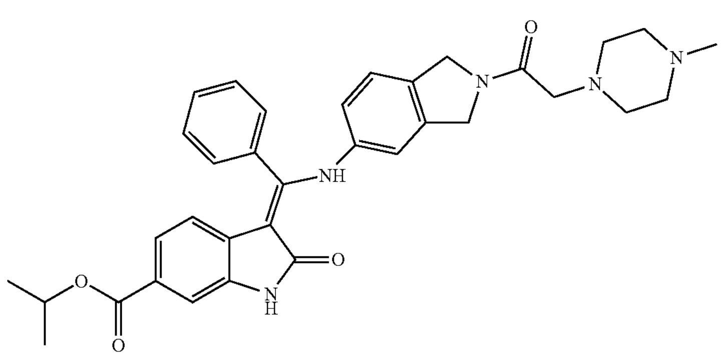 [SMILES: CC(C)OC(=O)c1ccc2c(c1)NC(=O)/C2=C(\Nc1ccc2c(c1)CN(C(=O)CN1CCN(C)CC1)C2)c1ccccc1] |

-continued

| Compound | Structure |
|---|---|
| 29 | 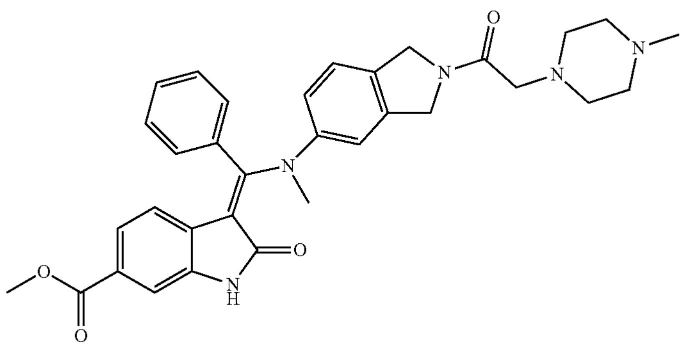 |
| 30 | 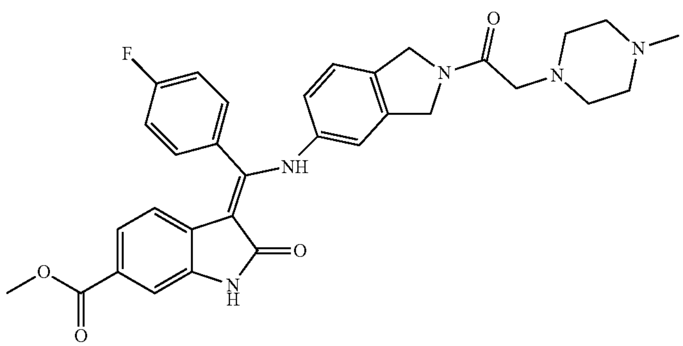 |
| 31 | 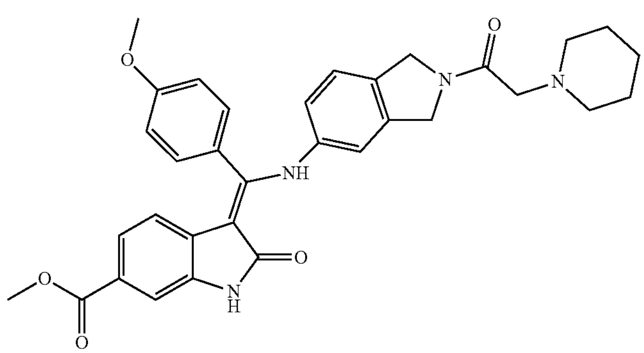 [SMILES: COC(=O)c1ccc2c(c1)NC(=O)/C2=C(\Nc1ccc2c(c1)CN(C(=O)CN1CCCCC1)C2)c1ccc(OC)cc1] |
| 32 | 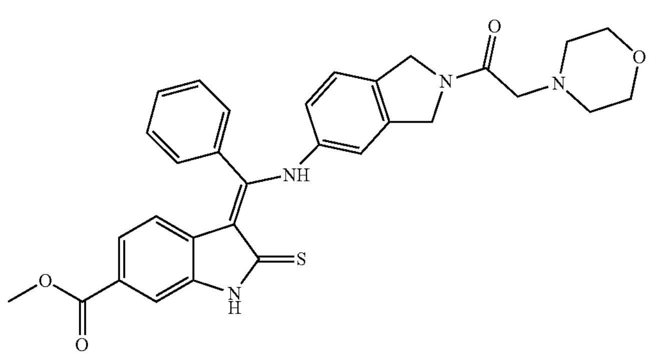 [SMILES: COC(=O)c1ccc2c(c1)NC(=S)/C2=C(\Nc1ccc2c(c1)CN(C(=O)CN1CCOCC1)C2)c1ccccc1] |

-continued

| Compound | Structure |
|---|---|
| 33 | 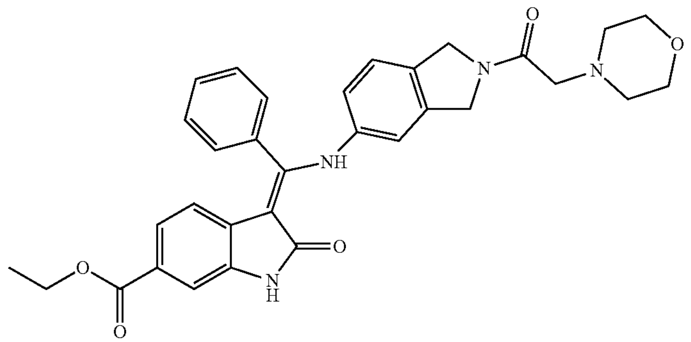 [SMILES: CCOC(=O)c1ccc2c(c1)NC(=O)/C2=C(\Nc1ccc2c(c1)CN(C(=O)CN1CCOCC1)C2)c1ccccc1] |
| 34 | 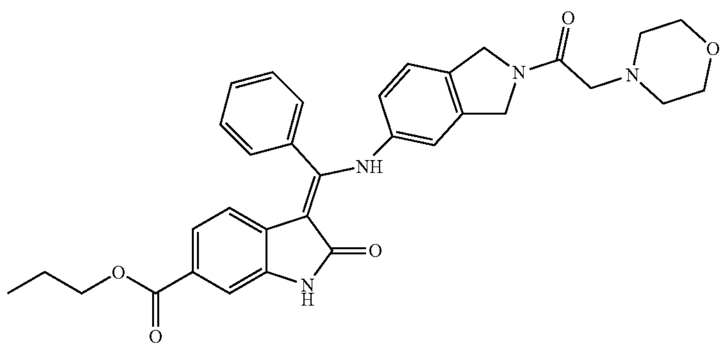 [SMILES: CCCOC(=O)c1ccc2c(c1)NC(=O)/C2=C(\Nc1ccc2c(c1)CN(C(=O)CN1CCOCC1)C2)c1ccccc1] |
| 35 | 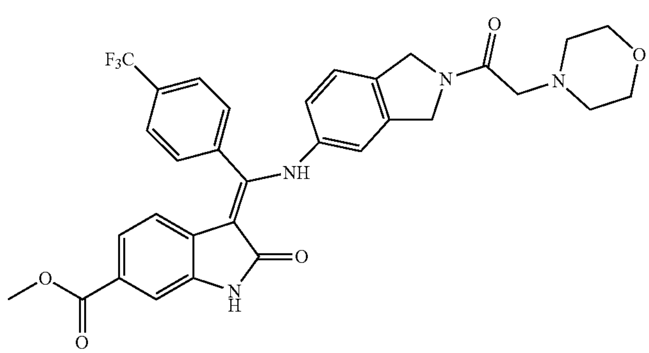 [SMILES: COC(=O)c1ccc2c(c1)NC(=O)/C2=C(\Nc1ccc2c(c1)CN(C(=O)CN1CCOCC1)C2)c1ccc(C(F)(F)F)cc1] |
| 36 | 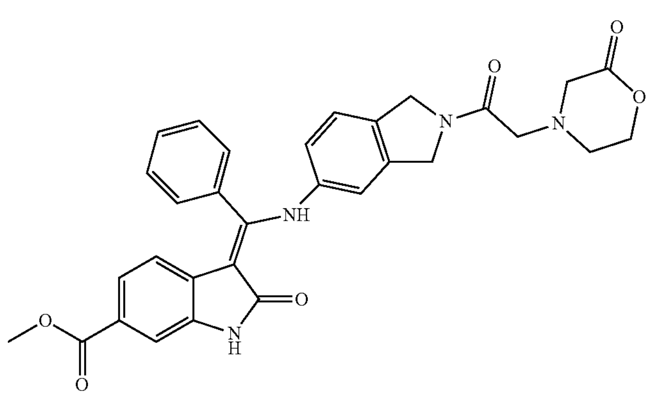 [SMILES: COC(=O)c1ccc2c(c1)NC(=O)/C2=C(\Nc1ccc2c(c1)CN(C(=O)CN1CCOC(=O)C1)C2)c1ccccc1] |

-continued
| Compound | Structure |
|---|---|
| 37 | 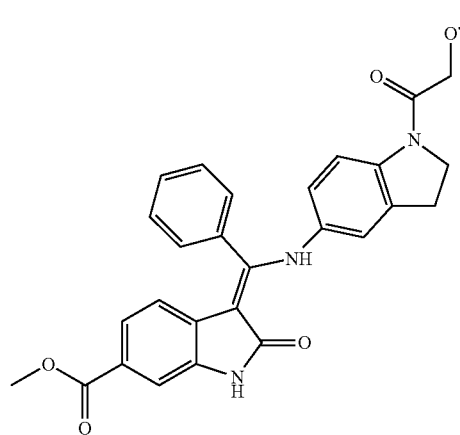 |
| 38 | 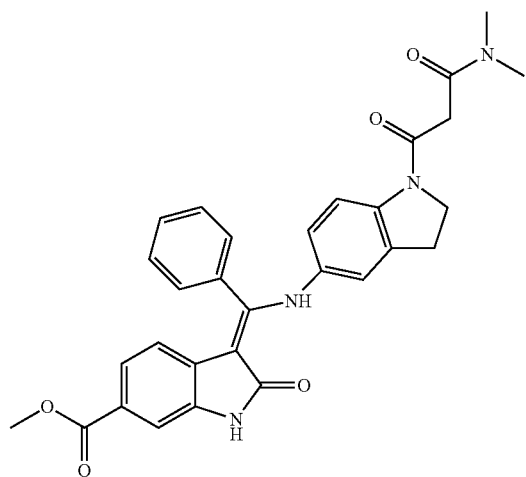 |
| 39 | 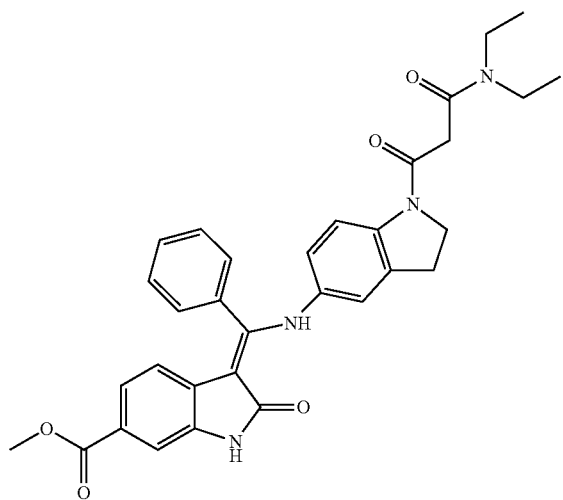 [SMILES: CCN(CC)C(=O)CC(=O)N1CCc2cc(N/C(=C3\C(=O)Nc4cc(C(=O)OC)ccc43)c3ccccc3)ccc21] |

-continued
| Compound | Structure |
|---|---|
| 40 | 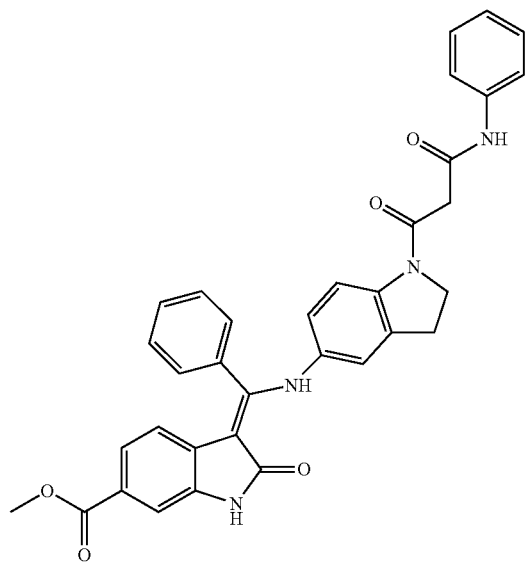 [SMILES: COC(=O)c1ccc2c(c1)NC(=O)/C2=C(\Nc1ccc2c(c1)CCN2C(=O)CC(=O)Nc1ccccc1)c1ccccc1] |
| 41 | 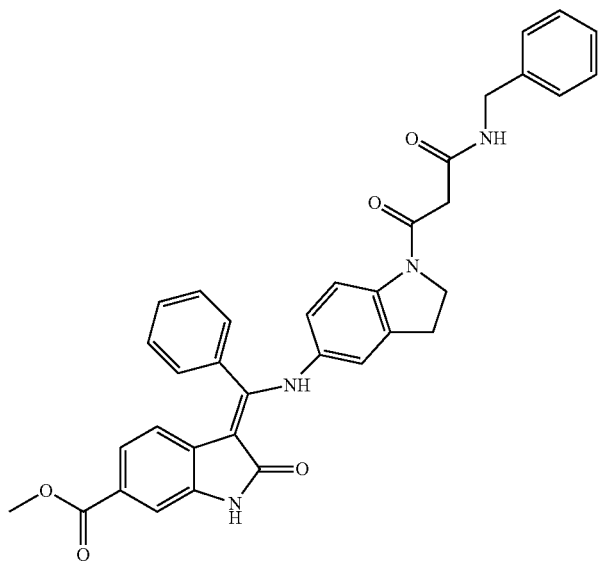 [SMILES: COC(=O)c1ccc2c(c1)NC(=O)/C2=C(\Nc1ccc2c(c1)CCN2C(=O)CC(=O)NCc1ccccc1)c1ccccc1] |
| 42 | 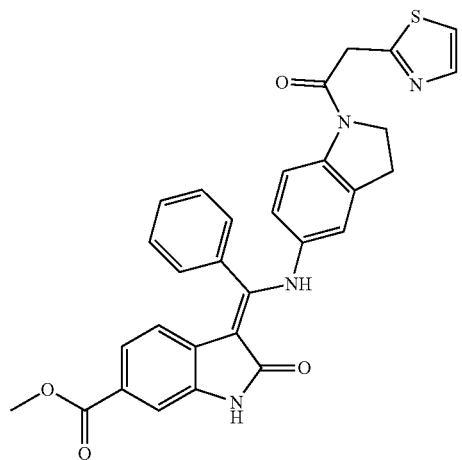 [SMILES: COC(=O)c1ccc2c(c1)NC(=O)/C2=C(\Nc1ccc2c(c1)CCN2C(=O)Cc1nccs1)c1ccccc1] |

-continued
| Compound | Structure |
|---|---|
| 43 | 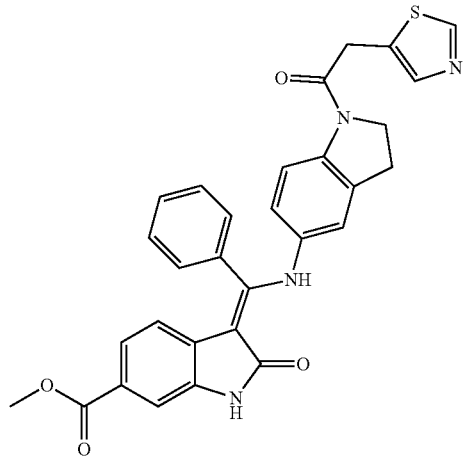 [SMILES: COC(=O)c1ccc2c(c1)NC(=O)/C2=C(\Nc1ccc2c(c1)CCN2C(=O)Cc1cncs1)c1ccccc1] |
| 44 | 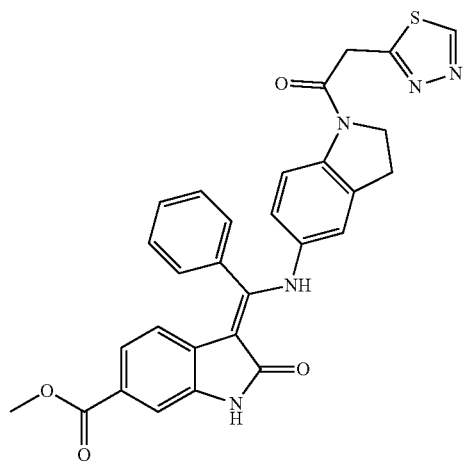 [SMILES: COC(=O)c1ccc2c(c1)NC(=O)/C2=C(\Nc1ccc2c(c1)CCN2C(=O)Cc1nncs1)c1ccccc1] |
| 45 | 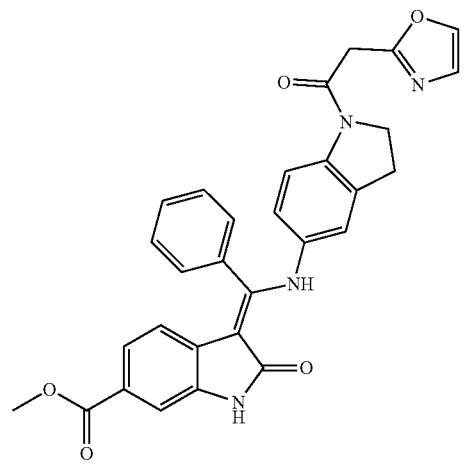 [SMILES: COC(=O)c1ccc2c(c1)NC(=O)/C2=C(\Nc1ccc2c(c1)CCN2C(=O)Cc1ncco1)c1ccccc1] |

| Compound | Structure |
|---|---|
| 46 | 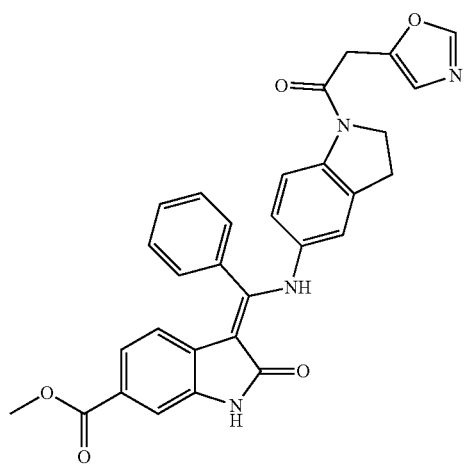 |
| 47 | 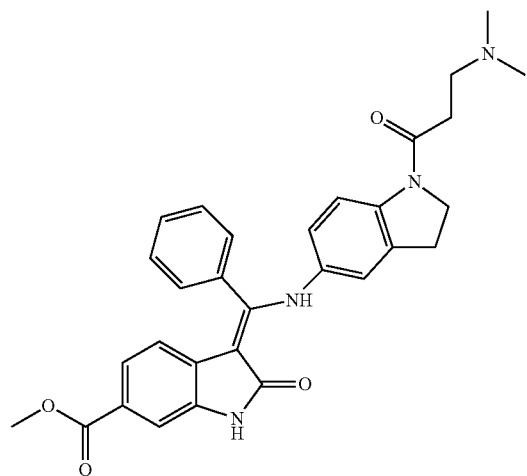 |
| 48 | 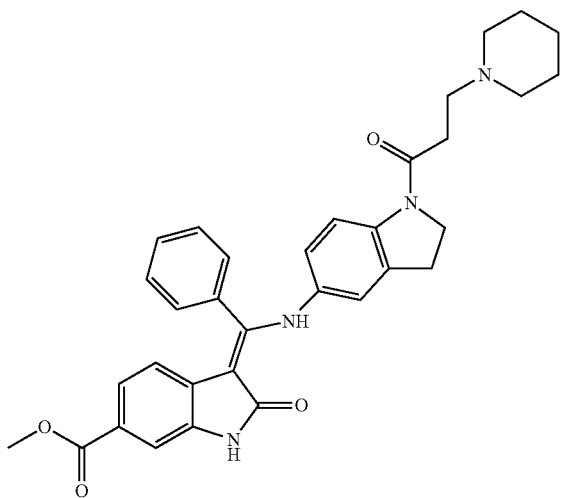 [SMILES: COC(=O)c1ccc2c(c1)NC(=O)/C2=C(\Nc1ccc2c(c1)CCN2C(=O)CCN1CCCCC1)c1ccccc1] |

-continued
| Compound | Structure |
|---|---|
| 49 | 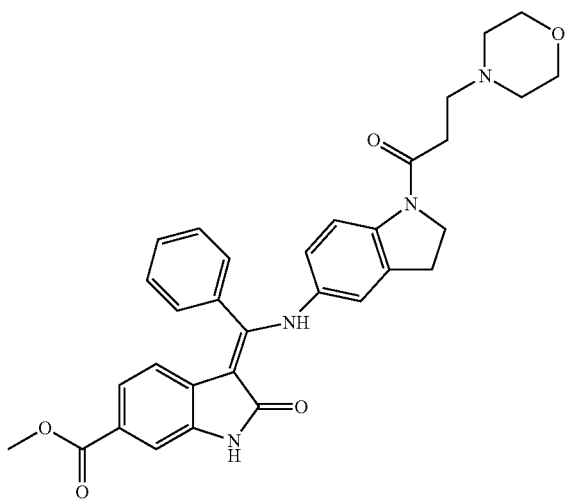 [SMILES: COC(=O)c1ccc2c(c1)NC(=O)/C2=C(\Nc1ccc2c(c1)CCN2C(=O)CCN1CCOCC1)c1ccccc1] |
| 50 | 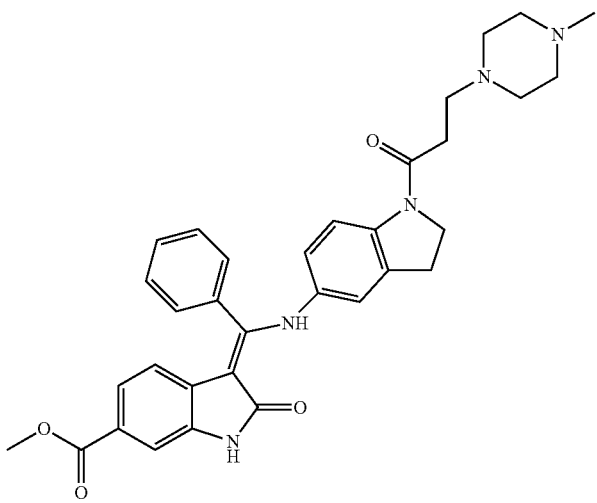 |
| 51 | 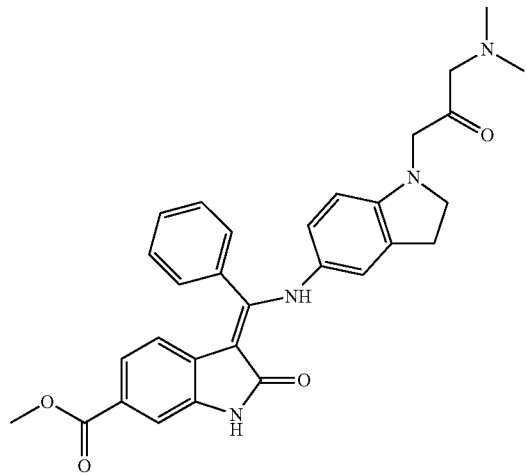 |

-continued
| Compound | Structure |
|---|---|
| 52 | 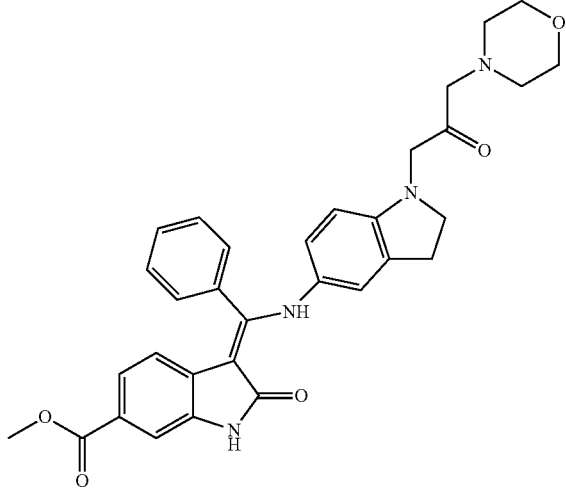 [SMILES: COC(=O)c1ccc2c(c1)NC(=O)/C2=C(\Nc1ccc2c(c1)CCN2CC(=O)CN1CCOCC1)c1ccccc1] |
| 53 | 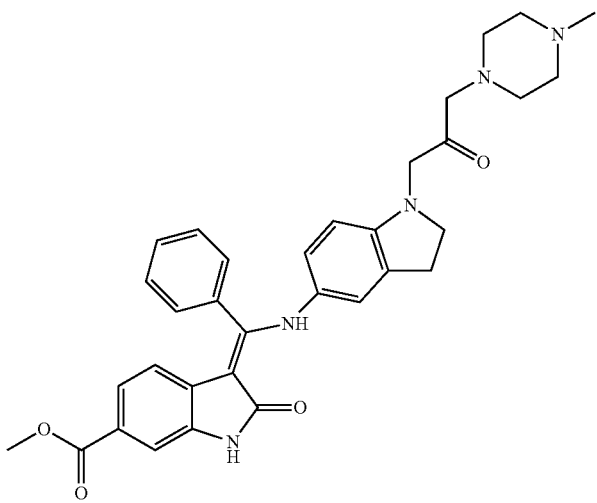 |
| 54 | 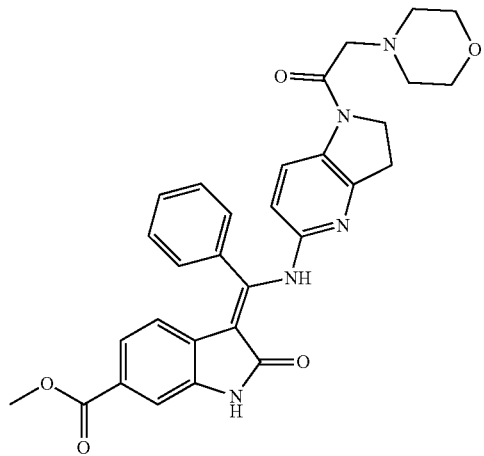 [SMILES: COC(=O)c1ccc2c(c1)NC(=O)/C2=C(\Nc1ccc2c(n1)CCN2C(=O)CN1CCOCC1)c1ccccc1] |

-continued
| Compound | Structure |
|---|---|
| 55 | 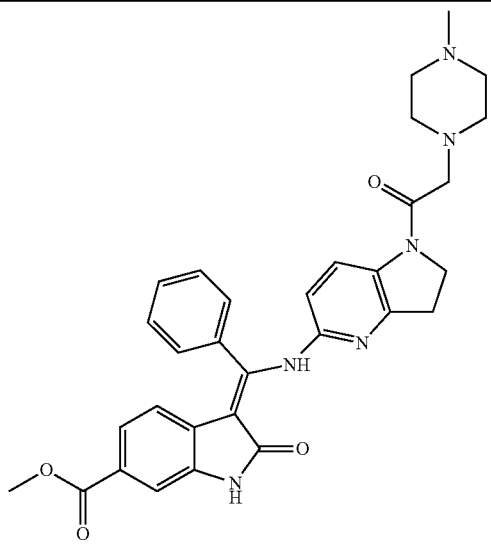 |
| 56 | 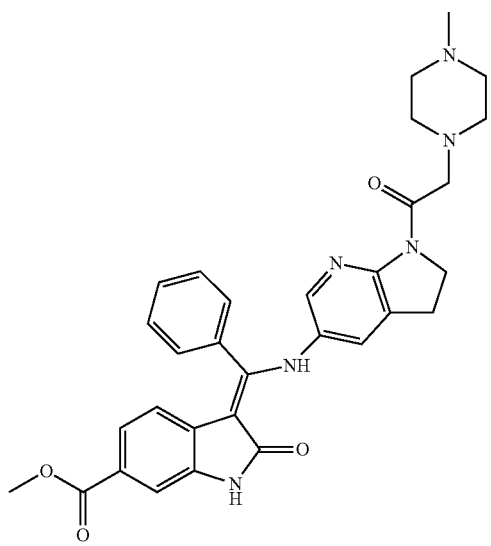 |
The particularly preferable compound according to the present invention are:

| Compound | Structure |
|---|---|
| 1b | 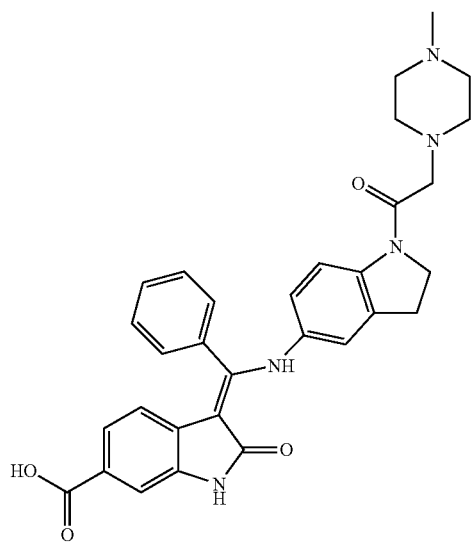 [SMILES: CN1CCN(CC(=O)N2CCc3cc(N/C(=C4\C(=O)Nc5cc(C(=O)O)ccc54)c4ccccc4)ccc32)CC1] |
| 2b | 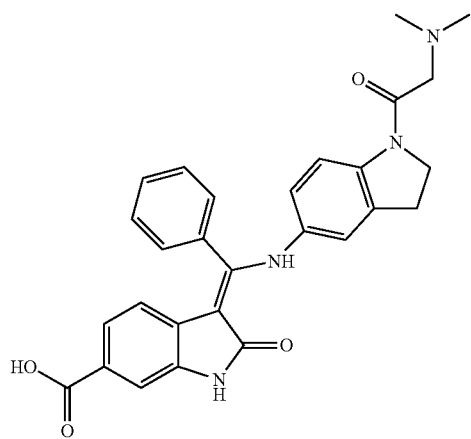 [SMILES: CN(C)CC(=O)N1CCc2cc(N/C(=C3\C(=O)Nc4cc(C(=O)O)ccc43)c3ccccc3)ccc21] |
| 3b | 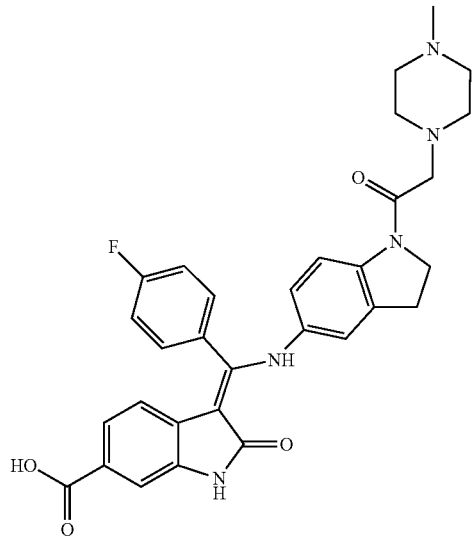 [SMILES: CN1CCN(CC(=O)N2CCc3cc(N/C(=C4\C(=O)Nc5cc(C(=O)O)ccc54)c4ccc(F)cc4)ccc32)CC1] |

-continued
| Compound | Structure |
|---|---|
| 4b | 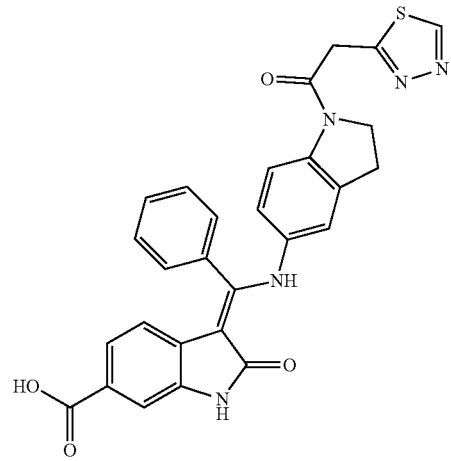 [SMILES: O=C1Nc2cc(C(=O)O)ccc2/C1=C(/Nc1ccc2c(c1)CCN2C(=O)Cc1nncs1)c1ccccc1] |
| 5b | 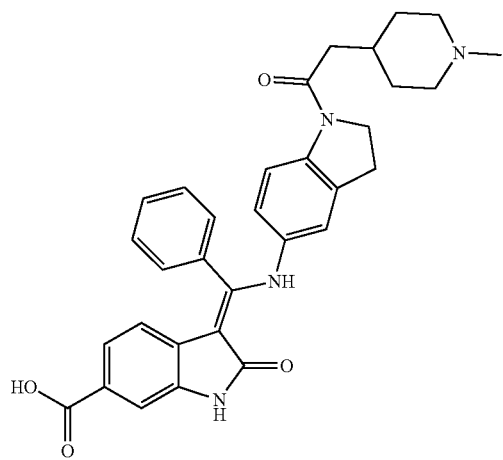 [SMILES: CN1CCC(CC(=O)N2CCc3cc(N/C(=C4\C(=O)Nc5cc(C(=O)O)ccc54)c4ccccc4)ccc32)CC1] |
| 6b | 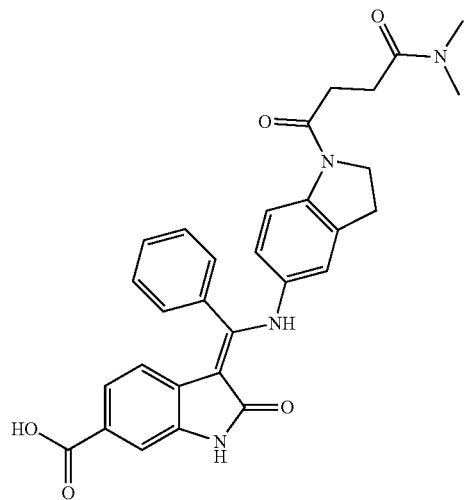 [SMILES: CN(C)C(=O)CCC(=O)N1CCc2cc(N/C(=C3\C(=O)Nc4cc(C(=O)O)ccc43)c3ccccc3)ccc21] |

| Compound | Structure |
|---|---|
| 7b | 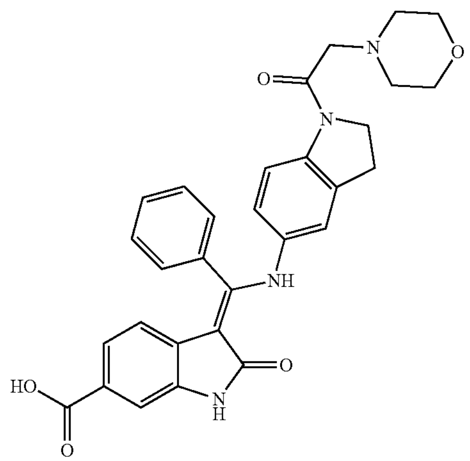 [SMILES: O=C1Nc2cc(C(=O)O)ccc2/C1=C(/Nc1ccc2c(c1)CCN2C(=O)CN1CCOCC1)c1ccccc1] |
| 8b | 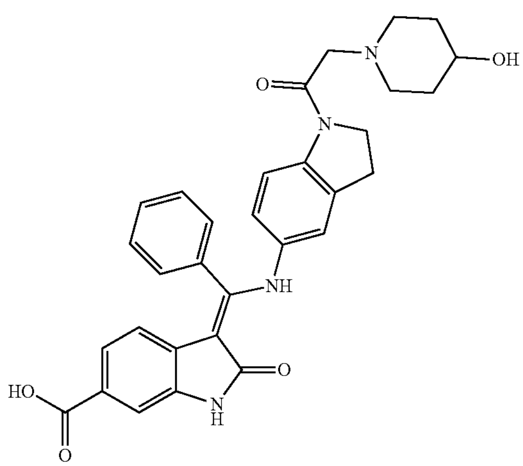 [SMILES: O=C1Nc2cc(C(=O)O)ccc2/C1=C(/Nc1ccc2c(c1)CCN2C(=O)CN1CCC(O)CC1)c1ccccc1] |
| 9b | 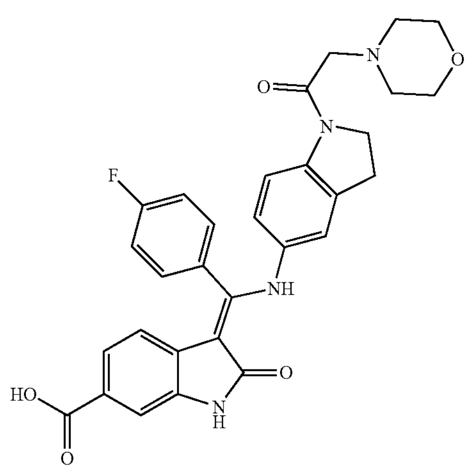 [SMILES: O=C1Nc2cc(C(=O)O)ccc2/C1=C(/Nc1ccc2c(c1)CCN2C(=O)CN1CCOCC1)c1ccc(F)cc1] |

-continued
| Compound | Structure |
|---|---|
| 10b | 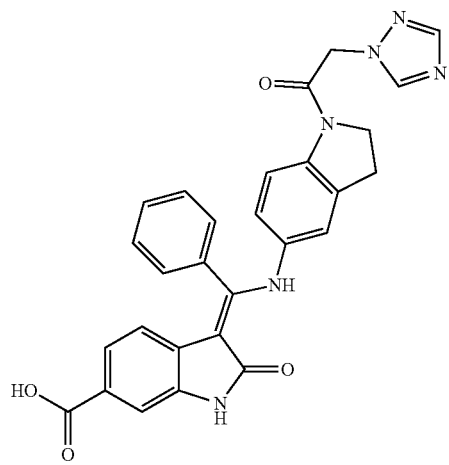 [SMILES: O=C1Nc2cc(C(=O)O)ccc2/C1=C(/Nc1ccc2c(c1)CCN2C(=O)Cn1cncn1)c1ccccc1] |
| 11b | 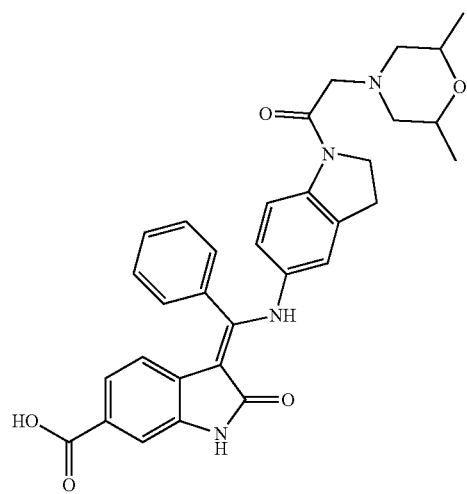 [SMILES: CC1CN(CC(=O)N2CCc3cc(N/C(=C4\C(=O)Nc5cc(C(=O)O)ccc54)c4ccccc4)ccc32)CC(C)O1] |
| 12b | 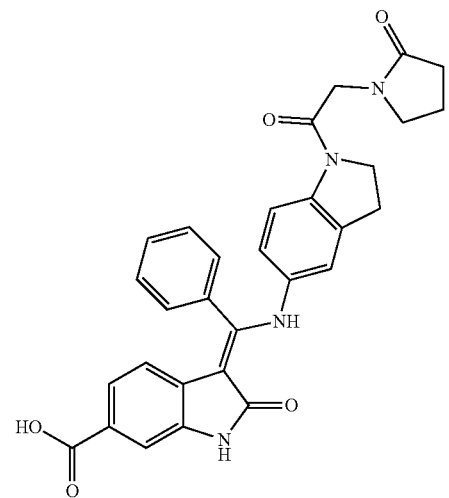 [SMILES: O=C1Nc2cc(C(=O)O)ccc2/C1=C(/Nc1ccc2c(c1)CCN2C(=O)CN1CCCC1=O)c1ccccc1] |

-continued
| Compound | Structure |
|---|---|
| 13b | 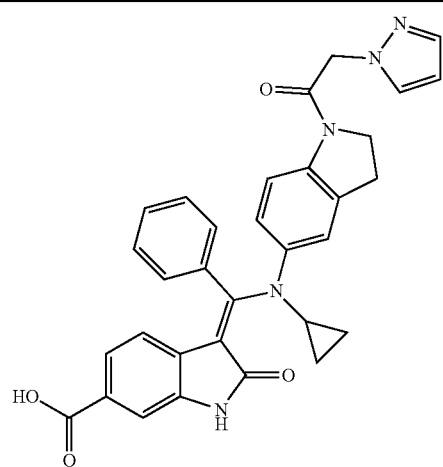 |
| 14b | 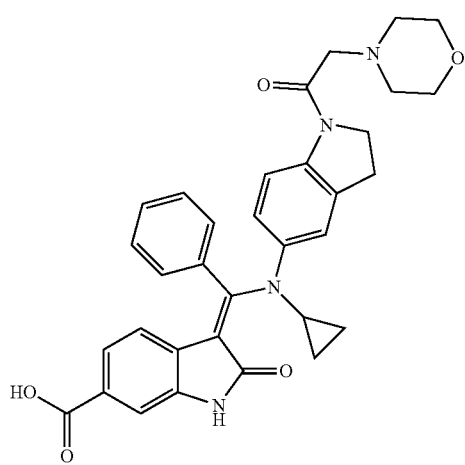 |
| 15b | 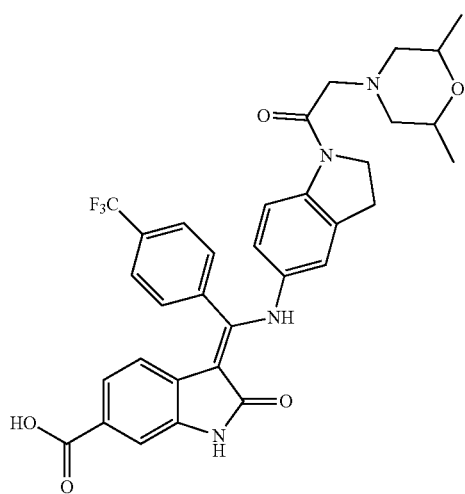 [SMILES: CC1CN(CC(=O)N2CCc3cc(N/C(=C4\C(=O)Nc5cc(C(=O)O)ccc54)c4ccc(C(F)(F)F)cc4)ccc32)CC(C)O1] |

-continued

| Compound | Structure |
|---|---|
| 16b | 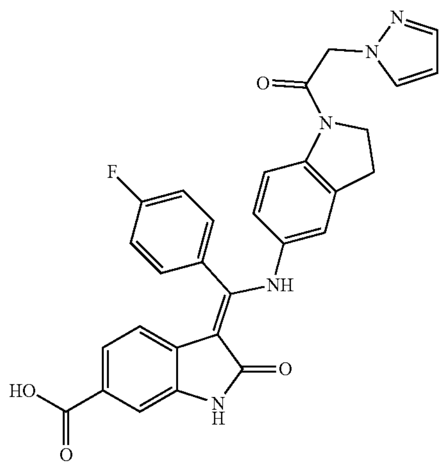 [SMILES: O=C1Nc2cc(C(=O)O)ccc2/C1=C(/Nc1ccc2c(c1)CCN2C(=O)Cn1cccn1)c1ccc(F)cc1] |
| 17b | 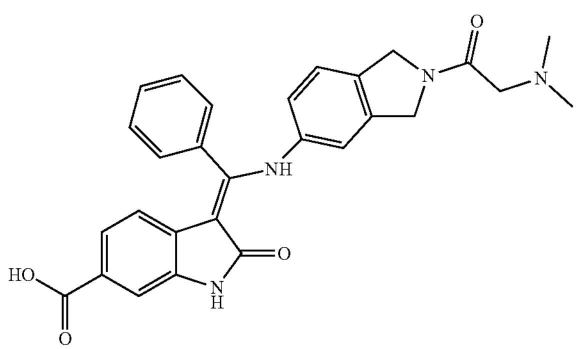 [SMILES: CN(C)CC(=O)N1Cc2ccc(N/C(=C3\C(=O)Nc4cc(C(=O)O)ccc43)c3ccccc3)cc2C1] |
| 18b | 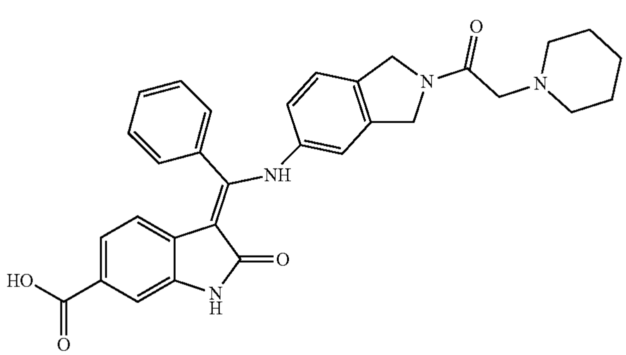 [SMILES: O=C1Nc2cc(C(=O)O)ccc2/C1=C(/Nc1ccc2c(c1)CN(C(=O)CN1CCCCC1)C2)c1ccccc1] |
| 19b | 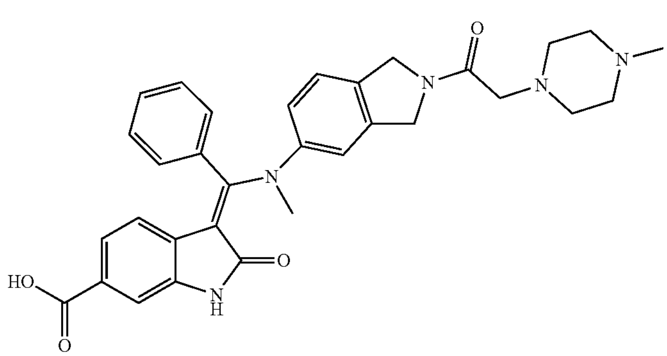 [SMILES: CN1CCN(CC(=O)N2Cc3ccc(N(C)/C(=C4\C(=O)Nc5cc(C(=O)O)ccc54)c4ccccc4)cc3C2)CC1] |

-continued
| Compound | Structure |
|---|---|
| 20b | 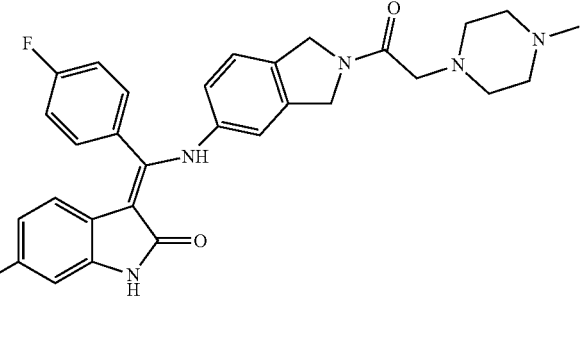 |
| 21b | 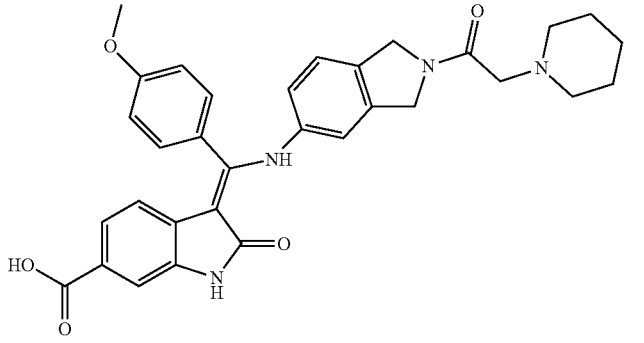 [SMILES: COc1ccc(/C(Nc2ccc3c(c2)CN(C(=O)CN2CCCCC2)C3)=C2/C(=O)Nc3cc(C(=O)O)ccc32)cc1] |
| 22b | 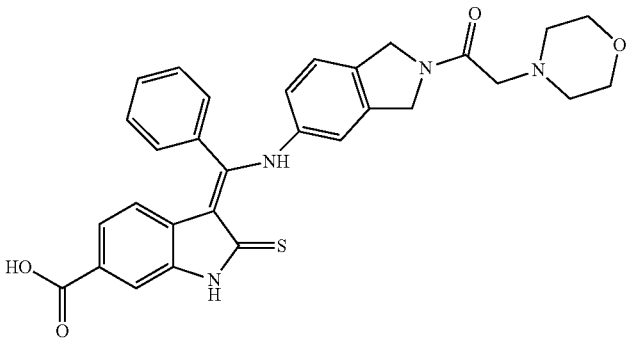 [SMILES: O=C(O)c1ccc2c(c1)NC(=S)/C2=C(\Nc1ccc2c(c1)CN(C(=O)CN1CCOCC1)C2)c1ccccc1] |
| 23b | 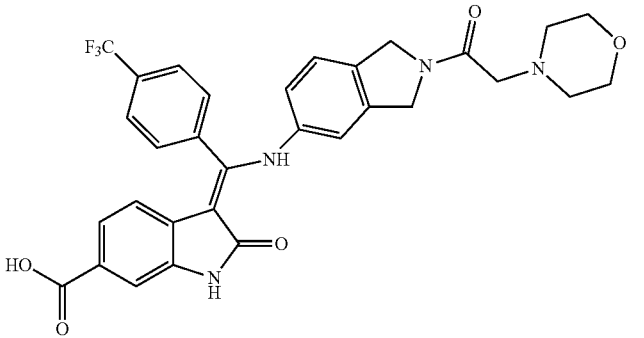 [SMILES: O=C1Nc2cc(C(=O)O)ccc2/C1=C(/Nc1ccc2c(c1)CN(C(=O)CN1CCOCC1)C2)c1ccc(C(F)(F)F)cc1] |

-continued

| Compound | Structure |
|---|---|
| 24b | 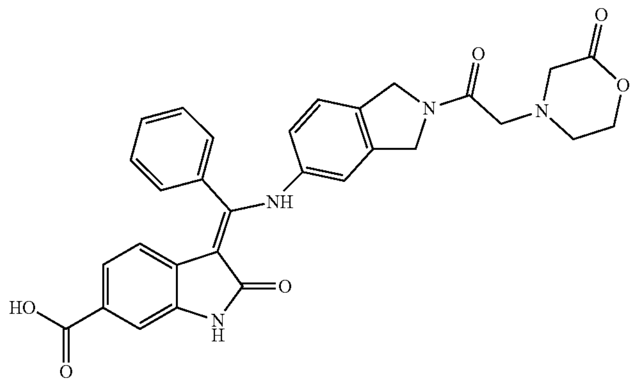 [SMILES: O=C1CN(CC(=O)N2Cc3ccc(N/C(=C4\C(=O)Nc5cc(C(=O)O)ccc54)c4ccccc4)cc3C2)CCO1] |
| 25b | 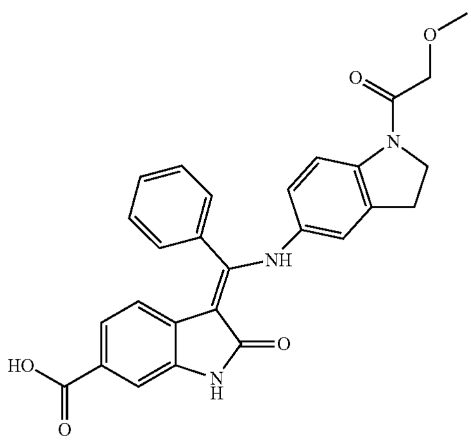 [SMILES: COCC(=O)N1CCc2cc(N/C(=C3\C(=O)Nc4cc(C(=O)O)ccc43)c3ccccc3)ccc21] |
| 26b | 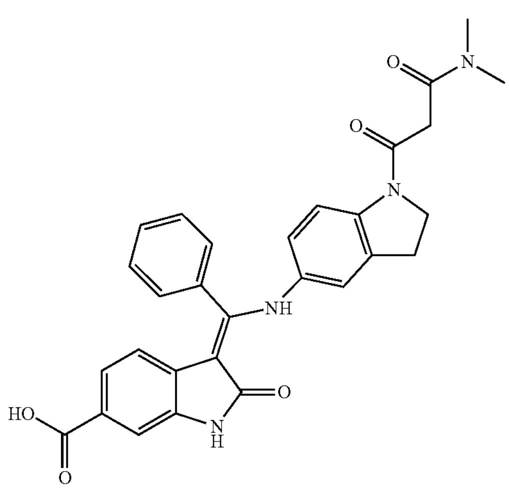 [SMILES: CN(C)C(=O)CC(=O)N1CCc2cc(N/C(=C3\C(=O)Nc4cc(C(=O)O)ccc43)c3ccccc3)ccc21] |

-continued
| Compound | Structure |
|---|---|
| 27b | 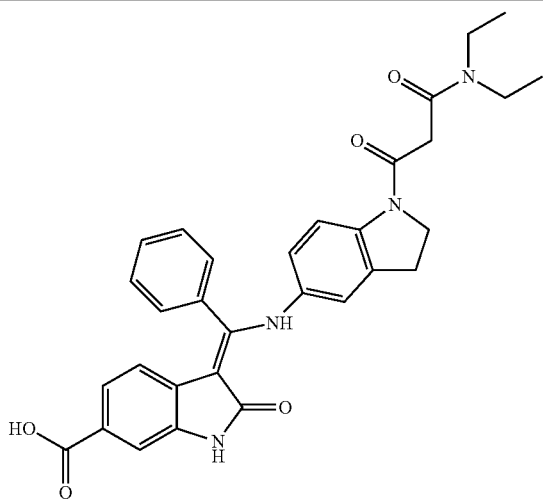 [SMILES: CCN(CC)C(=O)CC(=O)N1CCc2cc(N/C(=C3\C(=O)Nc4cc(C(=O)O)ccc43)c3ccccc3)ccc21] |
| 28b | 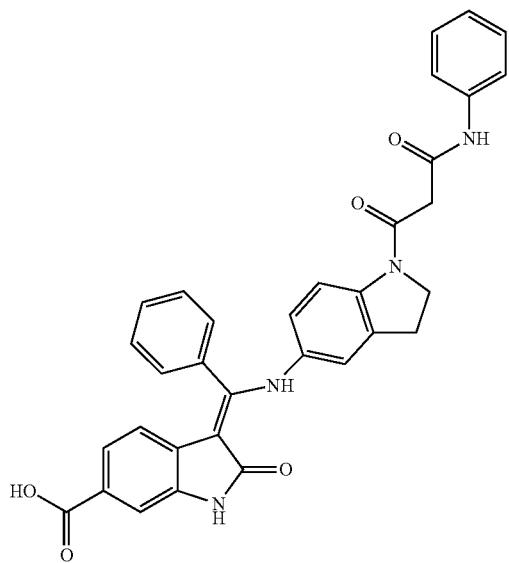 [SMILES: O=C(CC(=O)N1CCc2cc(N/C(=C3\C(=O)Nc4cc(C(=O)O)ccc43)c3ccccc3)ccc21)Nc1ccccc1] |
| 29b | 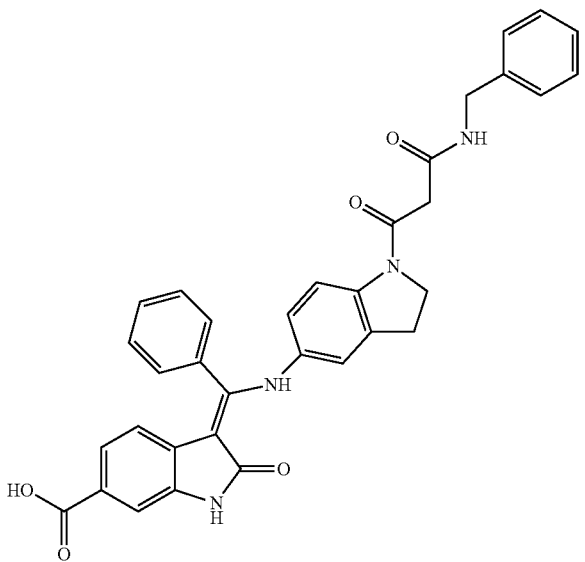 [SMILES: O=C(CC(=O)N1CCc2cc(N/C(=C3\C(=O)Nc4cc(C(=O)O)ccc43)c3ccccc3)ccc21)NCc1ccccc1] |

-continued

| Compound | Structure |
|---|---|
| 30b | 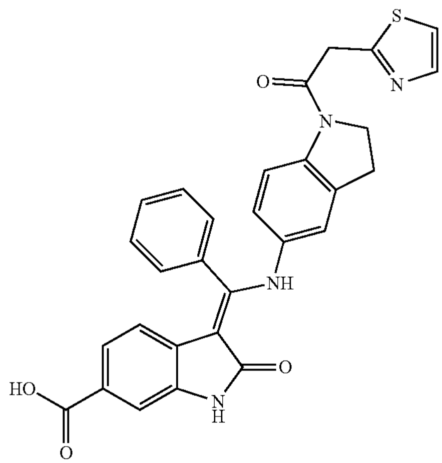 [SMILES: O=C1Nc2cc(C(=O)O)ccc2/C1=C(/Nc1ccc2c(c1)CCN2C(=O)Cc1nccs1)c1ccccc1] |
| 31b | 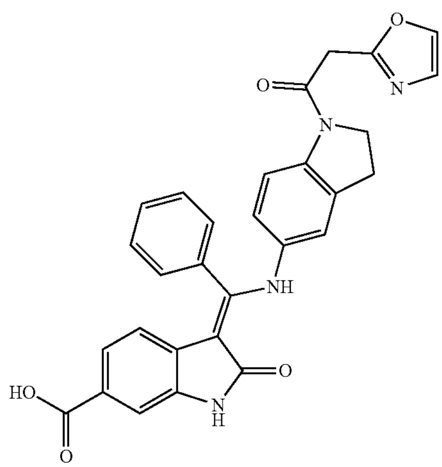 [SMILES: O=C1Nc2cc(C(=O)O)ccc2/C1=C(/Nc1ccc2c(c1)CCN2C(=O)Cc1ncco1)c1ccccc1] |
| 32b | 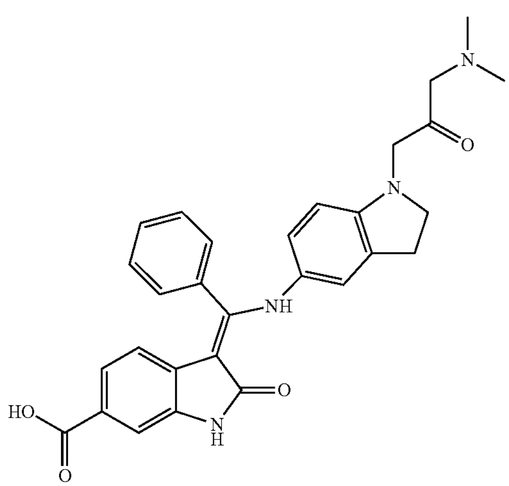 [SMILES: CN(C)CC(=O)CN1CCc2cc(N/C(=C3\C(=O)Nc4cc(C(=O)O)ccc43)c3ccccc3)ccc21] |

-continued
| Compound | Structure |
|---|---|
| 33b | 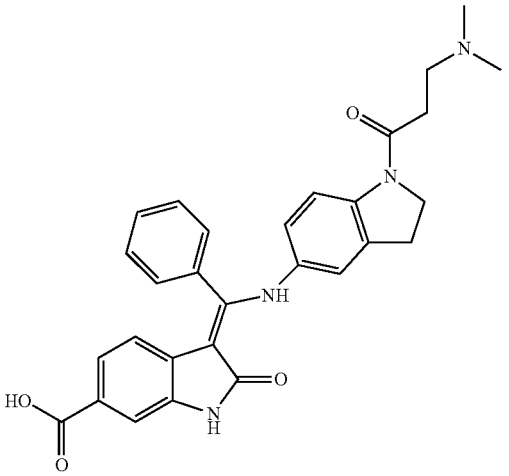 [SMILES: CN(C)CCC(=O)N1CCc2cc(N/C(=C3\C(=O)Nc4cc(C(=O)O)ccc43)c3ccccc3)ccc21] |
| 34b | 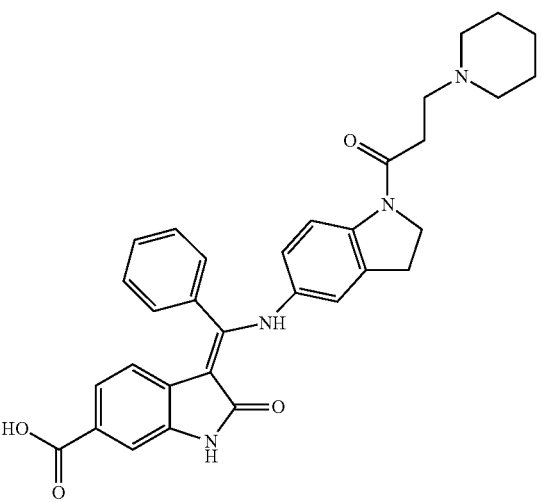 [SMILES: O=C1Nc2cc(C(=O)O)ccc2/C1=C(/Nc1ccc2c(c1)CCN2C(=O)CCN1CCCCC1)c1ccccc1] |
| 35b | 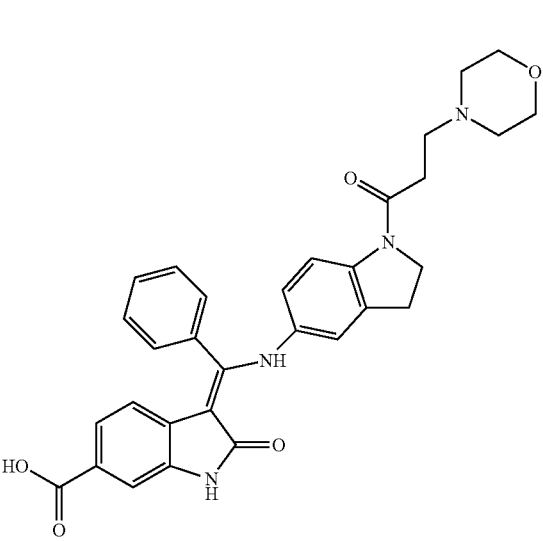 [SMILES: O=C1Nc2cc(C(=O)O)ccc2/C1=C(/Nc1ccc2c(c1)CCN2C(=O)CCN1CCOCC1)c1ccccc1] |

-continued

| Compound | Structure |
|---|---|
| 36b | (structure shown) |
| 37b | (structure shown) |
| 38b | (structure shown) |

DETAILED DESCRIPTION OF THE INVENTION

Unless other specified in the context, it should be understood that the terms used herein have the following meanings.

In the present invention, the term "halogen" means fluoro, chloro, bromo or iodo.

In the present invention, the term "$C_{1-6}$alkyl" means a straight or branched alkyl derived from a hydrocarbon containing 1-6 carbon atoms by removing one hydrogen atom. Its example includes methyl, ethyl, n-propyl, iso-propyl, n-butyl, iso-butyl, sec-butyl, tert-butyl, n-pentyl, iso-pentyl, 2-methylbutyl, neo-pentyl, 1-ethylpropyl, n-hexyl, iso-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-methyl-2-methylpropyl and the like. In the present invention, the term "$C_{1-6}$alkyl" means the specific examples having 1-4 carbon atoms among the above examples.

In the present invention, the term "$C_{1-6}$alkyloxycarbonyl" means a group that is formed by attaching "$C_{1-6}$alkyl" to an oxygen atom and then attaching the oxygen atom to a carbonyl group and is attached to another group via the carbonyl group. Its example includes methoxycarbonyl, ethyloxycarbonyl, propyloxycarbonyl, iso-propyloxycarbonyl, butyloxycarbonyl, iso-butyloxycarbonyl, tert-butyloxycarbonyl, sec-butyloxycarbonyl, pentyloxycarbonyl, neo-pentyloxycarbonyl, hexyloxycarbonyl and the like. In the present invention, the term "$C_{1-4}$alkyloxycarbonyl" means the specific examples having 1-4 carbon atoms among the above examples.

In the present invention, the term "$C_{1-3}$alkyloxy" means a group that is formed by attaching "$C_{1-3}$alkyl" to an oxygen atom and is attached to another group via the oxygen atom. Its example includes methoxy, ethyloxy, propyloxy, iso-propyloxy and the like.

In the present invention, the term "3-14-membered cycloalkyl" means a cyclic group derived from a cyclic hydrocarbon by removing one hydrogen atom, wherein the ring members of the cyclic hydrocarbon are all carbon atoms. Its example includes 3-8-membered monocyclic cycloalkyl and 6-14-membered fused cycloalkyl.

The term "3-8-membered monocyclic cycloalkyl" includes 3-8-membered saturated monocyclic cycloalkyl and 3-8-membered partially-saturated monocyclic cycloalkyl. The term "3-8-membered saturated monocyclic cycloalkyl" means that the monocyclic ring is a completely saturated carbonaceous ring. Its example includes but is not limited to: cyclopropyl, cyclobutyl, cyclopentyl, cyclohexyl, cycloheptyl, cyclooctanyl, methylcyclopropyl, dimethylcyclopropyl, methylcyclobutyl, dimethylcyclobutyl, methylcyclopentyl, dimethylcyclopentyl, methylcyclohexyl, dimethylcyclohexyl and the like. The term "3-8-membered partially-saturated monocyclic cycloalkyl" means that the monocyclic ring is a partially saturated carbonaceous ring. Its example includes but is not limited to cyclopropenyl, cyclobutenyl, cyclopentenyl, cyclohexenyl, 1,4-cyclohexadienyl, cycloheptenyl, 1,4-cycloheptadienyl, cyclooctene, 1,5-cyclooctadienyl and the like.

In the present invention, the term "3-6-membered monocyclic cycloalkyl" means a cycloalkyl having 3-6 carbon atoms.

The term "6-14-membered fused cycloalkyl" means a fused cycloalkyl group, which is formed by two or more cyclic structures in said fused ring via sharing two adjacent carbon atoms with each other, and includes "6-14-membered saturated fused cycloalkyl" and "6-14-membered partially saturated fused cycloalkyl". The term "6-14-membered saturated fused cycloalkyl" means that the fused ring is a completely saturated carbonaceous ring. Its example includes but is not limited to biscyclo[3.1.0]hexyl, biscyclo[4.1.0]heptyl, biscyclo[2.2.0]hexyl, biscyclo[3.2.0]heptyl, biscyclo[4.2.0]octanyl, octahydropentalenyl, octahydro-1H-indenyl, decahydronaphthalenyl, tetradecahydrophenanthrenyl and the like. The term "6-14-membered partially saturated fused cycloalkyl" means that at least one ring in the fused ring is a partially saturated carbonaceous ring. Its example includes but is not limited to biscyclo[3.1.0]hex-2-enyl, biscyclo[4.1.0]hept-3-enyl, biscyclo[3.2.0]hept-3-enyl, biscyclo[4.2.0]oct-3-enyl, 1,2,3,3α-tetrahydropentalenyl, 2,3,3α,4,7,7α-hexahydro-1H-indenyl, 1,2,3,4,4α,5,6,8α-octahydronaphthalenyl, 1,2,4α,5,6,8α-hexahydronaphthalenyl, 1,2,3,4,5,6,7,8,9,10-decahydrophenanthrenyl and the like.

In the present invention, the term "6-14-membered aryl" means a cyclic aromatic group, whose ring members are all the carbon atoms, and includes 6-8-membered monocyclic aryl and 8-14-membered fused aryl.

The term "6-8-membered monocyclic aryl" means a completely unsaturated aryl, for example, phenyl, cyclooctatetraeneyl and the like.

The term "8-14-membered fused aryl" means a cyclic group that is formed by two or more cyclic structures via sharing two adjacent carbon atoms with each other and in which at least one ring is a completely unsaturated aromatic ring, and includes 8-14-membered completely unsaturated fused aryl, e.g. naphthyl, phenanthrenyl and the like, and further includes 8-14-membered partially saturated fused aryl, e.g. benzene-fused 3-8-membered saturated monocyclic cycloalkyl, benzene-fused 3-8-membered partially-saturated monocyclic cycloalkyl. Its specific example includes, for example, 2,3-dihydro-1H-indenyl, 1H-indenyl, 1,2,3,4-tetrahydronaphthalenyl, 1,4-dihydronaphthalenyl and the like. In the present invention, the term "6-10-membered unsaturated aryl" means a monocyclic aryl and a fused aryl, both of which are completely unsaturated and have 6-10 carbon atoms.

In the present invention, the term "7-12-membered bridged ring group" means a structure that is formed by any two rings sharing two indirectly attached atoms and contains 7-12 carbon atoms and/or hetero atoms, wherein said hetero atom includes N, O, S and the like. The term "7-12-membered bridged ring" includes "7-12-membered saturated bridged ring", and "7-12-membered partially saturated bridged ring".

The term "7-12-membered saturated bridged ring" means that all of the rings in the bridged ring are the saturated cyclic groups, and is preferably "7-8-membered saturated bridged ring". Its specific example includes but is not limited to

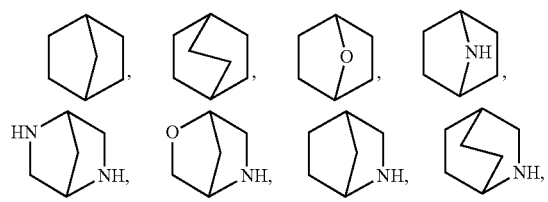

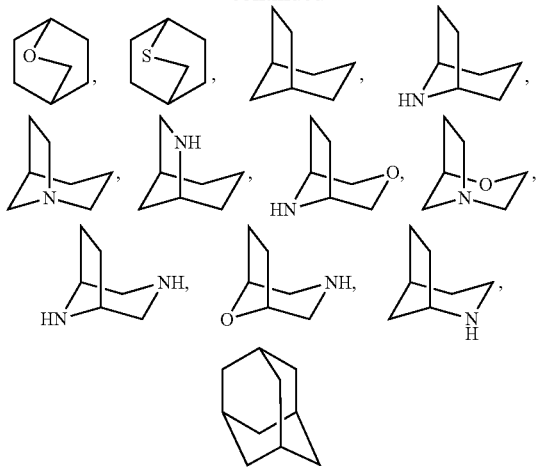

and the like.

The term "7-12-membered partially saturated bridged ring" means that at least one ring in the bridged ring is an unsaturated cyclic group, and is preferably "7-8-membered partially saturated bridged ring". Its specific example includes but is not limited to

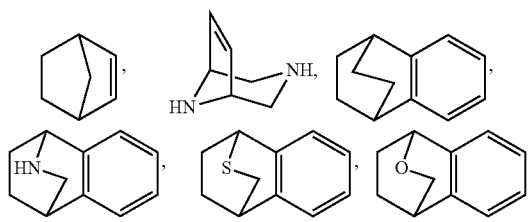

and the like.

In the present invention, the term "7-12-membered spiro ring" means a structure that is formed by at least two rings sharing the same atom and contains 7-12 carbon atoms and/or hetero atoms, wherein said hetero atom includes N, O, S and the like. The term "7-12-membered spiro ring" includes "7-12-membered saturated spiro ring, and "7-12-membered partially saturated spiro ring".

The term "7-12-membered saturated spiro ring" means all of the rings in the spiro ring are the saturated cyclic groups. Its specific example includes but is not limited to

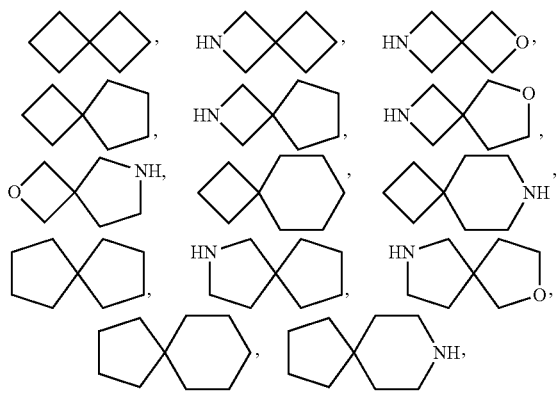

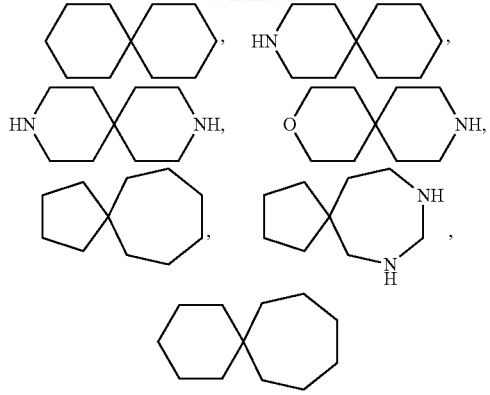

and the like.

The term "7-12-membered partially saturated spiro ring" means that at least one ring in the spiro ring is an unsaturated cyclic group. Its specific example includes but is not limited to

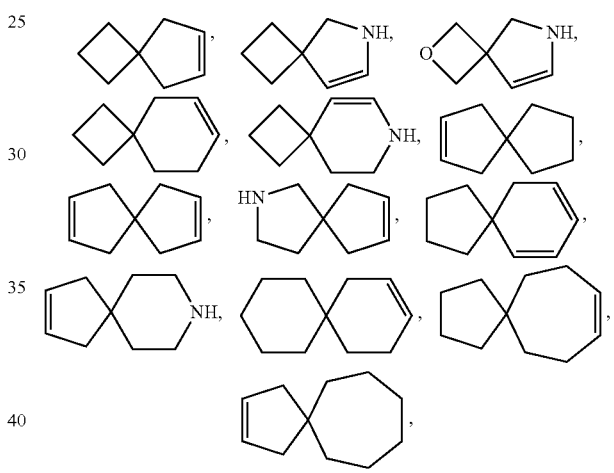

and the like.

In the present invention, the term "3-14-membered heterocyclyl" means a cyclic group containing 3-14 ring atoms (and containing at least one hetero atom as the ring atom), and comprises 3-8-membered monocyclic heterocyclyl, 6-14-membered fused heterocyclyl, 4-10-membered heterocyclyl, 5-10-membered heterocyclyl and the like. The hetero atom can comprise nitrogen, oxygen, sulfur and the like.

The term "3-8-membered monocyclic heterocyclyl" means a monocyclic heterocyclyl containing 3-8 ring atoms (and containing at least one hetero atom as the ring atom), and includes 3-8-membered unsaturated monocyclic heterocyclyl, 3-8-membered partially saturated monocyclic heterocyclyl, and 3-8-membered saturated monocyclic heterocyclyl. 5-6-membered monocyclic heterocyclyl is preferable. The term "3-8-membered unsaturated monocyclic heterocyclyl" means an aromatic cyclic group containing at least one hetero atom. 5-6-membered unsaturated monocyclic heterocyclyl is preferable. Its specific example includes but is not limited to piperidinyl, furyl, thienyl, pyrrolyl, thiazolyl, thiodiazolyl, oxazolyl, oxdiazolyl, imidazolyl, pyrazolyl, pyridyl, pyrimidinyl, 1,4-dioxinyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,2,4-triazinyl, 1,3,5-triazinyl, 1,2,4,5-tetrazinyl, oxepinyl, thiepinyl, azepinyl, 1,3-diazepinyl, azocinyl and the like. The term "3-8-membered partially saturated monocyclic heterocyclyl" mean a cyclic group containing at least one double bond and containing at least one hetero atom. 5-6-membered partially saturated monocyclic heterocyclyl is preferable. Its specific example includes but is not limited to 2,5-dihydrothienyl, 4,5-dihydropyrazolyl, 3,4-dihydro-2H-pyranyl, 5,6-dihydro-4H-1,3-oxazinyl and the like. The term "3-8-membered saturated monocyclic heterocyclyl" means a cyclic group containing at least one hetero atom and not containing any unsaturated bond. 5-6-membered saturated monocyclic heterocyclyl is preferable. Its specific example includes but is not limited to aziridinyl, azetidinyl, thietanyl, tetrahydrofuryl, tetrahydropyrrolyl, imidazolidinyl, pyrazolidinyl, tetrahydrofuryl, 1,4-dioxanyl, 1,3-dioxanyl, 1,3-dithianyl, morpholinyl, piperazinyl and the like.

The term "6-14-membered fused heterocyclyl" means a fused cyclic structure, which contains 6-14 ring atoms (and containing at least one hetero atom), and which is formed by linking via two or more cyclic structures sharing two adjacent atoms with each other, and includes 6-14-membered unsaturated fused heterocyclyl, 6-14-membered partially saturated fused heterocyclyl, and 6-14-membered saturated fused heterocyclyl.

The term "6-14-membered unsaturated fused heterocyclyl" means a fused cyclic structure in which all rings are unsaturated, e.g. a structure formed by fusing a benzene ring with 3-8-membered unsaturated monocyclic heterocyclyl, a structure formed by fusing 3-8-membered unsaturated monocyclic heterocyclyl with 3-8-membered unsaturated monocyclic heterocyclyl. Its specific example includes but is not limited to benzofuryl, benzoisofuryl, benzothienyl, indolyl, benzoxazolyl, benzimidazolyl, indazolyl, benzotriazolyl, quinolinyl, isoquinolinyl, acridinyl, phenanthridinyl, benzopyridazinyl, phthalazinyl, quinazolinyl, quinoxalyl, phenazinyl, pteridinyl, purinyl, naphthyridinyl, and the like.

The term "6-14-membered partially saturated fused heterocyclyl" means a fused cyclic structure containing at least one partially saturated ring, e.g. a structure formed by fusing a benzene ring with 3-8-membered partially saturated monocyclic heterocyclyl, a structure formed by fusing 3-8-membered partially saturated monocyclic heterocyclyl with 3-8-membered partially saturated monocyclic heterocyclyl, and the like. Its specific example includes but is not limited to 1,3-dihydrobenzofuryl, benzo[d][1,3]dioxolyl, isoindolinyl, chromanyl, 1,2,3,4-tetrahydropyrrolo[3,4-c]pyrrolyl and the like.

The term "6-14-membered saturated fused heterocyclyl" means a fused cyclic structure, in which all rings are saturated, e.g. a structure formed by fusing 3-8-membered saturated monocyclic heterocyclyl with 3-8-membered saturated monocyclic heterocyclyl. Its specific example includes but is not limited to cyclobutane-fused tetrahydropyrrolyl, cyclopentane-fused tetrahydropyrrolyl, azetidine-fused imidazolidinyl and the like.

In the present invention, the terms "4-10-membered heterocyclyl" and "5-10-membered heterocyclyl" means the monocyclic heterocyclyl and the fused heterocyclyl containing 4-10 ring atoms and 5-10 ring atoms respectively.

In the present invention, the term "prodrug group" means a protecting group on the nitrogen atom of lactam. Its specific example includes but is not limited to an acyl group, an ester group, an sulfonylurea group and the like.

In the present invention, the term "6-12-membered fused ring group-$C_{0-3}$alkyl", "7-12-membered spiro ring group-$C_{0-3}$alkyl" or "6-12-membered bridged ring group-$C_{0-3}$alkyl" means "6-12-membered fused ring group", "7-12-membered spiro ring group", and "6-12-membered bridged ring group" are attached to the other structure via $C_{0-3}$alkylene, and includes "6-9-membered fused ring group-$C_{0-3}$alkyl", "7-10-membered spiro ring group-$C_{0-3}$alkyl" or "7-8-membered bridged ring group-$C_{0-3}$alkyl". Its specific example includes but is not limited to

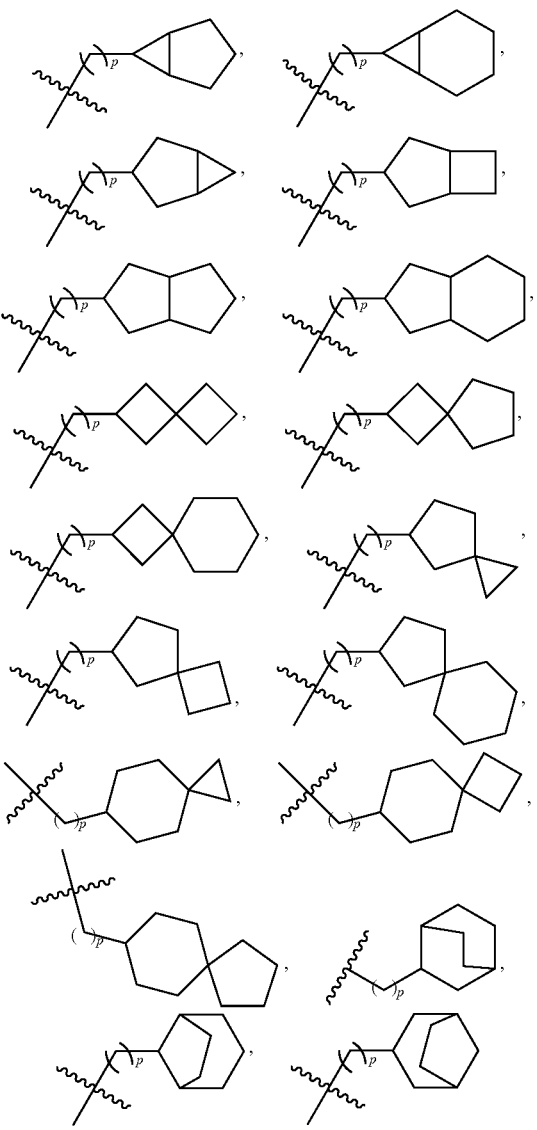

and the like. (Moreover, 1-3 carbon atoms in the rings can be replaced with 1-3 same or different groups selected from $N(H)_m$, $N(C_{1-3}alkyl)$, O, $S(O)_m$, and C(O), and p represents 0, 1, 2 or 3).

The above compounds of the present invention can be synthesized according to the methods described in the following reaction scheme and/or other methods well known to those skilled in the art. The synthesis method is not limited to the following methods.

Reaction Steps:

Intermediate 4 is synthesized according to *J. Med. Chem.* 2009, 52, 4466-4480.

Step 1: Preparation of Intermediate 1

Starting material 1 and an organic base are dissolved in DCM. Starting material 2 is added dropwise under an ice-water bath. The reaction mixture is warmed to room temperature and reacted for 0.5 hour. Water is added. The resulting mixture is extracted with DCM. The organic phase is dried and rotary-evaporated to dryness. The resulting solid is dried in vacuum to produce Intermediate 1.

Step 2: Preparation of Intermediate 2

Intermediate 1 and an organic base are dissolved in DCM. Starting material 3 is added dropwise. The reaction mixture is reacted at room temperature for 12 hours. The resulting mixture is extracted with DCM. The organic layer is dried over anhydrous sodium sulfate, and rotary-evaporated to dryness to produce Intermediate 2.

Step 3: Preparation of Intermediate 3

Intermediate 2 is dissolved in DCM. TFA is added. The reaction is conducted at room temperature. After the completion of the reaction, the reaction mixture is concentrated to produce Intermediate 3. Alternatively, Intermediate 2 is dissolved in methanol. The mixture is subjected to the hydrogenation reduction with Pd/C overnight, and then filtered. The resulting filtrate is concentrated to produce Intermediate 3. The product is not purified and directly used in the next reaction step.

Step 4: Preparation of the Compound Represented by Formula (I)

Intermediate 4 and Intermediate 3 are dissolved in DMF. The mixture is heated to 80° C. and reacted for 5 hours. The reaction mixture is cooled to room temperature, and the reaction is further conducted for 2 hours. Water is added. The resulting mixture is filtered. The resulting solid is dried in vacuum to produce the compound of formula (I).

Starting material 2 is a halide; see the specific Examples for Starting material 2; see the specific Examples for Starting material 3.

Reaction scheme:

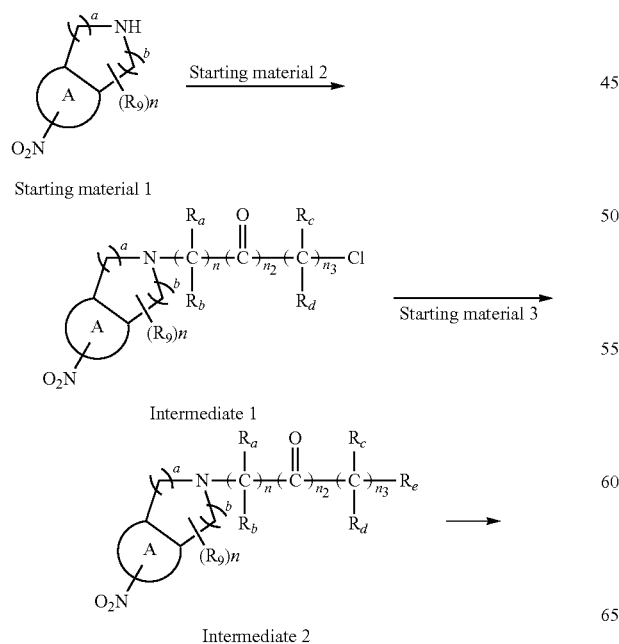

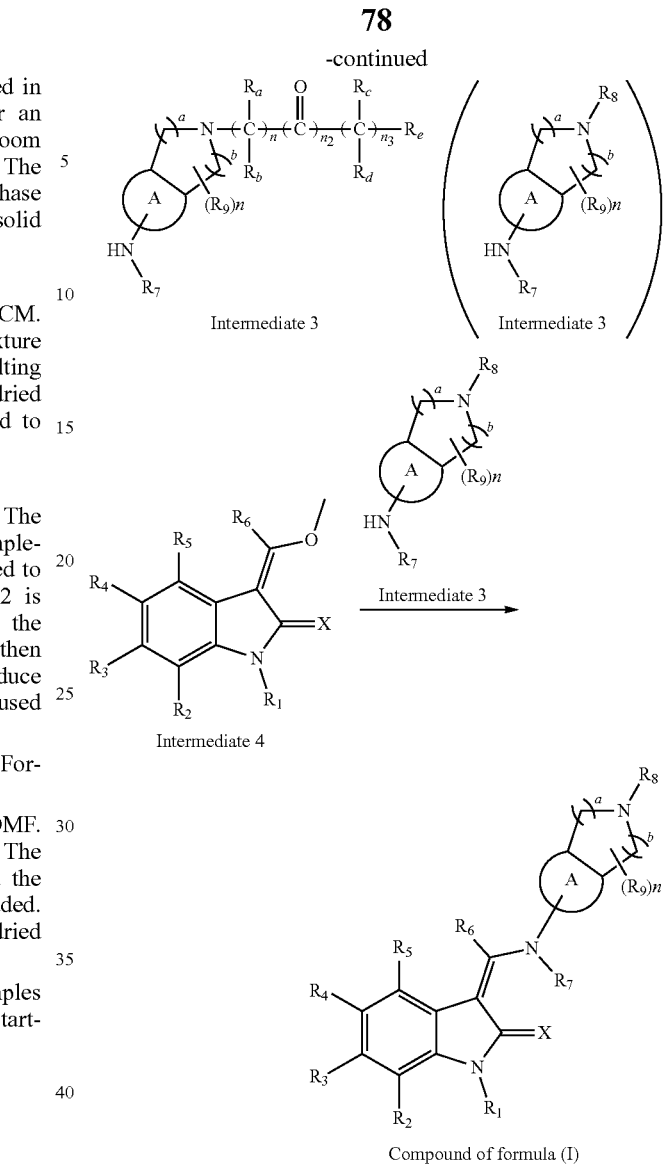

In the reaction equations, $R_1$, $R_2$, $R_3$, $R_4$, $R_5$, $R_6$, $R_7$, $R_8$, $R_9$, $R_a$, $R_b$, $R_c$, $R_d$, $R_e$, X, n, a, b, and Ring A are defined as hereinbefore.

In addition, the above compound can be converted, as follows:

-continued

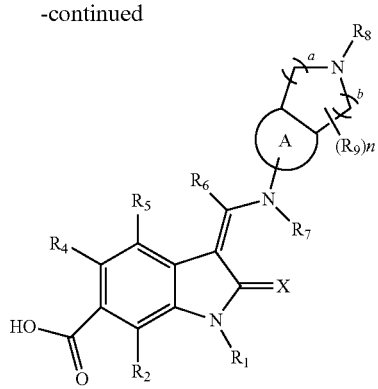

wherein, $R_x$ is methyl, ethyl, $R_1$, $R_2$, $R_4$, $R_5$, $R_6$, $R_7$, $R_8$, $R_9$, $R_a$, $R_b$, $R_c$, $R_d$, X, n, a, b, and Ring A are defined as above.

The starting material can be dissolved in an organic solvent (e.g. methanol, ethanol, THF, dioxane and the like); then an aqueous solution of inorganic base (e.g. sodium hydroxide, potassium hydroxide, and potassium carbonate) is added; the reaction is stirred until the completion of reaction; the resulting mixture is concentrated, washed with water, adjusted to the acidity with hydrochloric acid, and filtered; and the filtrate is washed with water, and dried to produce the product.

The pharmaceutically acceptable salt of any of the above compounds according to the present invention refers to a salt formed from a pharmaceutically acceptable, non-toxic base or acid, including a salt of an organic acid, a salt of an inorganic acid, a salt of an organic base, and a salt of an inorganic base.

The salt of the organic acid comprises a salt of formic acid, acetic acid, benzenesulfonic acid, benzoic acid, para-bisulfonic acid, camphor sulfonic acid, citric acid, mesylate, ethyl sulfonic acid, propionic acid, fumaric acid, gluconic acid, glutamate, hydroxy ethyl sulfonic acid, lactic acid, maleic acid, malic acid, mandelic acid, viscous acid, pamoic acid, pantothenic acid, succinic acid, tartaric acid, or the like. The salt of the inorganic acid comprises a salt of hydrobromic acid, hydrochloric acid, nitric acid, sulfuric acid, phosphoric acid, or the like.

The salt of the organic base comprises salts of primary, secondary and tertiary amines, substituted amines, including naturally occurring substituted amines, cyclic amines, and alkaline ion-exchange resin, selected from betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, meglumine, glucosamine, hydrabamine, iso-propylamine, methylglucamine, morpholine, piperazine, piperidine, procaine, purine, theobromine, triethylamine, trimethylamine, tripropylamine, tromethamine and the like, as well as salts of natural amino acids such as glycine, alanine, valine, leucine, isoleucine, norleucine, tyrosine, cystine, cysteine, methionine, proline, hydroxyproline, histidine, ornithine, lysine, arginine and serine. The salt of the inorganic base comprises ammonium salts, as well as salts of Li, Na, K, Ca, Mg, Zn, Ba, Al, Fe, Cu, $Fe^{2+}$, Mn, $Mn^{2+}$ and the like.

The present invention further relates to a pharmaceutical composition, wherein the pharmaceutical composition contains any of the above compounds, or a pharmaceutically acceptable salt, a deuteride or a stereoisomer thereof, and optionally one or more pharmaceutically acceptable carriers. The pharmaceutical composition can further contain a second therapeutical agent selected from an antineoplastic agent and an immunosuppressive agent, wherein the second therapeutical agent is selected from antimetabolites, including but being not limited to capecitabine, gemcitabine and the like; growth factor inhibitors, including but being not limited to gefitinib, lapatinib, pazopanib, imatinib and the like; antibodies, including but being not limited to herceptin, bevacizumab and the like; mitotic inhibitors, including but being not limited to paclitaxel, vinorelbine, docetaxel, doxorubicin and the like; antineoplastic hormones, including but being not limited to letrozole, tamoxifen, fulvestrant and the like; alkylating agents, including but being not limited to cyclophosphamide, carmustine and the like; metallic platinums, including but being not limited to carboplatin, cisplatin, oxaliplatin and the like; topoismerase inhibitors, including but being not limited to topotecan and the like; immunosuppressive agents, including but being not limited to everolimus and the like.

The present invention further relates to a pharmaceutical formulation, which comprises a compound represented by the above general formula (I), or a pharmaceutically acceptable salt, a deuteride or a stereoisomer thereof and one or more pharmaceutically acceptable carriers.

The present compound can be formulated into any pharmaceutical formulation in a well known manner in the art, and administrated in an oral, parenteral, rectal or pulmonary admininstration or the like to a subject in need thereof. For the oral administration, the present compound can be formulated into a conventional solid formulation, such as tablet, capsule, pill, granule, or the like; or the oral liquid formulation, such as an oral solution, an oral suspension, a syrup, or the like. For preparing the oral formulation, suitable filler, binder, disintegrant, lubricant, diluent, or the like can be added. For the parenteral administration, the present compounds can be formulated into an injectable formulation, including an injection solution, a sterile injection powder and a concentrated injection solution. For preparing the injectable formulation, a conventional method in the pharmaceutical production can be used. For preparing the injectable formulation, an additive can be optionally added, depending on the nature of drug. For the rectal administration, the present compounds can be formulated into a suppository or the like. For the pulmonary administration, the present compounds can be formulated into an inhalant, a spraying agent, or the like.

The present invention also provides the use of a compound represented by the above general formula (I), or a pharmaceutically acceptable salt, a deuteride or a stereoisomer thereof in manufacture of a medicament for treating or preventing a fibrous degeneration disease, wherein said fibrous degeneration disease includes but is not limited to: fibrous degeneration and remodeling of pulmonary tissue in chronic obstructive pulmonary disease, fibrous degeneration and remodeling of pulmonary tissue in chronic bronchitis, fibrous degeneration and remodeling of pulmonary tissue in emphysema, pulmonary fibrous degeneration as well as pulmonary disease with fibrosis components, fibrous degeneration and remodeling in asthma, fibrous degeneration in rheumatoid arthritis, virus-induced hepatic cirrhosis, radiation-induced fibrous degeneration, postangioplasty restenosis, chronic glomerulonephritis, renal fibrous degeneration in a cyclosporin-administrated patient and hypertension-induced renal fibrous degeneration, skin disease having fibrosis components, and over cicatrization.

The disease is selected from the group consisting of pulmonary fibrous degeneration and the pulmonary disease having fibrous degeneration components, including but not limited to idiopathic pulmonary fibrosis degeneration, giant cell interstitial pneumonia, sarcoidosis, cystic fibrous degeneration, respiratory distress syndrome, drug-induced pulmonary fibrous degeneration, granulomatosis, silicosis, asbestosis, systemic sclerosis, virus-induced hepatic cirrhosis (e.g. C-hepatitis induced hepatic cirrhosis), and skin disease having fibrous degeneration components (e.g. scleroderma, sarcoidosis and the systemic lupus erythematosus).

The present invention also provides the use of the present compound represented by the above general formula (I), or a pharmaceutically acceptable salt, a deuteride or a stereoisomer thereof in manufacture of a medicament for treating the excessive proliferation disease, inhibiting the angiogenesis and/or reducing the vascular permeability, wherein the excessive proliferation disease includes a cancer and a non-carcinomatous disease, including but not limited to: cerebroma, pulmonary carcinoma, nonsmall cell pulmonary carcinoma, squamous cell carcinoma, bladder carcinoma, gastric carcinoma, ovarian carcinoma, peritoneal carcinoma, pancreatic carcinoma, breast carcinoma, head and neck carcinoma, uterocervical carcinoma, endometrial carcinoma, rectal carcinoma, hepatoma, renal carcinoma, adenocarcinoma of esophagus, esophageal squamous cell carcinoma, solid tumor, non-Hodgkin lymphoma, central nervous system neuroplasm (glioma, glioblastoma multiforme, glioma sarcomatosum), prostatic carcinoma, thyroid carcinoma, female genital tract carcinoma, carcinoma in situ, lymphoma, histocytic lymphoma, neurofibromatosis, thyroid carcinoma, osteocarcinoma, skin cancer, brain carcinoma, colon carcinoma, carcinoma of testis, small cell pulmonary carcinoma, gastrointestinal stromal tumor, prostate tumor, mast cell tumor, multiple myeloma, melanoma, glioma, glioblastoma multiforme, astrocytoma, neuroblastoma, sarcoma, or the like. The non-carcinomatous disease includes but is not limited to the benign skin or prostate hyperplasia or the like.

The present invention relates to a "stereoisomer" of the compound of formula (I). The compound of the present invention may contain one or more asymmetric centers and can thus occur as racemates and racemic mixtures, single enantiomers, diastereomeric mixtures and individual diastereomers. The compound of the present invention may have at least one asymmetric center. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. The present compound of formula (I) or a pharmaceutically acceptable salt thereof can exist in an optical isomer form due to the presence of at least one asymmetric carbon atom. Thus, the present invention further comprises these optical isomers and mixture thereof. It is intended that all of isomerism (e.g. enantiomorphism, diastereoisomerism and geometric isomerism (or conformational isomerism)) forms of the structures as described herein are included herein; for example, R and S configurations for each asymmetric center, Z and E isomers for each double bond, and Z and E conformational isomers. Therefore, the individual stereoisomer of the present compound and a mixture of enantiomers, diastereoisomers, or geometric isomers (or confomational isomers) can be in the scope of the present invention. Unless stated to the contrary, all of tautomers of the present compound are in the scope of the present invention.

The present invention relates to a "deuteride" of the compound of formula (I). The present invention also comprises such a compound which is characterized by containing one or more isotope-enriched atoms. For example, a compound having the structure of the present invention but being enriched in deuterium or tritium that substitutes hydrogen or being enriched in the $^{13}C$ or $^{14}C$ atom that substitute the $^{12}C$ atom can be in the scope of the present invention. This kind of compounds can be for example used as an analysis tool, a probe in the biological analysis, or a therapeutic agent of the present invention. In some embodiments, the compound of formula (I) can have one or more deuterium atoms.

The indolinone-containing compound as the tyrosine kinase inhibitor of the present invention contains two or more chiral centers. The compound obtained by synthesis is a racemate. The desired enantiomerically pure compound can be obtained through a chiral resolution, for example, through a chiral stationary phase chromatography (e.g. high pressure preparation chromatography, supercritical fluid chromatography). The chiral filler includes but is not limited to: Chiralcel O J-H, Chiralpak A D-H, Chiralpak I A, Chiralpak A S-H.

The present invention also provides a method for preparing a compound represented by formula (I), or a pharmaceutically acceptable salt, a deuteride or a stereoisomer thereof, wherein said method comprises reacting a compound represented by formula (III) with a compound represented by formula (IV) to produce the compound represented by formula (I),

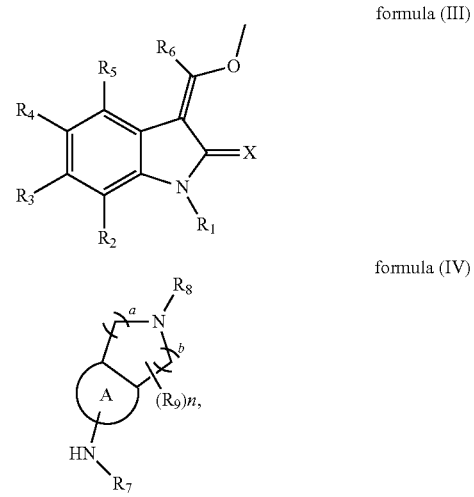

wherein $R_1$, $R_2$, $R_3$, $R_4$, $R_5$, $R_6$, $R_7$, $R_8$, $R_9$, a, b, n and ring A are defined as hereinbefore.

In comparison to the closest prior art, the present compound has the following advantages:

(1) As a small molecule tyrosine kinase inhibitor, the present compound can prevent or treat the fibrous degeneration disease, inhibit the cell proliferation and the angiogenesis, have a good antineoplastic activity, and have good effect in treating and/or preventing various fibrosis diseases and/or neoplastic diseases of mammals (including human).

(2) The present compound has a low toxicity and a low side-effect, and has a large safety window.

(3) The preparation process for the present compound is simple, and the present compound has a good photochemical property and a stable quality, which makes the present compound be easily produced on a large industrial scale.

Hereinafter, the beneficial effect of the present compound will be illustrated by the pharmacological experiments. However, it should be noted that the beneficial effect of the present compound is not limited to those as illustrated below.

Assay:

1. In Vitro Enzymology Inhibitory Activity of the Present Compounds

Materials:

| Material | Chinese Name | Source |
|---|---|---|
| VEGFR2 | vascular endothelial growth factor 2 | Carna |
| FGFR1 | fibroblast growth factor 1 | Carna |
| FGFR3 | fibroblast growth factor 3 | Carna |
| PDGFRβ | platelet derived growth factor β | BPS |
| EDTA | ethylenediamine tetraacetic acid | Sigma |
| Peptide FAM-P22 | fluorescein labelled peptide 22 | GL Biochem |
| ATP | adenosine triphosphate | Sigma |
| DMSO | dimethyl sulfoxide | Sigma |
| Staurosporine | Staurosporine | Sigma |

The present compounds were synthesized in laboratory. Chemical names, structures, and preparation methods were shown in their examples respectively.

Experiment Method:
(1) Preparation of agents and compounds
① 1-fold kinase buffer without $MnCl_2$ (50 mM HEPES, pH=7.5, 0.0015% Brij-35, 10 mM $MgCl_2$, 2 mM DTT)
② 1-fold kinase buffer with $MnCl_2$ (50 mM HEPES, pH=7.5, 0.0015% Brij-35, 10 mM $MgCl_2$, 10 mM $MnCl_2$, 2 mM DTT);
③ Termination solution (100 mM HEPES, pH=7.5, 0.015% Brij-35, 0.2% Coating Reagent #3, 50 mM EDTA);
④ 2.5-fold kinase solution (the VEGFR2, FGFR1, FGFR3, PDGFRβ kinases were added to the 1-fold kinase buffer respectively to prepare the corresponding 2.5-fold kinase solutions);
⑤ 2.5-fold substrate solution: FAM-labelled peptide and ATP were added to the 1-fold kinase buffer to prepare a peptide solution;
⑥ 4-fold dilution of the compound solution: the compound was accurately weighed, and dissolved in DMSO. The mixture was mixed sufficiently and evenly to prepare a 10 mM solution. Then the solution was diluted with DMSO to 500 μM, and 4-fold serial dilutions were done at 10 concentrations with a highest concentration of 50μM. The resulting diluted solutions were kept for use.
(2) 5 μL of a 5-fold compound solution was added to a 384-well plate.
(3) 10 μL of the 2.5-fold kinase solution was added and incubated for 10 min.
(4) Then 10 μL of the 2.5-fold substrate solution was added at 28° C. and the reaction was conducted for 1 hour (except for the PGDFRβ kinase, for which the reaction was conducted for 5 hour).
(5) Finally, 25 μL of termination solution was added to terminate the reaction, and the data was read from the Caliper.
(6) $IC_{50}$ was obtained by the curve fitting.

The calculated inhibition ratio (%)=(max. conversion−sample conversion)/(max. conversion−min. conversion)×100

The curve fitting was done with the software Xlfit to obtain the $IC_{50}$ value.

The experiment result was shown in the below table.

TABLE 1

In vitro enzymology inhibitory activity of the present compounds

| Compound | enzymology inhibitory activity $IC_{50}$(μM) | | | |
|---|---|---|---|---|
| | FGFR1 | FGFR3 | VEGFR2 | PDGFRβ |
| Compound 1 | 0.10 | 0.23 | 0.017 | 0.0076 |
| Compound 2 hydrochloride | 0.14 | 0.28 | 0.065 | 0.015 |
| Compound 9 hydrochloride | / | 9.80 | 0.77 | 0.085 |
| Compound 10 hydrochloride | 7.96 | 5.30 | 0.63 | 0.065 |
| Compound 12 hydrochloride | 1.77 | 1.72 | 0.23 | 0.019 |
| Compound 13 hydrochloride | 0.70 | 0.54 | 0.10 | 0.014 |
| Compound 14 hydrochloride | 4.67 | 4.02 | 0.31 | 0.024 |

"/" means no detection.

It can be seen from Table 1 that the present compounds have the inhibitory activities on FGFR1, FGFR3, VEGFR2, and PDGFRβ kinases. Among others, the present compounds have stronger inhibitory activities on the PDGFRβ kinase.

2. In Vitro Cellular Inhibitory Activity of the Present Compounds

Materials:

| Materials | Source |
|---|---|
| Human VEGF-A | HumanZyme |
| Human PDGF-BB | PeproTech |
| HI-FBS | Gibco |
| Calf serum | Gibco |

The present compounds were synthesized in laboratory. Chemical names, structures, and preparation methods were shown in their examples respectively.

Experiment Method:
(1) Thawing cells and Passing cells.
(2) Plating Cells:

The 3T3 cells were resuspended in a culture medium containing 10% fetal bovine serum, wherein the cell concentration was $5\times10^4$/ml. The cell suspension was added to a 96-well plate with 100 μL per well, and incubated overnight; the HUVEC cells were resuspended in a culture medium containing 10% heat-inactivated fetal bovine serum, wherein the cell concentration was $7.5\times10^4$/ml. The cell suspension was added to a 96-well plate with 100 μL per well.

(3) Treating with drugs: the compounds were diluted to different concentrations, and 60 μLh-PDGF-BB (3T3 cells) and 40 ng/ml h-VEGF-A (HUVEC cells) were added and incubated for 1 hour.
(4) 100 μL of a solution containing the compound and h-PDGF-BB (h-VEGF-A, for the HUVEC cells) was added to a cell culture plate, wherein the final concentration of h-PDGF-BB was 10 ng/ml, the final concentration of h-VEGF-A was 10 ng/ml, and the final concentration for the compounds were 10, 3.3333, 1.1111, 0.3704, 0.1235, 0.0412, 0.0137, 0.0046, and 0.0015 μM. The plate was incubated for 40 hours, and the HUVEC cells were incubated for 89 hours. To each well was added 20 μL Promega Substrate, and the plate was incubated at 37° C. for 7.5 hours, and the HUVEC cells were incubated for 11.5 hours. Then the plate was placed in a microplate reader to read the absorbance at 490 nm.

(5) Data processing

The curve of the compound concentration vs. Net OD was plotted, wherein Net OD=Compound OD−min. OD. ED50 was calculated according to the following equation: Conc. $ED_{50}(x)=(y-b)/a$, y=Calculated Net OD for $IC_{50}$, a=slope, b=intercept.

The experiment result was shown in the below tables.

TABLE 2

In vitro cellular inhibitory activity of the present compounds

| Compound | $ED_{50}(\mu M)$ for the HUVEC in vitro cells |
|---|---|
| Compound 1 | 0.056-0.084 |
| Compound 3 | 0.18-0.26 |
| Compound 4 | 0.12-0.17 |
| Compound 5 | 0.1-0.15 |
| Compound 6 hydrochloride | 0.19-0.28 |
| Compound 7 | 0.07-0.1 |
| Compound 8 | 0.07-0.1 |
| Compound 9 hydrochloride | 0.13-0.19 |
| Compound 10 hydrochloride | 0.09-0.14 |
| Compound 11 hydrochloride | 0.05-0.08 |
| Compound 12 hydrochloride | 0.02-0.03 |
| Compound 13 hydrochloride | 0.06-0.09 |
| Compound 14 hydrochloride | 0.07-0.10 |

TABLE 3

In vitro cellular inhibitory activity of the present compounds

| Compound | $ED_{50}(\mu M)$ for the 3T3 in vitro cells |
|---|---|
| Compound 1 | 0.06-0.08 |
| Compound 3 | 1.3-1.9 |
| Compound 5 | 0.82-1.24 |
| Compound 7 hydrochloride | 0.05-0.07 |

It can be seen from Tables 2 and 3 that the present compounds had the inhibitory effect on the proliferation of the HUVEC cells and the 3T3 cells.

3. Detection of the Inhibitory Effect of the Present Compounds on hERG Potassium Channel with the Patch Clamp Method Materials:

| Material | Source |
|---|---|
| Amitriptyline hydrochloride | Sigma-Aldrich |
| DMSO | Merck |
| CHO-hERG | AVIVA |

The present compounds were synthesized in laboratory. Chemical names, structures, and preparation methods were shown in their examples respectively.

The control drug, Intedanib (BIBF-1120), was synthesized in laboratory according to WO0127081A1.

Experiment Method:

1. Preparations of the Solutions and the Compounds

Extracellular fluid (mM): N-2-hydroxyethylpiperazine-N'-2-ethanesulfonic acid (HEPES) 10, NaCl 145, KCl 4, $CaCl_2$ 2, $MgCl_2$ 1, Glucose 10, adjusted with 1N sodium hydroxide to pH=7.4; the osmotic pressure was adjusted to 290-300 mOsm; filtered and preserved at 4° C.

Intracellular solution (mM): KCl 120, KOH 31.25, $CaCl_2$ 5.374, $MgCl_2$ 1.75, Ethylene glycol-bis(β-aminoethyl ether)-N,N,N',N'-tetraacetic acid (EGTA) 10, HEPES 10, Na2-ATP 4, adjusted with 1N potassium hydroxide to pH=7.2; the osmotic pressure was adjusted to 280-290 mOsm; filtered and preserved at −20° C.

Preparation of the compounds: The positive control drug, amitriptyline hydrochloride, two samples, Intedanib, and the compounds were firstly dissolved in 100% DMSO (Merck, 61850125001730) to prepare 10 or 30 mM of stock solutions (see the below table). Before the experiments, the above stock solutions were diluted with DMSO to the levels that were 333 or 1000 times higher than the experiment concentrations, and then diluted by 333 or 1000 folds with the extracellular fluid to the desired concentrations. The final concentration of DMSO in the extracellular fluid was 0.3% or 0.1%.

2. Electrophysiological experiment. The hERG current was recorded with whole cell patch clamp technique. A cell suspension was added to a 35 mm petri dish, and placed on the object stage of an inverted microscope. After the adherence of cells, the perfusion with the extracellular fluid was done in a perfusion rate of 1-2 ml/min. The glass microelectrode was made by a two-step pulling with a pipette puller, and had an electric resistance of 2-5 MΩ upon coming into solution. After establishing a whole-cell record, the holding potential was kept at −80 mV. In the voltage stimulation, the depolarization was made at the potential of +60 mV. Then, the repolarization was made at the potential of −50 mV and the hERG tail current was recorded. All of the recordings were conducted after the currents became stable. The extracellular perfusion administration started from the lower concentration, and the administration at each concentration was conducted for 5-10 mines until the current became stable and then the administration at the next concentration was conducted.

3. The Experiment Included the Following Aspects:

The hERG current was recoded on the CHO-K1 cell line stably expressing the hERG channel with the manual patch clamp technology; the inhibition ratio at each concentration was calculated according to the hERG tail current; each of the compounds was measured at five concentrations to deduce the $IC_{50}$ value; two cells were measured at each concentration; and one positive control drug was used.

4. Data Collection and Processing

The stimulation and the signal collection were accomplished through A/D-D/A digital-analog conversions with Digidata 1440 (Molecular Devices) and pCLAMP software (Version 10.2, Molecular Devices); the signal was amplified with a patch clamp amplifier (Multiclamp 700B, Molecular Devices), and filtered at 1 KHz. The data were further analyzed and subjected to the curve fitting with Clampfit (Version 10.2, Molecular Devices) and Prism. The data were expressed as mean value±standard deviation. The $IC_{50}$ value was obtained by the fitting based on the Logistic equation:

$$y = \left[\frac{max - min}{1 + \left(\frac{[drug]}{IC_{50}}\right)^{n_H}}\right] + min$$

y: the inhibitory percent; max: 100%; min: 0%; [drug]: the concentration of the tested substance; $n_H$: the slope rate; $IC_{50}$: the half maximal inhibitory concentration of the tested substance.

Results:

Table 4: $IC_{50}$ values of the compounds for the hERG currents recorded on CHO-K1 stable cell line

| Sample | IC$_{50}$ (μM) |
|---|---|
| Amitriptyline hydrochloride | 2.35 |
| Intedanib (BIBF-1120) | 4.90 |
| Compound 7 hydrochloride | >30.00 |
| Compound 9 hydrochloride | >30.00 |
| Compound 10 hydrochloride | >30.00 |
| Compound 11 hydrochloride | >30.00 |
| Compound 12 hydrochloride | >30.00 |
| Compound 13 hydrochloride | >30.00 |
| Compound 14 hydrochloride | >30.00 |

The positive control drug, amitriptyline, was one of the widely used drugs for blocking the hERG current. In the present experiment, the IC$_{50}$ value of the positive control drug for blocking the hERG current was 2.35 μM, which was consistent with those reported in the literatures. This showed that the result of the present experiment was convincing. In the present experiment, the hERG current blocking at the highest testing concentration (30.00 μM) of for each of Compounds 7, 9, 10, 11, 12, 13 and 14 did not reach the level of IC$_{50}$, which showed that the present compounds had no remarkable blocking of the hERG channel in the tested concentration range. The IC$_{50}$ value of the control drug (BIBF-1120) for the hERG current was 4.90 μM, which showed a remarkable blocking of the hERG channel. Therefore, the present compounds were safer in comparison with the control drug BIBF-1120.

Reference: Blockade of the HERG human cardiac K+ channel by the antidepressant drug amitriptyline. British Journal of Pharmacology, (2000) 129:1474-1480.

4. Specific Embodiments

Hereinafter, the present invention will be further illustrated in details by the following specific examples. It should be understood that the scope of the present invention is not limited by the following examples.

Example 1

Preparation of Methyl(Z)-3-((1-(2-(4-methylpiperazin-1-yl)acetyl)indol-5-ylamino)(phenyl)methylene)-2-oxoindoline-6-carboxylate (Compound 1)

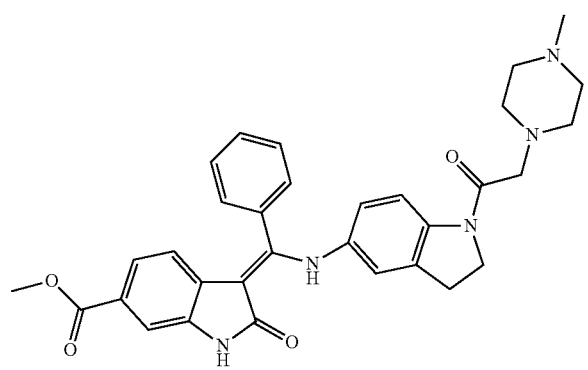 [SMILES: COC(=O)c1ccc2c(c1)NC(=O)/C2=C(\Nc1ccc2c(c1)CCN2C(=O)CN1CCN(C)CC1)c1ccccc1]

(1) Preparation of 1-(2-chloroacetyl)-5-nitroindoline

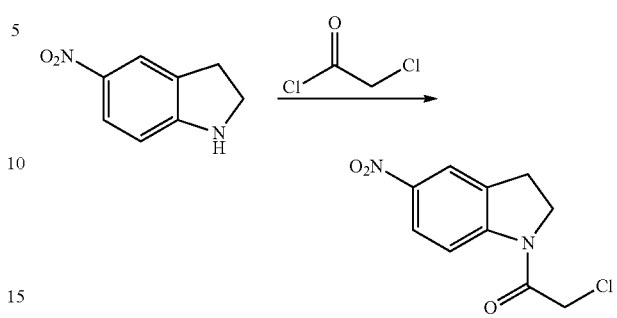

5-nitroindoline (16.4 g, 100 mmol) was dissolved in ethyl acetate (200 ml), and then chloroacetyl chloride (9.6 ml 120 mmol) was slowly added at 40° C. The resulting mixture was heated to 80° C., and reacted for 0.5 hour. The reaction mixture was cooled and filtered by suction. The filtrate was crystallized to produce 1-(2-chloroacetyl)-5-nitroindoline (22 g) as a grey solid in a yield of 92%.

(2) Preparation of 2-(4-methylpiperazin-1-yl)-1-(5-nitroindol-1-yl)ethanone

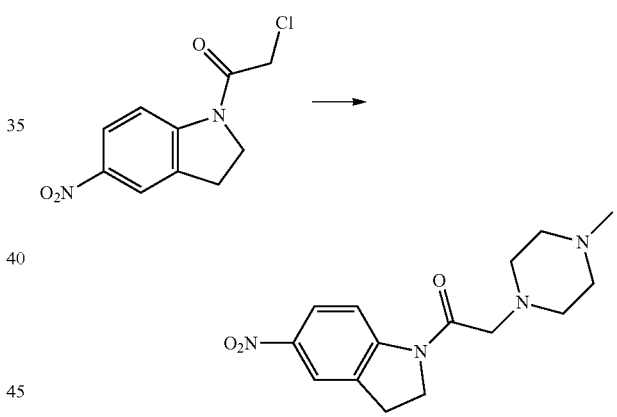

2-chloro-1-(5-nitroindol-1-yl)ethanone (22 g, 92 mmol) was dissolved in toluene (200 ml). The mixture was heated to 70° C., and then N-methylpiperazine was slowly added dropwise. The reaction was conducted overnight, and the solvent was dried by rotary evaporation. The residue was purified with a column chromatography to produce 2-(4-methylpiperazin-1-yl)-1-(5-nitroindol-1-yl)ethanone as a white floccular solid (15.8 g) in a yield of 56%.

(3) Preparation of 1-(5-aminoindol-1-yl)-2-(4-methylpiperazin-1-yl)ethanone

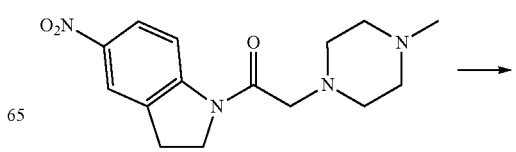

-continued

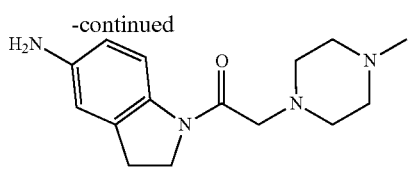

2-(4-methylpiperazin-1-yl)-1-(5-nitroindol-1-yl)ethanone (500 mg, 1.64 mmol) was added to methanol (100 ml), and then Pd/C (50 mg, 10%) was carefully added. The resulting mixture was subjected to a reduction reaction under hydrogen for 4 hours at room temperature. After the completion of the reaction, the Pd/C was filtered. The filtrate was concentrated to produce 1-(5-aminoindol-1-yl)-2-(4-methylpiperazin-1-yl)ethanone (300 mg) in a yield of 66%.

(4) Preparation of methyl(Z)-3-((1-(2-(4-methylpiperazin-1-yl)acetyl)indol-5-ylamino)(phenyl)methylene)-2-oxoindoline-6-carboxylate

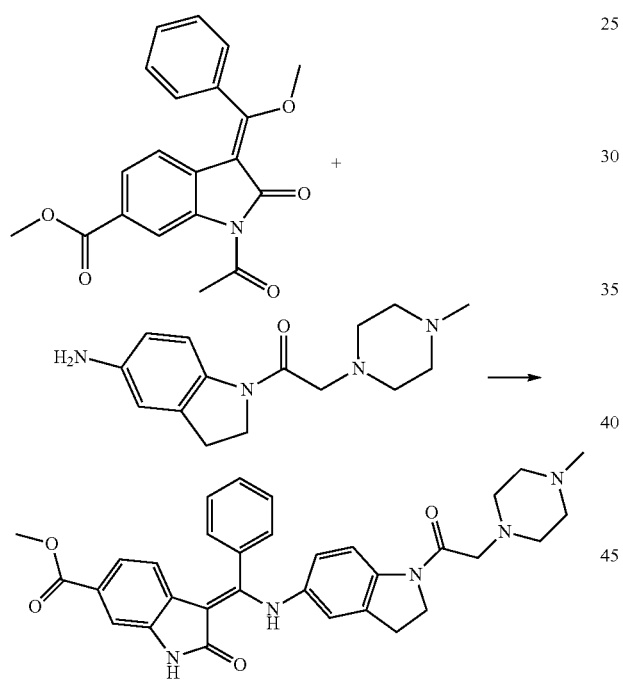

To methanol (50 mL) were added 1-(5-aminoindol-1-yl)-2-(4-methylpiperazin-1-yl)ethanone (300 mg, 1.09 mmol), methyl(Z)-methyl-1-acetyl-3-(methoxy(phenyl)methylene)-2-oxoindoline-6-carboxylate (338 mg, 1.09 mmol) and KOH (30 mg, 0.54 mmol). The mixture was stirred into dissolution, and reacted under reflux for 7 hours. Then the reaction was concentrated to produce a crude product, which was purified with a column chromatography (MeOH/DCM=1:30) to produce methyl(Z)-methyl-3-((1-(2-(4-methylpiperazin-1-yl)acetyl)indol-5-ylamino)(phenyl)methylene)-2-oxoindoline-6-carboxylate (150 mg) in a yield of 24.8%.

Formula: $C_{32}H_{33}N_5O_4$; MW: 552; Mass Spectrum (m/e): 552.3 (M+1)

$^1$H NMR (400M, DMSO-d$^6$, $\delta_{ppm}$): 12.16 (s, 1H), 10.93 (s, 1H), 7.77 (d, 1H), 7.56 (m, 3H), 7.48 (d, 2H), 7.40 (s, 1H), 7.17 (d, 1H), 6.79 (s, 1H), 6.66 (d, 1H), 5.79 (d, 1H), 4.09 (t, 2H), 3.75 (s, 3H), 3.16 (t, 2H), 2.95 (t, 2H), 2.30 (m, 4H), 2.29 (m, 4H), 2.12 (s, 3H).

Example 2

Preparation of methyl(Z)-3-((1-(2-(dimethylamino)acetyl)indolin-5-ylamino)(phenyl)methylene)-2-oxoindoline-6-carboxylate (Compound 2) and its hydrochloride

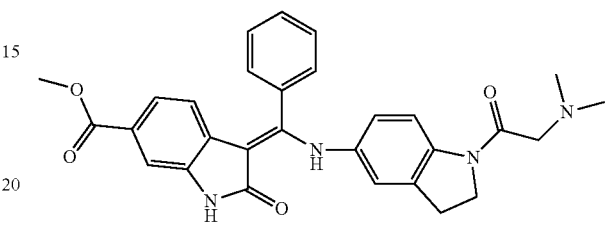

(1) Preparation of 1-(2-(dimethylamino)acetyl)-5-nitroindoline

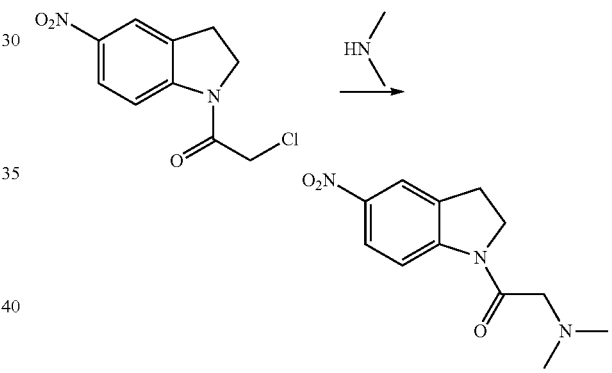

1-(2-chloroacetyl)-5-nitroindoline (22 g, 92 mmol), dimethylamine hydrochloride (22 g, 276 mmol), and potassium carbonate (32.5 g, 276 mmol) were respectively added to toluene (200 ml). The resulting mixture was added to 70° C., and reacted overnight. The solvent was removed by concentration. The residue was purified with a silica gel column chromatography (methanol/methylene chloride=0-1/10) to produce 1-(2-(dimethylamino)acetyl)-5-nitroindoline as a white solid (11.5 g) in a yield of 50%.

(2) Preparation of 1-(2-(dimethylamino)acetyl)-5-aminoindoline

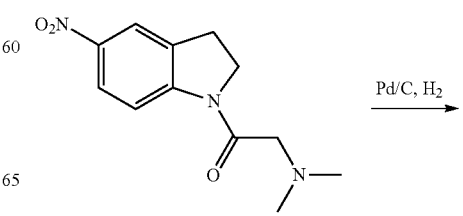

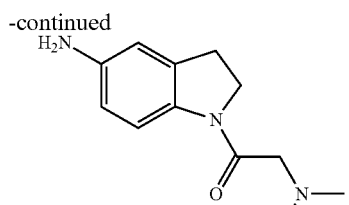

1-(2-(dimethylamino)acetyl)-5-nitroindoline (5 g, 16.4 mmol) and Pd/C (1 g) were added to methanol (200 ml). Hydrogen gas was introduced to the reaction system overnight. After the completion of the reaction, the solvent was removed by rotary-evaporation to produce 1-(2-(dimethylamino)acetyl)-5-aminoindoline as a white solid (5g, 99%).

(3) Preparation of methyl(Z)-3-((1-(2-(dimethylamino)acetyl)indolin-5-ylamino)(phenyl)methylene)-2oxoindoline-6-carboxylate and its hydrochloride

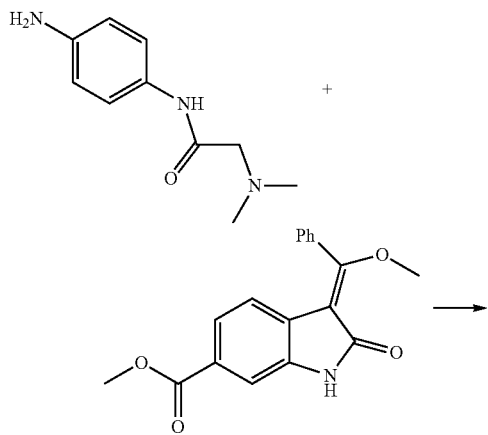

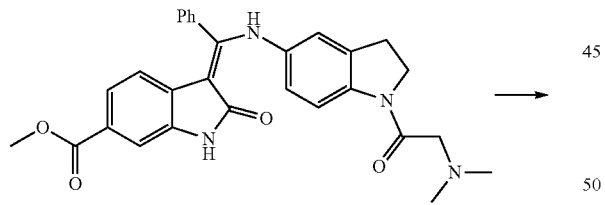

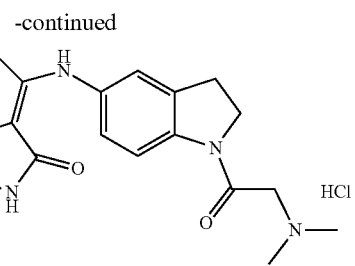

1-(2-(dimethylamino)acetyl)-5-aminoindoline (0.082 g, 0.3 mmol) and methyl(E)-3-(methoxy(phenyl)methylene)-2-oxoindoline-6-carboxylate (0.086 g, 0.28 mmol) was added to MeOH (2 ml). The resulting mixture was heated to 70° C. and kept for 7 hours. After being cooled naturally, the mixture was filtered by suction. The filtrate was dried to produce a yellow solid (61 mg) in a yield of 35.4%.

Methanol (10 ml) was added to a concentrated hydrochloric acid (1 ml). The above crude product was added to the resulting solution. The mixture was stirred at room temperature for 2 hours, and filtered by suction. The filtrate was dried in vacuum to produce methyl(Z)-3-((1-(2-(dimethylamino)acetyl)indolin-5-ylamino)(phenyl)methylene)-2oxoindoline-6-carboxylate hydrochloride (68 mg) as a yellow solid.

Formula: $C_{29}H_{28}N_4O_4$; MW: 496.2; Mass Spectrum (m/e): 497.3 (M+1)

$^1$H NMR (400 MHz; hydrochloride, DMSO-d$^6$, δppm): 12.16 (s, 1H), 10.96 (s, 1H), 9.77 (br. s., 1H), 7.79 (d, J=8.8 1H), 7.56 (m, 3H), 7.45 (m, 2H), 7.26 (s, 1H), 7.17(m, 1H), 6.88 (s, 1H), 6.74 (s, 1H), 5.81(d, J=8.4, 1H), 4.25 (m, 2H), 3.96(m, 2H), 3.76 (s, 3H), 3.04 (m, 2H), 2.83 (m, 6H).

Example 3

Preparation of methyl(Z)-3-((4-fluorophenyl)(1-(2-(4-methylpiperazin-1-yl)acetyl)indol-5-ylamino)methylene)-2-oxoindoline-6-carboxylate (Compound 3) and its hydrochloride

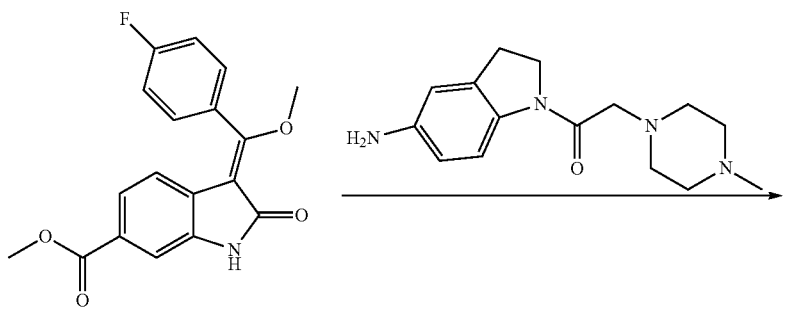

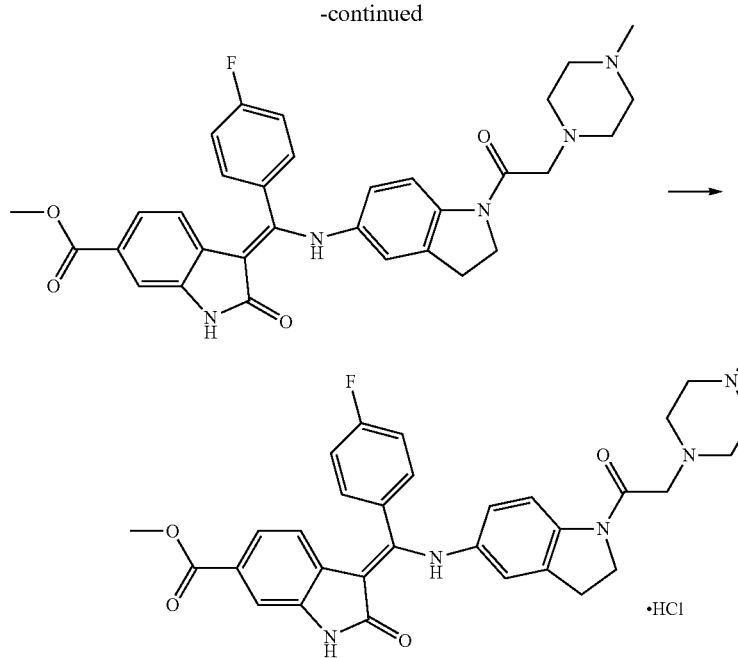
The preparation method was identical to those of Examples 1 and 2, and the yield was 24%.
Formula: $C_{32}H_{32}FN_5O_4$; Mass Spectrum (m/e): 569.8 (M+1)
$^1$H NMR (hydrochloride, DMSO-d$^6$, 400 MHz, δppm): 12.10 (s, 1H), 11.5(br s, 1H), 10.97 (s, 1H), 7.80 (d, 1H), 7.51-7.55 (m, 2H), 7.36-7.42 (m, 3H), 7.22-7.25 (m, 1H), 6.89 (s, 1H), 6.73 (d, 1H), 5.89 (d, 1H), 4.39-4.05 (m, 2H), 3.76 (s, 3H), 3.25-3.27 (m, 10H), 3.04 (t, 2H), 2.79 (s, 3H).
Example 4
Preparation of ethyl(Z)-3-((1-(2-(4-methylpiperazin-1-yl)acetyl)indol-5-ylamino)(phenyl)methylene)-2-oxoindoline-6-carboxylate (Compound 4) and its hydrochloride
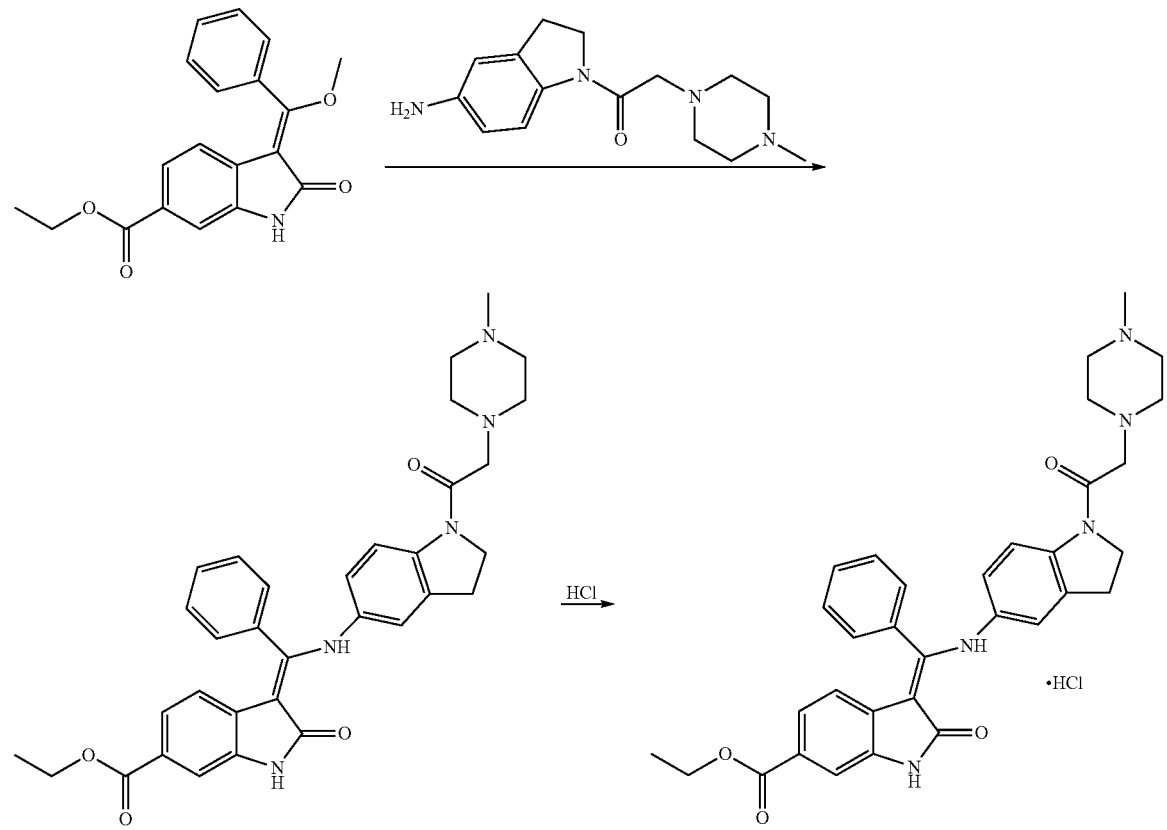

The preparation method was identical to those of Examples 1 and 2, and the yield was 7%.

Formula: $C_{33}H_{35}N_5O_4$; Mass Spectrum (m/e): 565.8 (M+1)

$^1$HNMR (hydrochloride, DMSO-d$^6$, 400 MHz, δppm): 1.25(m, 3H), 2.80(s, 3H), 3.02(m, 2H), 3.45(m, 8H), 4.01(m, 2H), 4.25(m, 4H), 5.80(d, 1H), 6.73(d, 1H), 6.87(s, 1H), 7.16 (m, 1H), 7.44 (m, 3H), 7.55 (m, 3H), 7.77 (d, 1H), 10.94 (s, 1H), 11.5(br s, 1H), 12.13 (s, 1H).

Example 5

Preparation of methyl(Z)-3-((1-(2-(1-methylpiperidine-4-yl)acetyl)indol-5-ylamino)(phenyl)methylene)-2-oxoindoline-6-carboxylate (Compound 5) and its hydrochloride

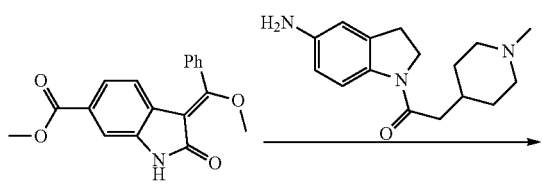

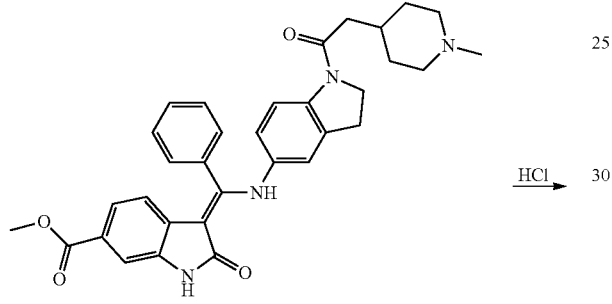

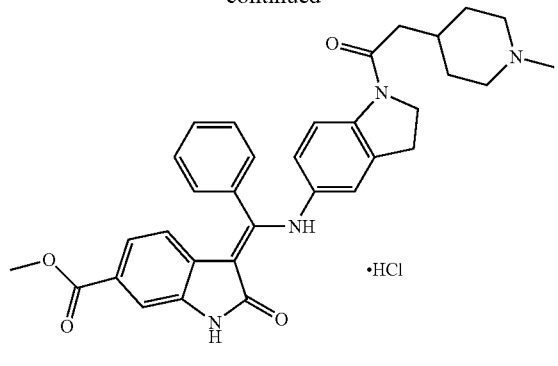

The preparation method was identical to those of Examples 1 and 2, and the yield was 21.7%.

Formula: $C_{33}H_{34}N_4O_4$; Mass Spectrum (m/e): 551.3 (M+1)

$^1$H NMR (hydrochloride, DMSO-d$^6$, 400 MHz, δppm): 12.14 (s, 1H), 10.94 (s, 1H), 10.2(br m, 1H), 7.79 (d, 1H), 7.51-7.66 (m, 3H), 7.40-7.45 (m, 3H), 7.16 (d, 1H), 6.80 (s, 1H), 6.65 (d, 1H), 5.79 (d, 1H), 3.98-4.05 (m, 2H), 3.75 (s, 3H), 2.86-2.97 (m, 4H), 2.67-2.71(m, 4H), 2.34 (d, 2H), 1.84-2.01 (m, 4H), 1.44-1.51 (m, 2H).

Example 6

Preparation of methyl(Z)-3-((1-(4-(dimethylamino)-4-oxobutanoyl)indol-5-ylamino)(phenyl)methylene)-2-oxoindoline-6-carboxylate (Compound 6) and its hydrochloride

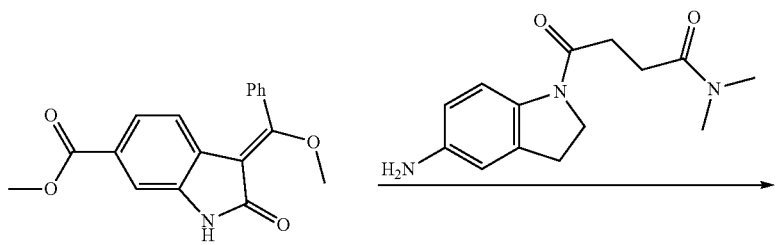

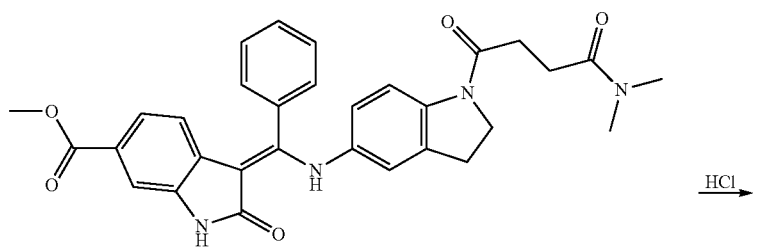

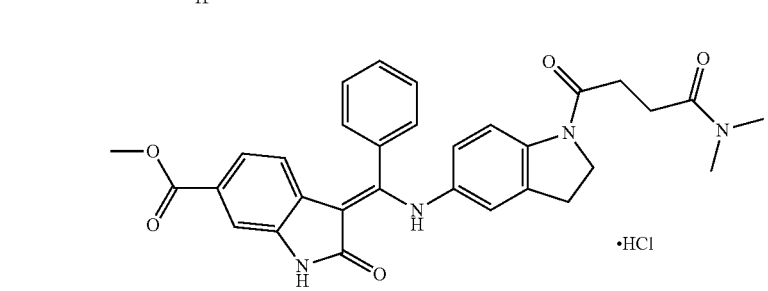

The preparation method was identical to those of Examples 1 and 2, and the yield was 64%.

Formula: $C_{31}H_{30}N_4O_5$; Mass Spectrum (m/e): 539.3 (M+1)

$^1$H NMR (DMSO-d$^6$, 400 MHz, δppm): 12.15 (s, 1H), 10.91 (s, 1H), 7.76 (d, 1H), 7.53-7.55 (m, 3H), 7.40-7.46 (m, 3H), 7.17 (d, 1H), 6.80 (s, 1H), 6.64 (d, 1H), 5.80 (d, 1H), 4.06 (t, 2H), 3.75 (s, 3H), 2.97 (m, 5H), 2.78 (s, 3H), 2.56(s, 4H).

Example 7

Preparation of methyl(Z)-3-((1-(2-morpholinylacetyl)indol-5-ylamino)(phenyl)methylene)-2-oxoindoline-6-carboxylate (Compound 7) and its hydrochloride

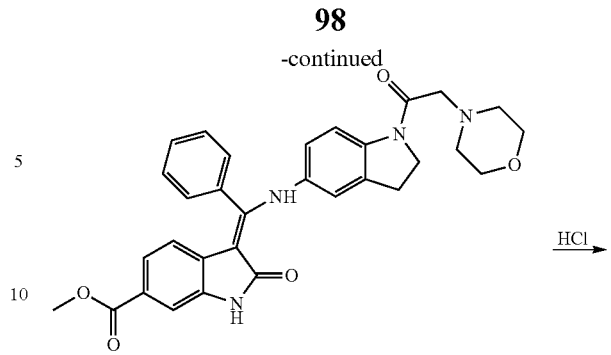

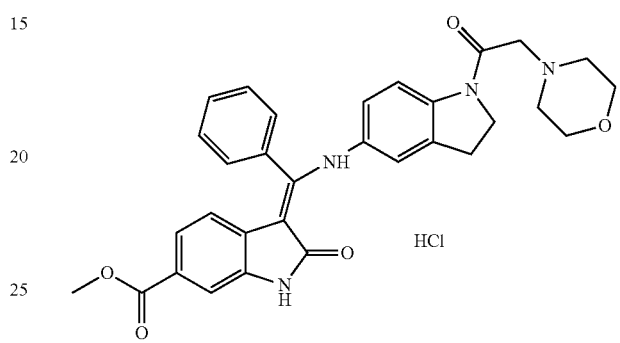

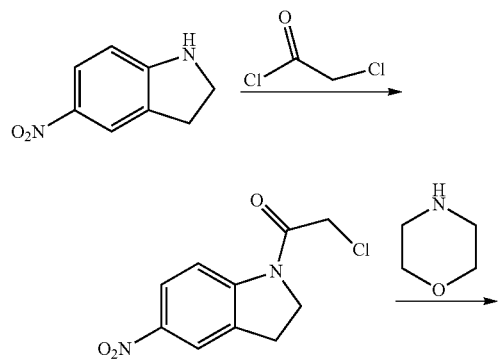

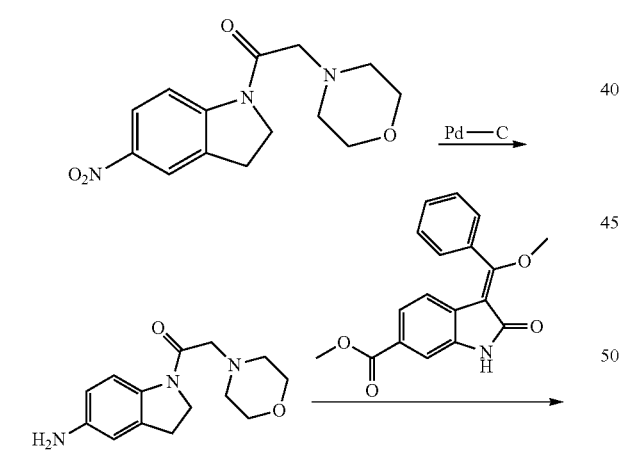

The title compound was synthesized with reference to Examples 1 and 2 in a yield of 57.4%.

Formula: $C_{31}H_{30}N_4O_5$; Mass Spectrum (m/e): 538.8 (M+1)

$^1$H NMR (hydrochloride, DMSO-d$^6$, 400 MHz, δppm): 3.15(s, 2H), 3.20(t, 4H), 3.75(s, 3H), 3.80(t, 2H), 4.00(t, 4H), 4.35(m, 2H), 5.80(d, 1H), 6.75(d, 1H), 6.87(s, 1H), 7.18(d, 1H), 7.44 (s, 1H), 7.46 (d, 2H), 7.59 (m, 3H), 7.79 (d, 1H), 10.49 (s, 1H), 10.97 (s, 1H), 12.16 (s, 1H).

Example 8

Preparation of methyl(Z)-3-((1-(2-(4-hydroxypiperidinyl)acetyl)indol-5-ylamino)(phenyl)methylene)-2-oxoindoline-6-carboxylate (Compound 8) and its hydrochloride

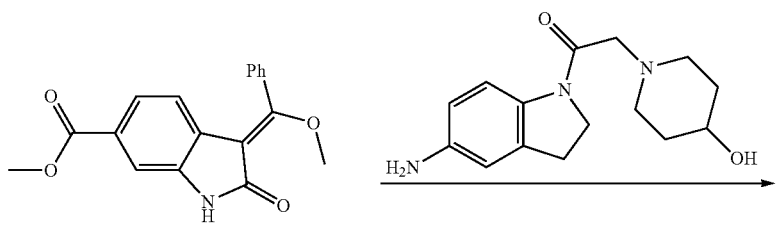

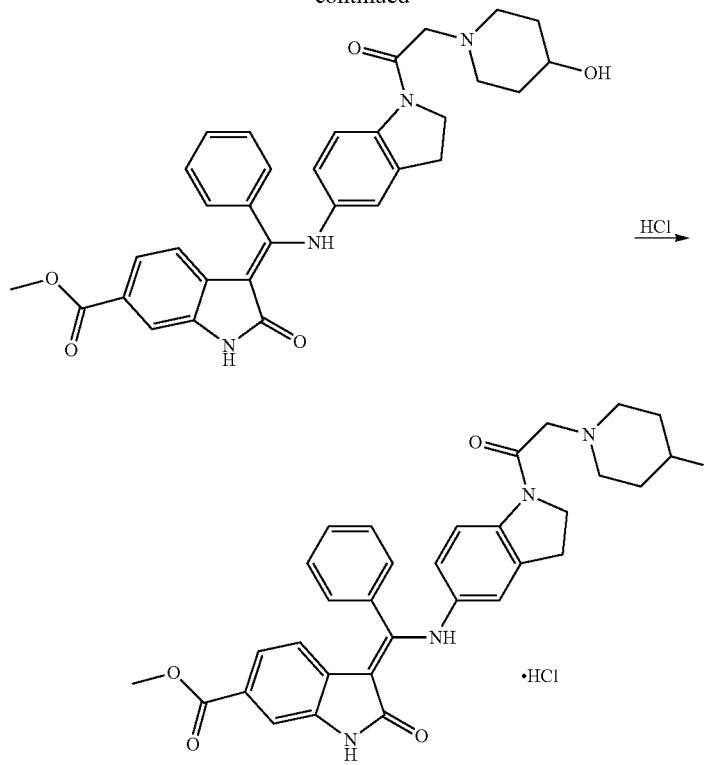

The title compound was synthesized with reference to Examples 1 and 2 in a yield of 56%.

Formula: $C_{32}H_{32}N_4O_5$; Mass Spectrum (m/e): 553.3 (M+1)

$^1$H NMR (hydrochloride, DMSO-d$^6$, 400 MHz, δppm): 1.72(m, 2H), 1.94(m, 2H), 3.03(m, 4H), 3.25(m, 2H), 3.45 (m, 1H), 3.75(s, 3H), 3.99(s, 2H), 4.29(m, 2H), 5.05(d, 1H), 5.80(d, 1H), 6.75(d, 1H), 6.87(s, 1H), 7.18(d, 1H), 7.44 (s, 1H), 7.46 (d, 2H), 7.59 (m, 3H), 7.79 (d, 1H), 10.49 (s, 1H), 10.97 (s, 1H), 12.16 (s, 1H).

Example 9

Preparation of methyl(Z)-3-((4-fluorophenyl)(1-(2-morpholinylacetyl)indolin-5-ylamino)methylene)-2-oxoindoline-6-carboxylate (Compound 9) and its hydrochloride

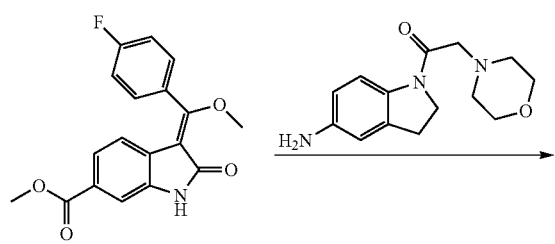

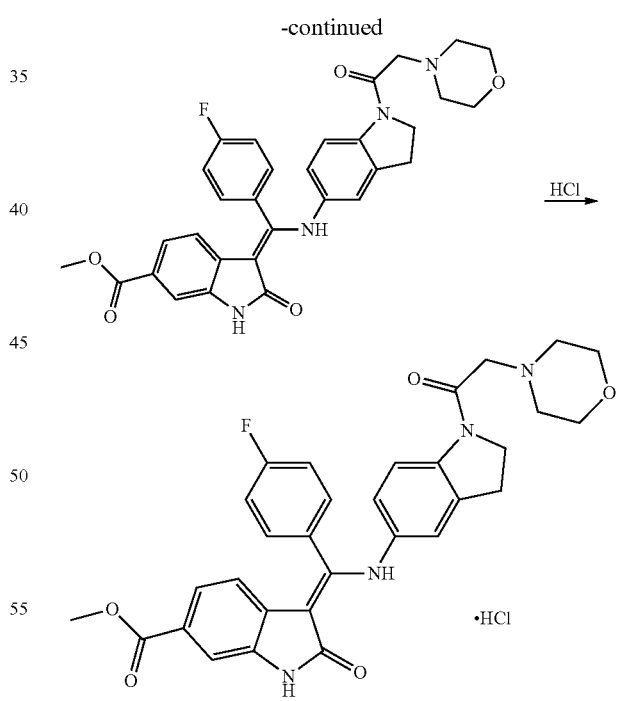

Methyl(Z)-3-((4-fluorophenyl)(methoxy)methylene)-2-oxoindoline-6-carboxylate (500 mg, 1.53 mmol), potassium hydroxide (43 mg, 0.76 mmol) and 1-(5-aminoindolin-1-yl)-2-morpholineethanone (400 mg, 1.53 mmol) were dissolved in methanol (10 mL). The resulting mixture was reacted at room temperature for 10 hours. The reaction mixture was cooled to room temperature, and water was added. The resulting mixture was extracted with methylene chloride.

The organic phase was dried, concentrated, and subjected to a preparation separation to obtain a product (100 mg) in a yield of 12%.

Formula: $C_{31}H_{29}FN_4O_5$; MW: 556; Mass Spectrum (m/e): 556.5 (M+1).

$^1$H NMR (400 MHz, hydrochloride, DMSO-d$^6$, δppm): 12.10 (s, 1H), 10.97 (s, 1H), 10.45(br s, 1H), 7.81 (d, 1H), 7.51-7.55 (m, 2H), 7.39 (t, 3H), 7.22 (d, 1H), 6.90 (s, 1H), 6.75 (d, 1H), 5.89 (d, 1H), 4.37 (s, 2H), 3.93-4.02 (m, 5H), 3.76-3.83 (m, 5H), 3.15-3.19 (m, 3H), 3.07 (t, 2H).

Example 10

Preparation of ethyl(Z)-3-((1-(2-morpholinylacetyl)indolin-5-ylamino)(phenyl)methylene)-2-oxoindoline-6-carboxylate (Compound 10) and its hydrochloride

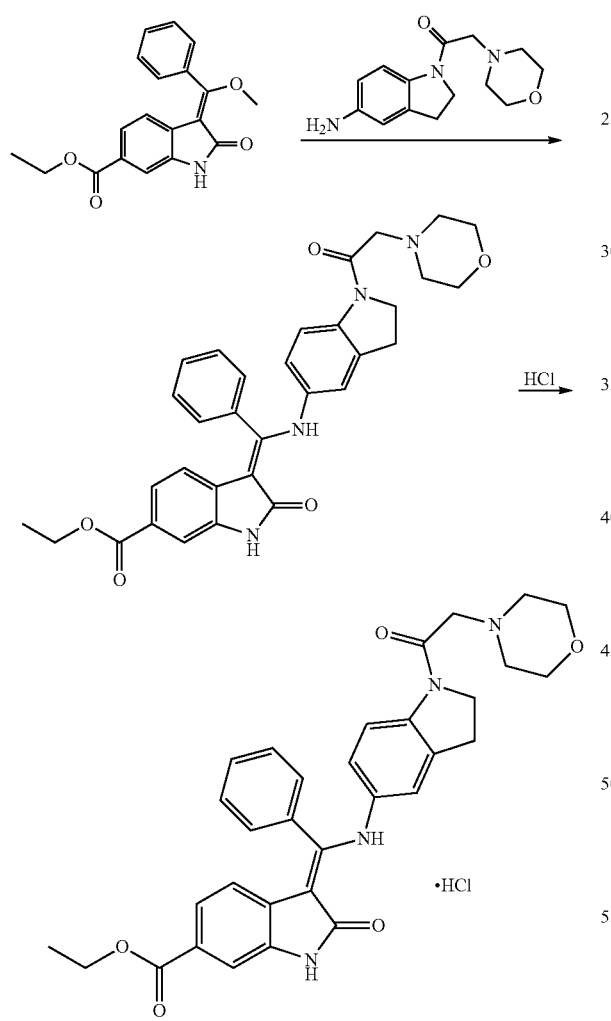

The title compound was synthesized with reference to Example 1 and Example 2 in a yield of 33%.

Formula: $C_{32}H_{32}N_4O_5$; MW: 552; Mass Spectrum (m/e): 552.7 (M+1).

$^1$H NMR (400 MHz, hydrochloride, DMSO-d$^6$, δppm): 12.11 (s, 1H), 10.93 (s, 1H), 10.25(br s, 1H), 7.78 (d, 1H), 7.51-7.57 (m, 3H), 7.41-7.45(m, 3H), 7.17(d, 1H), 6.87 (s, 1H), 6.72-6.75 (m, 1H), 5.79 (d, 1H), 4.35 (s, 2H), 4.17-4.23 (m, 2H), 3.96-4.00 (m, 2H), 3.76-3.79 (br, 6H), 3.14-3.19 (br, 2H), 3.03 (t, 2H), 1.24 (t, 3H).

Example 11

Preparation of methyl(Z)-3-((1-(2-(2,6-dimethylmorpholine)acetyl)indolin-5-ylamino)(phenyl)methylene)-2-oxoindoline-6-carboxylate (Compound 11) and its hydrochloride

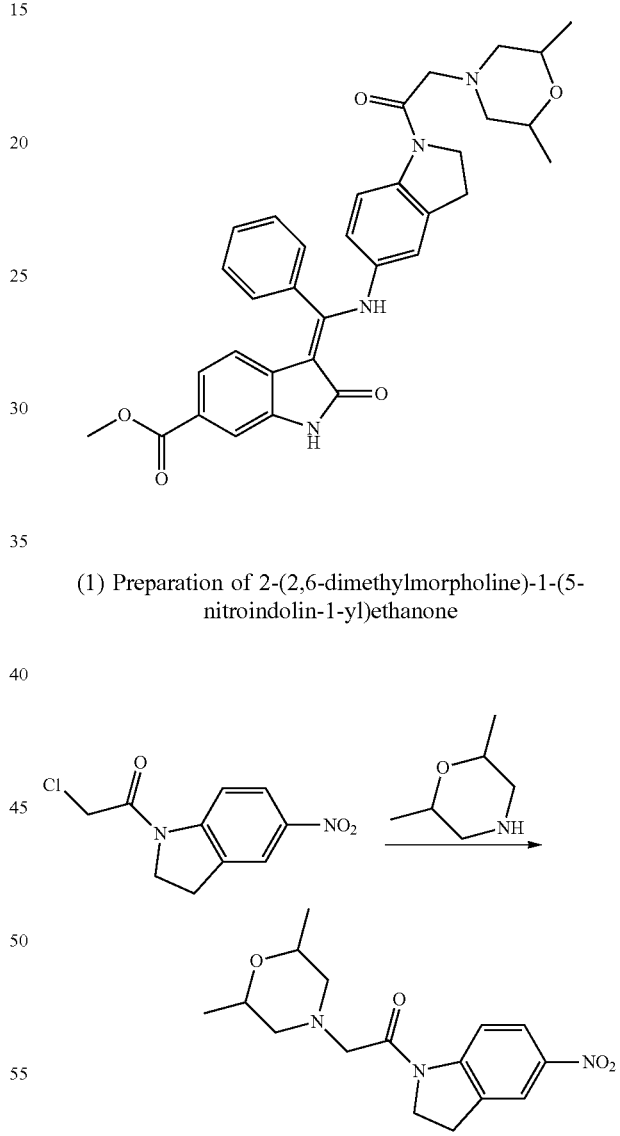

(1) Preparation of 2-(2,6-dimethylmorpholine)-1-(5-nitroindolin-1-yl)ethanone 2-chloro-N-methyl-N-(4-nitrophenyl)acetamide (1.0 g, 4.2 mmol), 2,6-dimethylmorpholine (1.15 g, 10 mmol) and triethylamine (1 mL, 7 mmol) were dissolved in DCM (50 mL). The resulting mixture was reacted under stirring at room temperature for 1 hour. The reaction product was washed with water, extracted with methylene chloride, dried, concentrated, and directly used in the next reaction step.

(2) Preparation of 1-(5-aminoindolin-1-yl)-2-(2,6-dimethylmorpholine)ethanone

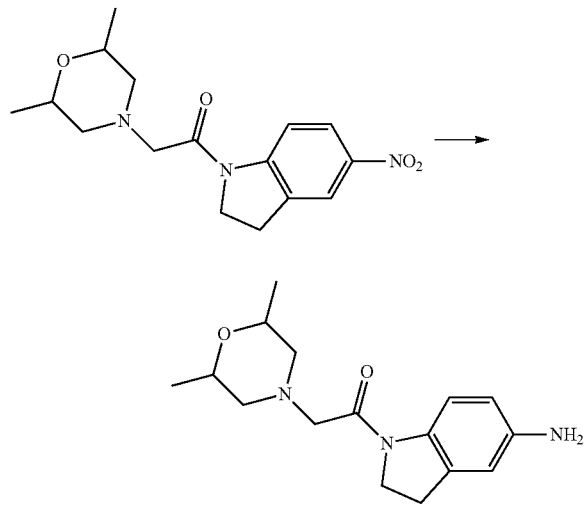

The above crude 2-(2,6-dimethylmorpholine)-1-(5-nitroindolin-1-yl)ethanone was dissolved in methanol (50 mL). Pd/C (200 mg, 10%) was added. The resulting mixture was subjected to a hydrogenation reduction for 2 hours, and filtered. The filtrate was concentrated and directly used in the next step.

(3) Preparation of methyl(Z)-3-((1-(2-(2,6-dimethylmorpholine)acetyl)indolin-5-ylamino)(phenyl)methylene)-2-oxoindoline-6-carboxylate and its hydrochloride

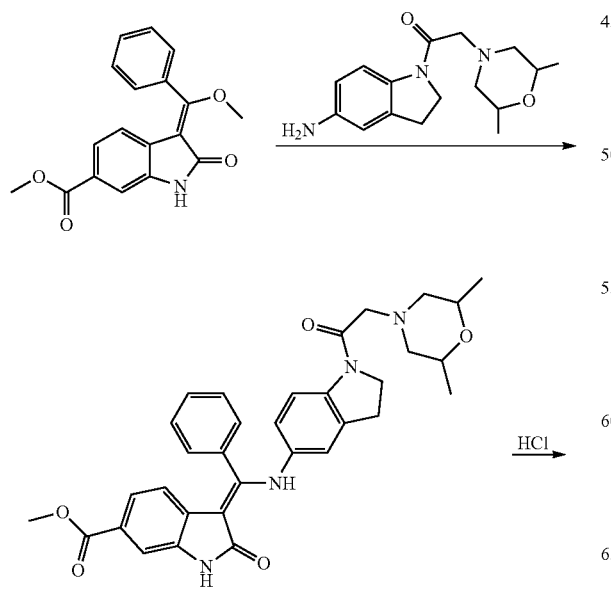

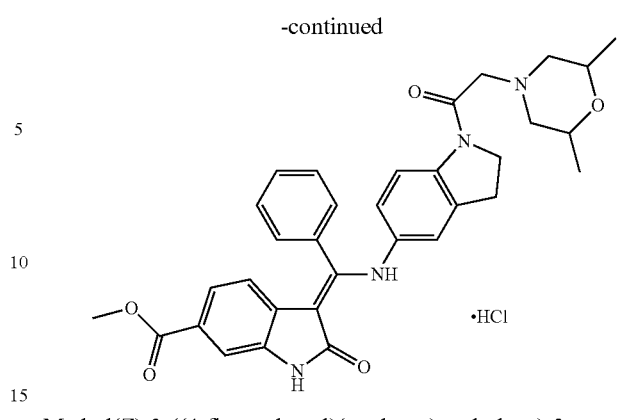

Methyl(Z)-3-((4-fluorophenyl)(methoxy)methylene)-2-oxoindoline-6-carboxylate (1.0 g, 3.2 mmol), potassium hydroxide (57 mg, 1 mmol) and the product from the previous step, 1-(5-aminoindolin-1-yl)-2-(2,6-dimethylmorpholine)ethanone were dissolved in methanol (50 mL). The resulting mixture was reacted at 60° C. for 2 hours. After cooling, water was added to the cooled mixture. The resulting mixture was extracted with methylene chloride, and the resulting organic phase was dried, concentrated, and purified with a silica gel column chromatography (methylene chloride:methanol=100:1) to obtain a product. The resulting product was dissolved in methylene chloride (20 mL). To the resulting solution was added hydrochloric acid (1 mL, 2N). After concentration, the target hydrochloride (130 mg) was obtained in a yield of 7.2%.

Formula: $C_{33}H_{34}N_4O_5$; MW: 566; Mass Spectrum (m/e): 567.1 $(M+H)^+$.

$^1$HNMR(400 MHz, DMSO, hydrochloride, δppm): 12.13 (s, 1H), 10.95(s 1H), 10.50(s, 1H), 7.79(s, 1H), 7.51(m, 6H), 7.18(s, 1H), 6.89(s, 1H), 6.74(s, 1H), 5.81(s, 1H), 4.29(s, 2H), 3.98(s, 4H), 3.76(m, 3H), 3.16(s, 2H), 3.06(t, 2H), 2.74(d, 2H), 1.09(d, 6H).

Example 12

Preparation of methyl(Z)-3-((1-(2-(2-pyrrolidon-1-yl)acetyl)indolin-5-ylamino)(phenyl)methylene)-2-oxoindoline-6-carboxylate (Compound 12) and its hydrochloride

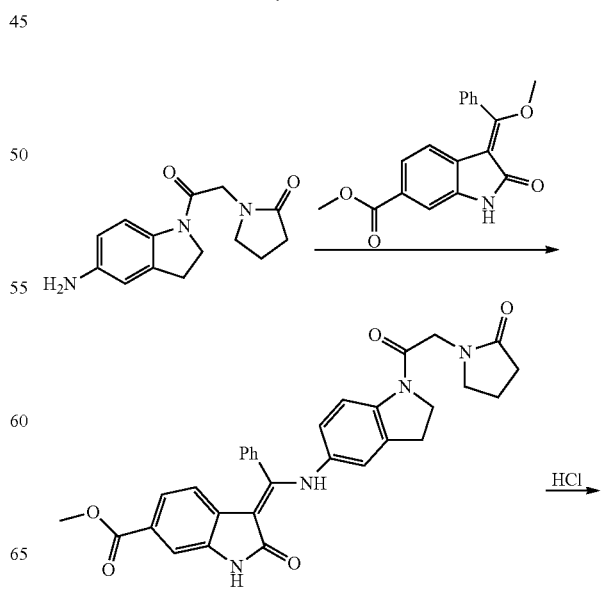

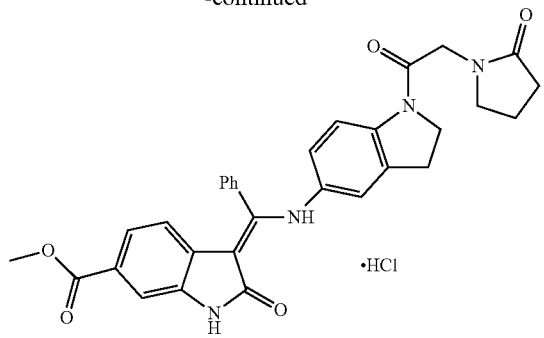

The title compound was synthesized with reference to Example 11 in a yield of 43%.

Formula: $C_{31}H_{28}N_4O_5$; MW: 536; Mass Spectrum (m/e): 537 (M+1).

$^1$H NMR (400 MHz, DMSO-d$^6$, δppm): 12.15 (s, 1H), 10.93(s, 1H), 7.73 (d, 1H), 7.55 (m, 3H), 7.43-7.40 (m, 2H), 7.41 (d, 1H), 7.17 (d, 1H), 6.83 (d, 1H), 6.67 (d, 1H), 5.81 (d, 1H), 4.10 (s, 2H), 4.04(t, 2H), 3.75(s, 3H), 3.00 (t, 2H), 2.24 (m, 2H), 1.95(m, 2H), 1.22(m, 2H).

Example 13

Preparation of methyl(Z)-3-((1-(2-(1H-1,2,4-triazol-1-yl)acetyl)indolin-5-ylamino)(phenyl)methylene)-2-oxoindoline-6-carboxylate (Compound 13) and its hydrochloride

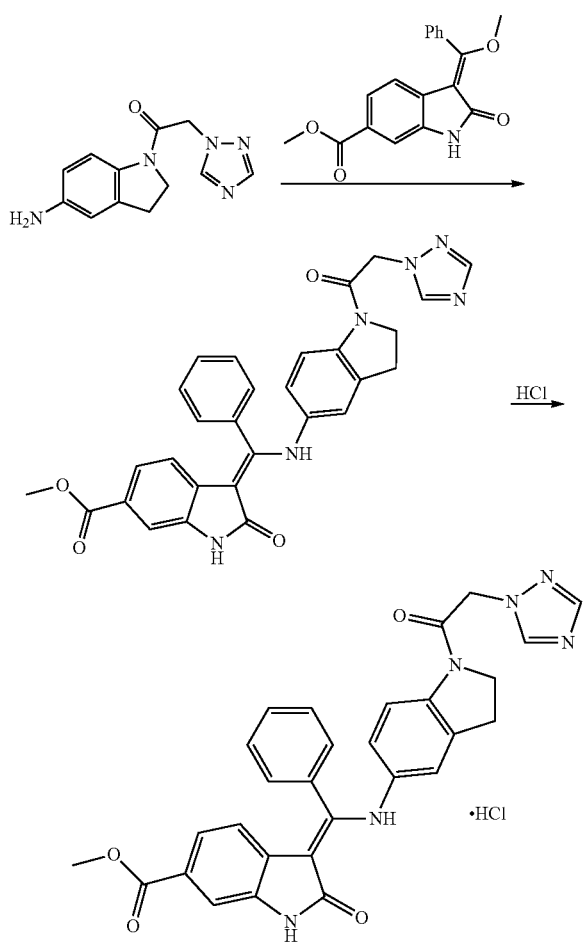

The title compound was synthesized with reference to Example 11 in a yield of 8%.

Formula: $C_{29}H_{24}N_6O_4$; MW: 520; Mass Spectrum (m/e): 521 (M+1).

$^1$H NMR (400 MHz, hydrochloride, DMSO-d$^6$, δppm): 12.17(s, 1H), 10.93(s, 1H), 7.80(d, 1H), 7.50(m, 6H), 7.19 (m, 1H), 6.83(s, 1H), 6.69(m, 1H), 5.83(d, 1H), 4.09(s, 2H), 3.92(t, 3H), 3.76(s, 3H), 2.96(t, 2H) (All of active hydrogens were not shown).

Example 14

Preparation of methyl(Z)-3-((1-(2-(1H-pyrazol-1-yl)acetyl)indolin-5-ylamino)(phenyl)methylene)-2-oxoindoline-6-carboxylate (Compound 14) and its hydrochloride

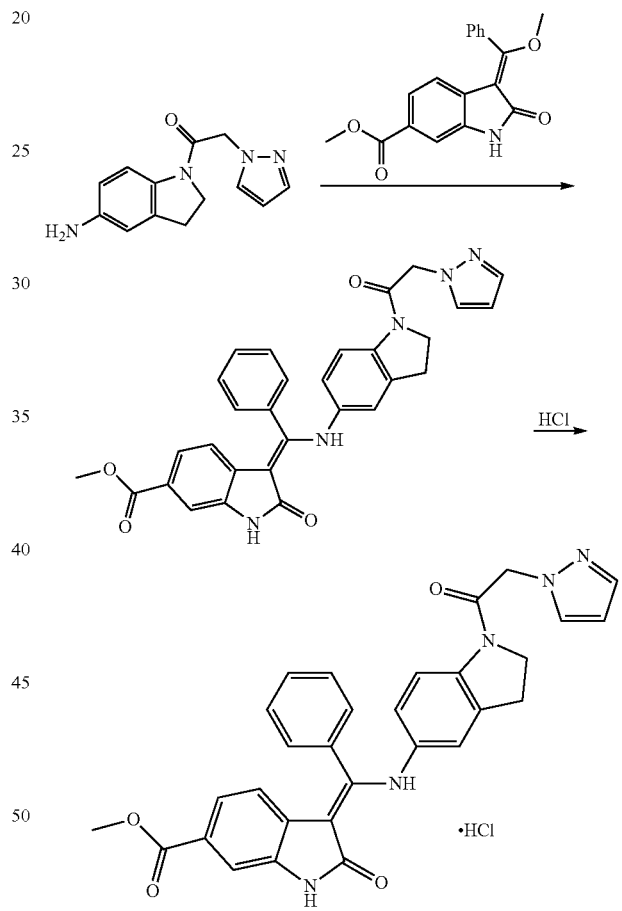

The title compound was synthesized with reference to Example 11 in a yield of 65%.

Formula: $C_{30}H_{25}N_5O_4$; MW: 519; Mass Spectrum (m/e): 520 (M+1).

$^1$H NMR (400 MHz, DMSO-d$^6$, δppm): 12.09 (s, 1H), 10.93 (s, 1H), 7.69 (d, 1H), 7.64 (d, 1H), 7.52-7.54 (m, 3H), 7.42 (d, 4H), 7.14-7.18 (m, 1H), 6.83 (s, 1H), 6.65 (d, 1H), 6.26 (t, 1H), 5.80 (d, 1H), 5.14 (s, 2H), 4.09 (t, 2H), 3.74 (s, 3H), 3.01 (t, 2H).

The following compounds were prepared according to the methods similar to those for preparing the above compounds:

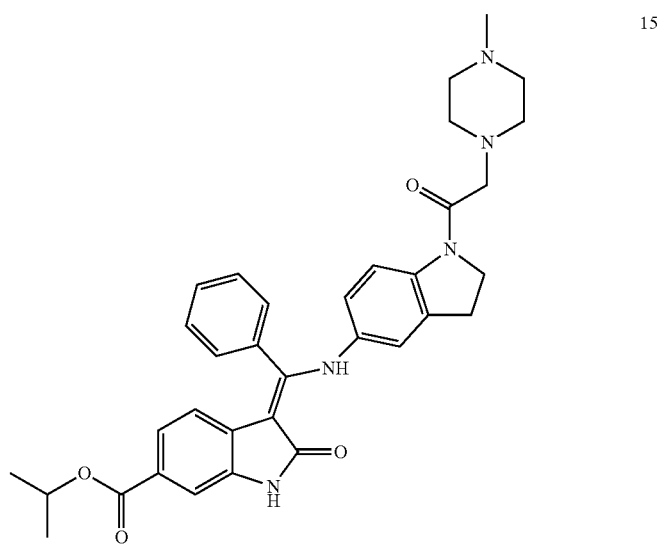
15
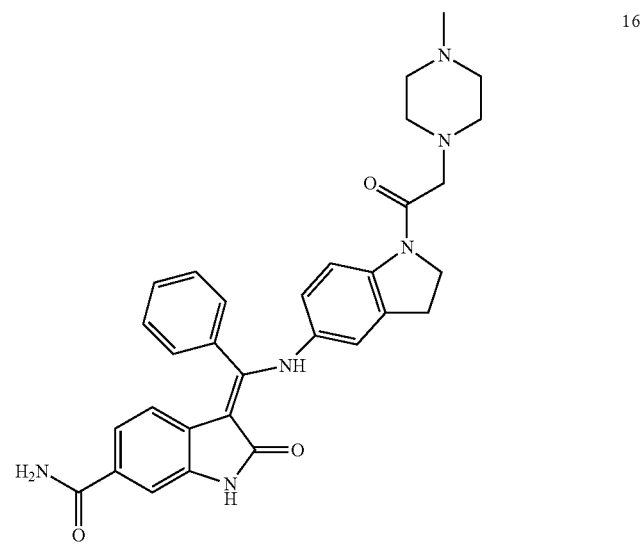
16
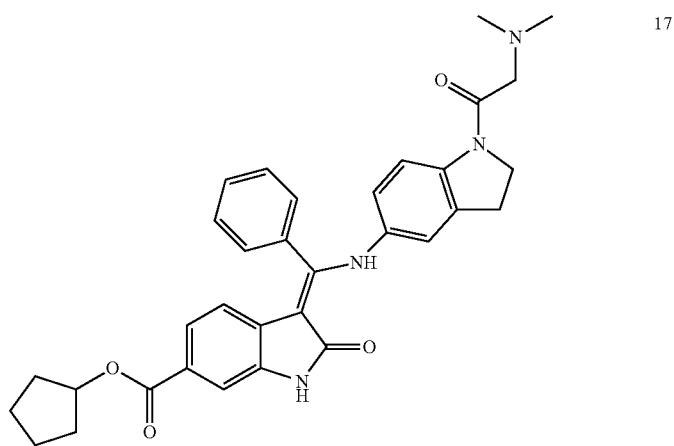
17

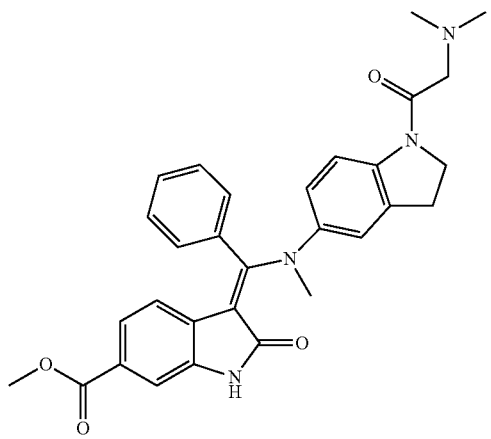
18
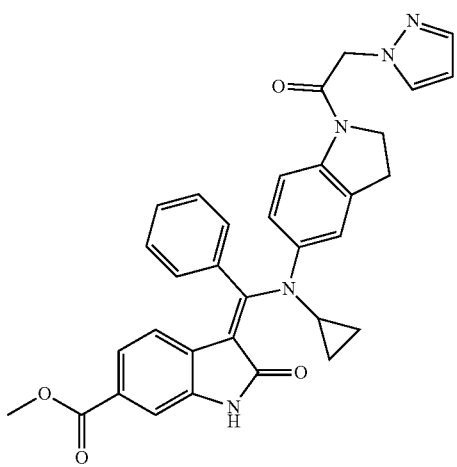 [SMILES: COC(=O)c1ccc2c(c1)NC(=O)/C2=C(/c1ccccc1)N(c1ccc2c(c1)CCN2C(=O)Cn1cccn1)C1CC1]
19
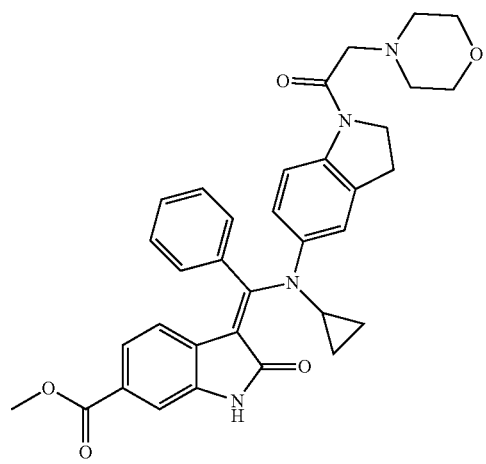 [SMILES: COC(=O)c1ccc2c(c1)NC(=O)/C2=C(/c1ccccc1)N(c1ccc2c(c1)CCN2C(=O)CN1CCOCC1)C1CC1]
20

-continued
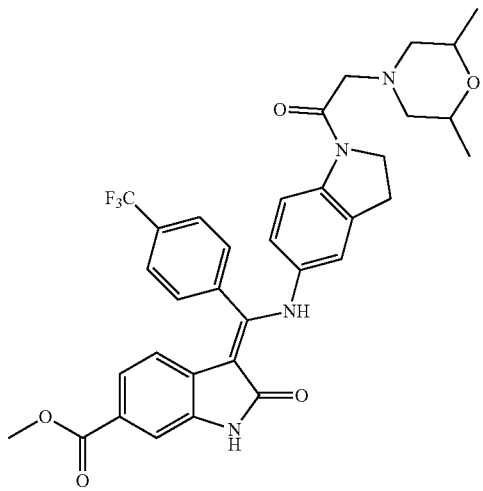
21
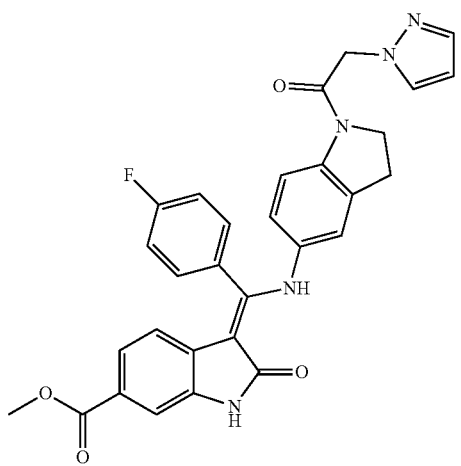 [SMILES: COC(=O)c1ccc2c(c1)NC(=O)/C2=C(\Nc1ccc2c(c1)CCN2C(=O)Cn1cccn1)c1ccc(F)cc1]
22
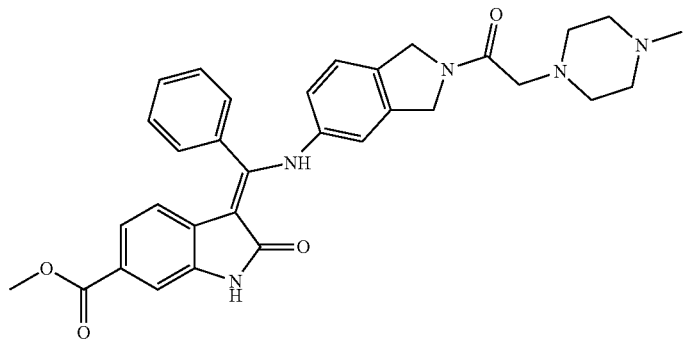
23
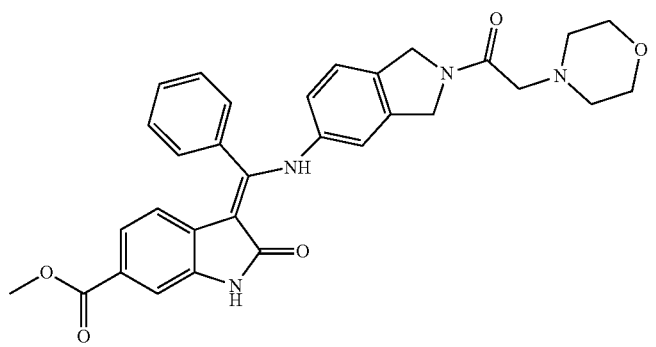
24

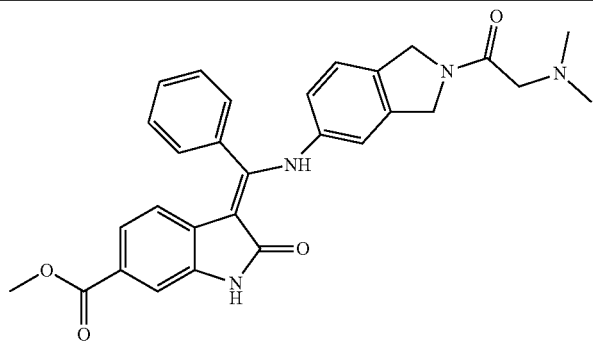
25
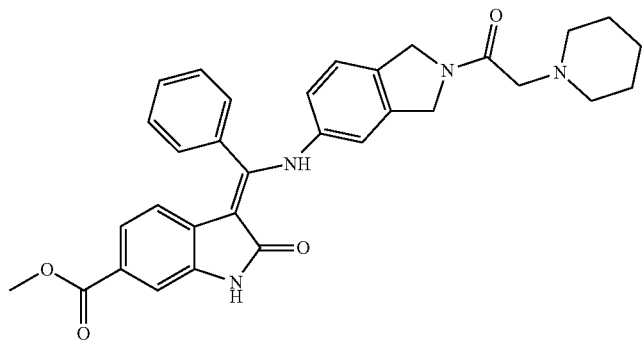 [SMILES: COC(=O)c1ccc2c(c1)NC(=O)/C2=C(\Nc1ccc2c(c1)CN(C(=O)CN1CCCCC1)C2)c1ccccc1]
26
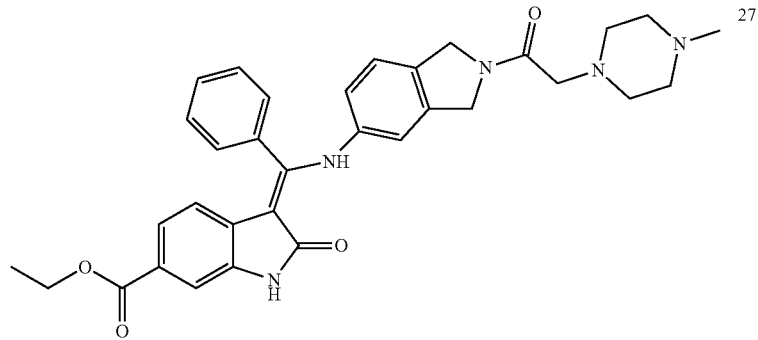
27
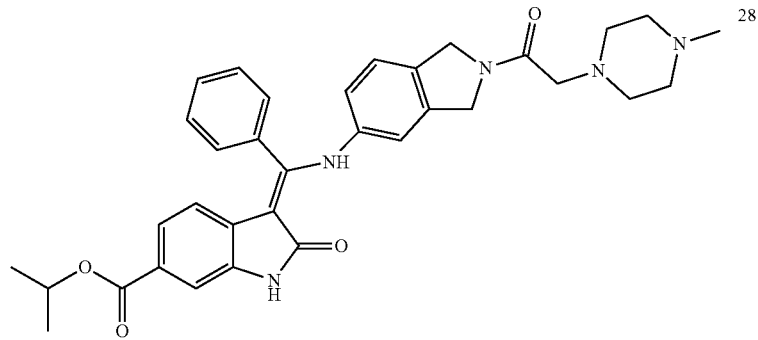
28

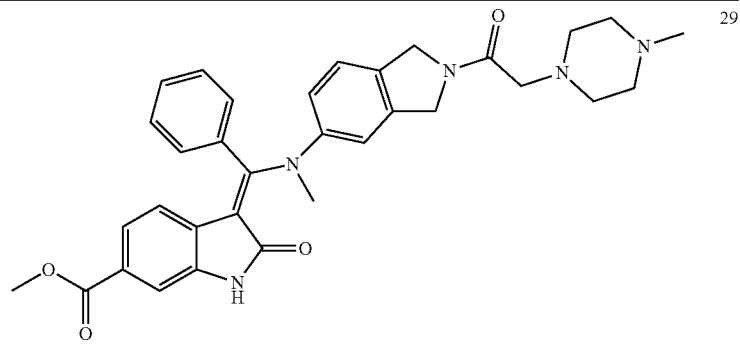
29
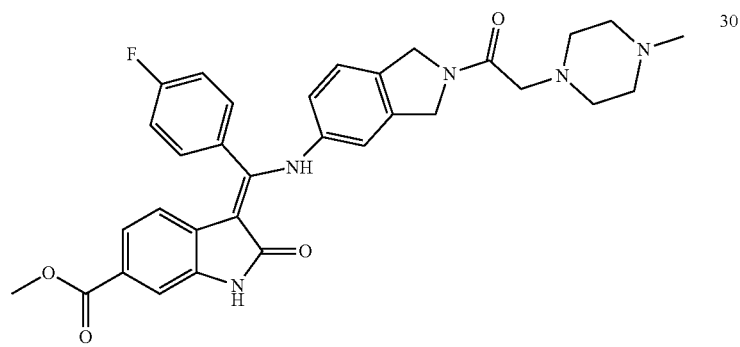
30
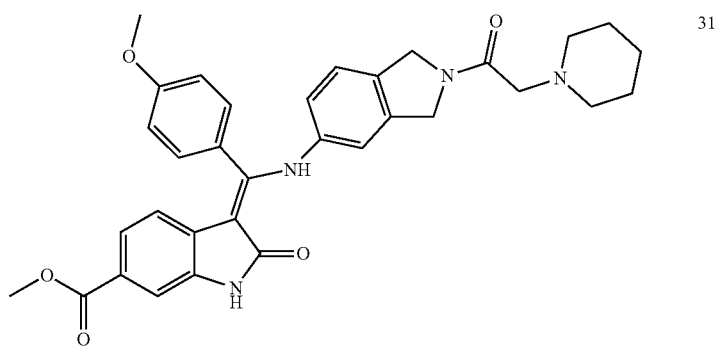
31
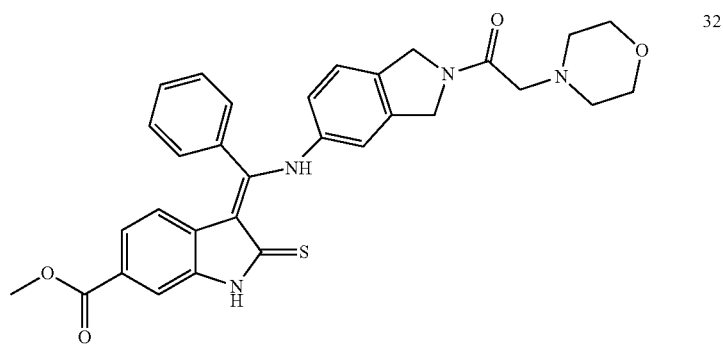
32

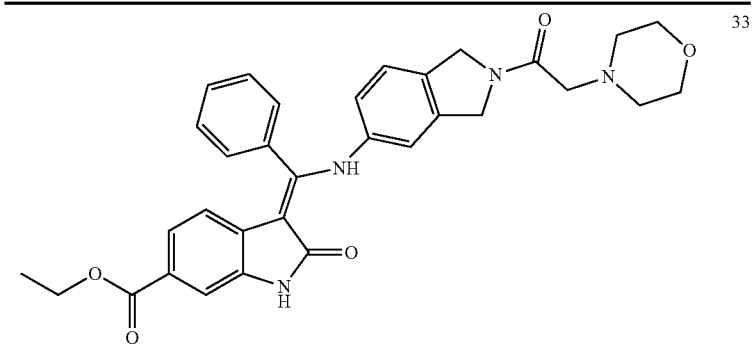
33
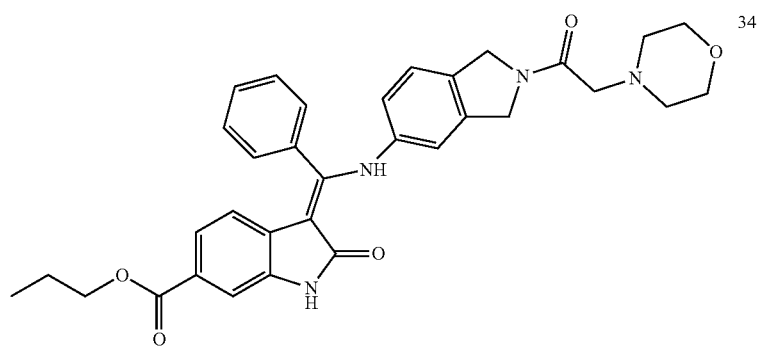
34
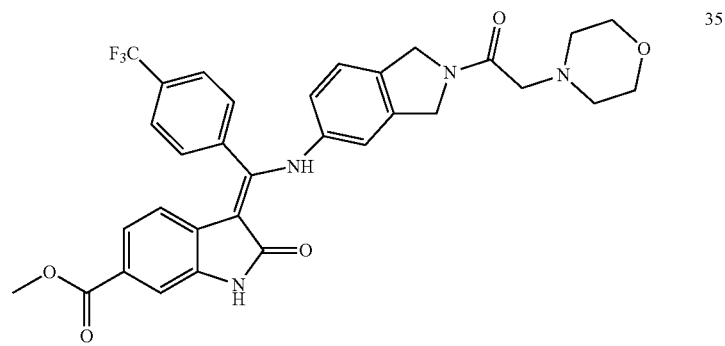
35
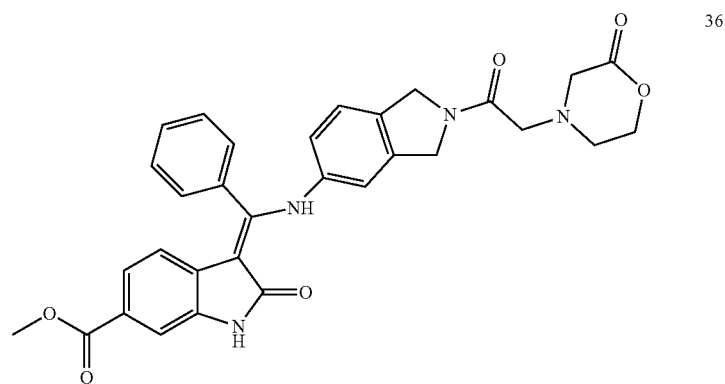
36

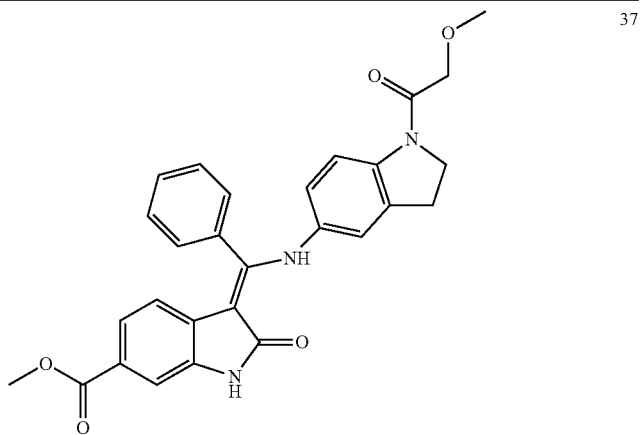
37
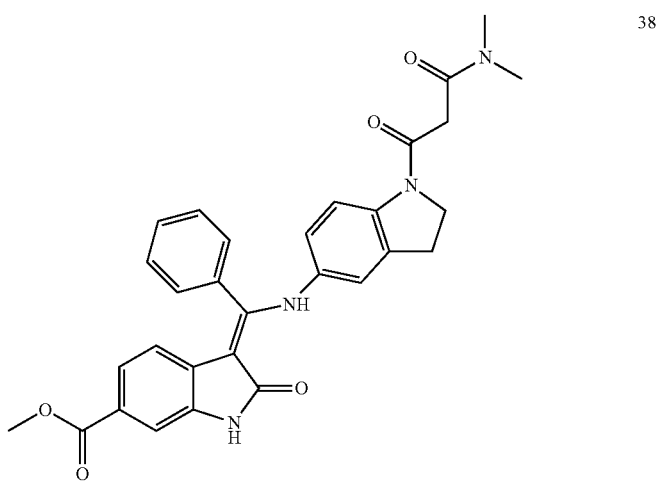
38
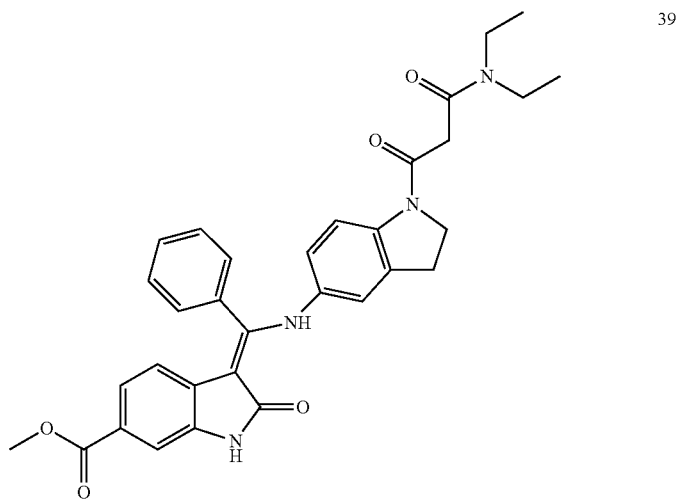
39

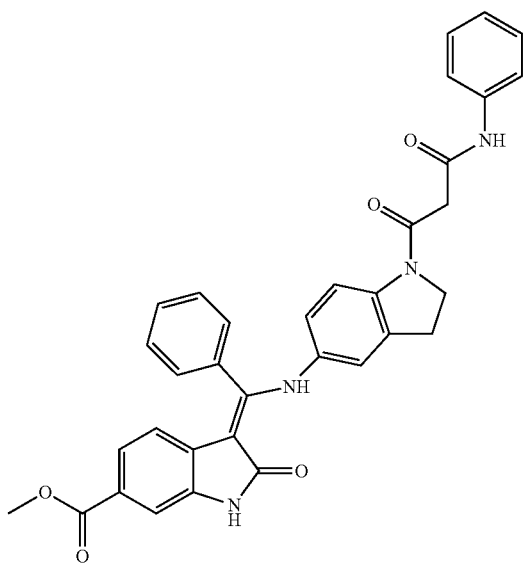 [SMILES: COC(=O)c1ccc2c(c1)NC(=O)/C2=C(\Nc1ccc2c(c1)CCN2C(=O)CC(=O)Nc1ccccc1)c1ccccc1]
40
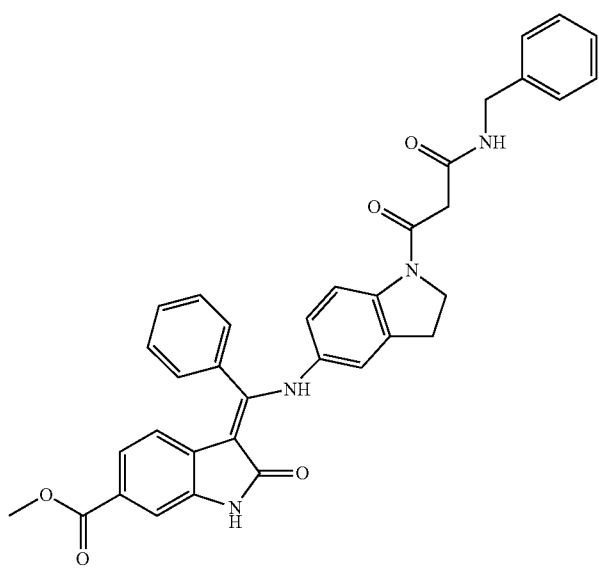 [SMILES: COC(=O)c1ccc2c(c1)NC(=O)/C2=C(\Nc1ccc2c(c1)CCN2C(=O)CC(=O)NCc1ccccc1)c1ccccc1]
41
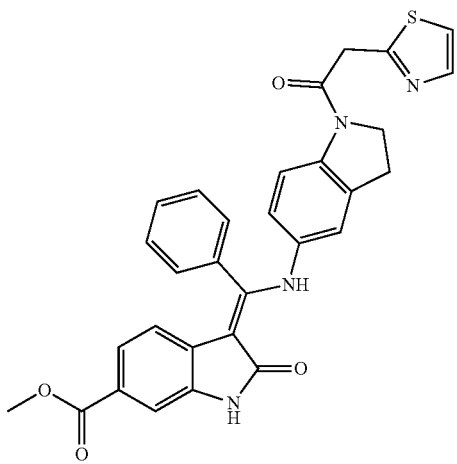
42

| | |
|---|---|
| 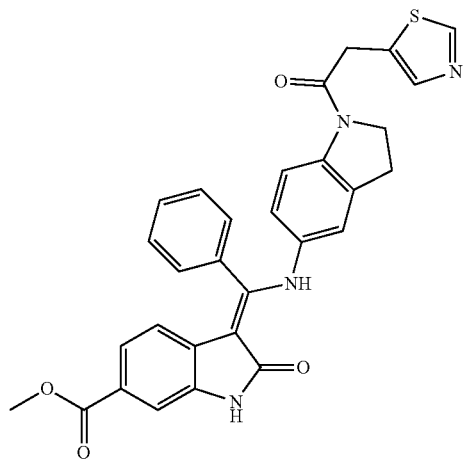 [SMILES: COC(=O)c1ccc2c(c1)NC(=O)/C2=C(\Nc1ccc2c(c1)CCN2C(=O)Cc1cncs1)c1ccccc1] | 43 |
| 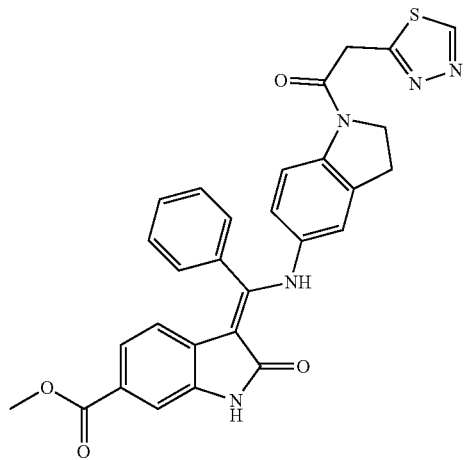 [SMILES: COC(=O)c1ccc2c(c1)NC(=O)/C2=C(\Nc1ccc2c(c1)CCN2C(=O)Cc1nncs1)c1ccccc1] | 44 |
| 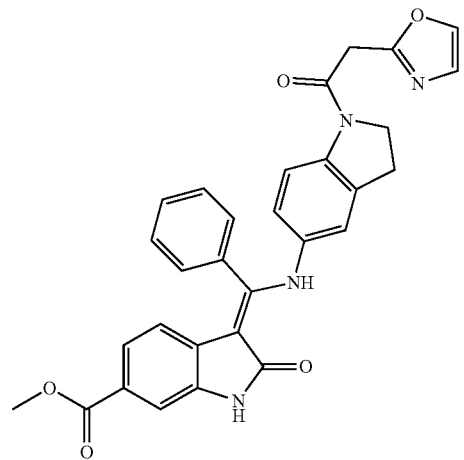 | 45 |

-continued
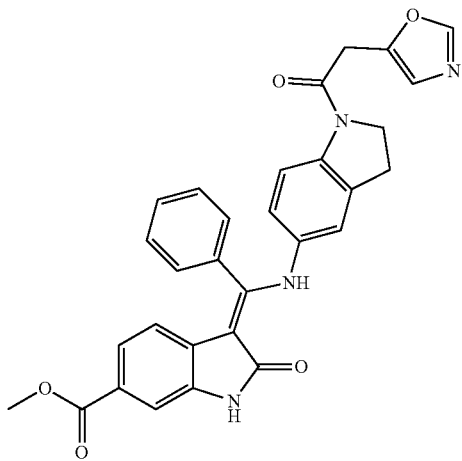
46
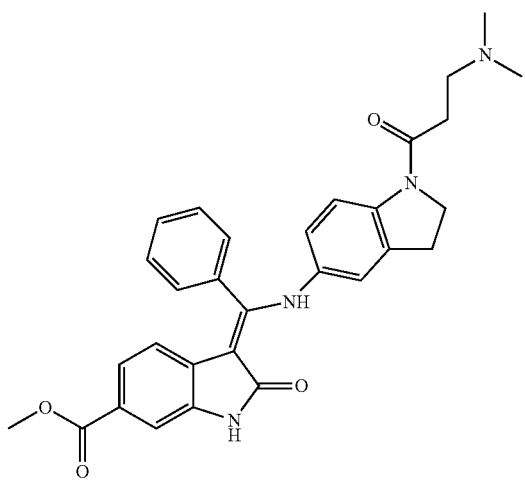
47
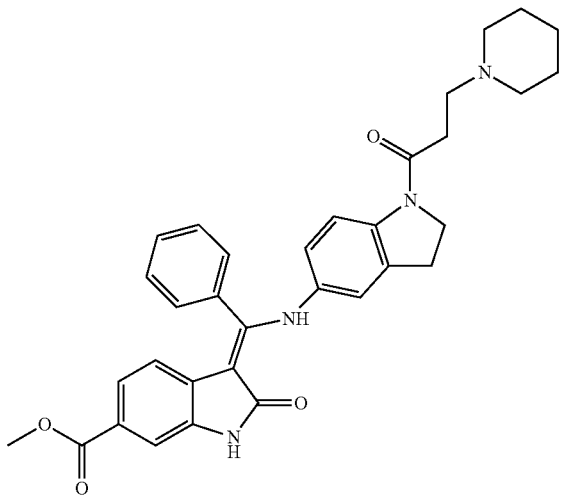 [SMILES: COC(=O)c1ccc2c(c1)NC(=O)/C2=C(\Nc1ccc2c(c1)CCN2C(=O)CCN1CCCCC1)c1ccccc1]
48

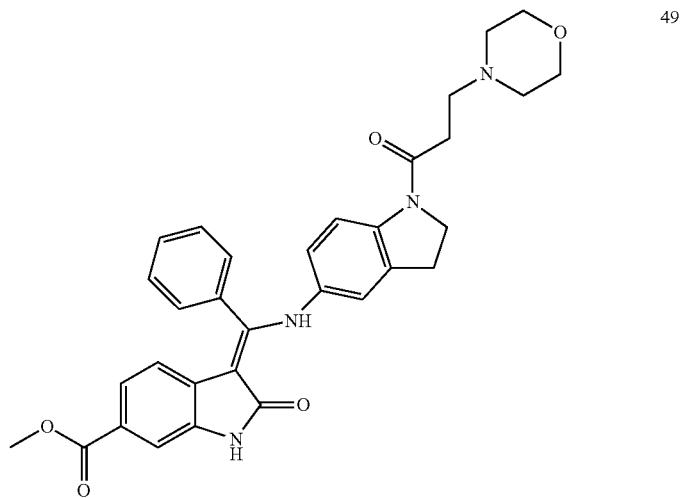
49
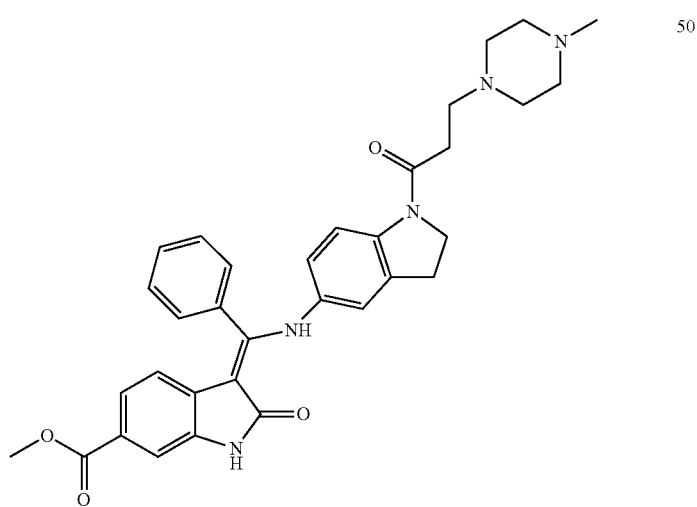
50
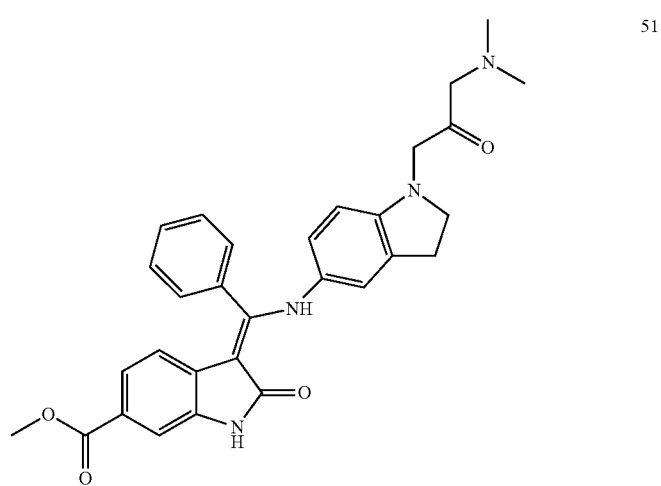
51

-continued
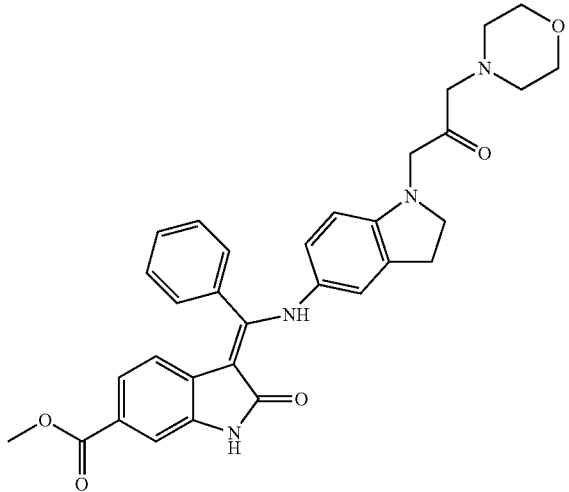 [SMILES: COC(=O)c1ccc2c(c1)NC(=O)/C2=C(\Nc1ccc2c(c1)CCN2CC(=O)CN1CCOCC1)c1ccccc1]
52
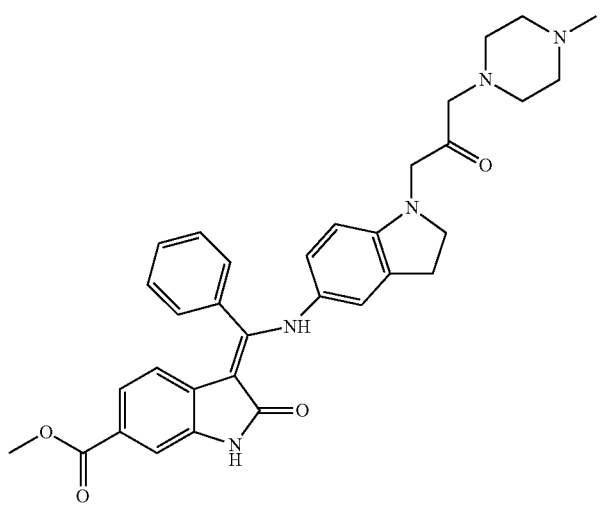
53
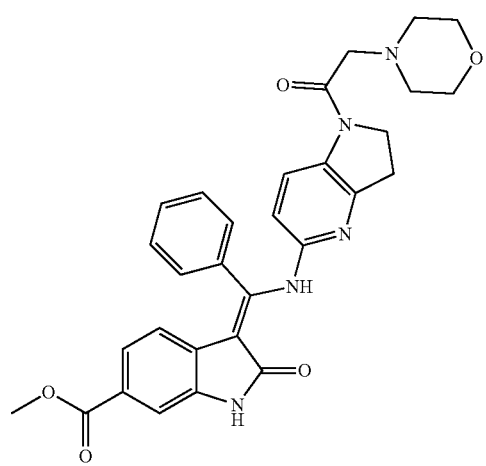 [SMILES: COC(=O)c1ccc2c(c1)NC(=O)/C2=C(\Nc1ccc2c(n1)CCN2C(=O)CN1CCOCC1)c1ccccc1]
54

-continued
55
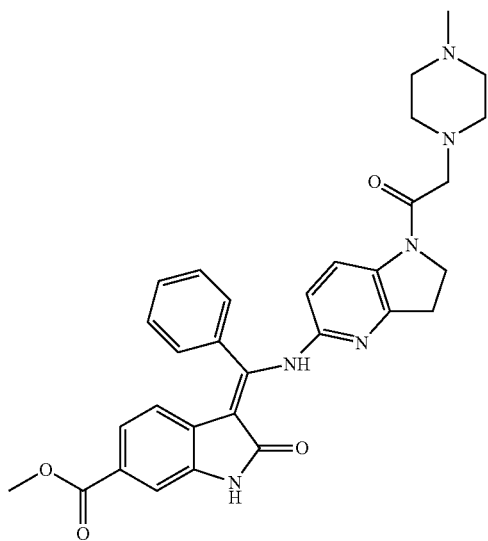
56
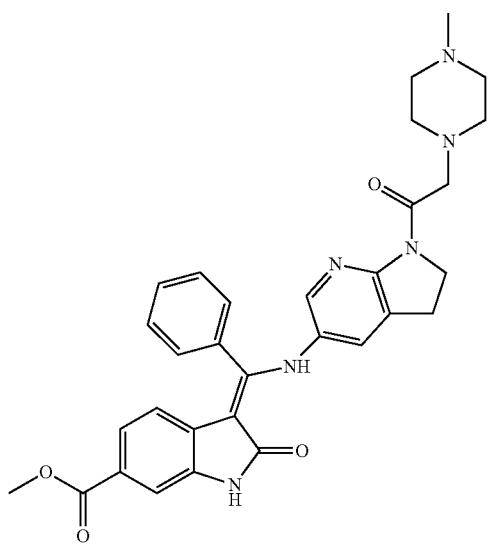
57
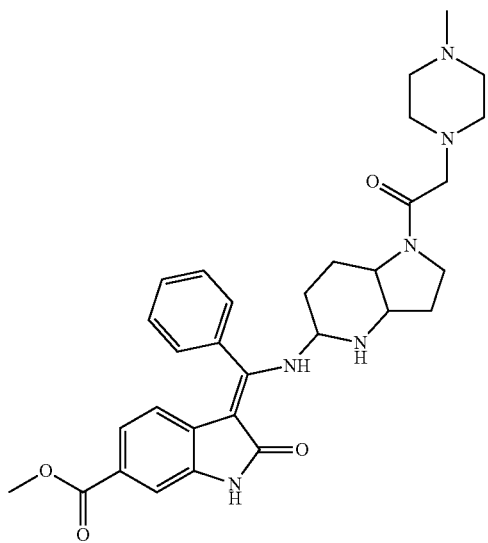 [SMILES: COC(=O)c1ccc2c(c1)NC(=O)/C2=C(\NC1CCC2C(CCN2C(=O)CN2CCN(C)CC2)N1)c1ccccc1]

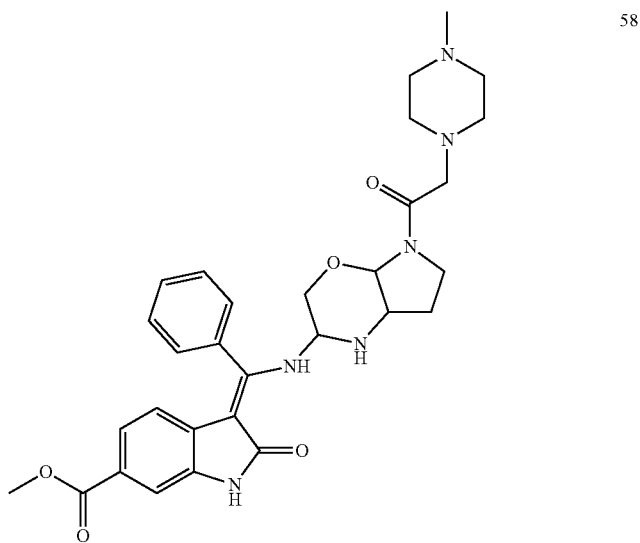
58
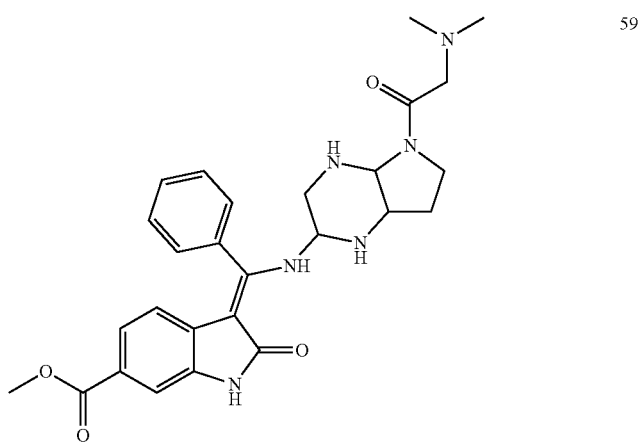
59
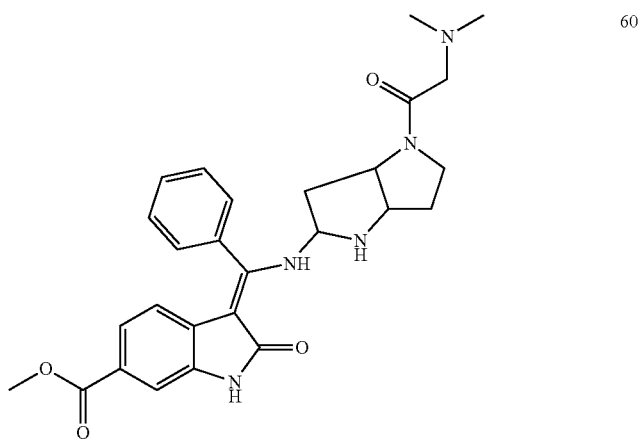
60

-continued
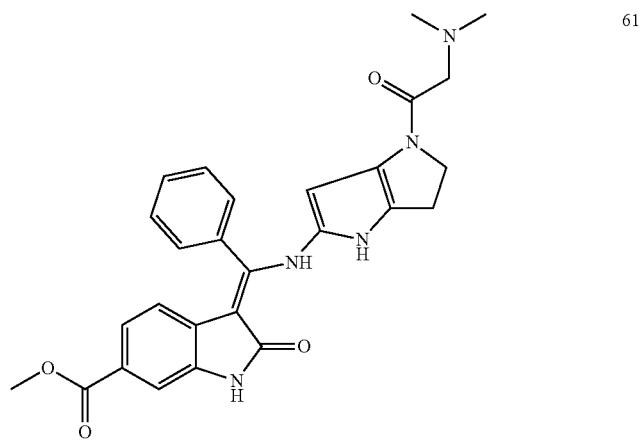
61
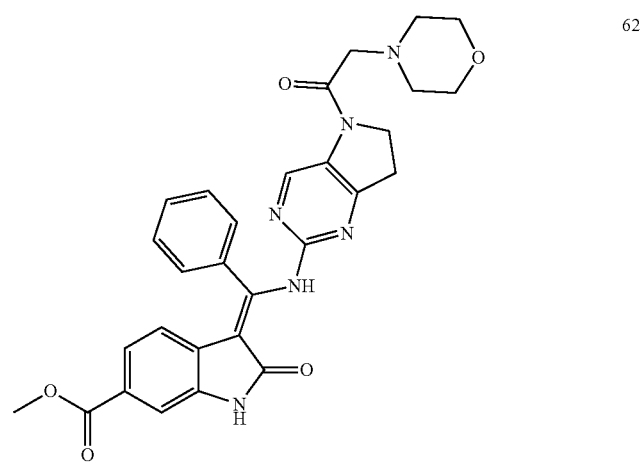
62
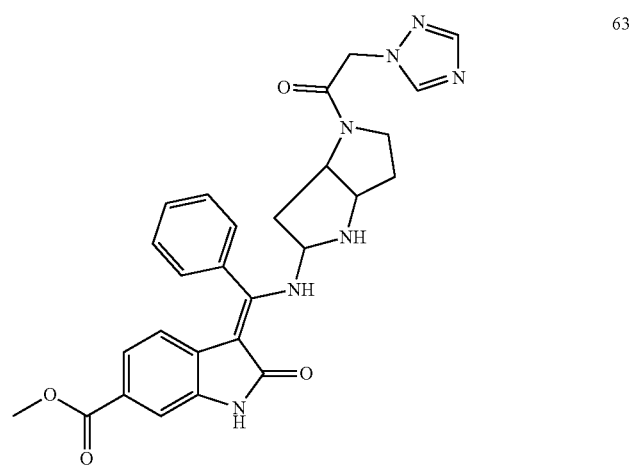
63

-continued
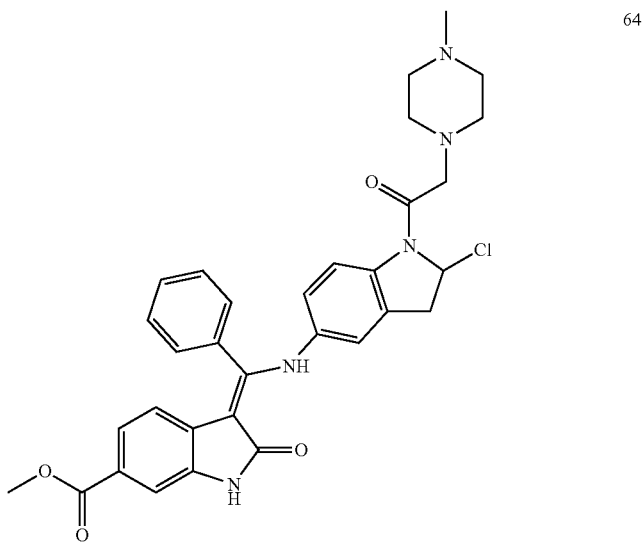
64
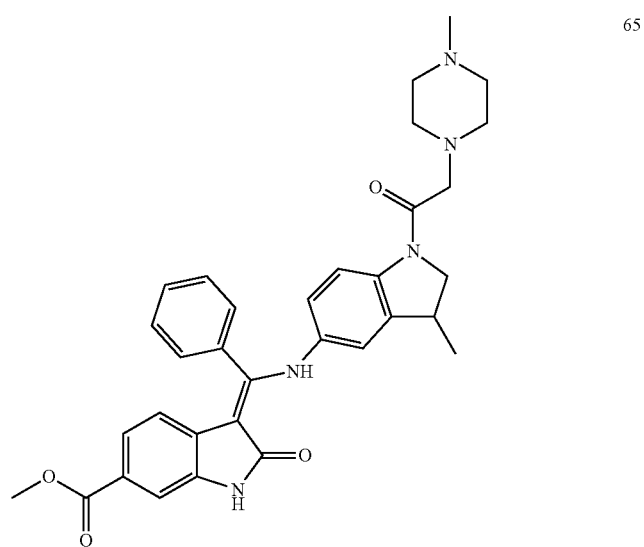
65
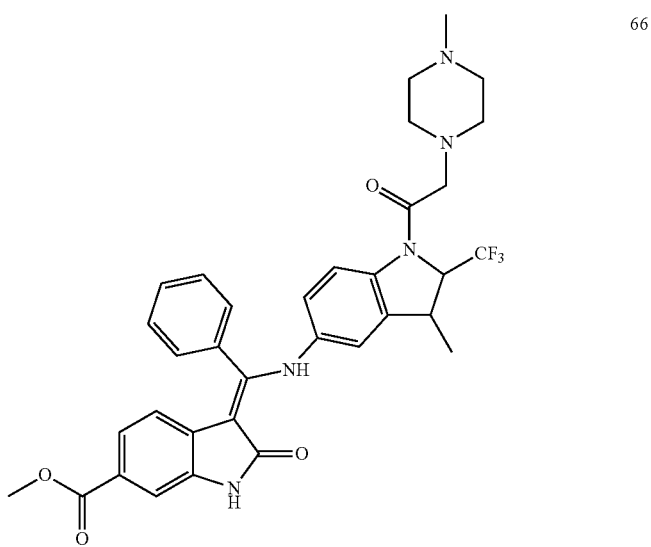
66

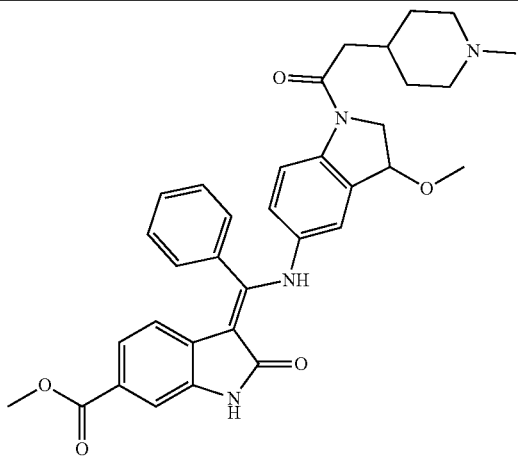
67
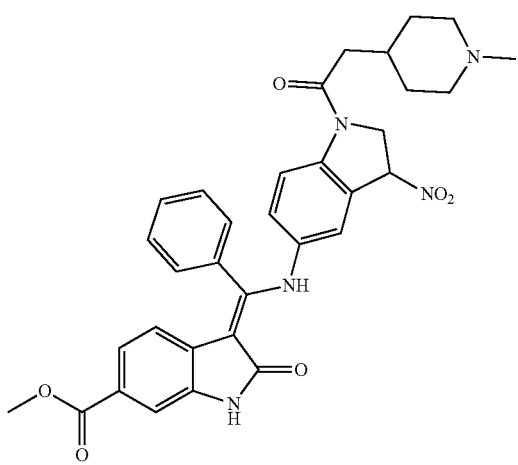
68
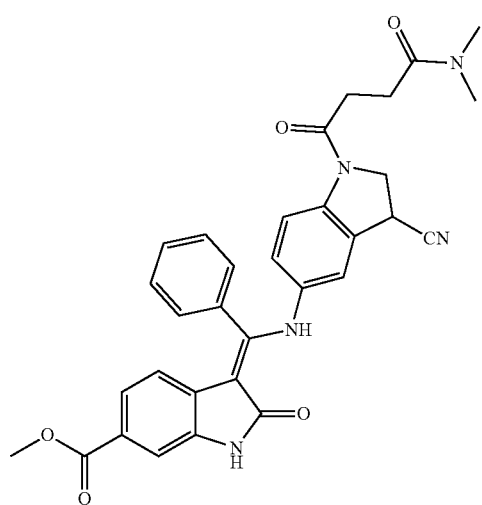
69

-continued
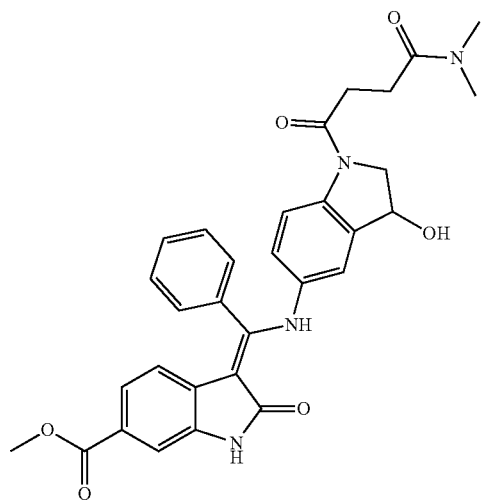
70
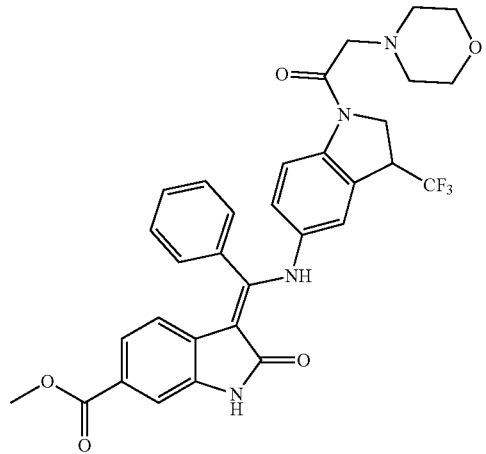 [SMILES: COC(=O)c1ccc2c(c1)NC(=O)/C2=C(\Nc1ccc2c(c1)C(C(F)(F)F)CN2C(=O)CN1CCOCC1)c1ccccc1]
71
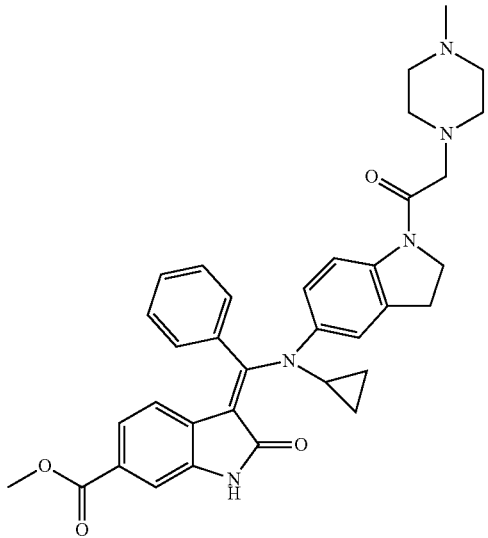 [SMILES: COC(=O)c1ccc2c(c1)NC(=O)/C2=C(/c1ccccc1)N(c1ccc2c(c1)CCN2C(=O)CN1CCN(C)CC1)C1CC1]
15a

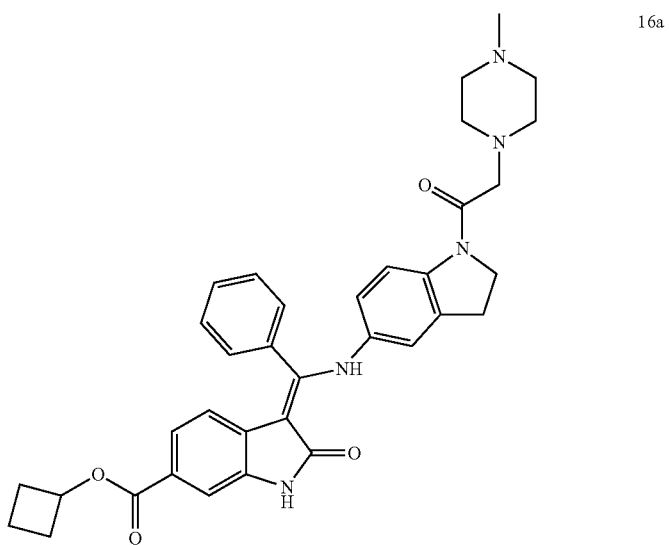
16a
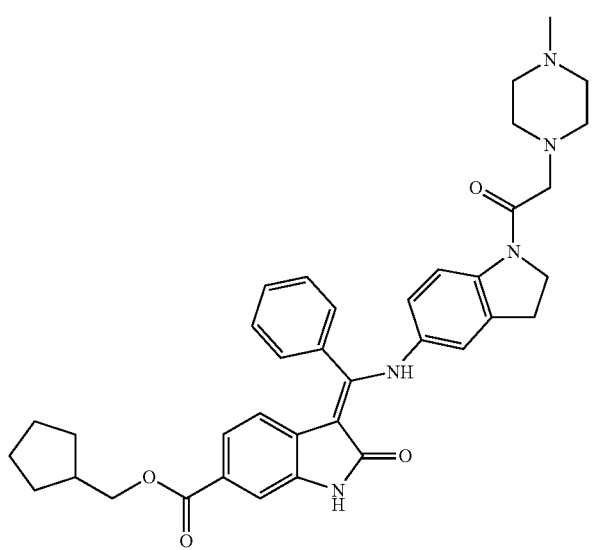 [SMILES: CN1CCN(CC(=O)N2CCc3cc(N/C(=C4\C(=O)Nc5cc(C(=O)OCC6CCCC6)ccc54)c4ccccc4)ccc32)CC1]
17a
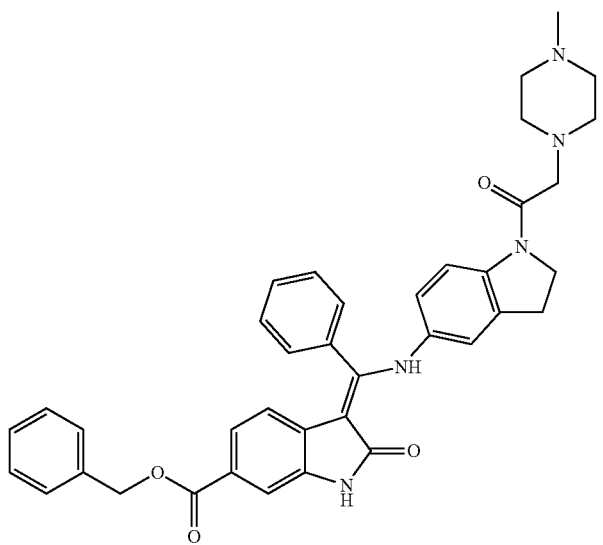 [SMILES: CN1CCN(CC(=O)N2CCc3cc(N/C(=C4\C(=O)Nc5cc(C(=O)OCc6ccccc6)ccc54)c4ccccc4)ccc32)CC1]
18a

-continued
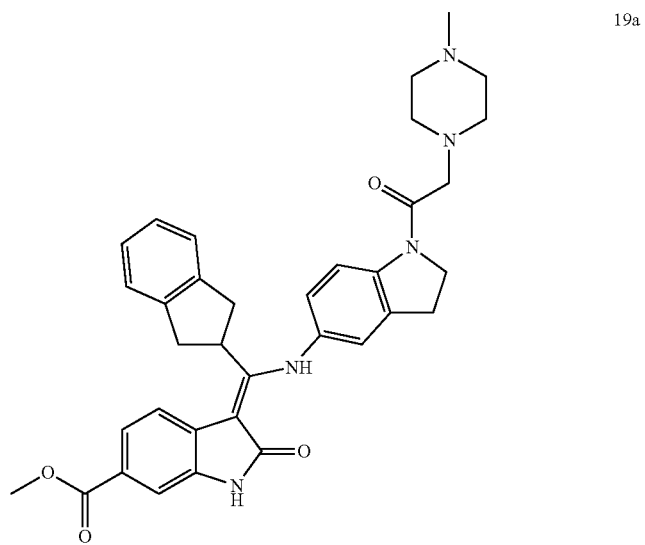
19a
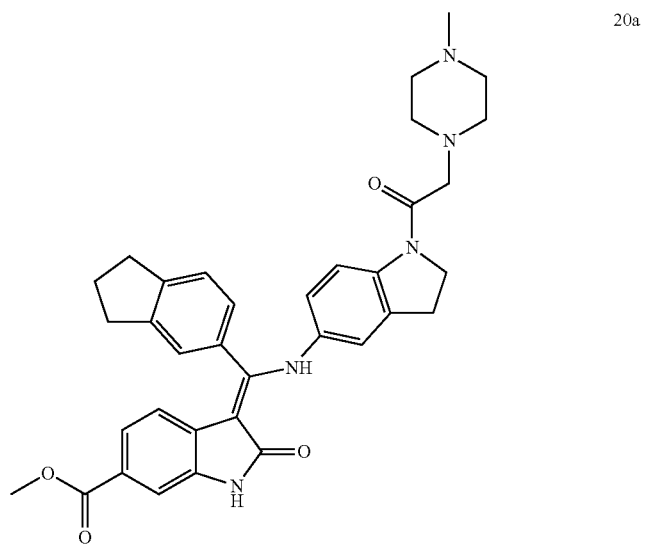
20a
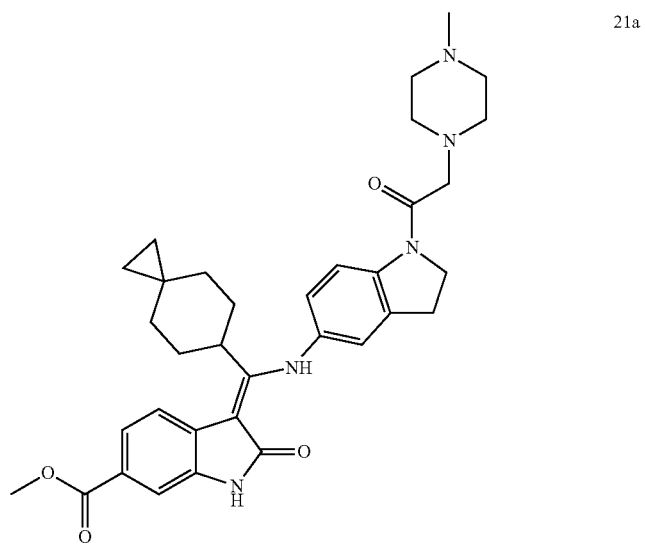
21a

-continued
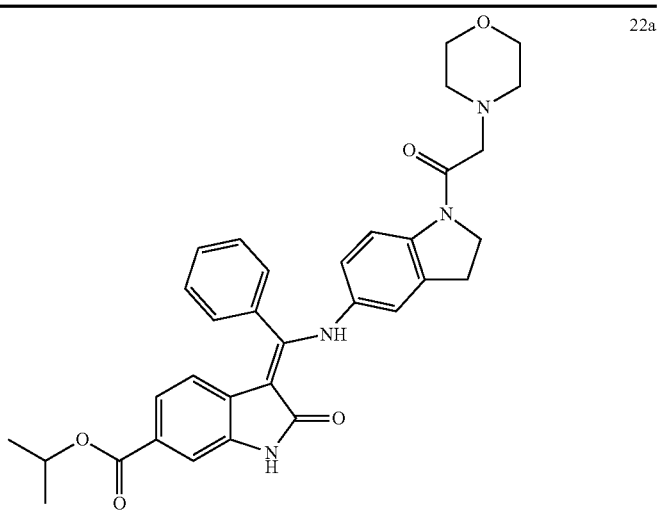
22a
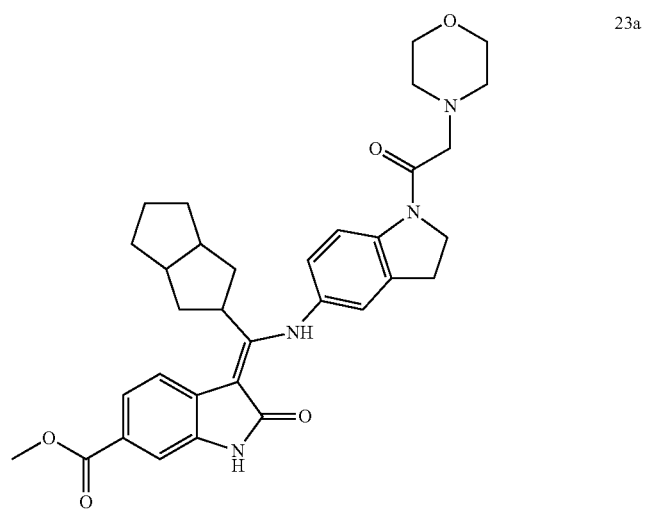
23a
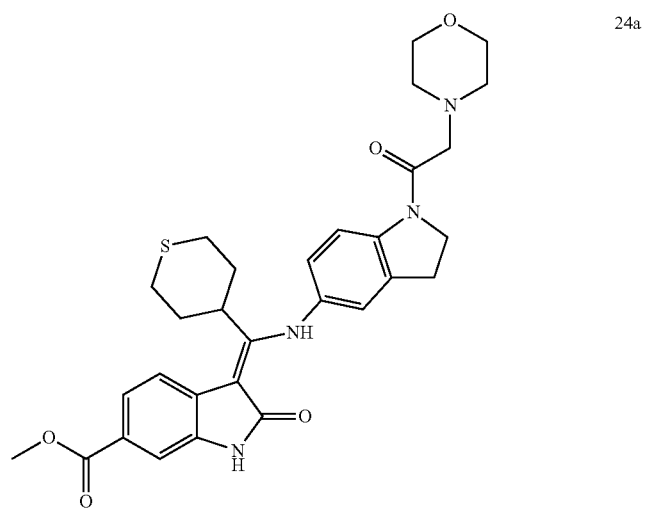
24a

-continued
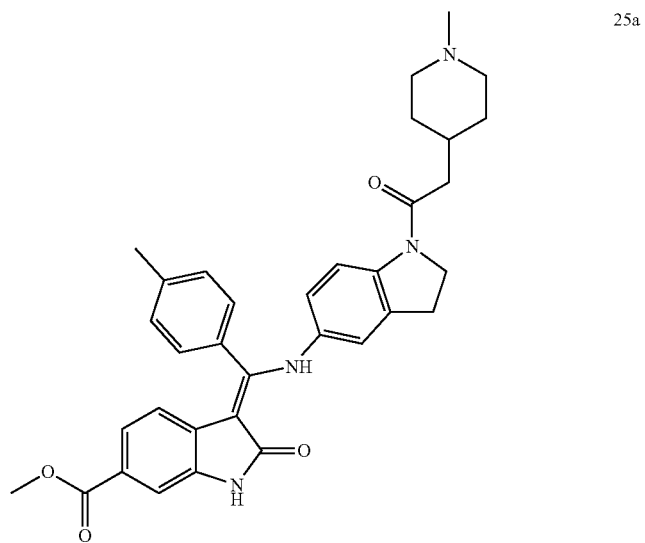
25a
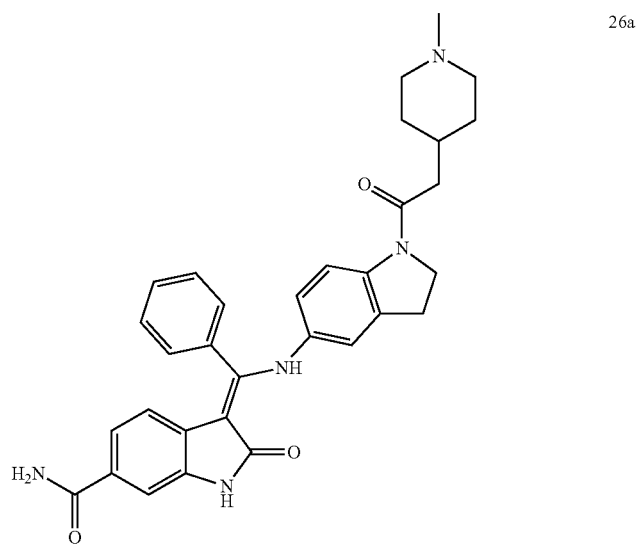
26a
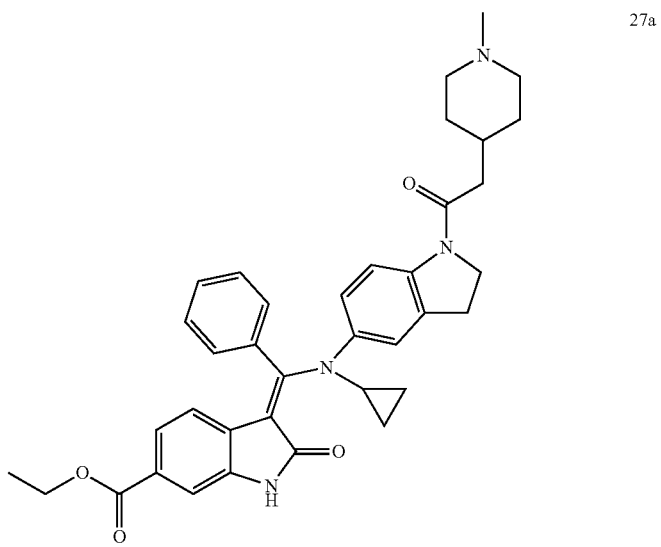
27a

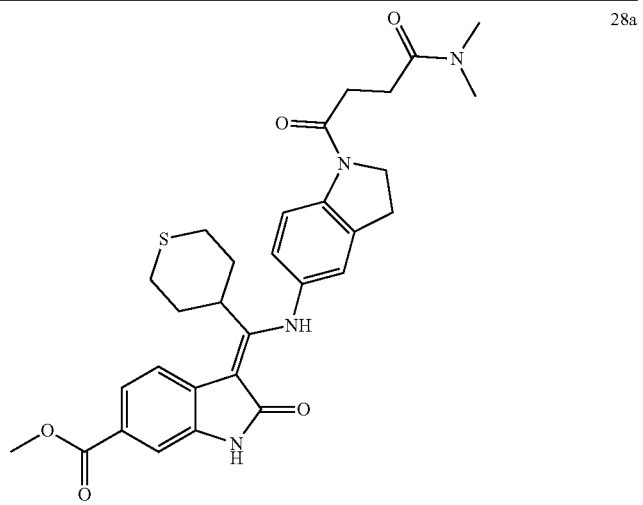
28a
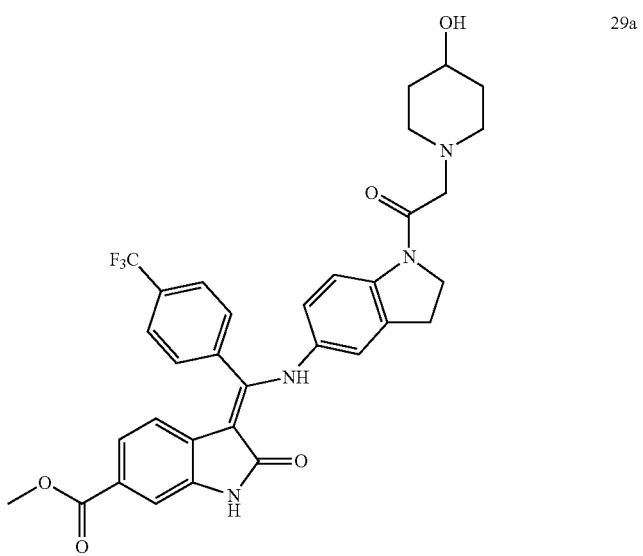
29a
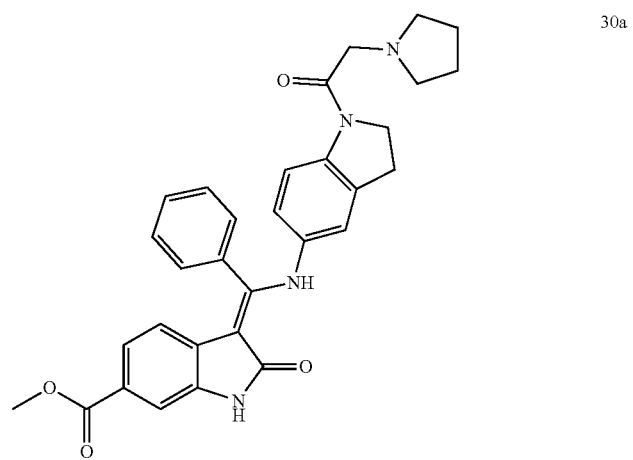
30a

-continued
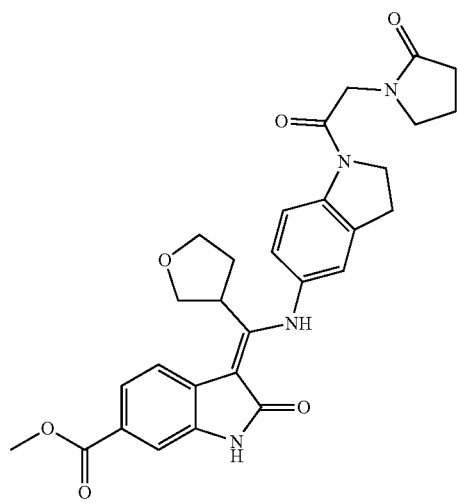 [SMILES: COC(=O)c1ccc2c(c1)NC(=O)/C2=C(\Nc1ccc2c(c1)CCN2C(=O)CN1CCCC1=O)C1CCOC1]
31a
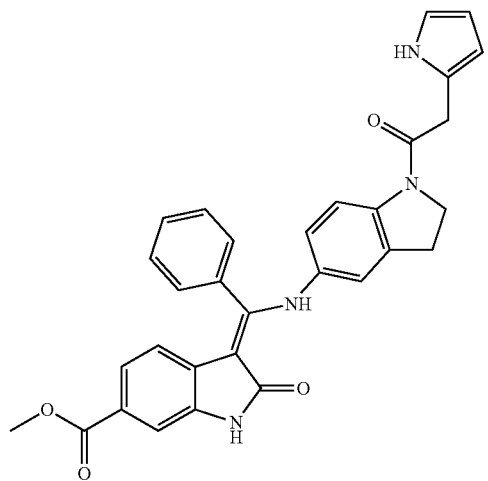 [SMILES: COC(=O)c1ccc2c(c1)NC(=O)/C2=C(\Nc1ccc2c(c1)CCN2C(=O)Cc1ccc[nH]1)c1ccccc1]
32a
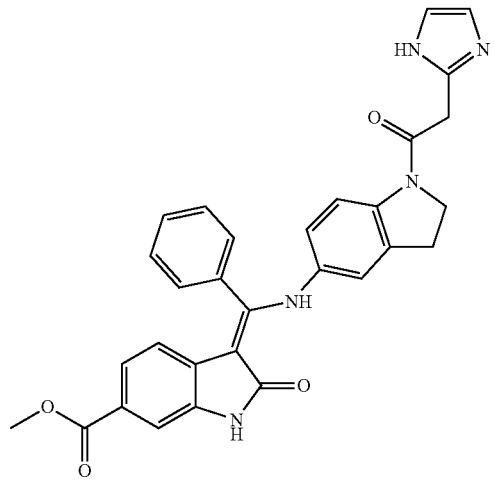 [SMILES: COC(=O)c1ccc2c(c1)NC(=O)/C2=C(\Nc1ccc2c(c1)CCN2C(=O)Cc1ncc[nH]1)c1ccccc1]
33a

-continued
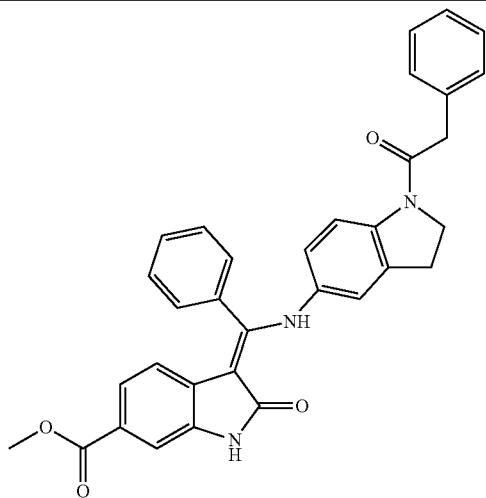
34a
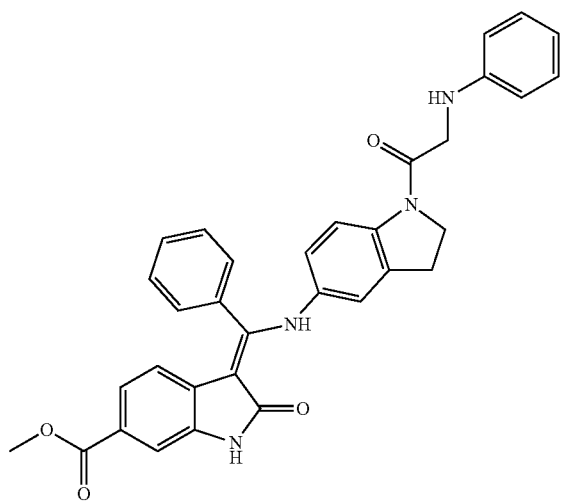 [SMILES: COC(=O)c1ccc2c(c1)NC(=O)/C2=C(\Nc1ccc2c(c1)CCN2C(=O)CNc1ccccc1)c1ccccc1]
35a
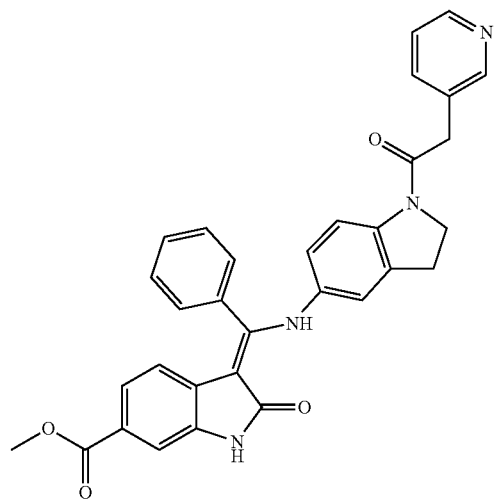 [SMILES: COC(=O)c1ccc2c(c1)NC(=O)/C2=C(\Nc1ccc2c(c1)CCN2C(=O)Cc1cccnc1)c1ccccc1]
36a

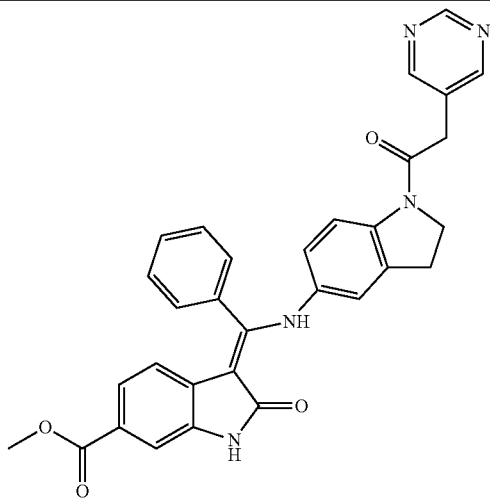

37a

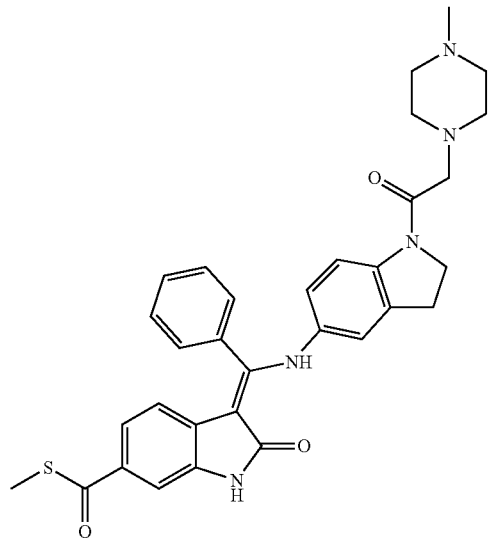 [SMILES: CSC(=O)c1ccc2c(c1)NC(=O)/C2=C(\Nc1ccc2c(c1)CCN2C(=O)CN1CCN(C)CC1)c1ccccc1]

38a

Hydrolysis of an Ester into an Acid

The compounds prepared as above can be hydrolyzed into their corresponding free acids with the conventional methods. For example, the compounds can be dissolved in an organic solvent (e.g. methanol, ethanol, THF, dioxane and the like); then an aqueous solution of inorganic base (e.g. sodium hydroxide, potassium hydroxide, and potassium carbonate) is added; the reaction is stirred until the completion of reaction; the resulting mixture is concentrated, washed with water, adjusted to the acidity with hydrochloric acid, and filtered; and the filtrate is washed with water, and dried to produce the following acids:

| Compound | Structure |
|---|---|
| 1b | 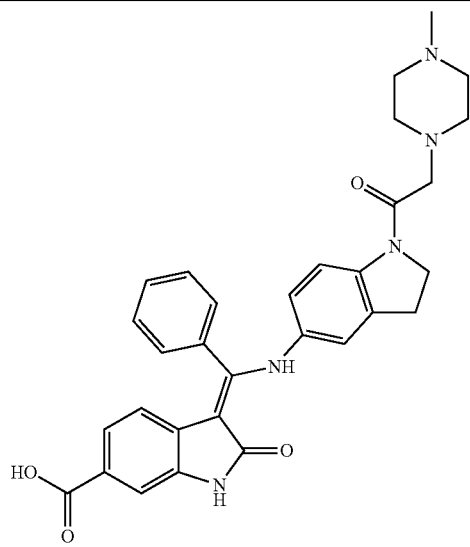 |
| 2b | 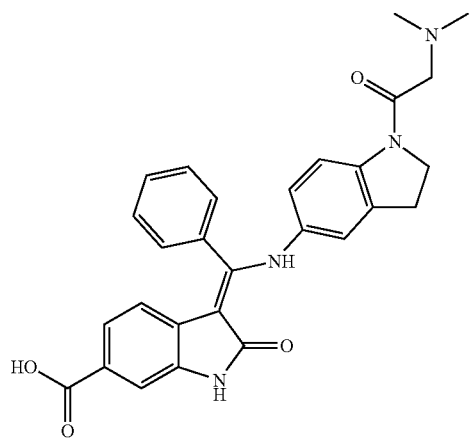 [SMILES: CN(C)CC(=O)N1CCc2cc(N/C(=C3\C(=O)Nc4cc(C(=O)O)ccc43)c3ccccc3)ccc21] |
| 3b | 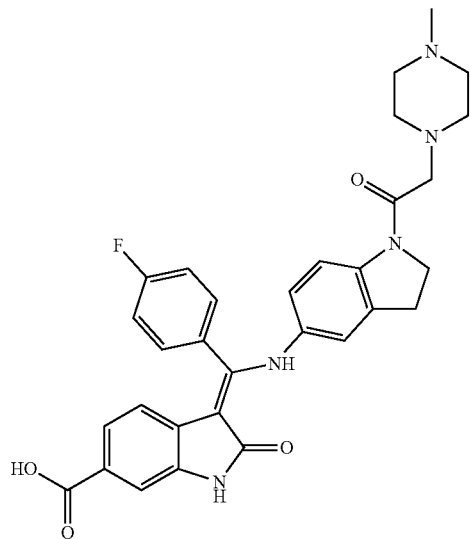 [SMILES: CN1CCN(CC(=O)N2CCc3cc(N/C(=C4\C(=O)Nc5cc(C(=O)O)ccc54)c4ccc(F)cc4)ccc32)CC1] |

-continued
| Compound | Structure |
|---|---|
| 4b | 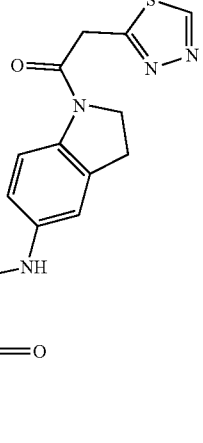 |
| 5b | 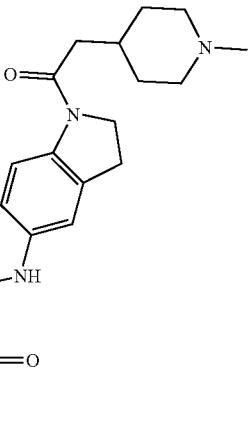 |
| 6b | 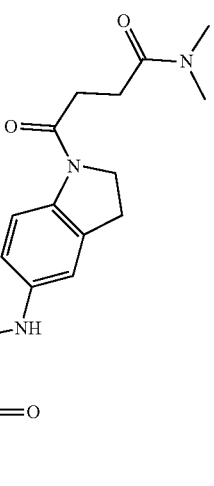 |

-continued
| Compound | Structure |
|---|---|
| 7b | 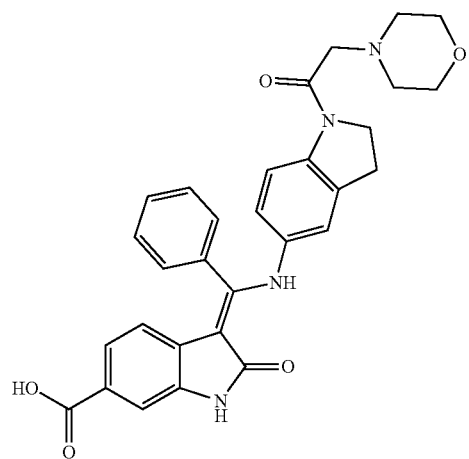 [SMILES: O=C1Nc2cc(C(=O)O)ccc2/C1=C(/Nc1ccc2c(c1)CCN2C(=O)CN1CCOCC1)c1ccccc1] |
| 8b | 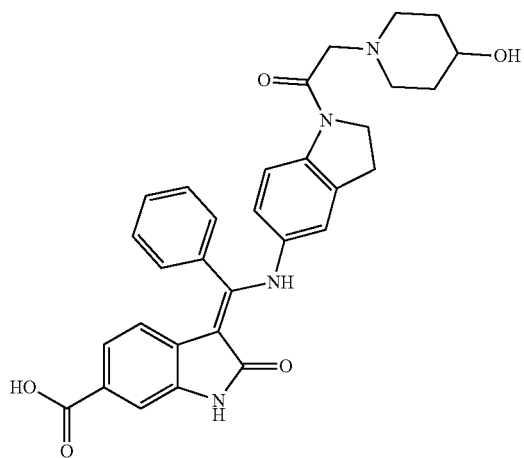 [SMILES: O=C1Nc2cc(C(=O)O)ccc2/C1=C(/Nc1ccc2c(c1)CCN2C(=O)CN1CCC(O)CC1)c1ccccc1] |
| 9b | 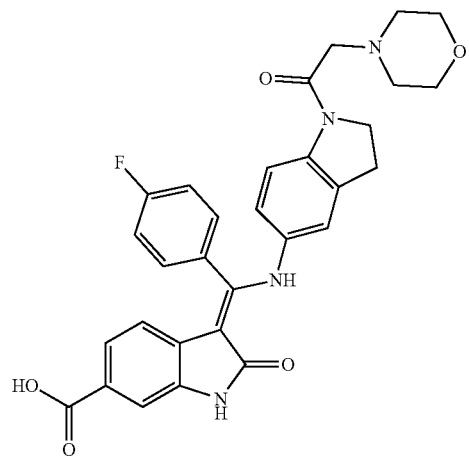 [SMILES: O=C1Nc2cc(C(=O)O)ccc2/C1=C(/Nc1ccc2c(c1)CCN2C(=O)CN1CCOCC1)c1ccc(F)cc1] |

-continued
| Compound | Structure |
|---|---|
| 10b | 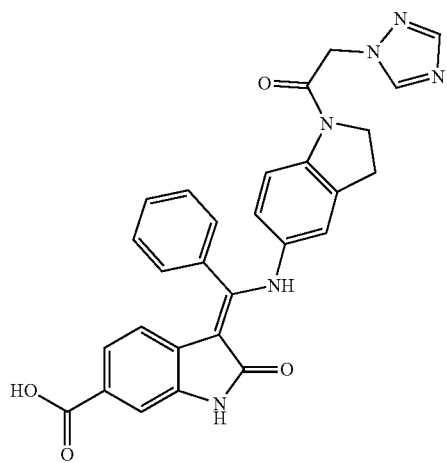 [SMILES: O=C1Nc2cc(C(=O)O)ccc2/C1=C(/Nc1ccc2c(c1)CCN2C(=O)Cn1cncn1)c1ccccc1] |
| 11b | 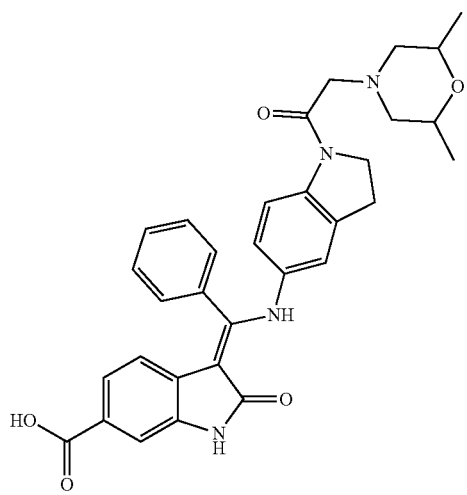 [SMILES: CC1CN(CC(=O)N2CCc3cc(N/C(=C4\C(=O)Nc5cc(C(=O)O)ccc54)c4ccccc4)ccc32)CC(C)O1] |
| 12b | 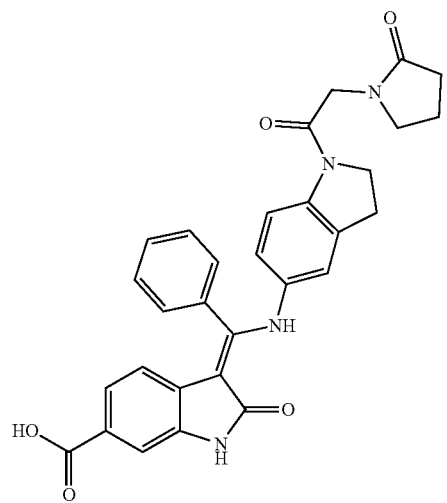 [SMILES: O=C1Nc2cc(C(=O)O)ccc2/C1=C(/Nc1ccc2c(c1)CCN2C(=O)CN1CCCC1=O)c1ccccc1] |

| Compound | Structure |
|---|---|
| 13b | 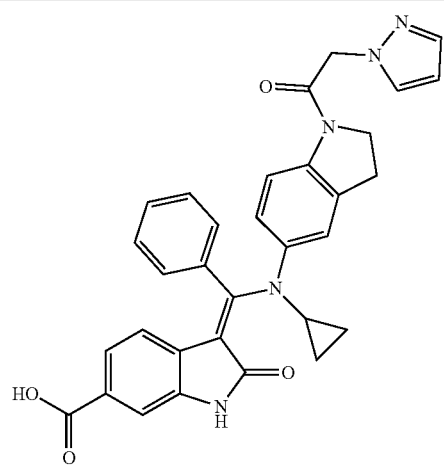 [SMILES: O=C1Nc2cc(C(=O)O)ccc2/C1=C(\c1ccccc1)N(c1ccc2c(c1)CCN2C(=O)Cn1cccn1)C1CC1] |
| 14b | 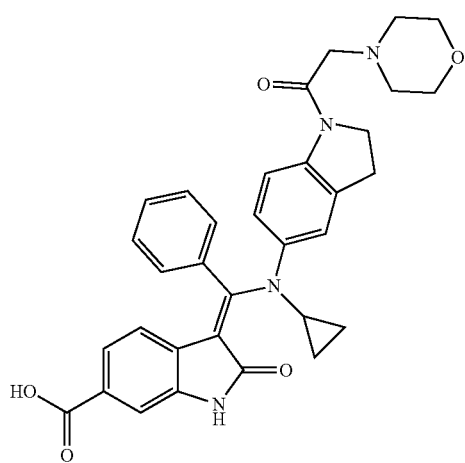 [SMILES: O=C1Nc2cc(C(=O)O)ccc2/C1=C(\c1ccccc1)N(c1ccc2c(c1)CCN2C(=O)CN1CCOCC1)C1CC1] |
| 15b | 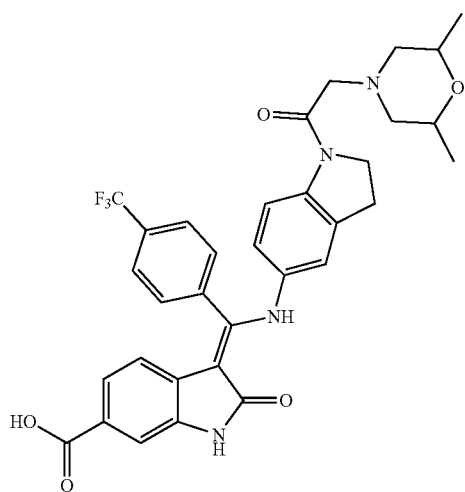 [SMILES: CC1CN(CC(=O)N2CCc3cc(N/C(=C4\C(=O)Nc5cc(C(=O)O)ccc54)c4ccc(C(F)(F)F)cc4)ccc32)CC(C)O1] |

| Compound | Structure |
|---|---|
| 16b | 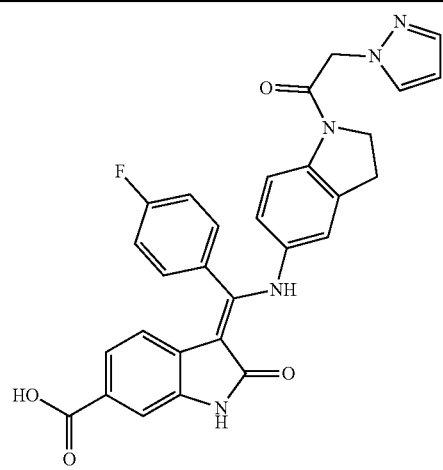 |
| 17b | 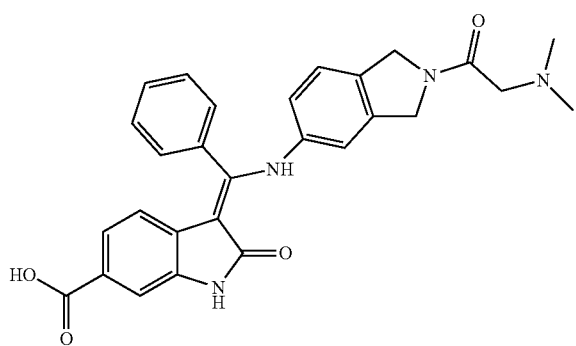 [SMILES: CN(C)CC(=O)N1Cc2ccc(N/C(=C3\C(=O)Nc4cc(C(=O)O)ccc43)c3ccccc3)cc2C1] |
| 18b | 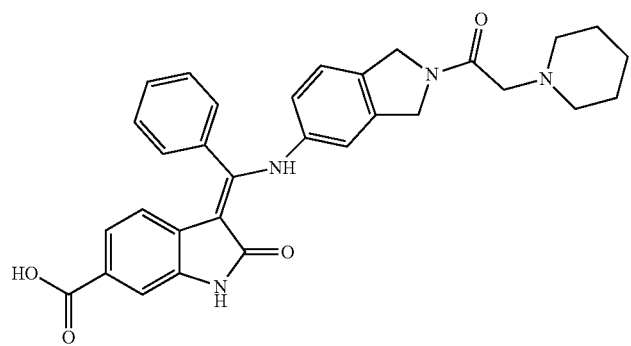 [SMILES: O=C1Nc2cc(C(=O)O)ccc2/C1=C(/Nc1ccc2c(c1)CN(C(=O)CN1CCCCC1)C2)c1ccccc1] |
| 19b | 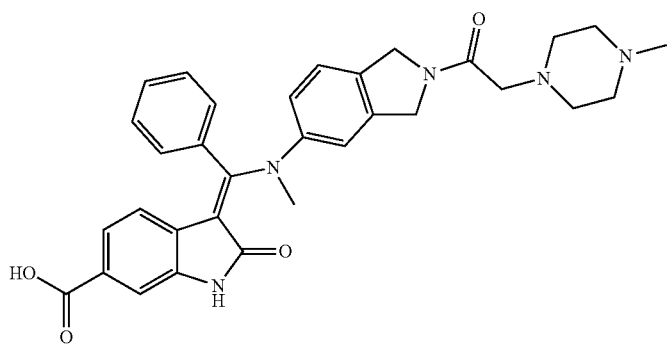 [SMILES: CN1CCN(CC(=O)N2Cc3ccc(N(C)/C(=C4\C(=O)Nc5cc(C(=O)O)ccc54)c4ccccc4)cc3C2)CC1] |

-continued

| Compound | Structure |
|---|---|
| 20b | (4-fluorophenyl)(NH-isoindoline-N-CO-CH2-N-methylpiperazine) methylene-2-oxoindoline-6-carboxylic acid |
| 21b | (4-methoxyphenyl)(NH-isoindoline-N-CO-CH2-piperidine) methylene-2-oxoindoline-6-carboxylic acid |
| 22b | phenyl(NH-isoindoline-N-CO-CH2-morpholine) methylene-2-thioxoindoline-6-carboxylic acid |
| 23b | (4-trifluoromethylphenyl)(NH-isoindoline-N-CO-CH2-morpholine) methylene-2-oxoindoline-6-carboxylic acid |

-continued
| Compound | Structure |
|---|---|
| 24b | 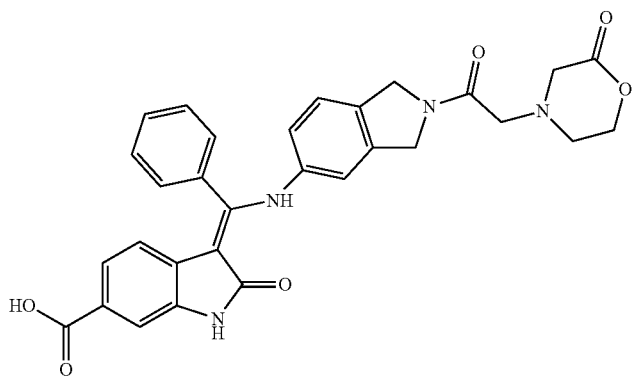 [SMILES: O=C1CN(CC(=O)N2Cc3ccc(N/C(=C4\C(=O)Nc5cc(C(=O)O)ccc54)c4ccccc4)cc3C2)CCO1] |
| 25b | 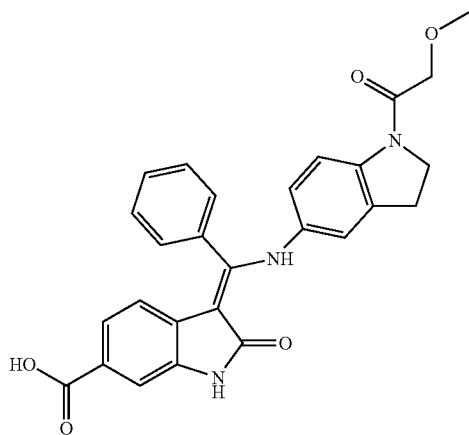 [SMILES: COCC(=O)N1CCc2cc(N/C(=C3\C(=O)Nc4cc(C(=O)O)ccc43)c3ccccc3)ccc21] |
| 26b | 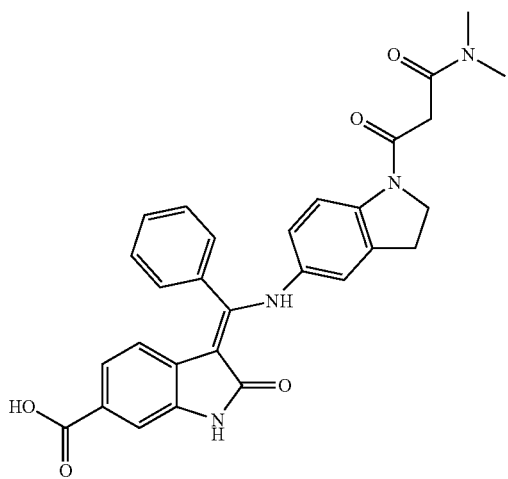 [SMILES: CN(C)C(=O)CC(=O)N1CCc2cc(N/C(=C3\C(=O)Nc4cc(C(=O)O)ccc43)c3ccccc3)ccc21] |

-continued
| Compound | Structure |
|---|---|
| 27b | 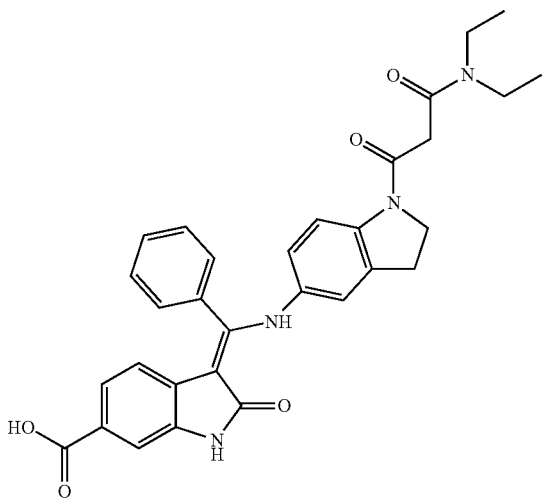 [SMILES: CCN(CC)C(=O)CC(=O)N1CCc2cc(N/C(=C3\C(=O)Nc4cc(C(=O)O)ccc43)c3ccccc3)ccc21] |
| 28b | 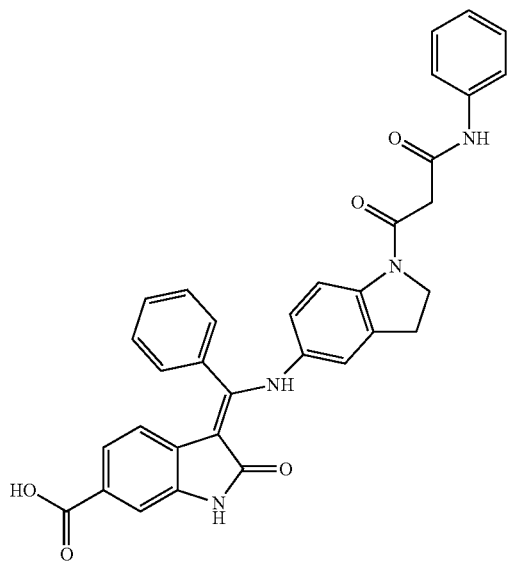 [SMILES: O=C(CC(=O)N1CCc2cc(N/C(=C3\C(=O)Nc4cc(C(=O)O)ccc43)c3ccccc3)ccc21)Nc1ccccc1] |
| 29b | 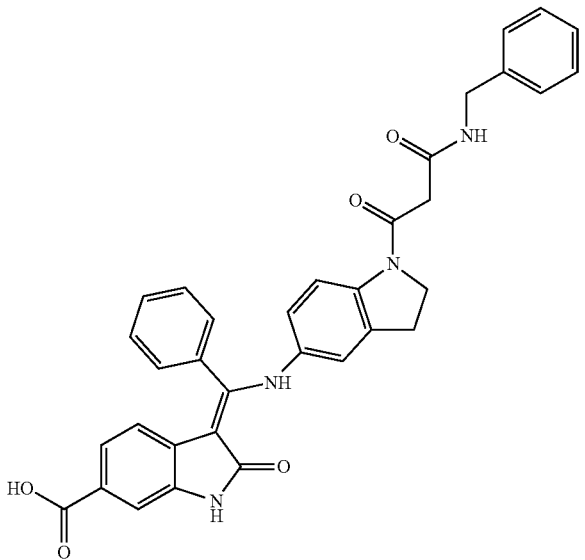 [SMILES: O=C(CC(=O)N1CCc2cc(N/C(=C3\C(=O)Nc4cc(C(=O)O)ccc43)c3ccccc3)ccc21)NCc1ccccc1] |

-continued
| Compound | Structure |
|---|---|
| 30b | 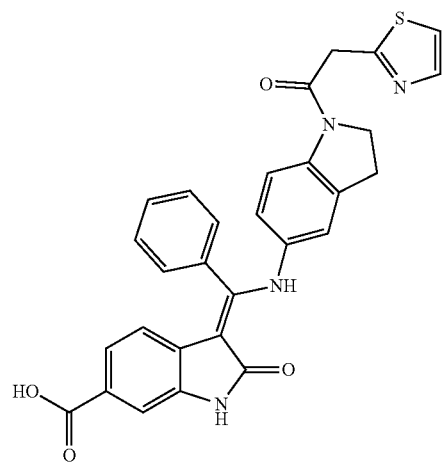 |
| 31b | 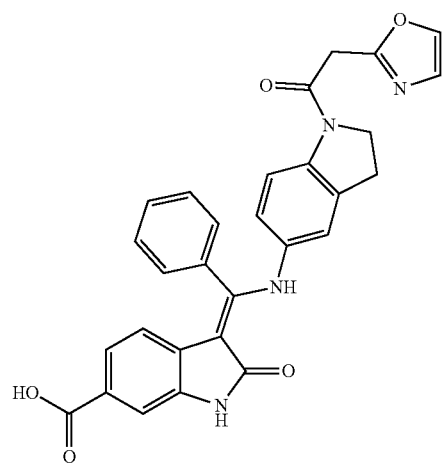 [SMILES: O=C1Nc2cc(C(=O)O)ccc2/C1=C(/Nc1ccc2c(c1)CCN2C(=O)Cc1ncco1)c1ccccc1] |
| 32b | 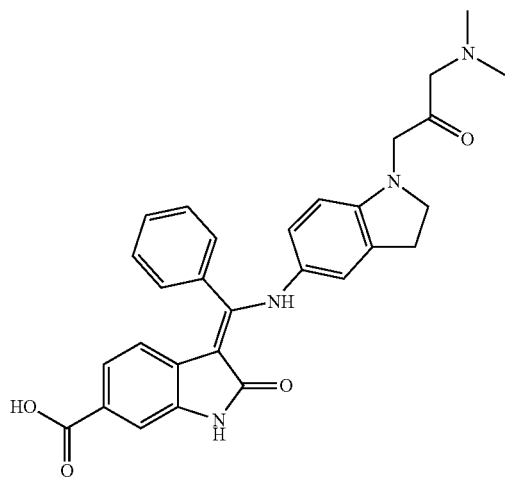 [SMILES: CN(C)CC(=O)CN1CCc2cc(N/C(=C3\C(=O)Nc4cc(C(=O)O)ccc43)c3ccccc3)ccc21] |

-continued
| Compound | Structure |
|---|---|
| 33b | 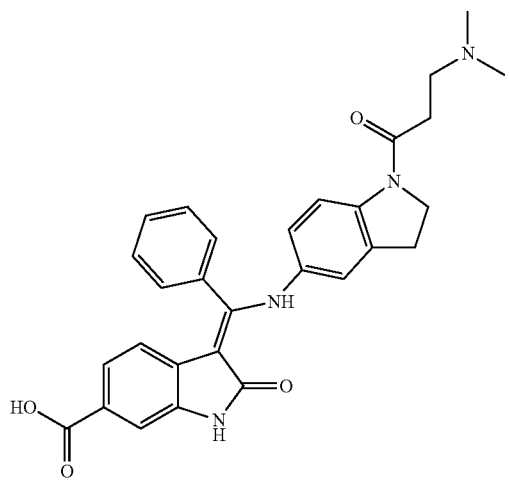 [SMILES: CN(C)CCC(=O)N1CCc2cc(N/C(=C3\C(=O)Nc4cc(C(=O)O)ccc43)c3ccccc3)ccc21] |
| 34b | 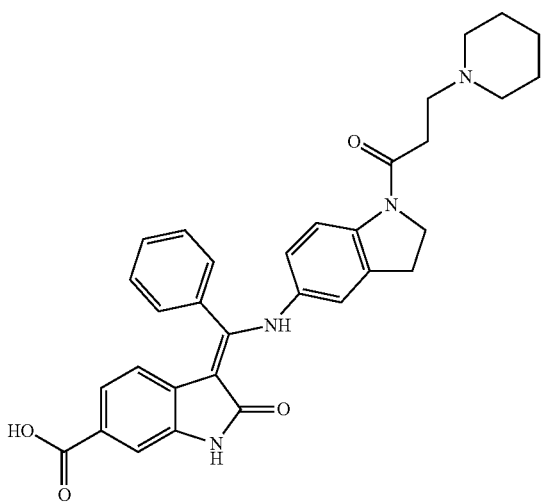 [SMILES: O=C1Nc2cc(C(=O)O)ccc2/C1=C(/Nc1ccc2c(c1)CCN2C(=O)CCN1CCCCC1)c1ccccc1] |
| 35b | 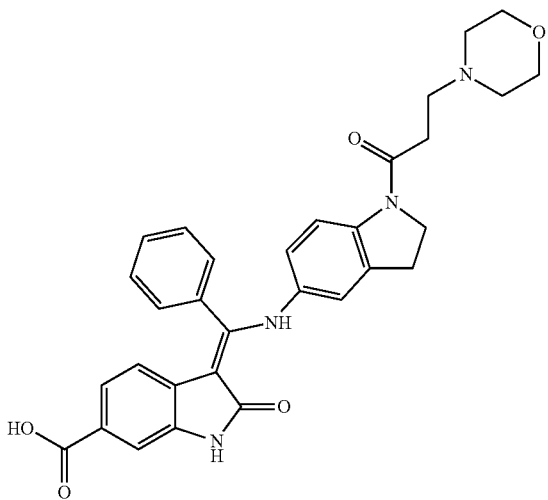 [SMILES: O=C1Nc2cc(C(=O)O)ccc2/C1=C(/Nc1ccc2c(c1)CCN2C(=O)CCN1CCOCC1)c1ccccc1] |

| Compound | Structure |
|---|---|
| 36b | 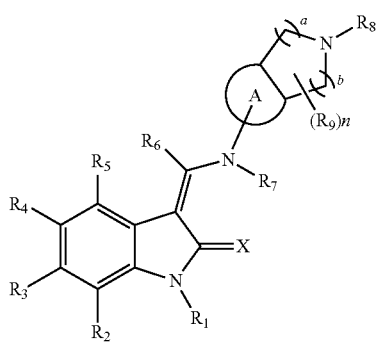 |

The invention claimed is:

1. A compound represented by general formula (I), a pharmaceutically acceptable salt, a deuteride or a stereoisomer thereof:

(I)

wherein, X represents O or S;

$R_1$ represents H or a prodrug group thereof;

$R_2$, $R_4$ and $R_5$ each independently represent H;

$R_3$ represents carboxyl, $C_{1-6}$alkyl-OC(O)—, $C_{1-6}$alkyl-SC(O)—, 3-14-membered cycloalkyl-OC(O)—, or carbamoyl, which is unsubstituted or substituted by 1-3 groups represented by $Q_1$;

$Q_1$ represents 6-14-membered aryl, or 3-14-membered cycloalkyl;

$R_6$ represents 6-14-membered aryl, 7-12-membered bridged ring group-$C_{0-3}$alkyl, 7-12-membered spiro ring group-$C_{0-3}$alkyl or 3-14-membered heterocyclyl$C_{0-3}$alkyl, which is unsubstituted or substituted by 1-3 groups represented by $Q_2$, $Q_2$ represents halogen, trifluoromethyl, $C_{1-3}$alkyl, or $C_{1-3}$alkyloxy;

$R_7$ represents H, $C_{1-3}$alkyl, or 3-14-membered cycloalkyl;

Ring A represents phenyl or 5-7-membered heterocyclyl;

$R_8$ represents formula (IIa),

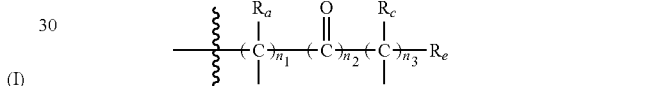

formula (IIa)

wherein, $R_a$, $R_b$, $R_c$ and $R_d$ each independently represent H, $R_e$ represents $C_{1-3}$alkyloxy, amino, $C_{1-3}$alkylamino, di($C_{1-3}$alkyl)amino, di($C_{1-3}$alkyl)carbamoyl, phenylamino, phenyl, or 3-8-membered monocyclic heterocyclyl, the carbon atom on the 3-8-membered monocyclic heterocyclyl can be replaced with 1-3 groups selected from C(O), the $C_{1-3}$alkyl and the 3-8-membered monocyclic heterocyclyl can be substituted by 1-3 groups as represented by $Q_3$;

$Q_3$ represents hydroxyl or $C_{1-3}$alkyl;

$R_9$ represents H;

a represents 0 or 1;

b represents 1 or 2;

n represents 0, 1 or 2, when n is 2, the substituents represented by $R_9$ can be identical or different;

$n_1$ represents 0 or 1;

$n_2$ represents 1; and $n_3$ represents 1 or 2.

2. The compound of claim 1, a pharmaceutically acceptable salt, a deuteride or a stereoisomer thereof:

wherein, X represents O or S;

$R_1$ represents H or a prodrug group thereof;

$R_2$, $R_4$ and $R_5$ each independently represent H;

$R_3$ represents carboxyl, $C_{1-3}$alkyl-OC(O)—, 3-8-membered monocyclic cycloalkylOC(O)—, or carbamoyl, which is unsubstituted or substituted by 1-3 groups represented by $Q_1$, $Q_1$ represents phenyl, or 3-6-membered cycloalkyl;

R₆ represents the following groups, which are unsubstituted or substituted by 1-3 groups represented by Q₂:

(1) 6-14 -membered aryl, or (2)

p represents 0, 1, 2 or 3,
r represents 0, 1 or 2,
s represents 0, 1 or 2,
$Q_2$ represents halogen, trifluoromethyl, C1-3alkyl, or $C_{1-3}$alkyloxy;
$R_7$ represents H, $C_{1-3}$alkyl, or 3-6-membered monocyclic cycloalkyl;
Ring A represents phenyl, pyrrolyl, pyridyl, pyrimidinyl, pyrrolidinyl, piperidinyl, piperazinyl or morpholinyl;
$R_8$ represents formula (IIa)

formula (IIa)

wherein,
$R_a$, $R_b$, $R_c$ and $R_d$ each independently represent H,
$R_e$ represents $C_{1-3}$alkyloxy, amino, $C_{1-3}$alkylamino, di($C_{1-3}$alkyl)amino, di($C_{1-3}$alkyl)carbamoyl, phenylamino, phenyl or 5-7-membered monocyclic heterocyclyl,
the carbon atom on the 5-7-membered monocyclic heterocyclyl can be replaced with 1-3 groups selected from C(O),
the $C_{1-3}$alkyl and the 5-7-membered monocyclic heterocyclyl can be substituted by 1-3 groups represented by $Q_3$,
$Q_3$ represents hydroxyl or $C_{1-3}$alkyl;
$R_9$ represents H;
a represents 0 or 1;
b represents 1 or 2;
n represents 0, 1 or 2, when n is 2, the substituents represented by $R_9$ can be identical or different;
$n_1$ represents 0 or 1;
$n_2$ represents 1; and
$n_3$ represents 1 or 2.

3. The compound of claim 2, a pharmaceutically acceptable salt, a deuteride or a stereoisomer thereof:
wherein, X represents O;
$R_1$ represents H;
$R_2$, $R_4$ and $R_5$ each independently represent H;
$R_3$ represents $C_{1-3}$alkylOC(O)— or carbamoyl;
$R_6$ represents the following groups, which are unsubstituted or substituted by 1-3 groups represented by $Q_2$:

(1) phenyl, or (2)

-continued

[chemical structure fragments]

p represents 0, 1, 2 or 3,
r represents 1,
s represents 1,
$Q_2$ represents halogen, trifluoromethyl, $C_{1-3}$alkyl, or $C_{1-3}$alkyloxy;
$R_7$ represents H or 3-5-membered monocyclic cycloalkyl;
Ring A represents phenyl or pyridyl;
$R_8$ represents formula (IIa)

formula (IIa)

[chemical structure]

wherein,
$R_a$, $R_b$, $R_c$ and $R_d$ each independently represent H,
$R_e$ represents $C_{1-3}$alkyloxy, amino, $C_{1-3}$alkylamino, di($C_{1-3}$alkyl)amino, di($C_{1-3}$alkyl)carbamoyl, phenylamino, phenyl or 5-7-membered monocyclic heterocyclyl,
the carbon atom on the 5-7-membered monocyclic heterocyclyl can be replaced with 1-3 groups selected from C(O), the $C_{1-3}$alkyl and the 5-7-membered monocyclic heterocyclyl can be substituted by 1-3 groups represented by $Q_3$,
$Q_3$ represents, hydroxy, or methyl;
$R_9$ represents H;
a represents 0 or 1;
b represents 1 or 2;
n represents 0 or 1;
$n_1$ represents 0 or 1;
$n_2$ represents 1; and
$n_3$ represents 1 or 2.

4. The compound of claim 3, a pharmaceutically acceptable salt, a deuteride or a stereoisomer thereof, the compound has a structure represented by the below general formula (II):

(II)

[chemical structure]

wherein, X represents O;
$R_1$ represents H;
$R_2$, $R_4$ and $R_5$ each independently represent H;
$R_3$ represents $CH_3OC(O)$—, $CH_3CH_2OC(O)$—, $(CH_3)_2CHOC(O)$— or $NH_3C(O)$—;
$R_6$ represents the following groups, which are unsubstituted or substituted by 1-3 groups represented by $Q_2$: phenyl, tetrahydrofuryl, tetrahydropyranyl,

[chemical structures]

$Q_2$ represents halogen, trifluoromethyl, methyl, or methoxy;
$R_7$ represents H or cyclopropyl;

R₈ represents formula (IIb)

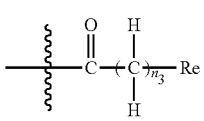

formula (IIb)

wherein, R_e represents $C_{1-3}$alkyloxy, di($C_{1-3}$alkyl)amino, di($C_{1-3}$alkyl)carbamoyl, phenylamino, pyrrolyl, pyrazolyl, imidazolyl, triazolyl, pyridyl, pyrimidinyl, pyrrolidinyl, pyrrolidonyl, piperidinyl, piperazinyl or morpholinyl, said pyrrolyl, pyrazolyl, imidazolyl, triazolyl, pyridyl, pyrimidinyl, pyrrolidinyl, pyrrolidonyl, piperidinyl, piperazinyl, and morpholinyl can be substituted by 1-3 groups represented by $Q_3$, $Q_3$ represents halogen, or methyl;

$R_9$ represents H;

a represents 0 or 1;

b represents 1 or 2;

n represents 0; and $n_3$ represents 1 or 2.

5. The compound of claim 4, a pharmaceutically acceptable salt, a deuteride or a stereoisomer thereof:
wherein, X represents O;
$R_1$ represents H;
$R_2$, $R_4$ and $R_5$ each independently represent H;
$R_3$ represents $CH_3OC(O)$—, or $CH_3CH_2OC(O)$—;
$R_6$ represents the following groups, which are unsubstituted or substituted by 1-3 groups selected from halogen, trifluoromethyl and methoxy:

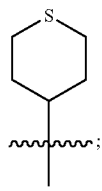 [SMILES: *C1CCSCC1]

phenyl, tetrahydrofuryl, tetrahydropyranyl or
$R_7$ represents H or cyclopropyl;
$R_8$ represents formula (IIb)

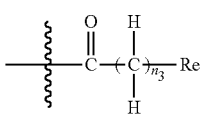

formula (IIb)

wherein R_e represents dimethylamino, dimethylcarbamoyl, pyrrolyl, pyrazolyl, imidazolyl, triazolyl, pyridyl, pyrimidinyl, pyrrolidinyl, pyrrolidonyl, piperidinyl, piperazinyl or morpholinyl, said pyrrolyl, pyrazolyl, imidazolyl, triazolyl, pyridyl, pyrimidinyl, pyrrolidinyl, pyrrolidonyl, piperidinyl, piperazinyl, and morpholinyl can be substituted by 1-2 groups selected from $Q_3$, $Q_3$ represents methyl;

$R_9$ represents H;

a represents 0;

b represents 2;

n represents 0; and $n_3$ represents 1 or 2.

6. The compound of claim 5, a pharmaceutically acceptable salt, a deuteride or a stereoisomer thereof:
wherein, X represents O;
$R_1$ represents H;
$R_2$, $R_4$ and $R_5$ each independently represent H;
$R_3$ represents $CH_3OC(O)$—, or $CH_3CH_2OC(O)$—;
$R_6$ represents phenyl, 4-fluorophenyl, 4-trifluoromethylphenyl, or 4-methoxyphenyl;
$R_7$ represents H;
$R_8$ represents formula (IIb)

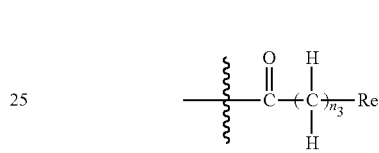

formula (IIb)

wherein R_e represents dimethylamino, dimethylcarbamoyl, pyrazolyl, triazolyl, pyrrolidinyl, pyrrolidonyl, piperidinyl, N-methylpiperidinyl, 4-hydroxypiperidinyl, N-methylpiperazinyl, morpholinyl, or 3,5-dimethylmorpholinyl;

$R_9$ represents H;

a represents 0;

b represents 2;

n represents 0; and $n_3$ represents 1 or 2.

7. A compound, or a pharmaceutically acceptable salt, a deuteride or a stereoisomer thereof, wherein the compound is selected from the group consisting of:

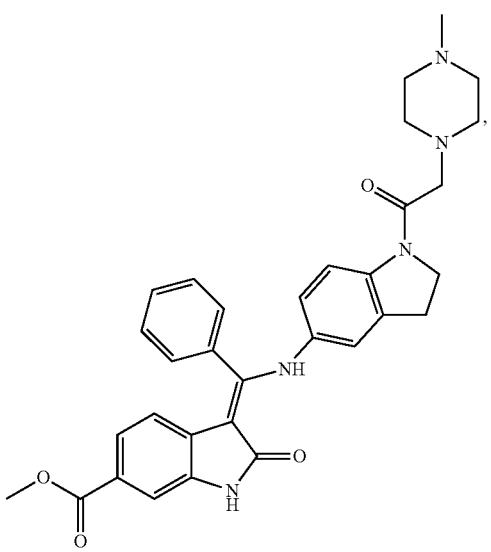

189
-continued
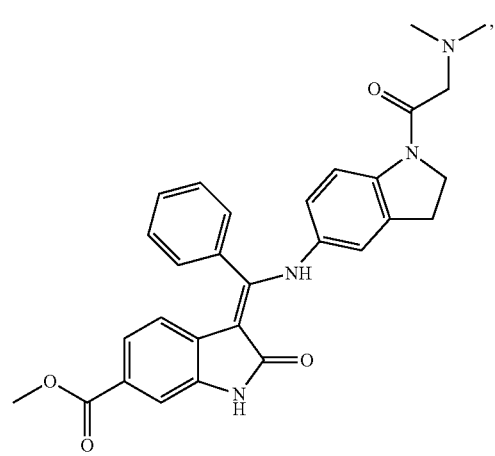
190
-continued
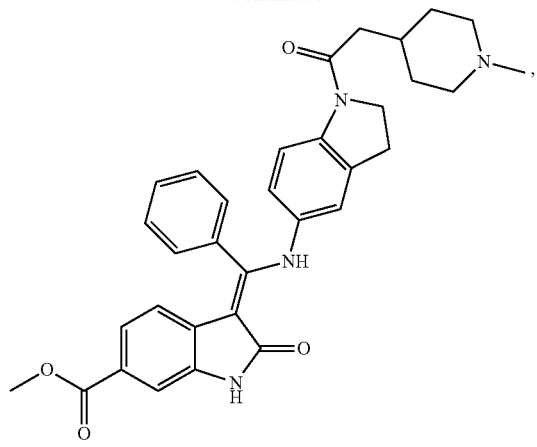
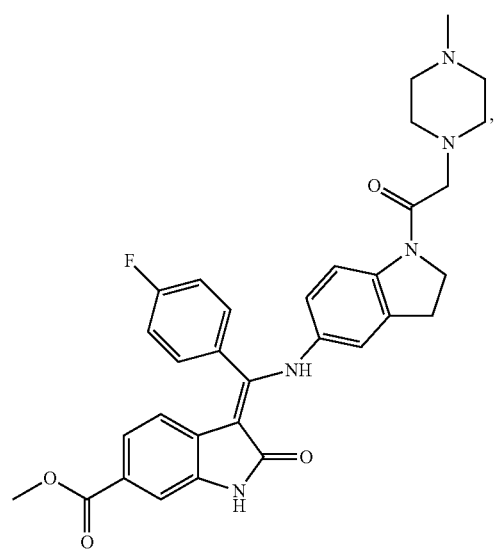
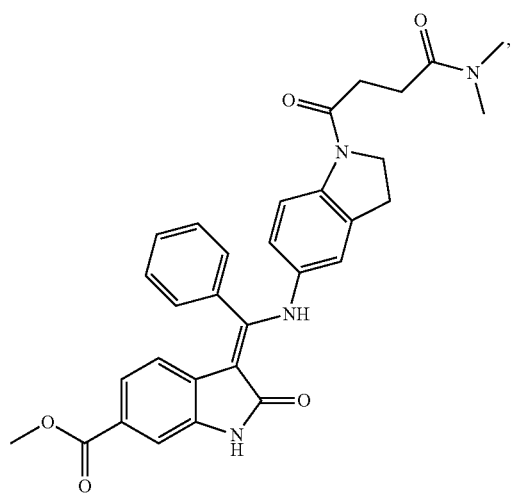
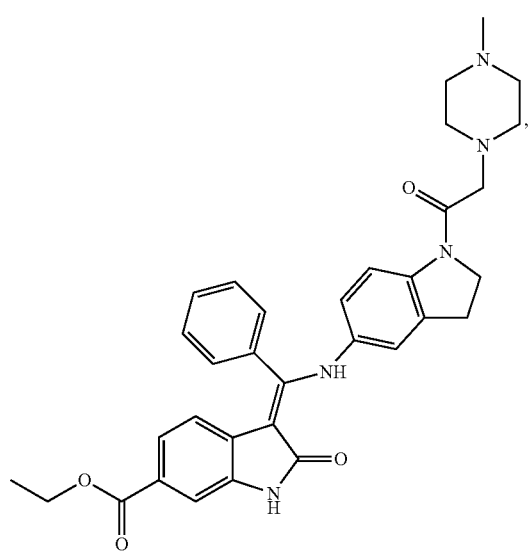
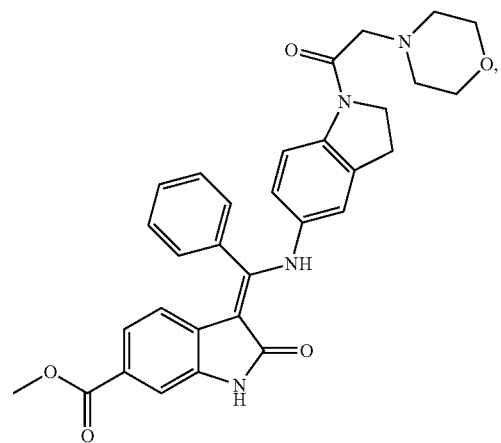

191
-continued
192
-continued
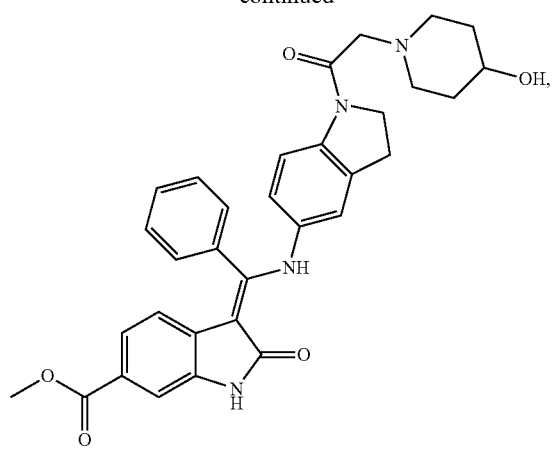
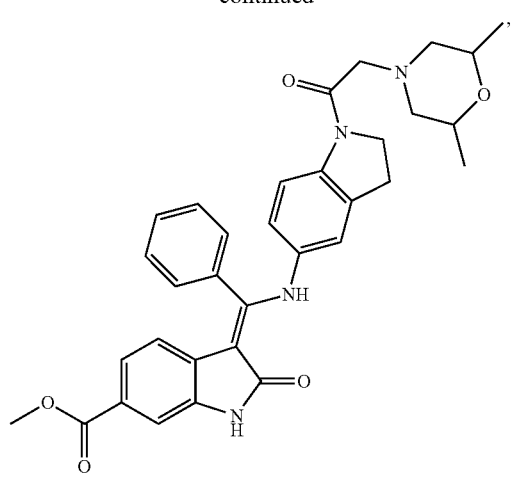
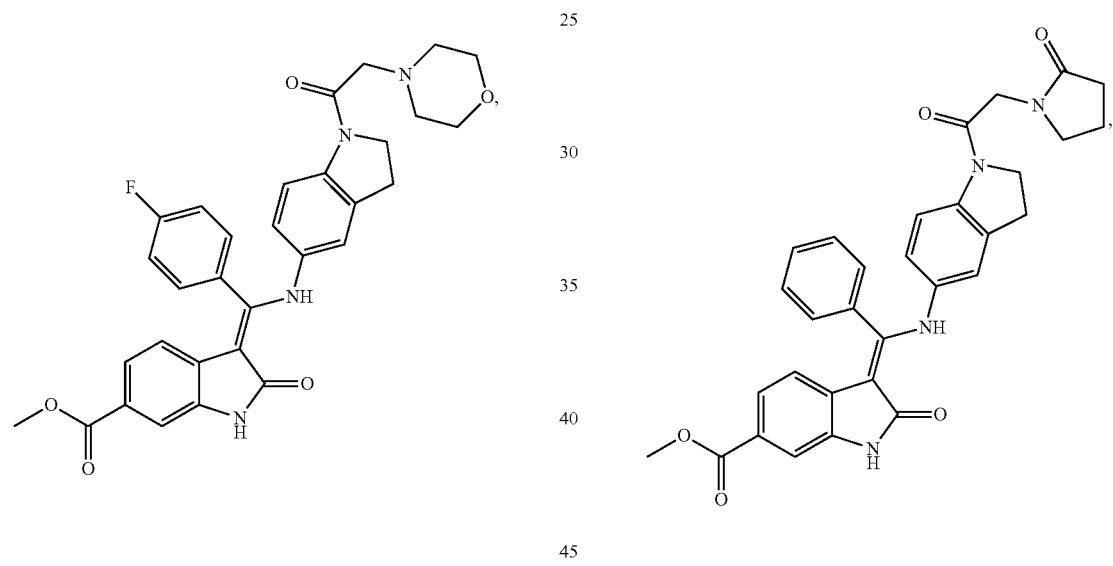
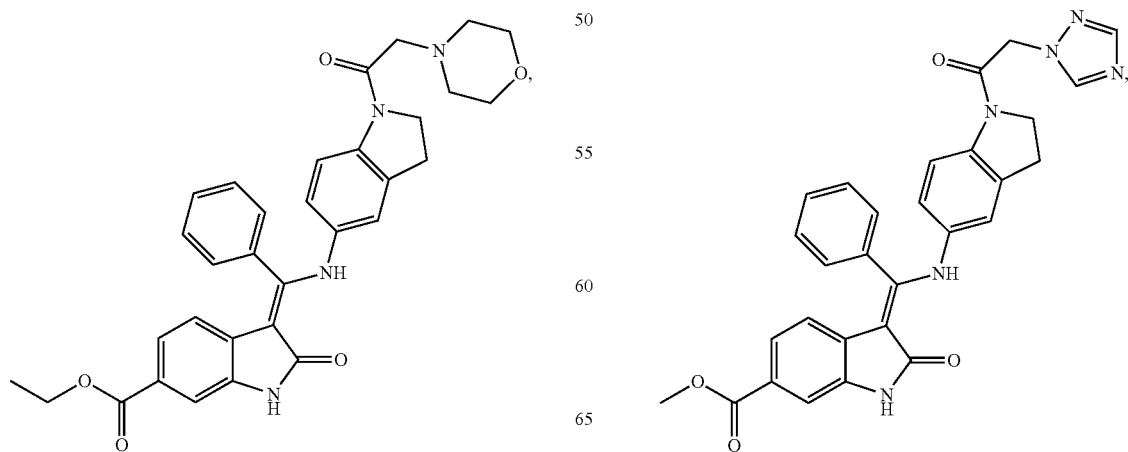

193
-continued
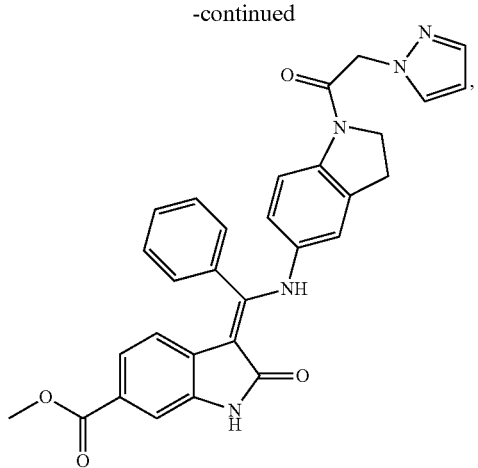
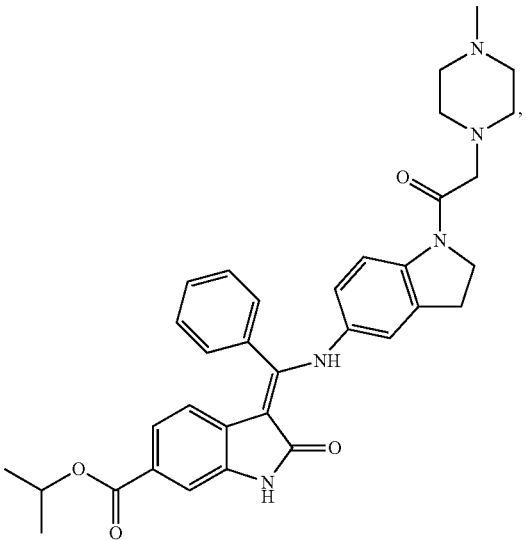
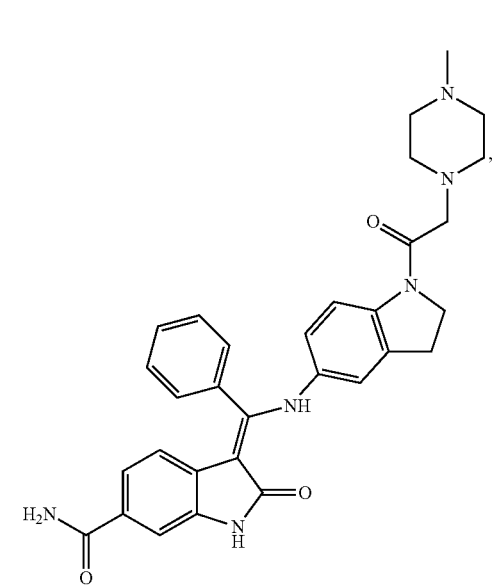
194
-continued
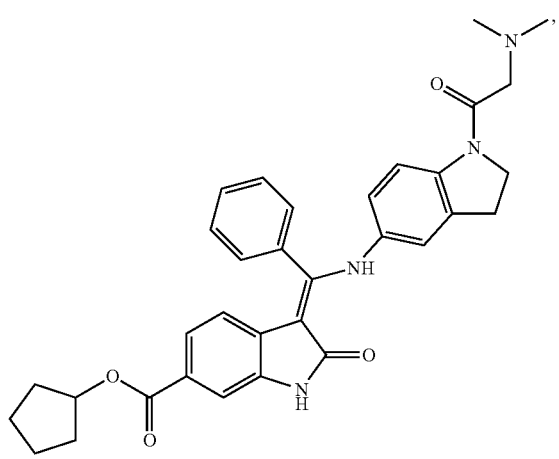
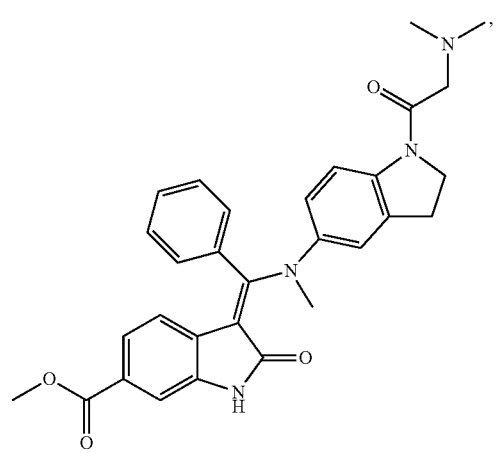
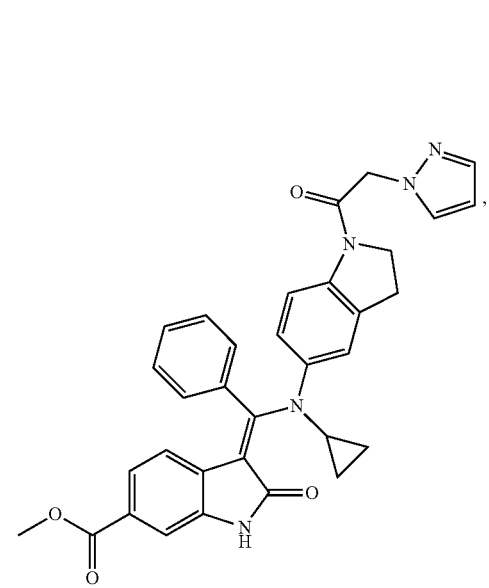

195
-continued
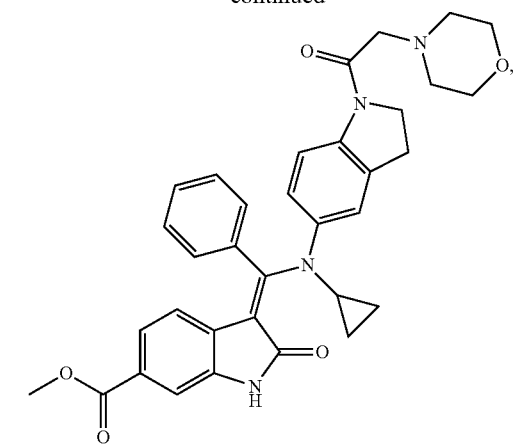
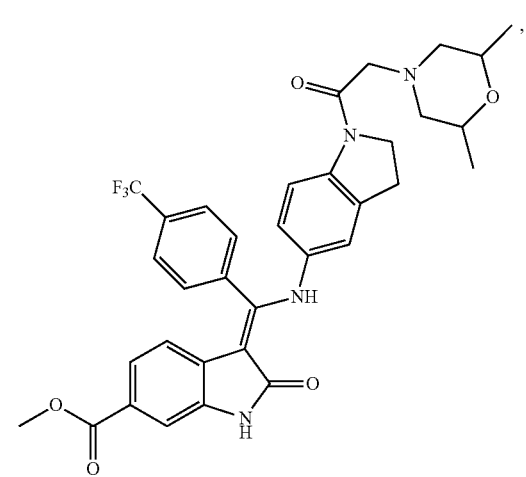
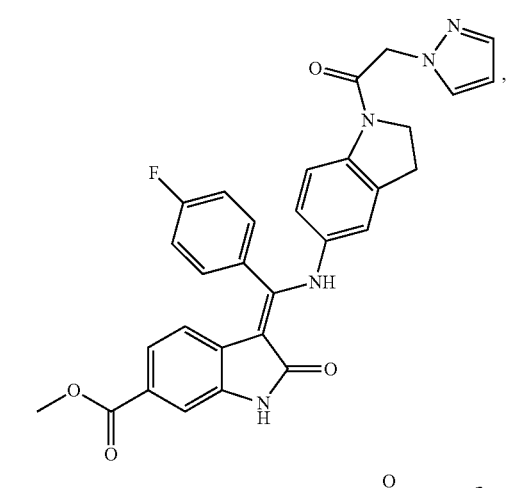
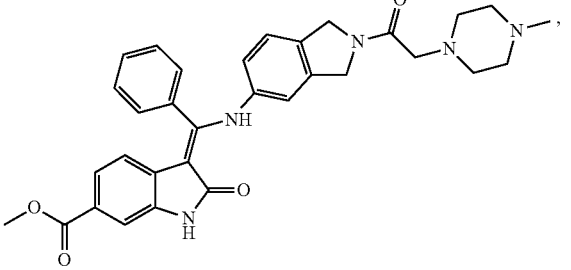
196
-continued
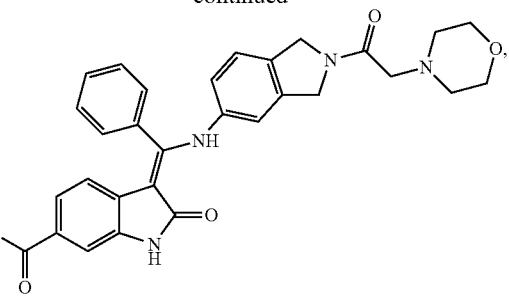
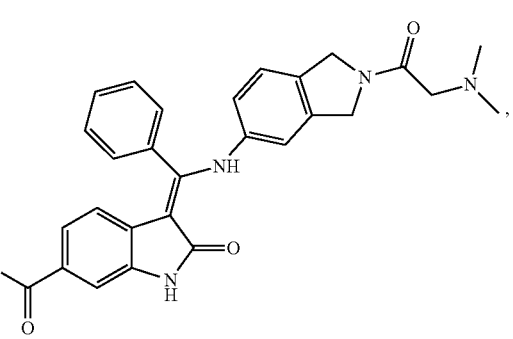
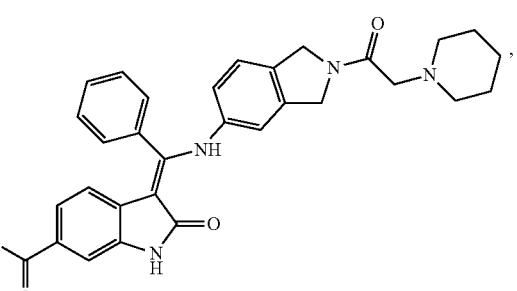
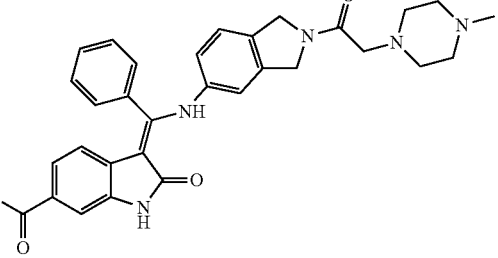
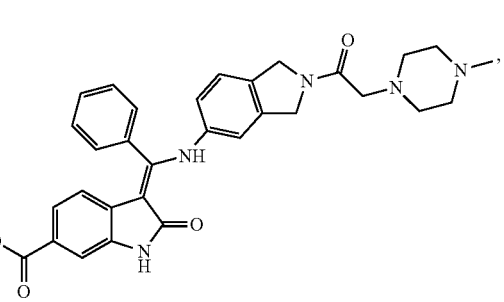

197
-continued
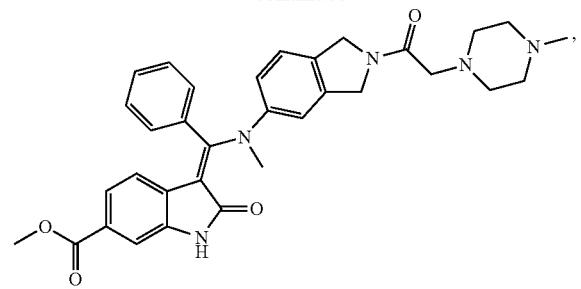
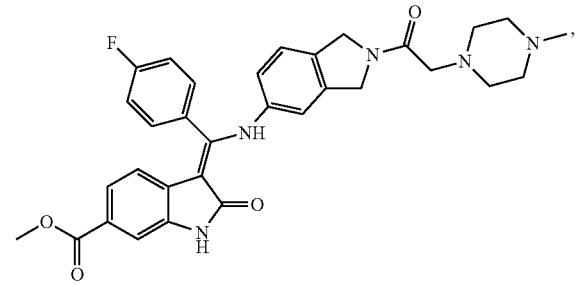
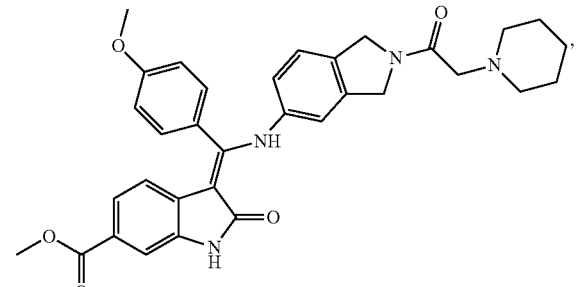
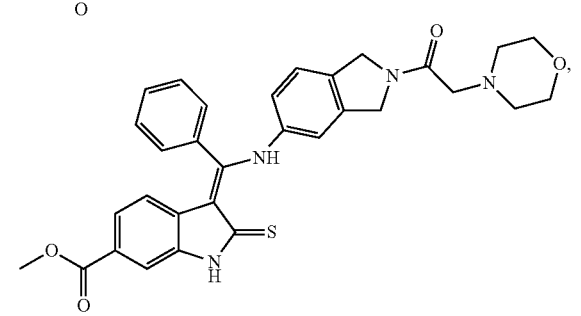
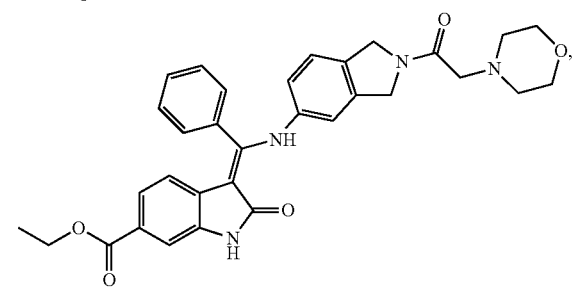
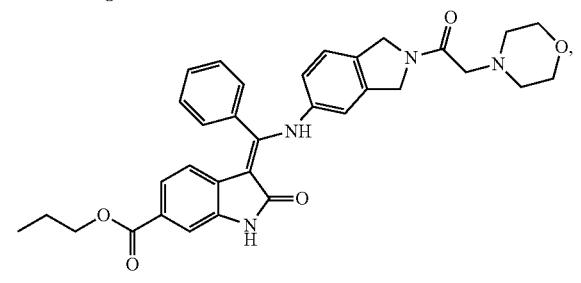
198
-continued
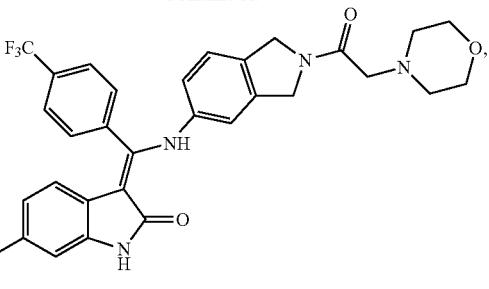
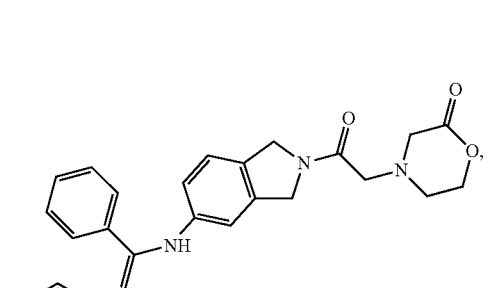
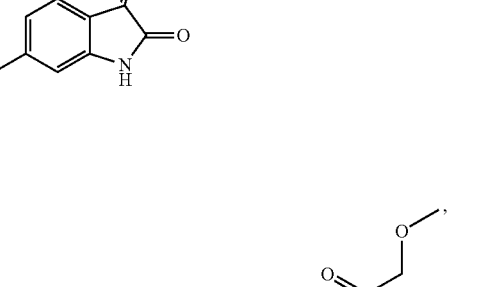
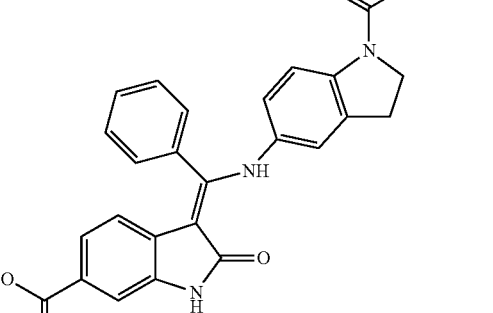
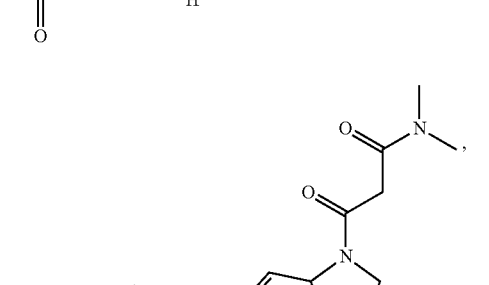
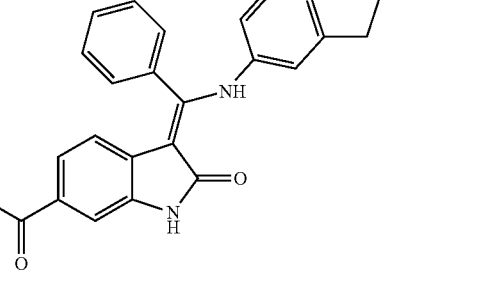

199
-continued
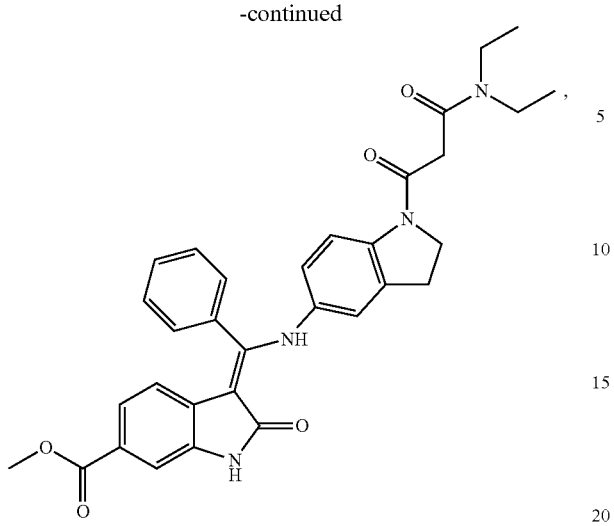
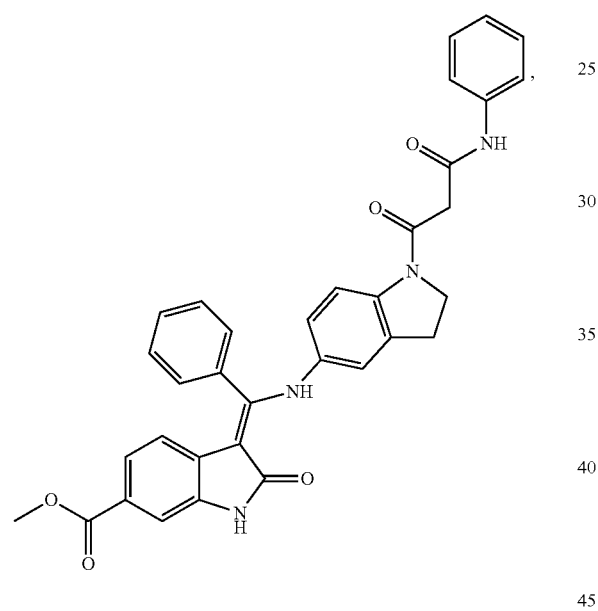
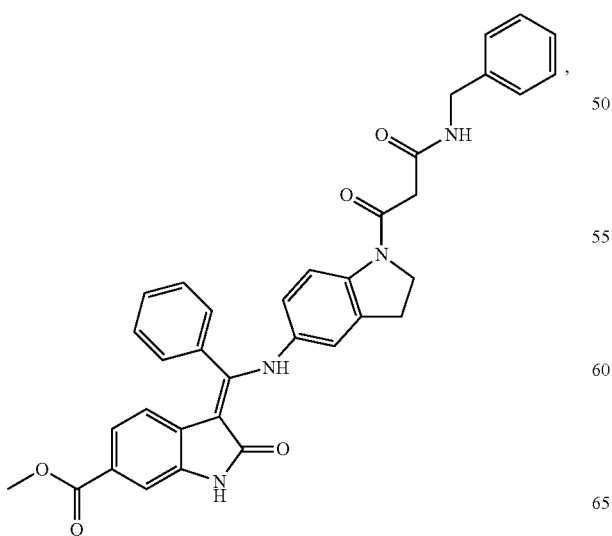
200
-continued
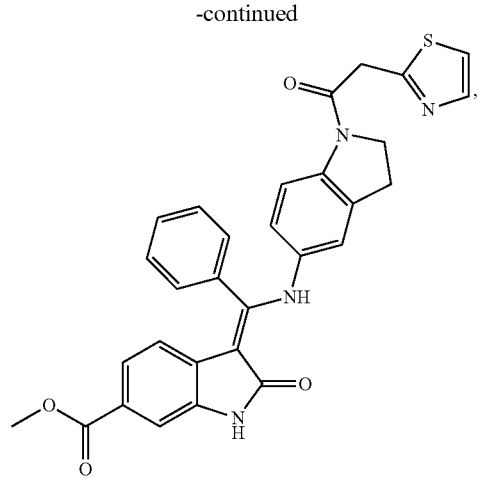
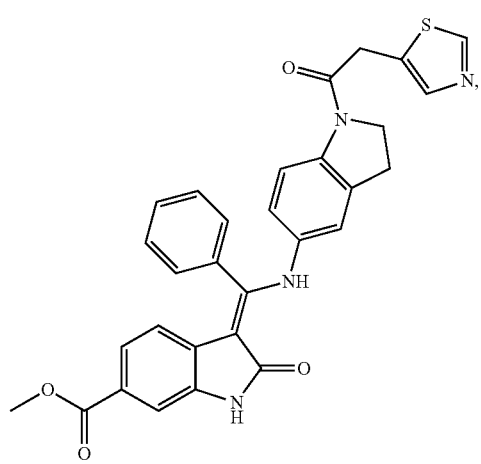
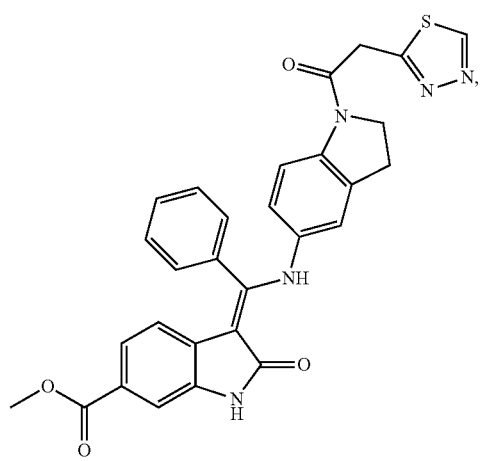

201
-continued
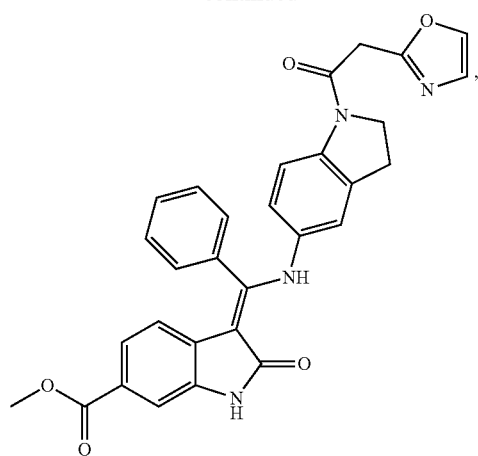
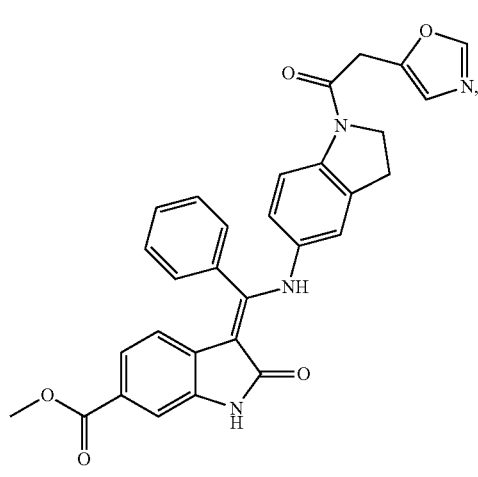
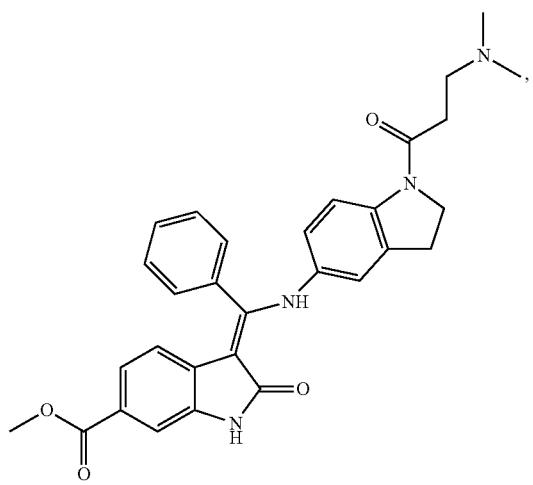
202
-continued
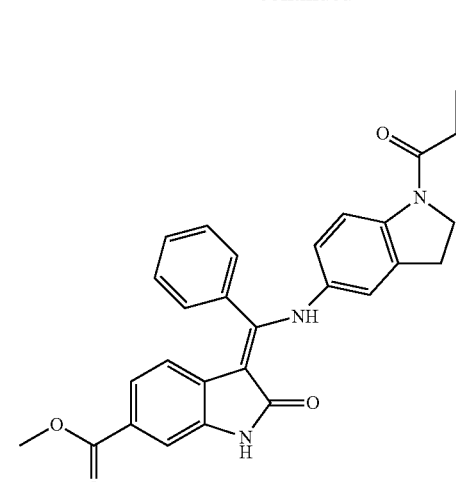
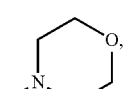
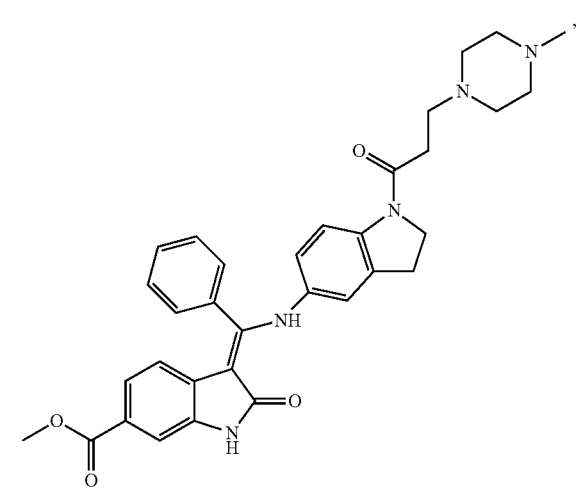

203
-continued
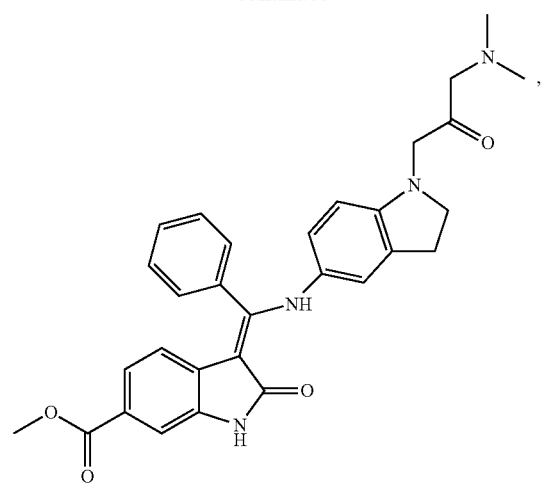
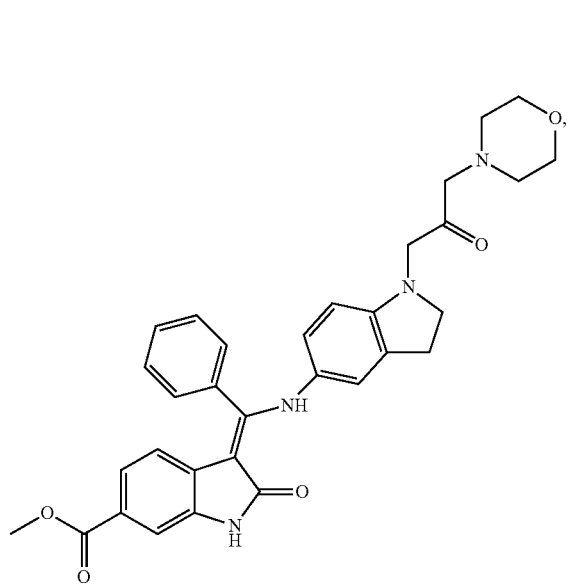
204
-continued
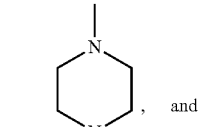
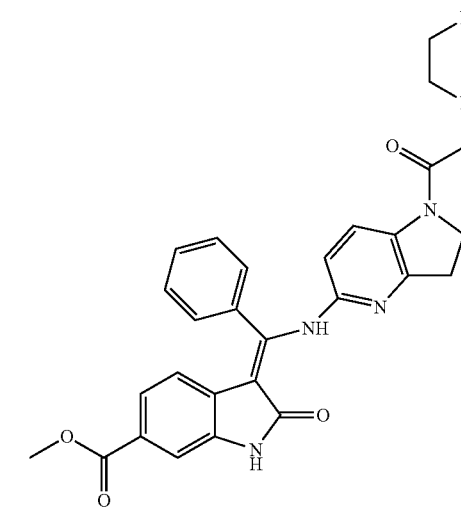
8. A compound, or a pharmaceutically acceptable salt, a deuteride or a stereoisomer thereof, wherein the compound is selected from the group consisting of:

205
-continued
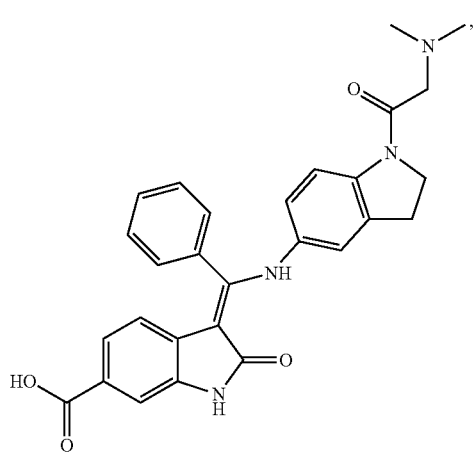
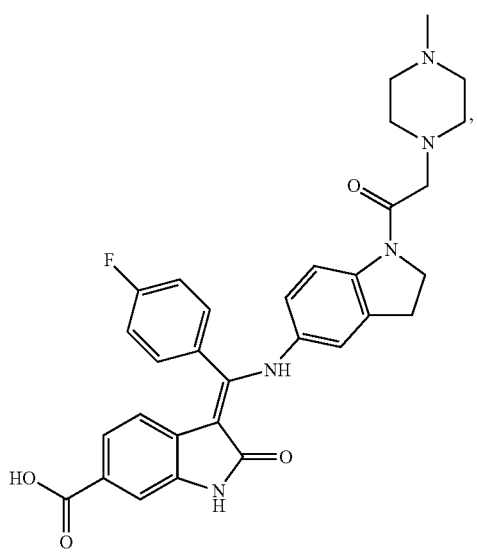
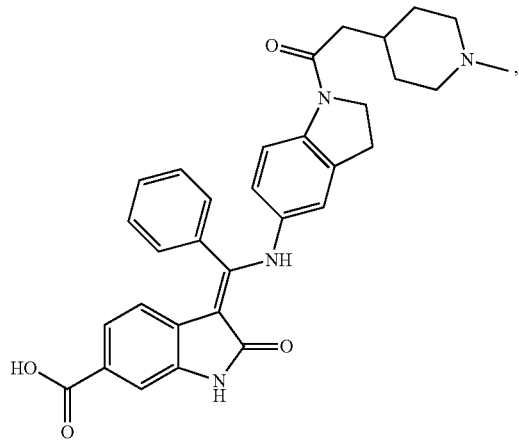
206
-continued
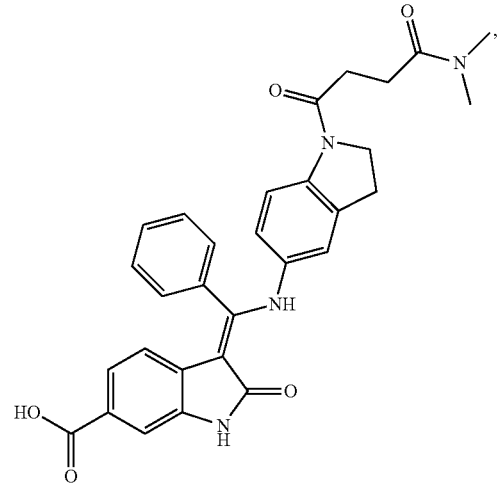
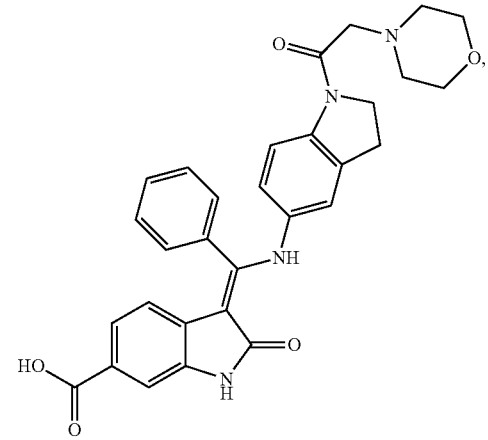
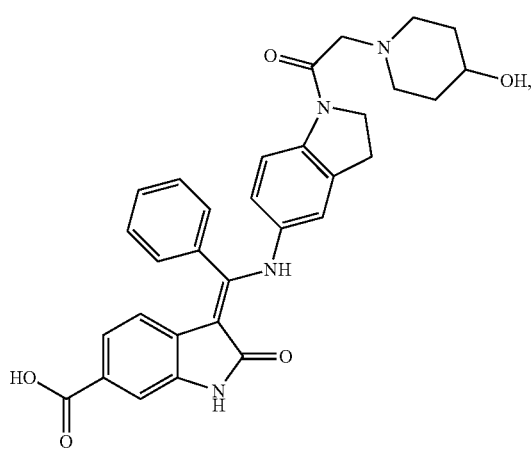

207
-continued
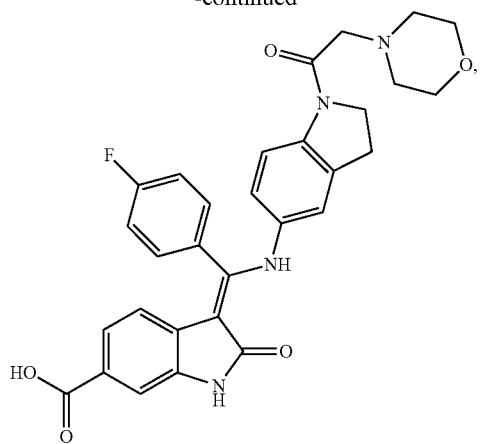
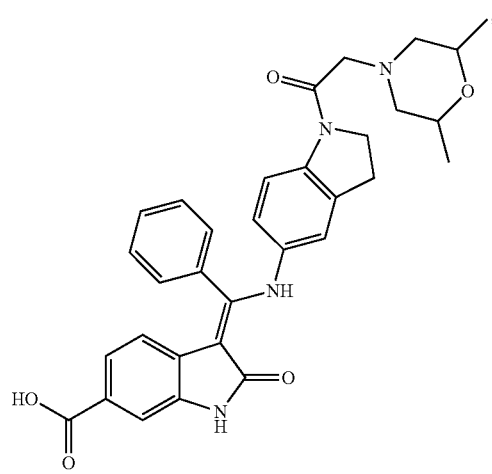
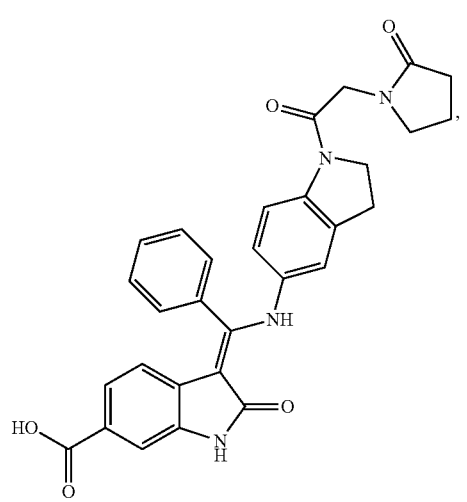
208
-continued
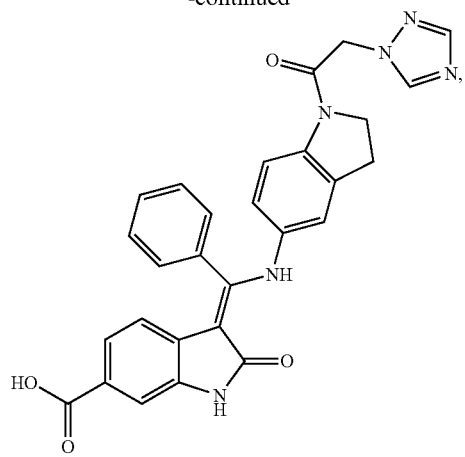
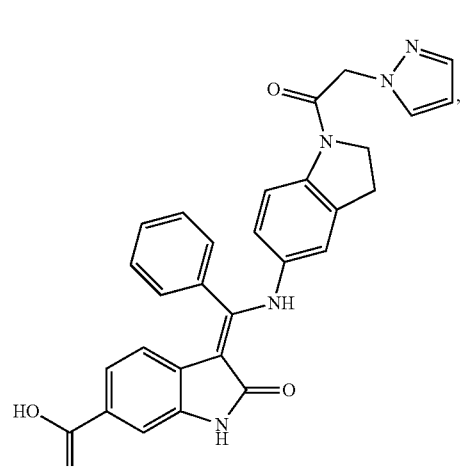
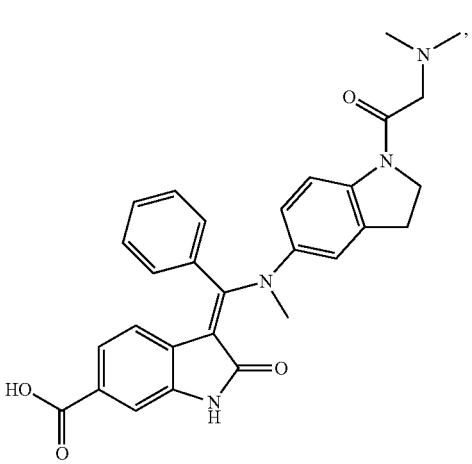

209
-continued
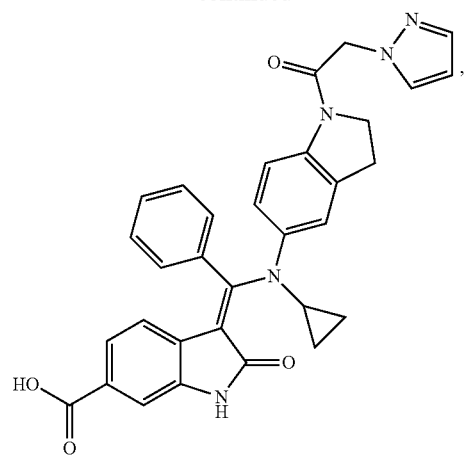
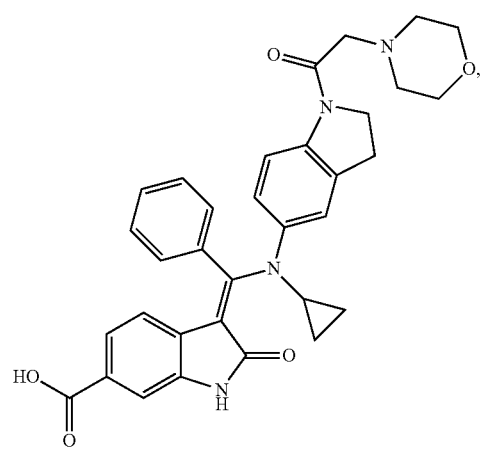
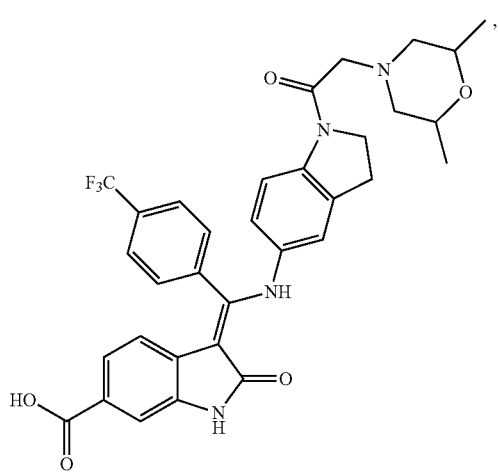
210
-continued
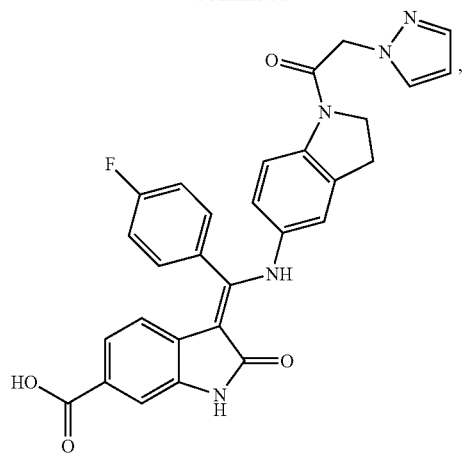
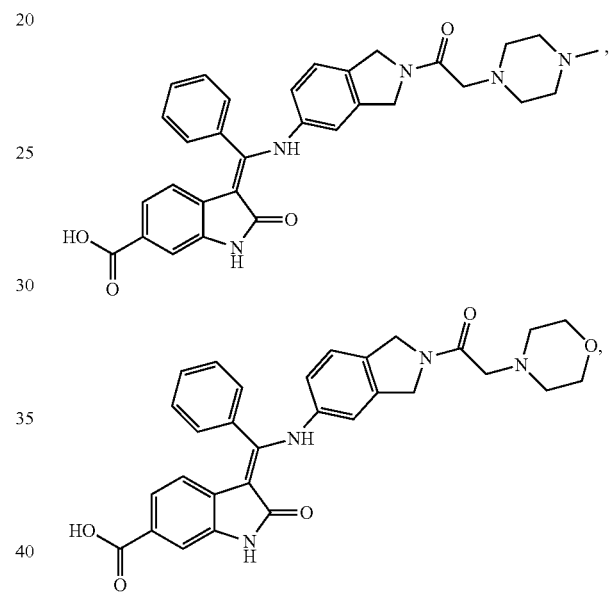
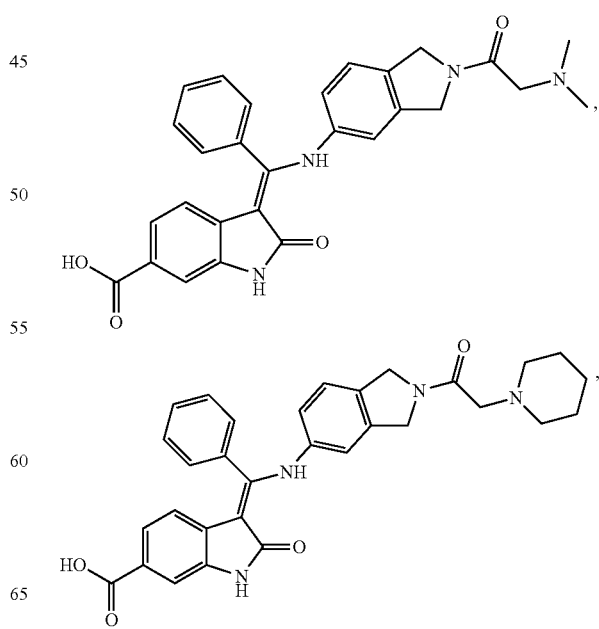

211
-continued
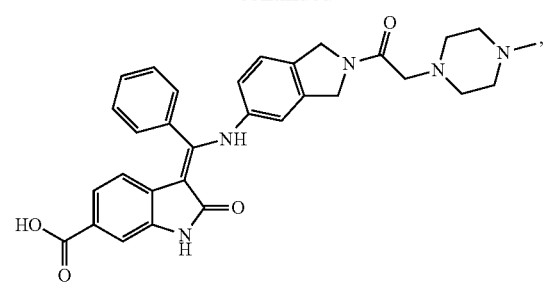
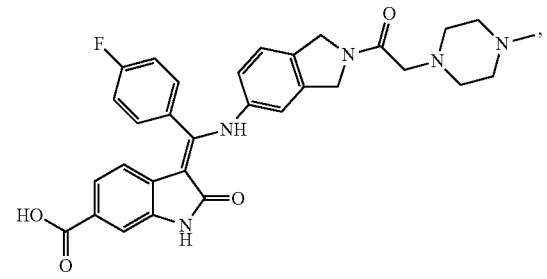
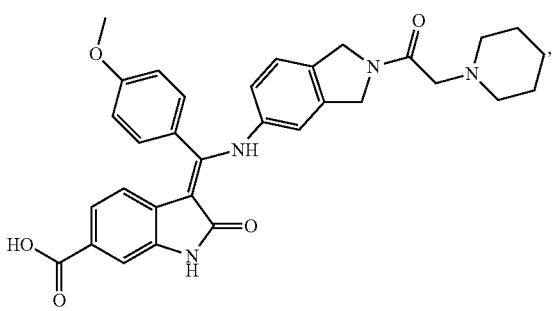
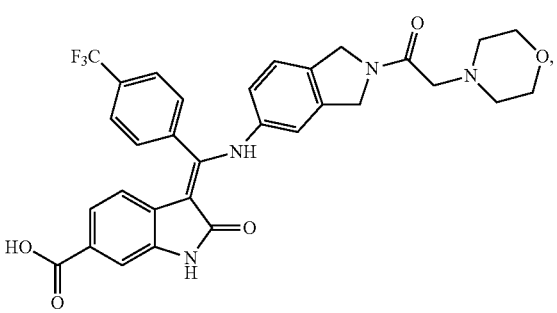
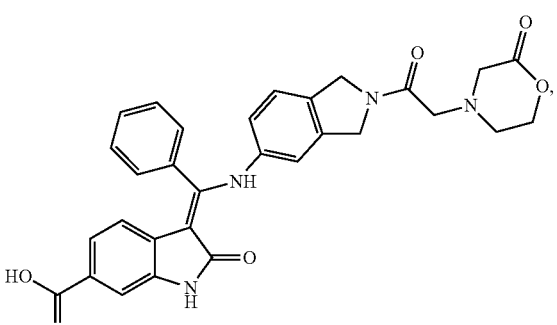
212
-continued
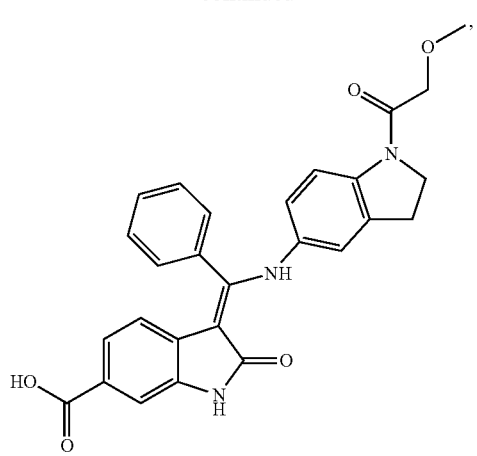
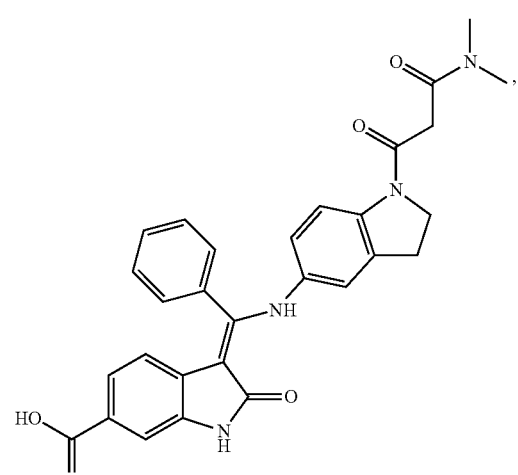
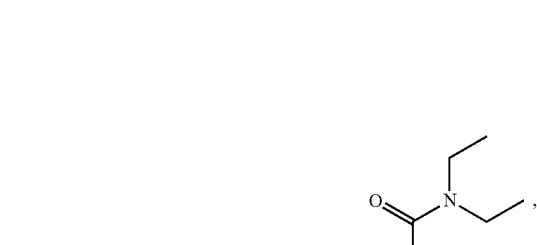
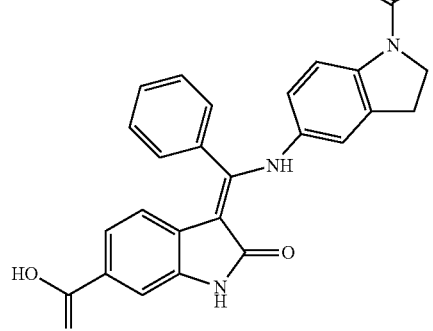

213
-continued
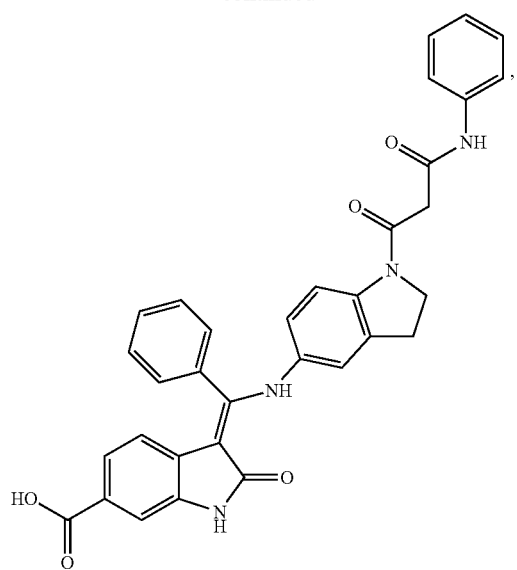
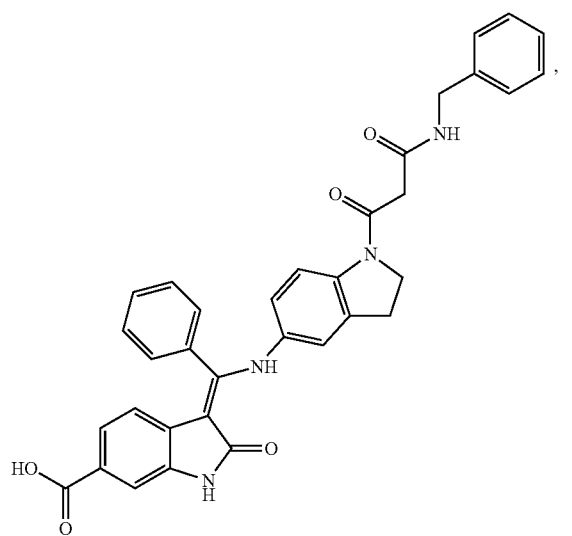
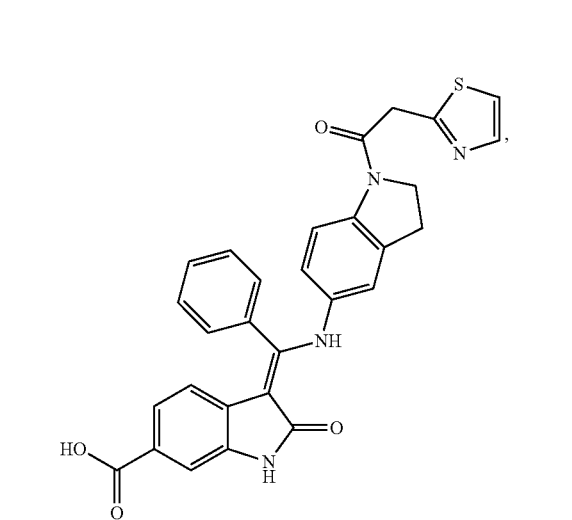
214
-continued
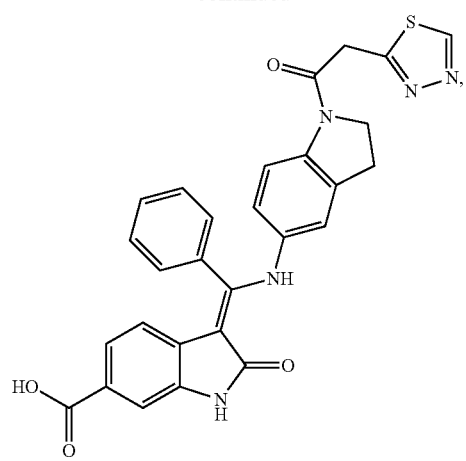
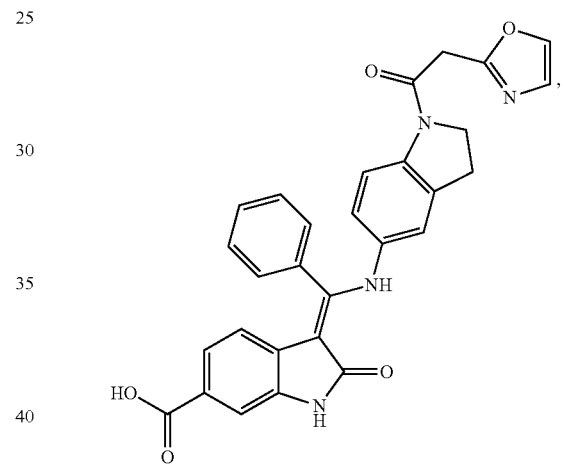
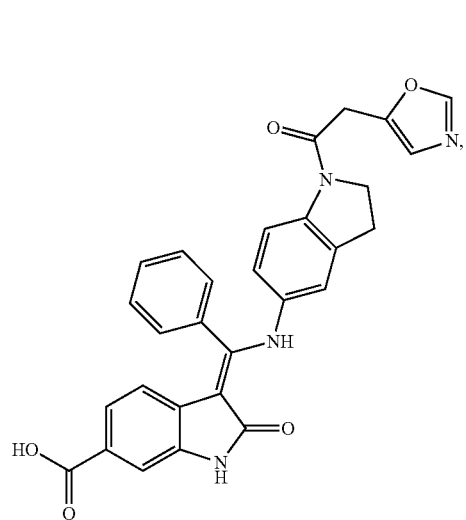

215
-continued
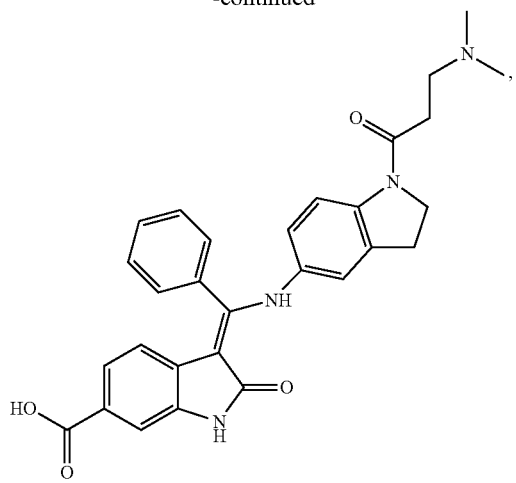
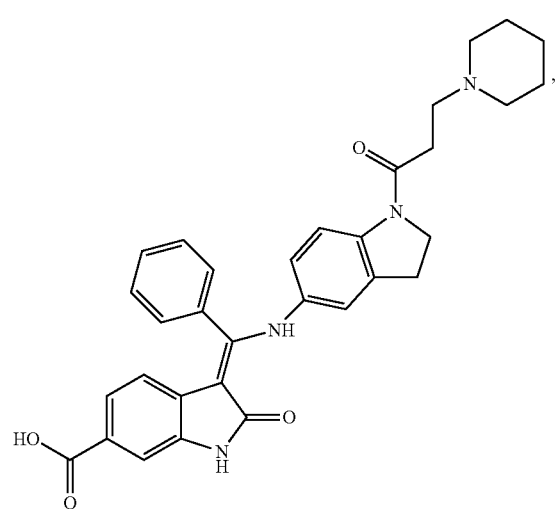
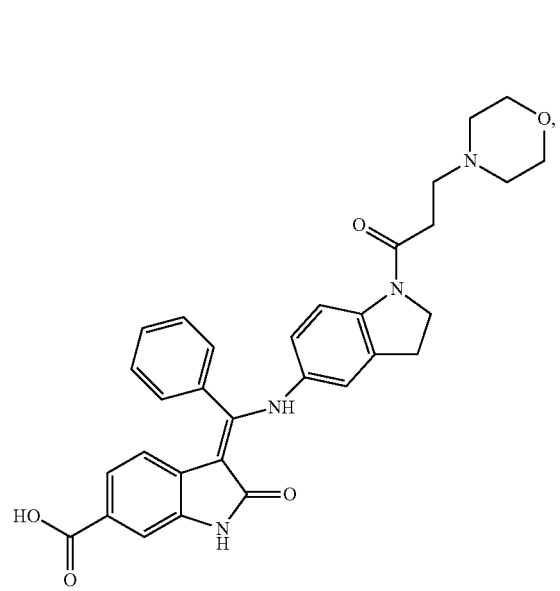
216
-continued
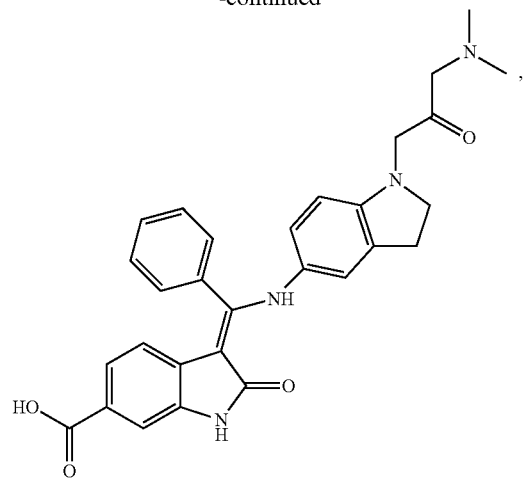
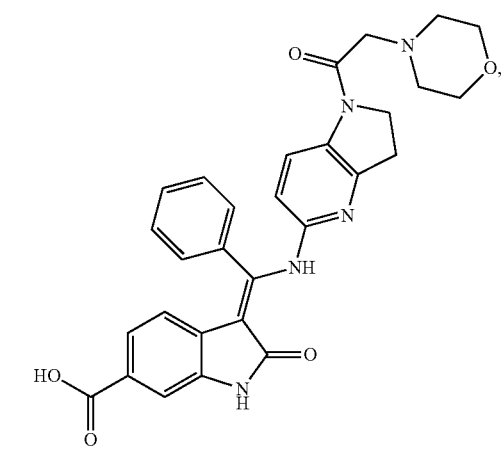
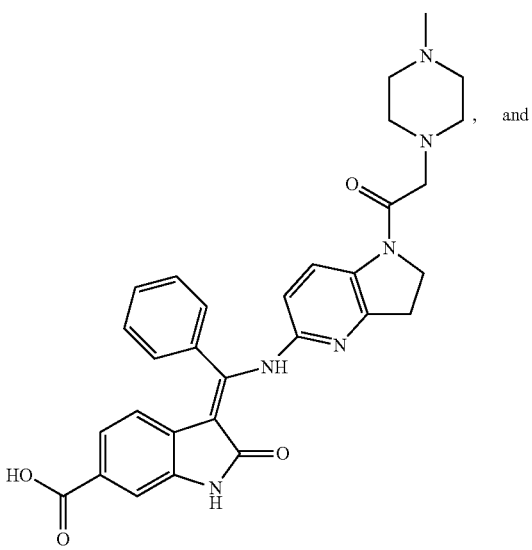

-continued

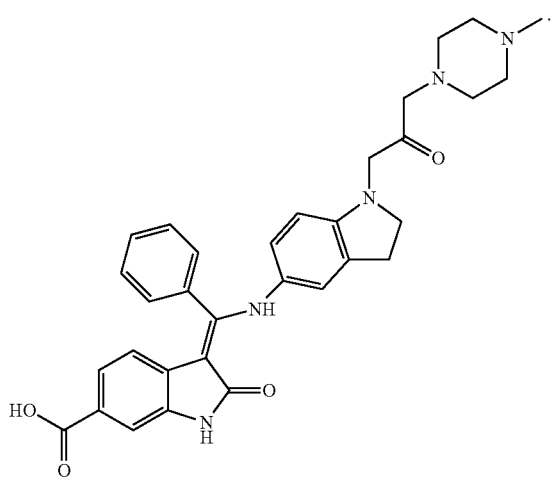 [SMILES: CN1CCN(CC(=O)CN2CCc3cc(N/C(=C4\C(=O)Nc5cc(C(=O)O)ccc54)c4ccccc4)ccc32)CC1]

9. A method for preparing a compound according to claim 1, or a pharmaceutically acceptable salt, a deuteride or a stereoisomer thereof, wherein said method comprises reacting a compound represented by formula (III) with a compound represented by formula (IV) to produce the compound represented by formula (I),

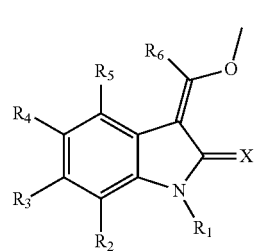

formula (III)

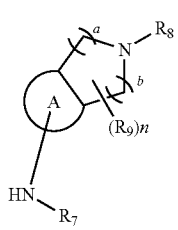

formula (IV)

10. The compound according to claim 1, a pharmaceutically acceptable salt, a deuteride or a stereoisomer thereof, wherein said salt is selected from the group consisting of hydrochloride, sulfate, esilate, mesilate, maleate, tosilate, benzenesulfonate, and oxalate.

11. A pharmaceutical composition comprising the compound according to claim 1, a pharmaceutically acceptable salt, a deuteride or a stereoisomer thereof, and optionally one or more pharmaceutically acceptable carriers.

12. The pharmaceutical composition of claim 11, wherein the pharmaceutical composition further comprises a second therapeutical agent selected from an antineoplastic agent or an immunosuppressive agent, wherein the second therapeutical agent is selected from antimetabolites, selected from the group consisting of capecitabine, and gemcitabine, or combinations thereof; growth factor inhibitors, selected from the group consisting of gefitinib, lapatinib, pazopanib, and imatinib, or combinations thereof; antibodies, selected from the group consisting of herceptin, and bevacizumab, or combinations thereof; mitotic inhibitors, selected from the group consisting of paclitaxel, vinorelbine, docetaxel, and doxorubicin, or combinations thereof; antineoplastic hormones, selected from the group consisting of letrozole, tamoxifen, and fulvestrant, or combinations thereof; alkylating agents, selected from the group consisting of cyclophosphamide, and carmustine, or combinations thereof; metallic platinums, selected from the group consisting of carboplatin, cisplatin, and oxaliplatin, or combinations thereof; topoismerase inhibitors; or immunosuppressive agents, selected from the group consisting of everolimus, anticholinergic agents, βcholine mimetics, steroids, PDE-IV inhibitors, p38 MAP kinase inhibitors, $NK_1$ antagonists, LTD4 antagonists, EGFR inhibitors, and endothelin antagonists, or combinations thereof.

13. A pharmaceutical formulation, wherein said pharmaceutical formulation comprises the compound according to claim 1, a pharmaceutically acceptable salt, a deuteride or a stereoisomer thereof, and one or more pharmaceutically acceptable carriers, wherein said pharmaceutical formulation is in any pharmaceutically acceptable dosage.

14. A method of treating at least one of fibrous degeneration disease, treating excessive proliferation disease, inhibiting the angiogenesis and reducing vascular permeability comprising the step of:
administering the compound according to claim 1, or a pharmaceutically acceptable salt, a deuteride, or a stereoisomer thereof,
wherein the fibrous degeneration disease is atleast one of fibrous degeneration and remodeling of pulmonary tissue in chronic obstructive pulmonary disease; fibrous degeneration and remodeling of pulmonary tissue in chronic bronchitis; fibrous degeneration and remodeling of pulmonary tissue in emphysema; pulmonary fibrous degeneration and pulmonary disease with fibrosis components; fibrous degeneration and remodeling in asthma; fibrous degeneration in rheumatoid arthritis; virus-induced hepatic cirrhosis; radiation-induced fibrous degeneration; postangioplasty restenosis; chronic glomerulonephritis; renal fibrous degeneration in a cyclosporin-administrated patient and hypertension-induced renal fibrous degeneration; and skin disease having fibrosis components and over cicatrization;
wherein the excessive proliferation disease is at least one of cancer and non-carcinomatous disease; the cancer is selected from the group consisting of cerebroma, pulmonary carcinoma, nonsmall cell pulmonary carcinoma, squamous cell carcinoma, bladder carcinoma, gastric carcinoma, ovarian carcinoma, peritoneal carcinoma, pancreatic carcinoma, breast carcinoma, head and neck carcinoma, uterocervical carcinoma, endometrial carcinoma, colorectal carcinoma, hepatoma, renal carcinoma, adenocarcinoma of esophagus, esophageal squamous cell carcinoma, solid tumor, non-Hodgkin lymphoma, central nervous system neuroplasm selected from glioma, glioblastoma multiforme, glioma sarcomatosum, prostatic carcinoma, and thyroid carcinoma, or combinations thereof; non-carcinomatous disease selected from the group consisting of benign skin and prostate hyperplasia, or combinations thereof.

15. A method of treating at least one of fibrous degeneration disease, treating excessive proliferation disease, inhibiting the angiogenesis and reducing vascular permeability comprising the step of:

administering the compound according to claim 1, or a pharmaceutically acceptable salt, a deuteride, or a stereoisomer thereof, wherein pulmonary fibrous degeneration and the pulmonary disease having fibrous degeneration components is atleast one of idiopathic pulmonary fibrosis degeneration, giant cell interstitial pneumonia, sarcoidosis, cystic fibrous degeneration, respiratory distress syndrome, drug-induced pulmonary fibrous degeneration, granulomatosis, silicosis, asbestosis, systemic sclerosis, virus-induced hepatic cirrhosis, and skin disease having fibrous degeneration components selected from the group consisting of scleroderma, and systemic lupus erythematosus, or combinations thereof.

* * * * *